(12) United States Patent
Cromie et al.

(10) Patent No.: US 9,120,855 B2
(45) Date of Patent: Sep. 1, 2015

(54) BIOLOGIC COMPOUNDS DIRECTED AGAINST DEATH RECEPTOR 5

(75) Inventors: Karen Cromie, Merelbeke (BE); Bruno Dombrecht, Heusden (BE); Seth Ettenberg, Melrose, MA (US); Joost Kolkman, Sint-Martens-Latem (BE); Jing Li, Lexington, MA (US); Kris Meerschaert, Sint-Gillis-Waas (BE); David Raymond Stover, Sherman Oaks, CA (US); Jingxin Zhang, Walpole, MA (US)

(73) Assignee: NOVARTIS AG, Basel (CH)

(*) Notice: Subject to any disclaimer, the term of this patent is extended or adjusted under 35 U.S.C. 154(b) by 557 days.

(21) Appl. No.: 13/024,174

(22) Filed: Feb. 9, 2011

(65) Prior Publication Data

US 2011/0318366 A1    Dec. 29, 2011

Related U.S. Application Data

(60) Provisional application No. 61/303,173, filed on Feb. 10, 2010, provisional application No. 61/308,599, filed on Feb. 26, 2010.

(51) Int. Cl.
| | |
|---|---|
| *A61K 39/395* | (2006.01) |
| *A61P 35/00* | (2006.01) |
| *A61P 35/02* | (2006.01) |
| *C07K 16/28* | (2006.01) |
| *C07K 14/00* | (2006.01) |
| *A61K 39/00* | (2006.01) |

(52) U.S. Cl.
CPC ........ *C07K 16/2878* (2013.01); *A61K 2039/505* (2013.01); *C07K 2316/95* (2013.01); *C07K 2317/22* (2013.01); *C07K 2317/24* (2013.01); *C07K 2317/34* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | |
|---|---|---|
| 6,342,369 B1 | 1/2002 | Ashkenazi |
| 7,229,617 B2 | 6/2007 | Nasoff et al. |
| 7,279,160 B2 | 10/2007 | Zhou et al. |
| 7,595,046 B2 | 9/2009 | Adams et al. |
| 2003/0148455 A1 | 8/2003 | Adams |
| 2006/0088523 A1 | 4/2006 | Andya et al. |
| 2007/0128204 A1 | 6/2007 | Nasoff et al. |
| 2009/0258011 A1 | 10/2009 | Diamond et al. |

FOREIGN PATENT DOCUMENTS

| | | |
|---|---|---|
| WO | 01/77342 | 10/2001 |
| WO | WO 01/83560 A1 | 11/2001 |
| WO | WO 03/037913 A2 | 5/2003 |
| WO | WO 03/038043 A2 | 5/2003 |
| WO | 2005/100399 | 10/2005 |
| WO | WO 2005/114187 A2 | 12/2005 |
| WO | 2008020079 A1 | 2/2008 |
| WO | 2008066854 A2 | 6/2008 |
| WO | WO 2008/066854 A2 | 6/2008 |
| WO | WO 2009/030285 A1 | 3/2009 |
| WO | 2009/020079 | 12/2009 |

OTHER PUBLICATIONS

Shi et al (Cancer Research 2006, 66(24): 11946-11953).*
Rudikoff et al (Proc Natl Acad Sci USA 1982 vol. 79, 1979-1983).*
MacCallum et al. J. Mol. Biol. (1996) 262, 732-745.*
Vajdos et al. (2002) 320, 415-428.*
Wu et al. J. Mol. Biol. (1999) 294, 151-162.*
Adams et al.; "Structural and functional analysis of the interaction between the agonistic monoclonal antibody Apomab and the proapoptotic receptor DR5"; Cell Death and Differentiation; 15:751-761 (2008).
Ashkenazi et al.; "Safety and antitumor activity of recombinant soluble Apo2 ligand"; J. Clin. Invest.; 104:155-162 (1999).
Ashkenazi; "Targeting Death and Decoy Receptors of the Tumournecrosis Factor Superfamily"; Nature—Reviews; 2:420-430 (2002).
Buchsbaum et al.; "TRAIL-receptor antibodies as a potential cancer treatment"; Future Oncol.; 3(4):405-409 (2007).
Camidge; "The Potential of Death Receptor 4- and 5- Directed Therapies in the Treatment of Lung Cancer"; Clinical Lung Cancer; 8(7):413-419 (2007).
Chuntharapai et al.; "Isotype-Dependent Inhibition of Tumor Growth In Vivo by Monoclonal Antibodies to Death Receptor 4"; The Journal of Immunology; 166:4891-4898 (2001).
Clarke et al.; "Reovirus-Induced Apoptosis is Mediated by TRAIL"; Journal of Virology; 74(17):8135-8139 (2000).
Dong et al.; "The function of multiple IkB: NF-kB complexes in the resistance of cancer cells to Taxol-induced apoptosis"; Oncogene; 21:6510-6519 (2002).
Fulda et al.; "Smac agonists sensitize for Apo2L/TRAIL- or anticancer drug-induced apoptosis and induce regression of malignant glioma in vivo"; Nature Medicine; 8(8):808-815 (2002).
Griffith et al.; "Functional Analysis of TRAIL Receptors Using Monoclonal Antibodies"; The Journal of Immunology; 162:2597-2605 (1999).
Huisman et al.; "Paclitaxel Triggers Cell Death Primarily via Caspase-independent Routes in the Non-Small Cell Lung Cancer Cell Line NCI-H460"; Clinical Cancer Research; 8:596-606 (2002).
Hymowitz et al.; "Triggering Cell Death: The Crystal Structure of Apo2L/TRAIL in a Complex with Death Receptor 5"; Molecular Cell; 4:563-571 (1999).

(Continued)

*Primary Examiner* — Gerald R Ewoldt
*Assistant Examiner* — Marianne Dibrino
(74) *Attorney, Agent, or Firm* — Frank Wu

(57) ABSTRACT

The present invention relates to amino acid sequences that are directed against TRAIL cell surface receptor 2 (herein also "DR5"), as well as to compounds or constructs thereof, and in particular proteins and polypeptides and nucleotides that encode them (referred to herein in their entirety as "NB agents") and fragments thereof, and pharmaceutically effective variants thereof, and their use in the diagnosis and treatment of DR5 associated diseases and disorders.

17 Claims, 5 Drawing Sheets

(56) References Cited

OTHER PUBLICATIONS

Ichikawa et al.; "Tumoricidal activity of a novel anti-human DR5 monoclonal antibody without hepatocyte cytotoxicity"; Nature Medicine; 7(8):954-960 (2001).
Imgenex Catalog No. IMG-120A; "Polyclonal Antibody to DR5/Apo2/TRAIL-R2/TRAILR2/TRICK2/KILLER"; Datasheet [Downloaded/Printed off Internet—Sep. 17, 2009].
Kabat et al.; "Identical V Region Amino Acid Sequences and Segments of Sequences in Antibodies of Different Specificities: Relative Contributions of VH and VL Genes, Minigenes, and Complementarity-Determining Regions to Binding of Antibody-Combining Sites"; The Journal of Immunology; 147 (5):1709-1719 (1991).
Kim et al.; "Molecular Determinants of Response to TRAIL in Killing of Normal and Cancer Cells"; Clinical Cancer Research; 6:335-346 (2000).
Kreuz et al.; "NF-kB Inducers Upregulate cFLIP, a Cycloheximide-Sensitive Inhibitor of Death Receptor Signaling"; Molecular and Cellular Biology; 21(12):3964-3973 (2001).
Laguinge et al.; "DR5 Receptor Mediates Anoikis in Human Colorectal Carcinoma Cell Lines"; Cancer Res; 68 (3):909-917 (2008).
Li et al.; "Antitumor efficacy of LBY135, an anti-DR5 monoclonal antibody, alone or in combination with chemotherapy in human colon tumor cell lines and xenografts"; Therapeutic Approaches to Apoptosis: Poster Presentations-Abstract #4874; 98th AACR Annual Meeting—Apr. 14-18, 2007, Los Angeles, CA [Abstract only].
Li et al.; "LBY135, a Novel Anti-DR5 Agonistic Antibody Induces Tumor Cell-Specific Cytotoxic Activity in Human Colon Tumor Cell Lines and Xenografts"; Drug Development Research; 69:69-82 (2008).
Li et al.; "Activation of the Proapoptotic Death Receptor DR5 by Oligomeric Peptide and Antibody Agonists"; J. Mol. Biol.; 361:522-536 (2006).
Liu et al.; "Tumor Necrosis Factor—Related Apoptosis-Inducing Ligand and Chemotherapy Cooperate to Induce Apoptosis in Mesothelioma Cell Lines"; Am. J. Respir. Cell Mol. Biol.; 25:111-118 (2001).
Mitsiades et al.; "TRAIL/Apo2L ligand selectively induces apoptosis and overcomes drug resistance in multiple myeloma: therapeutic applications"; Blood; 98(3):795-804 (2001).
Mongkolsapaya et al.; "Structure of the TRAIL-DR5 complex reveals mechanisms conferring specificity in apoptotic initiation"; nature structural biology; 6(11):1048-1053 (1999).
Motoki et al.; "Enhanced Apoptosis and Tumor Regression Induced by a Direct Agonist Antibody to Tumor Necrosis Factor—Related Apoptosis-Inducing Ligand Receptor 2"; Clin. Cancer Res.; 11:3126-3135 (2005).
Nasoff et al.; "Generation and purification of NVP-LCR211"; RD-2005-51190—Release Ready Method/Study Report; Confidential (2005).
Natoni et al.; "TRAIL signals to apoptosis in chronic lymphocytic leukaemia cells primarily through TRAIL-R1 whereas cross-linked agonistic TRAIL-R2 antibodies facilitate signalling via TRAIL-R2"; British Journal of Haematology; 139:568-577 (2007).
Odoux et al.; "TRAIL, FASL and a Blocking Anti-DR5 Antibody Augment Paclitaxel-Induced Apoptosis in Human Non-Small-Cell Lung Cancer"; Int. J. Cancer; 97:458-465 (2002).
Pan et al.; "An Antagonist Decoy Receptor and a Death Domain-Containing Receptor for TRAIL"; Science; 277:815-818 (1997).
Poulaki et al.; "Regulation of Apo2L/Tumor Necrosis Factor-Related Apoptosis-Inducing Ligand-Induced Apoptosis in Thyroid Carcinoma Cells"; American Journal of Pathology; 161(2):643-654 (2002).
Ren et al.; "Differential Regulation of the Trail Death Receptors DR4 and DR5 by the Signal Recognition Particle"; Molecular Biology of the Cell; 15:5064-5074 (2004).
Rottmann et al.; "A TRAIL receptor-dependent synthetic lethal relationship between MYC activation and GSK3beta/FBW7 loss of function"; PNAS; 102(42):15195-15200 (2005).
Sheridan et al.; "Control of TRAIL-Induced Apoptosis by a Family of Signaling and Decoy Receptors"; Science; 277:818-821 (1997).
Shigeno et al.; "Interferon-alpha sensitizes human hepatoma cells to TRAIL-induced apoptosis through DR5 upregulation and NF-kB inactivation"; Oncogene; 22:1653-1662 (2003).
Wagner et al.; "Activation and Suppression of the TRAIL Death-Receptor Pathway in Chemotherapy Sensitive and Resistant Follicular Lymphoma Cells"; Cancer Biology & Therapy; 2(5):534-540 (2003).
Wang et al.; "Synthetic lethal targeting of MYC by activation of the DR5 death receptor pathway"; Cancer Cell; 5:501-512 (2004).
Weber et al.; "Vitamin E Succinate is a Potent Novel Antineoplastic Agent with High Selectivity and Cooperativity with Tumor Necrosis Factor-related Apoptosis-inducing Ligand (Apo2 Ligand) in Vivo"; Clinical Cancer Research; 8:863-869 (2002).
Cui et al., "IL-4 regulates COX-2 and PGE2 Production in Human Non-Small Cell Lung Cancer"; Biochemical and Biophysical Research Communications vol. 343: 995-1001 (2006).
Dohlsten et al., "Monoclonal Antibody-targeted Superantigens: A Different Class of Anti-tumor Agents"; Immunology, vol. 88: 9287-9291 (Oct. 1991).
Nilsson et al., "Sialosyllactotetraosylceramide, a Novel Ganglioside Antigen Detected in Human Carcinomas by a Monoclonal Antibody" Federation of European Biochemical Societies, vol. 182, No. 2 (Mar. 1985).
Pukac et al., "HGS-ETRI, a Fully Human TRAIL-receptor I Monoclonal Antibody, Induces Cell Death in Multiple Tumour Types in vitro and in vivo" British Journal of Cancer, vol. 92: 1430-1441 (2005).
Rudikoff et al., "Single Amino Acid Substitution Altering Antigen-binding Specificity"; Immunology, vol. 79: 1979-1983 (Mar. 1982).
Shi et al., "Therapeutic Expression of an Anti-Death Receptor 5 Single-Chain Fixed-Variable Region Prevents Tumor Growth in Mice" Cancer Research, vol. 66: 11946-11953 (2006).
Wang et al., "Induction of NAD(P)H:quinone Reductase by Vitamins A, E, and C in Colo205 Colon Cancer Cells" Cancer Letters, vol. 98: 63-69 (1995).
Weinberg et al., "Aromatase Inhibitors in Human Lung Cancer Therapy" Cancer Research, vol. 65: 11287-11291 (2005).
[No Author Listed] BCL2 Jurkat (ATCC® CRL-2899™). ATCC. 2003. Website. <http://www.atcc.org/Products/All/CRL-2899.aspx#generalinformation> Last Accessed May 2, 2014. 6 pages.
[No Author Listed] MOLT-4 (ATCC® CRL-1582™). ATCC. Website. <http://www.atcc.org/Products/All/CRL-1582.aspx#generalinformation> Last Accessed May 2, 2014. 6 pages.
[No Author Listed] NCI-H226 [H226] (ATCC® CRL-5826™). ATCC. 1980. Website. <http://www.atcc.org/Products/All/CRL-5826.aspx#generalinformation> Last Accessed May 2, 2014. 6 pages.
[No Author Listed] NCI-H2052 [H2052] (ATCC® CRL-5915™). ATCC. Website. <http://www.atcc.org/Products/All/CRL-5915.aspx#generalinformation> Last Accessed May 2, 2014. 6 pages.
[No Author Listed] NCI-H2122 [H2122] (ATCC® CRL-5985™). ATCC. Jan. 1989. Website. <http://www.atcc.org/Products/All/CRL-5985.aspx#generalinformation> Last Accessed May 2, 2014. 6 pages.
[No Author Listed] COLO 205 (ATCC® CCL-222™). ATCC. Website. <http://www.atcc.org/Products/All/CCL-222.aspx#generalinformation> Last Accessed May 2, 2014. 6 pages.

* cited by examiner

SEQUENCE LISTING

```
<160> NUMBER OF SEQ ID NOS: 114

<210> SEQ ID NO 1
<211> LENGTH: 126
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 1

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Phe Gly Ser Ile
                20                  25                  30

Arg Val Gly Trp Phe Arg Gln Thr Pro Gly Lys Glu Arg Glu Phe Val
            35                  40                  45

Ala Ala Ile Asn Arg Asn Asp Gly Thr Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Met Gln Met Ala Ser Leu Lys Pro Glu Asp Thr Ala Val Tyr Tyr Cys
                85                  90                  95

Ala Ala Gly Leu Gln Tyr Asn Arg Ser Ala Asp Arg Val Pro Val Gly
            100                 105                 110

Ala Val Tyr Trp Gly Gln Gly Thr Gln Val Thr Val Ser Ser
        115                 120                 125

<210> SEQ ID NO 2
<211> LENGTH: 124
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 2

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
                20                  25                  30

Ala Met Gly Trp Phe Arg Gln Ala Pro Gly Lys Glu Arg Glu Phe Val
            35                  40                  45

Ala Ala Leu Asn Trp Ser Gly Ser Thr Tyr Tyr Val Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Gly Ser Phe Ser Leu Gly Gly Arg Pro Tyr Gly Asp Asp
            100                 105                 110
```

Tyr Trp Gly Lys Gly Thr Leu Val Thr Val Ser Ser
            115                 120

<210> SEQ ID NO 3
<211> LENGTH: 126
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Ala Ile Asn Ser Gly Gly Asp Thr Tyr Tyr Arg Asp Ser Val
    50                  55                  60

Arg Gly Arg Phe Thr Ile Ser Arg Asp Asn Phe Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ala Glu Gly Pro Pro Thr Phe Ser Leu Ile Arg Thr Met Thr
            100                 105                 110

Val Asp Pro Gly Ala Gln Gly Thr Gln Val Thr Val Ser Ser
            115                 120                 125

<210> SEQ ID NO 4
<211> LENGTH: 122
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Asp Ser Ile Asn
            20                  25                  30

Asn Met Gly Trp Tyr Arg Gln Ala Pro Gly Lys Gln Arg Glu Leu Val
        35                  40                  45

Ala Glu Ile Thr Pro Arg Gly Arg Thr Asn Tyr Ala Asp Ser Glu Lys
    50                  55                  60

Ser Arg Phe Thr Ile Ser Arg Asp Asn Ala Lys Arg Thr Val Asn Leu
65                  70                  75                  80

Gln Met Asn Ser Leu Lys Pro Glu Asp Thr Ala Val Tyr Tyr Cys Asn
                85                  90                  95

Ala Glu Val Arg Glu Arg Gly Thr Ser Trp Tyr Arg Pro Asp Tyr Trp
            100                 105                 110

Gly Gln Gly Thr Gln Val Thr Val Ser Ser
            115                 120

<210> SEQ ID NO 5
<211> LENGTH: 122
<212> TYPE: PRT
<213> ORGANISM: Artificial Sequence

```
<220> FEATURE:
<223> OTHER INFORMATION: Description of Artificial Sequence: Synthetic
      recombinant polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
    50                  55                  60

Gly Arg Phe Thr Ile Ser Arg Asp Asn Ala Lys Asp Thr Met Tyr Leu
65                  70                  75                  80

Gln Met Asn Ser Leu Lys Pro Glu Asp Thr Ala Val Tyr Phe Cys Asn
                85                  90                  95

Ala Glu Ile Leu Lys Arg Ala Tyr Ile Asp Val Tyr Val Asn Tyr Trp
            100                 105                 110

Gly Gln Gly Thr Gln Val Thr Val Ser Ser
        115                 120

<210> SEQ ID NO 6
<211> LENGTH: 448
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 6

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Phe Gly Ser Ile
            20                  25                  30

Arg Val Gly Trp Phe Arg Gln Thr Pro Gly Lys Glu Arg Glu Phe Val
        35                  40                  45

Ala Ala Ile Asn Arg Asn Asp Gly Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Met Gln Met Ala Ser Leu Lys Pro Glu Asp Thr Ala Val Tyr Tyr Cys
                85                  90                  95

Ala Ala Gly Leu Gln Tyr Asn Arg Ser Ala Asp Arg Val Pro Val Gly
            100                 105                 110

Ala Val Tyr Trp Gly Gln Gly Thr Gln Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Ser Val Gln Ala Gly
                165                 170                 175

Asp Ser Leu Arg Leu Ser Cys Ala Ala Ser Gly Arg Thr Phe Gly Ser
            180                 185                 190

Ile Arg Val Gly Trp Phe Arg Gln Thr Pro Gly Lys Glu Arg Glu Phe
        195                 200                 205
```

Val Ala Ala Ile Asn Arg Asn Asp Gly Thr Thr Tyr Tyr Ala Asp Ser
            210                 215                 220

Val Lys Gly Arg Phe Thr Ile Ser Arg Asp Asn Ala Lys Asn Thr Val
225                 230                 235                 240

Tyr Met Gln Met Ala Ser Leu Lys Pro Glu Asp Thr Ala Val Tyr Tyr
                245                 250                 255

Cys Ala Ala Gly Leu Gln Tyr Asn Arg Ser Ala Asp Arg Val Pro Val
            260                 265                 270

Gly Ala Val Tyr Trp Gly Gln Gly Thr Gln Val Thr Val Ser Ser Gly
        275                 280                 285

Gly Gly Gly Ser Gly Gly Gly Ser Gly Gly Gly Ser Gly Gly
        290                 295                 300

Gly Gly Ser Gly Gly Gly Ser Gly Gly Gly Ser Gly Gly Gly
305                 310                 315                 320

Gly Ser Glu Val Gln Leu Val Glu Ser Gly Gly Ser Val Gln Ala
                325                 330                 335

Gly Asp Ser Leu Arg Leu Ser Cys Ala Ala Ser Gly Arg Thr Phe Gly
            340                 345                 350

Ser Ile Arg Val Gly Trp Phe Arg Gln Thr Pro Gly Lys Glu Arg Glu
        355                 360                 365

Phe Val Ala Ala Ile Asn Arg Asn Asp Gly Thr Thr Tyr Tyr Ala Asp
    370                 375                 380

Ser Val Lys Gly Arg Phe Thr Ile Ser Arg Asp Asn Ala Lys Asn Thr
385                 390                 395                 400

Val Tyr Met Gln Met Ala Ser Leu Lys Pro Glu Asp Thr Ala Val Tyr
                405                 410                 415

Tyr Cys Ala Ala Gly Leu Gln Tyr Asn Arg Ser Ala Asp Arg Val Pro
            420                 425                 430

Val Gly Ala Val Tyr Trp Gly Gln Gly Thr Gln Val Thr Val Ser Ser
        435                 440                 445

<210> SEQ ID NO 7
<211> LENGTH: 609
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 7

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Phe Gly Ser Ile
            20                  25                  30

Arg Val Gly Trp Phe Arg Gln Thr Pro Gly Lys Glu Arg Glu Phe Val
        35                  40                  45

Ala Ala Ile Asn Arg Asn Asp Gly Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Met Gln Met Ala Ser Leu Lys Pro Glu Asp Thr Ala Val Tyr Tyr Cys
                85                  90                  95

Ala Ala Gly Leu Gln Tyr Asn Arg Ser Ala Asp Arg Val Pro Val Gly
            100                 105                 110

Ala Val Tyr Trp Gly Gln Gly Thr Gln Val Thr Val Ser Ser Gly Gly

-continued

```
            115                 120                 125
Gly Gly Ser Gly Gly Gly Ser Gly Gly Gly Ser Gly Gly
    130                 135                 140
Gly Ser Gly Gly Gly Ser Gly Gly Gly Ser Gly Gly Gly
145                 150                 155                 160
Ser Glu Val Gln Leu Val Glu Ser Gly Gly Ser Val Gln Ala Gly
                165                 170                 175
Asp Ser Leu Arg Leu Ser Cys Ala Ala Ser Gly Arg Thr Phe Gly Ser
                180                 185                 190
Ile Arg Val Gly Trp Phe Arg Gln Thr Pro Gly Lys Glu Arg Glu Phe
                195                 200                 205
Val Ala Ala Ile Asn Arg Asn Asp Gly Thr Thr Tyr Tyr Ala Asp Ser
    210                 215                 220
Val Lys Gly Arg Phe Thr Ile Ser Arg Asp Asn Ala Lys Asn Thr Val
225                 230                 235                 240
Tyr Met Gln Met Ala Ser Leu Lys Pro Glu Asp Thr Ala Val Tyr Tyr
                245                 250                 255
Cys Ala Ala Gly Leu Gln Tyr Asn Arg Ser Ala Asp Arg Val Pro Val
                260                 265                 270
Gly Ala Val Tyr Trp Gly Gln Gly Thr Gln Val Thr Val Ser Ser Gly
                275                 280                 285
Gly Gly Gly Ser Gly Gly Gly Gly Ser Gly Gly Gly Ser Gly Gly
    290                 295                 300
Gly Gly Ser Gly Gly Gly Ser Gly Gly Gly Ser Gly Gly Gly
305                 310                 315                 320
Gly Ser Glu Val Gln Leu Val Glu Ser Gly Gly Ser Val Gln Ala
                325                 330                 335
Gly Asp Ser Leu Arg Leu Ser Cys Ala Ala Ser Gly Arg Thr Phe Gly
                340                 345                 350
Ser Ile Arg Val Gly Trp Phe Arg Gln Thr Pro Gly Lys Glu Arg Glu
                355                 360                 365
Phe Val Ala Ala Ile Asn Arg Asn Asp Gly Thr Thr Tyr Tyr Ala Asp
    370                 375                 380
Ser Val Lys Gly Arg Phe Thr Ile Ser Arg Asp Asn Ala Lys Asn Thr
385                 390                 395                 400
Val Tyr Met Gln Met Ala Ser Leu Lys Pro Glu Asp Thr Ala Val Tyr
                405                 410                 415
Tyr Cys Ala Ala Gly Leu Gln Tyr Asn Arg Ser Ala Asp Arg Val Pro
                420                 425                 430
Val Gly Ala Val Tyr Trp Gly Gln Gly Thr Gln Val Thr Val Ser Ser
                435                 440                 445
Gly Gly Gly Gly Ser Gly Gly Gly Ser Gly Gly Gly Ser Gly
    450                 455                 460
Gly Gly Ser Gly Gly Gly Ser Gly Gly Gly Ser Gly Gly
465                 470                 475                 480
Gly Gly Ser Glu Val Gln Leu Val Glu Ser Gly Gly Ser Val Gln
                485                 490                 495
Ala Gly Asp Ser Leu Arg Leu Ser Cys Ala Ala Ser Gly Arg Thr Phe
                500                 505                 510
Gly Ser Ile Arg Val Gly Trp Phe Arg Gln Thr Pro Gly Lys Glu Arg
                515                 520                 525
Glu Phe Val Ala Ala Ile Asn Arg Asn Asp Gly Thr Thr Tyr Tyr Ala
    530                 535                 540
```

Asp Ser Val Lys Gly Arg Phe Thr Ile Ser Arg Asp Asn Ala Lys Asn
545                 550                 555                 560

Thr Val Tyr Met Gln Met Ala Ser Leu Lys Pro Glu Asp Thr Ala Val
                565                 570                 575

Tyr Tyr Cys Ala Ala Gly Leu Gln Tyr Asn Arg Ser Ala Asp Arg Val
            580                 585                 590

Pro Val Gly Ala Val Tyr Trp Gly Gln Gly Thr Gln Val Thr Val Ser
        595                 600                 605

Ser

<210> SEQ ID NO 8
<211> LENGTH: 770
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 8

Glu Val Gln Leu Val Glu Ser Gly Gly Gly Ser Val Gln Ala Gly Asp
1               5                   10                  15

Ser Leu Arg Leu Ser Cys Ala Ala Ser Gly Arg Thr Phe Gly Ser Ile
            20                  25                  30

Arg Val Gly Trp Phe Arg Gln Thr Pro Gly Lys Glu Arg Glu Phe Val
        35                  40                  45

Ala Ala Ile Asn Arg Asn Asp Gly Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Met Gln Met Ala Ser Leu Lys Pro Glu Asp Thr Ala Val Tyr Tyr Cys
                85                  90                  95

Ala Ala Gly Leu Gln Tyr Asn Arg Ser Ala Asp Arg Val Pro Val Gly
            100                 105                 110

Ala Val Tyr Trp Gly Gln Gly Thr Gln Val Thr Val Ser Ser Gly Gly
        115                 120                 125

Gly Gly Ser Gly Gly Gly Ser Gly Gly Gly Ser Gly Gly Gly
    130                 135                 140

Gly Ser Gly Gly Gly Gly Ser Gly Gly Gly Ser Gly Gly Gly Gly
145                 150                 155                 160

Ser Glu Val Gln Leu Val Glu Ser Gly Gly Gly Ser Val Gln Ala Gly
                165                 170                 175

Asp Ser Leu Arg Leu Ser Cys Ala Ala Ser Gly Arg Thr Phe Gly Ser
            180                 185                 190

Ile Arg Val Gly Trp Phe Arg Gln Thr Pro Gly Lys Glu Arg Glu Phe
        195                 200                 205

Val Ala Ala Ile Asn Arg Asn Asp Gly Thr Thr Tyr Tyr Ala Asp Ser
    210                 215                 220

Val Lys Gly Arg Phe Thr Ile Ser Arg Asp Asn Ala Lys Asn Thr Val
225                 230                 235                 240

Tyr Met Gln Met Ala Ser Leu Lys Pro Glu Asp Thr Ala Val Tyr Tyr
                245                 250                 255

Cys Ala Ala Gly Leu Gln Tyr Asn Arg Ser Ala Asp Arg Val Pro Val
            260                 265                 270

Gly Ala Val Tyr Trp Gly Gln Gly Thr Gln Val Thr Val Ser Ser Gly
        275                 280                 285

Gly Gly Gly Ser Gly Gly Gly Ser Gly Gly Gly Ser Gly Gly
    290                 295                 300

Gly Gly Ser Gly Gly Gly Ser Gly Gly Gly Ser Gly Gly Gly
305                 310                 315                 320

Gly Ser Glu Val Gln Leu Val Glu Ser Gly Gly Ser Val Gln Ala
            325                 330                 335

Gly Asp Ser Leu Arg Leu Ser Cys Ala Ala Ser Gly Arg Thr Phe Gly
        340                 345                 350

Ser Ile Arg Val Gly Trp Phe Arg Gln Thr Pro Gly Lys Glu Arg Glu
        355                 360                 365

Phe Val Ala Ala Ile Asn Arg Asn Asp Gly Thr Thr Tyr Tyr Ala Asp
370                 375                 380

Ser Val Lys Gly Arg Phe Thr Ile Ser Arg Asp Asn Ala Lys Asn Thr
385                 390                 395                 400

Val Tyr Met Gln Met Ala Ser Leu Lys Pro Glu Asp Thr Ala Val Tyr
            405                 410                 415

Tyr Cys Ala Ala Gly Leu Gln Tyr Asn Arg Ser Ala Asp Arg Val Pro
        420                 425                 430

Val Gly Ala Val Tyr Trp Gly Gln Gly Thr Gln Val Thr Val Ser Ser
        435                 440                 445

Gly Gly Gly Gly Ser Gly Gly Gly Ser Gly Gly Gly Ser Gly
    450                 455                 460

Gly Gly Gly Ser Gly Gly Gly Ser Gly Gly Gly Ser Gly Gly
465                 470                 475                 480

Gly Gly Ser Glu Val Gln Leu Val Glu Ser Gly Gly Ser Val Gln
            485                 490                 495

Ala Gly Asp Ser Leu Arg Leu Ser Cys Ala Ala Ser Gly Arg Thr Phe
        500                 505                 510

Gly Ser Ile Arg Val Gly Trp Phe Arg Gln Thr Pro Gly Lys Glu Arg
        515                 520                 525

Glu Phe Val Ala Ala Ile Asn Arg Asn Asp Gly Thr Thr Tyr Tyr Ala
    530                 535                 540

Asp Ser Val Lys Gly Arg Phe Thr Ile Ser Arg Asp Asn Ala Lys Asn
545                 550                 555                 560

Thr Val Tyr Met Gln Met Ala Ser Leu Lys Pro Glu Asp Thr Ala Val
            565                 570                 575

Tyr Tyr Cys Ala Ala Gly Leu Gln Tyr Asn Arg Ser Ala Asp Arg Val
        580                 585                 590

Pro Val Gly Ala Val Tyr Trp Gly Gln Gly Thr Gln Val Thr Val Ser
        595                 600                 605

Ser Gly Gly Gly Gly Ser Gly Gly Gly Gly Ser Gly Gly Gly Gly Ser
    610                 615                 620

Gly Gly Gly Gly Ser Gly Gly Gly Ser Gly Gly Gly Ser Gly
625                 630                 635                 640

Gly Gly Gly Ser Glu Val Gln Leu Val Glu Ser Gly Gly Ser Val
            645                 650                 655

Gln Ala Gly Asp Ser Leu Arg Leu Ser Cys Ala Ala Ser Gly Arg Thr
        660                 665                 670

Phe Gly Ser Ile Arg Val Gly Trp Phe Arg Gln Thr Pro Gly Lys Glu
        675                 680                 685

Arg Glu Phe Val Ala Ala Ile Asn Arg Asn Asp Gly Thr Thr Tyr Tyr
    690                 695                 700

```
Ala Asp Ser Val Lys Gly Arg Phe Thr Ile Ser Arg Asp Asn Ala Lys
705                 710                 715                 720

Asn Thr Val Tyr Met Gln Met Ala Ser Leu Lys Pro Glu Asp Thr Ala
            725                 730                 735

Val Tyr Tyr Cys Ala Ala Gly Leu Gln Tyr Asn Arg Ser Ala Asp Arg
        740                 745                 750

Val Pro Val Gly Ala Val Tyr Trp Gly Gln Gly Thr Gln Val Thr Val
        755                 760                 765

Ser Ser
    770

<210> SEQ ID NO 9
<211> LENGTH: 442
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 9

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Leu Asn Trp Ser Gly Gly Ser Thr Tyr Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Gly Ser Phe Ser Leu Gly Gly Arg Pro Tyr Gly Asp Asp
            100                 105                 110

Tyr Trp Gly Lys Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Gly Leu Val Gln Ala Gly Gly Ser
                165                 170                 175

Leu Arg Leu Ser Cys Ala Ala Ser Gly Arg Thr Phe Ser Asn Tyr Ala
            180                 185                 190

Met Gly Trp Phe Arg Gln Ala Pro Gly Lys Glu Arg Glu Phe Val Ala
        195                 200                 205

Ala Leu Asn Trp Ser Gly Gly Ser Thr Tyr Tyr Val Asp Ser Val Lys
    210                 215                 220

Gly Arg Phe Thr Ile Ser Arg Asp Asn Ala Lys Asn Thr Val Tyr Leu
225                 230                 235                 240

Gln Met Asn Ser Leu Lys Pro Glu Asp Thr Ala Val Tyr Tyr Cys Ala
                245                 250                 255

Ala Ala Gly Ser Phe Ser Leu Gly Gly Arg Pro Tyr Gly Asp Asp Tyr
            260                 265                 270

Trp Gly Lys Gly Thr Leu Val Thr Val Ser Ser Gly Gly Gly Gly Ser
        275                 280                 285
```

```
Gly Gly Gly Gly Ser Gly Gly Gly Ser Gly Gly Gly Ser Gly
            290                 295                 300

Gly Gly Gly Ser Gly Gly Gly Ser Gly Gly Gly Ser Glu Val
305                 310                 315                 320

Gln Leu Val Glu Ser Gly Gly Leu Val Gln Ala Gly Gly Ser Leu
                325                 330                 335

Arg Leu Ser Cys Ala Ala Ser Gly Arg Thr Phe Ser Asn Tyr Ala Met
            340                 345                 350

Gly Trp Phe Arg Gln Ala Pro Gly Lys Glu Arg Glu Phe Val Ala Ala
        355                 360                 365

Leu Asn Trp Ser Gly Gly Ser Thr Tyr Tyr Val Asp Ser Val Lys Gly
    370                 375                 380

Arg Phe Thr Ile Ser Arg Asp Asn Ala Lys Asn Thr Val Tyr Leu Gln
385                 390                 395                 400

Met Asn Ser Leu Lys Pro Glu Asp Thr Ala Val Tyr Tyr Cys Ala Ala
                405                 410                 415

Ala Gly Ser Phe Ser Leu Gly Gly Arg Pro Tyr Gly Asp Asp Tyr Trp
            420                 425                 430

Gly Lys Gly Thr Leu Val Thr Val Ser Ser
        435                 440

<210> SEQ ID NO 10
<211> LENGTH: 601
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 10

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Leu Asn Trp Ser Gly Gly Ser Thr Tyr Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Gly Ser Phe Ser Leu Gly Gly Arg Pro Tyr Gly Asp Asp
            100                 105                 110

Tyr Trp Gly Lys Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Gly Leu Val Gln Ala Gly Gly Ser
                165                 170                 175

Leu Arg Leu Ser Cys Ala Ala Ser Gly Arg Thr Phe Ser Asn Tyr Ala
            180                 185                 190

Met Gly Trp Phe Arg Gln Ala Pro Gly Lys Glu Arg Glu Phe Val Ala
```

-continued

```
            195                 200                 205
Ala Leu Asn Trp Ser Gly Gly Ser Thr Tyr Tyr Val Asp Ser Val Lys
210                 215                 220

Gly Arg Phe Thr Ile Ser Arg Asp Asn Ala Lys Asn Thr Val Tyr Leu
225                 230                 235                 240

Gln Met Asn Ser Leu Lys Pro Glu Asp Thr Ala Val Tyr Tyr Cys Ala
                245                 250                 255

Ala Ala Gly Ser Phe Ser Leu Gly Gly Arg Pro Tyr Gly Asp Asp Tyr
                260                 265                 270

Trp Gly Lys Gly Thr Leu Val Thr Val Ser Ser Gly Gly Gly Gly Ser
                275                 280                 285

Gly Gly Gly Gly Ser Gly Gly Gly Ser Gly Gly Gly Gly Ser Gly
290                 295                 300

Gly Gly Gly Ser Gly Gly Gly Ser Gly Gly Gly Ser Glu Val
305                 310                 315                 320

Gln Leu Val Glu Ser Gly Gly Gly Leu Val Gln Ala Gly Gly Ser Leu
                325                 330                 335

Arg Leu Ser Cys Ala Ala Ser Gly Arg Thr Phe Ser Asn Tyr Ala Met
                340                 345                 350

Gly Trp Phe Arg Gln Ala Pro Gly Lys Glu Arg Glu Phe Val Ala Ala
                355                 360                 365

Leu Asn Trp Ser Gly Gly Ser Thr Tyr Tyr Val Asp Ser Val Lys Gly
                370                 375                 380

Arg Phe Thr Ile Ser Arg Asp Asn Ala Lys Asn Thr Val Tyr Leu Gln
385                 390                 395                 400

Met Asn Ser Leu Lys Pro Glu Asp Thr Ala Val Tyr Tyr Cys Ala Ala
                405                 410                 415

Ala Gly Ser Phe Ser Leu Gly Gly Arg Pro Tyr Gly Asp Asp Tyr Trp
                420                 425                 430

Gly Lys Gly Thr Leu Val Thr Val Ser Ser Gly Gly Gly Gly Ser Gly
                435                 440                 445

Gly Gly Gly Ser Gly Gly Gly Ser Gly Gly Gly Gly Ser Gly Gly
450                 455                 460

Gly Gly Ser Gly Gly Gly Ser Gly Gly Gly Ser Glu Val Gln
465                 470                 475                 480

Leu Val Glu Ser Gly Gly Gly Leu Val Gln Ala Gly Gly Ser Leu Arg
                485                 490                 495

Leu Ser Cys Ala Ala Ser Gly Arg Thr Phe Ser Asn Tyr Ala Met Gly
                500                 505                 510

Trp Phe Arg Gln Ala Pro Gly Lys Glu Arg Glu Phe Val Ala Ala Leu
                515                 520                 525

Asn Trp Ser Gly Gly Ser Thr Tyr Tyr Val Asp Ser Val Lys Gly Arg
                530                 535                 540

Phe Thr Ile Ser Arg Asp Asn Ala Lys Asn Thr Val Tyr Leu Gln Met
545                 550                 555                 560

Asn Ser Leu Lys Pro Glu Asp Thr Ala Val Tyr Tyr Cys Ala Ala Ala
                565                 570                 575

Gly Ser Phe Ser Leu Gly Gly Arg Pro Tyr Gly Asp Asp Tyr Trp Gly
                580                 585                 590

Lys Gly Thr Leu Val Thr Val Ser Ser
                595                 600
```

<210> SEQ ID NO 11

```
<211> LENGTH: 760
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 11

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Leu Asn Trp Ser Gly Gly Ser Thr Tyr Tyr Val Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Gly Ser Phe Ser Leu Gly Gly Arg Pro Tyr Gly Asp Asp
            100                 105                 110

Tyr Trp Gly Lys Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Ser Gly Gly Gly Ser Glu
145                 150                 155                 160

Val Gln Leu Val Glu Ser Gly Gly Gly Leu Val Gln Ala Gly Gly Ser
                165                 170                 175

Leu Arg Leu Ser Cys Ala Ala Ser Gly Arg Thr Phe Ser Asn Tyr Ala
            180                 185                 190

Met Gly Trp Phe Arg Gln Ala Pro Gly Lys Glu Arg Glu Phe Val Ala
        195                 200                 205

Ala Leu Asn Trp Ser Gly Gly Ser Thr Tyr Tyr Val Asp Ser Val Lys
    210                 215                 220

Gly Arg Phe Thr Ile Ser Arg Asp Asn Ala Lys Asn Thr Val Tyr Leu
225                 230                 235                 240

Gln Met Asn Ser Leu Lys Pro Glu Asp Thr Ala Val Tyr Tyr Cys Ala
                245                 250                 255

Ala Ala Gly Ser Phe Ser Leu Gly Gly Arg Pro Tyr Gly Asp Asp Tyr
            260                 265                 270

Trp Gly Lys Gly Thr Leu Val Thr Val Ser Ser Gly Gly Gly Gly Ser
        275                 280                 285

Gly Gly Gly Gly Ser Gly Gly Gly Gly Ser Gly Gly Gly Gly Ser Gly
    290                 295                 300

Gly Gly Gly Ser Gly Gly Gly Gly Ser Gly Gly Gly Gly Ser Glu Val
305                 310                 315                 320

Gln Leu Val Glu Ser Gly Gly Gly Leu Val Gln Ala Gly Gly Ser Leu
                325                 330                 335

Arg Leu Ser Cys Ala Ala Ser Gly Arg Thr Phe Ser Asn Tyr Ala Met
            340                 345                 350

Gly Trp Phe Arg Gln Ala Pro Gly Lys Glu Arg Glu Phe Val Ala Ala
        355                 360                 365

Leu Asn Trp Ser Gly Gly Ser Thr Tyr Tyr Val Asp Ser Val Lys Gly
```

```
                    370                 375                 380
Arg Phe Thr Ile Ser Arg Asp Asn Ala Lys Asn Thr Val Tyr Leu Gln
385                 390                 395                 400

Met Asn Ser Leu Lys Pro Glu Asp Thr Ala Val Tyr Tyr Cys Ala Ala
                405                 410                 415

Ala Gly Ser Phe Ser Leu Gly Gly Arg Pro Tyr Gly Asp Asp Tyr Trp
            420                 425                 430

Gly Lys Gly Thr Leu Val Thr Val Ser Ser Gly Gly Gly Gly Ser Gly
        435                 440                 445

Gly Gly Gly Ser Gly Gly Gly Ser Gly Gly Gly Gly Ser Gly Gly
450                 455                 460

Gly Gly Ser Gly Gly Gly Ser Gly Gly Gly Ser Glu Val Gln
465                 470                 475                 480

Leu Val Glu Ser Gly Gly Leu Val Gln Ala Gly Ser Leu Arg
                485                 490                 495

Leu Ser Cys Ala Ala Ser Gly Arg Thr Phe Ser Asn Tyr Ala Met Gly
            500                 505                 510

Trp Phe Arg Gln Ala Pro Gly Lys Glu Arg Glu Phe Val Ala Ala Leu
        515                 520                 525

Asn Trp Ser Gly Gly Ser Thr Tyr Tyr Val Asp Ser Val Lys Gly Arg
    530                 535                 540

Phe Thr Ile Ser Arg Asp Asn Ala Lys Asn Thr Val Tyr Leu Gln Met
545                 550                 555                 560

Asn Ser Leu Lys Pro Glu Asp Thr Ala Val Tyr Tyr Cys Ala Ala Ala
                565                 570                 575

Gly Ser Phe Ser Leu Gly Gly Arg Pro Tyr Gly Asp Asp Tyr Trp Gly
            580                 585                 590

Lys Gly Thr Leu Val Thr Val Ser Ser Gly Gly Gly Gly Ser Gly Gly
        595                 600                 605

Gly Gly Ser Gly Gly Gly Ser Gly Gly Gly Gly Ser Gly Gly Gly
    610                 615                 620

Gly Ser Gly Gly Gly Ser Gly Gly Gly Ser Glu Val Gln Leu
625                 630                 635                 640

Val Glu Ser Gly Gly Leu Val Gln Ala Gly Ser Leu Arg Leu
                645                 650                 655

Ser Cys Ala Ala Ser Gly Arg Thr Phe Ser Asn Tyr Ala Met Gly Trp
            660                 665                 670

Phe Arg Gln Ala Pro Gly Lys Glu Arg Glu Phe Val Ala Ala Leu Asn
        675                 680                 685

Trp Ser Gly Gly Ser Thr Tyr Tyr Val Asp Ser Val Lys Gly Arg Phe
    690                 695                 700

Thr Ile Ser Arg Asp Asn Ala Lys Asn Thr Val Tyr Leu Gln Met Asn
705                 710                 715                 720

Ser Leu Lys Pro Glu Asp Thr Ala Val Tyr Tyr Cys Ala Ala Ala Gly
                725                 730                 735

Ser Phe Ser Leu Gly Gly Arg Pro Tyr Gly Asp Asp Tyr Trp Gly Lys
            740                 745                 750

Gly Thr Leu Val Thr Val Ser Ser
        755                 760

<210> SEQ ID NO 12
<211> LENGTH: 396
<212> TYPE: PRT
<213> ORGANISM: Artificial Sequence
```

<220> FEATURE:
<223> OTHER INFORMATION: Description of Artificial Sequence: Synthetic
      recombinant polypeptide

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Ala Ile Asn Ser Gly Gly Gly Asp Thr Tyr Tyr Arg Asp Ser Val
50                  55                  60

Arg Gly Arg Phe Thr Ile Ser Arg Asp Asn Phe Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ala Glu Gly Pro Pro Thr Phe Ser Leu Ile Arg Thr Met Thr
            100                 105                 110

Val Asp Pro Gly Ala Gln Gly Thr Gln Val Thr Val Ser Ser Gly Gly
        115                 120                 125

Gly Gly Ser Gly Gly Gly Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Phe Thr Phe Ser Arg Tyr Trp Met Tyr Trp Val Arg Gln Ala Pro
                165                 170                 175

Gly Lys Gly Leu Glu Trp Val Ser Ala Ile Asn Ser Gly Gly Gly Asp
            180                 185                 190

Thr Tyr Tyr Arg Asp Ser Val Arg Gly Arg Phe Thr Ile Ser Arg Asp
        195                 200                 205

Asn Phe Lys Asn Thr Leu Tyr Leu Gln Met Asn Ser Leu Lys Ser Glu
    210                 215                 220

Asp Thr Ala Val Tyr Tyr Cys Ala Lys Ala Glu Gly Pro Pro Thr Phe
225                 230                 235                 240

Ser Leu Ile Arg Thr Met Thr Val Asp Pro Gly Ala Gln Gly Thr Gln
                245                 250                 255

Val Thr Val Ser Ser Gly Gly Gly Gly Ser Gly Gly Gly Ser Glu Val
            260                 265                 270

Gln Leu Val Glu Ser Gly Gly Gly Leu Val Gln Pro Gly Gly Ser Leu
        275                 280                 285

Arg Leu Ser Cys Ala Ala Ser Gly Phe Thr Phe Ser Arg Tyr Trp Met
    290                 295                 300

Tyr Trp Val Arg Gln Ala Pro Gly Lys Gly Leu Glu Trp Val Ser Ala
305                 310                 315                 320

Ile Asn Ser Gly Gly Gly Asp Thr Tyr Tyr Arg Asp Ser Val Arg Gly
                325                 330                 335

Arg Phe Thr Ile Ser Arg Asp Asn Phe Lys Asn Thr Leu Tyr Leu Gln
            340                 345                 350

Met Asn Ser Leu Lys Ser Glu Asp Thr Ala Val Tyr Tyr Cys Ala Lys
        355                 360                 365

Ala Glu Gly Pro Pro Thr Phe Ser Leu Ile Arg Thr Met Thr Val Asp
370                 375                 380

Pro Gly Ala Gln Gly Thr Gln Val Thr Val Ser Ser
```

385             390             395

<210> SEQ ID NO 13
<211> LENGTH: 418
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Ala Ile Asn Ser Gly Gly Gly Asp Thr Tyr Tyr Arg Asp Ser Val
    50                  55                  60

Arg Gly Arg Phe Thr Ile Ser Arg Asp Asn Phe Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ala Glu Gly Pro Pro Thr Phe Ser Leu Ile Arg Thr Met Thr
            100                 105                 110

Val Asp Pro Gly Ala Gln Gly Thr Gln Val Thr Val Ser Ser Gly Gly
        115                 120                 125

Gly Gly Ser Gly Gly Gly Ser Gly Gly Gly Ser Gly Gly Gly Gly Gly
    130                 135                 140

Gly Ser Glu Val Gln Leu Val Glu Ser Gly Gly Gly Leu Val Gln Pro
145                 150                 155                 160

Gly Gly Ser Leu Arg Leu Ser Cys Ala Ala Ser Gly Phe Thr Phe Ser
                165                 170                 175

Arg Tyr Trp Met Tyr Trp Val Arg Gln Ala Pro Gly Lys Gly Leu Glu
            180                 185                 190

Trp Val Ser Ala Ile Asn Ser Gly Gly Gly Asp Thr Tyr Tyr Arg Asp
        195                 200                 205

Ser Val Arg Gly Arg Phe Thr Ile Ser Arg Asp Asn Phe Lys Asn Thr
    210                 215                 220

Leu Tyr Leu Gln Met Asn Ser Leu Lys Ser Glu Asp Thr Ala Val Tyr
225                 230                 235                 240

Tyr Cys Ala Lys Ala Glu Gly Pro Pro Thr Phe Ser Leu Ile Arg Thr
                245                 250                 255

Met Thr Val Asp Pro Gly Ala Gln Gly Thr Gln Val Thr Val Ser Ser
            260                 265                 270

Gly Gly Gly Gly Ser Gly Gly Gly Ser Gly Gly Gly Gly Ser Gly
        275                 280                 285

Gly Gly Ser Glu Val Gln Leu Val Glu Ser Gly Gly Gly Leu Val
    290                 295                 300

Gln Pro Gly Gly Ser Leu Arg Leu Ser Cys Ala Ala Ser Gly Phe Thr
305                 310                 315                 320

Phe Ser Arg Tyr Trp Met Tyr Trp Val Arg Gln Ala Pro Gly Lys Gly
                325                 330                 335

Leu Glu Trp Val Ser Ala Ile Asn Ser Gly Gly Gly Asp Thr Tyr Tyr
            340                 345                 350

```
Arg Asp Ser Val Arg Gly Arg Phe Thr Ile Ser Arg Asp Asn Phe Lys
            355                 360                 365

Asn Thr Leu Tyr Leu Gln Met Asn Ser Leu Lys Ser Glu Asp Thr Ala
        370                 375                 380

Val Tyr Tyr Cys Ala Lys Ala Glu Gly Pro Pro Thr Phe Ser Leu Ile
385                 390                 395                 400

Arg Thr Met Thr Val Asp Pro Gly Ala Gln Gly Thr Gln Val Thr Val
                405                 410                 415

Ser Ser

<210> SEQ ID NO 14
<211> LENGTH: 448
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Tyr Trp Val Arg Gln Ala Pro Gly Lys Gly Leu Glu Trp Val
        35                  40                  45

Ser Ala Ile Asn Ser Gly Gly Gly Asp Thr Tyr Tyr Arg Asp Ser Val
    50                  55                  60

Arg Gly Arg Phe Thr Ile Ser Arg Asp Asn Phe Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Ala Glu Gly Pro Pro Thr Phe Ser Leu Ile Arg Thr Met Thr
            100                 105                 110

Val Asp Pro Gly Ala Gln Gly Thr Gln Val Thr Val Ser Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Leu Arg Leu Ser Cys Ala Ala Ser Gly Phe Thr Phe Ser Arg
            180                 185                 190

Tyr Trp Met Tyr Trp Val Arg Gln Ala Pro Gly Lys Gly Leu Glu Trp
        195                 200                 205

Val Ser Ala Ile Asn Ser Gly Gly Gly Asp Thr Tyr Tyr Arg Asp Ser
    210                 215                 220

Val Arg Gly Arg Phe Thr Ile Ser Arg Asp Asn Phe Lys Asn Thr Leu
225                 230                 235                 240

Tyr Leu Gln Met Asn Ser Leu Lys Ser Glu Asp Thr Ala Val Tyr Tyr
                245                 250                 255

Cys Ala Lys Ala Glu Gly Pro Pro Thr Phe Ser Leu Ile Arg Thr Met
            260                 265                 270

Thr Val Asp Pro Gly Ala Gln Gly Thr Gln Val Thr Val Ser Ser Gly
        275                 280                 285
```

-continued

Gly Gly Gly Ser Gly Gly Gly Ser Gly Gly Gly Ser Gly Gly
    290                 295                 300
Gly Gly Ser Gly Gly Gly Ser Gly Gly Gly Ser Gly Gly Gly
305                 310                 315                 320
Gly Ser Glu Val Gln Leu Val Glu Ser Gly Gly Gly Leu Val Gln Pro
                325                 330                 335
Gly Gly Ser Leu Arg Leu Ser Cys Ala Ala Ser Gly Phe Thr Phe Ser
            340                 345                 350
Arg Tyr Trp Met Tyr Trp Val Arg Gln Ala Pro Gly Lys Gly Leu Glu
        355                 360                 365
Trp Val Ser Ala Ile Asn Ser Gly Gly Gly Asp Thr Tyr Tyr Arg Asp
    370                 375                 380
Ser Val Arg Gly Arg Phe Thr Ile Ser Arg Asp Asn Phe Lys Asn Thr
385                 390                 395                 400
Leu Tyr Leu Gln Met Asn Ser Leu Lys Ser Glu Asp Thr Ala Val Tyr
                405                 410                 415
Tyr Cys Ala Lys Ala Glu Gly Pro Pro Thr Phe Ser Leu Ile Arg Thr
            420                 425                 430
Met Thr Val Asp Pro Gly Ala Gln Gly Thr Gln Val Thr Val Ser Ser
        435                 440                 445

<210> SEQ ID NO 15
<211> LENGTH: 609
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 15

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Arg Tyr
            20                  25                  30
Trp Met Tyr Trp Val Arg Gln Ala Pro Gly Lys Gly Leu Glu Trp Val
        35                  40                  45
Ser Ala Ile Asn Ser Gly Gly Gly Asp Thr Tyr Tyr Arg Asp Ser Val
    50                  55                  60
Arg Gly Arg Phe Thr Ile Ser Arg Asp Asn Phe Lys Asn Thr Leu Tyr
65                  70                  75                  80
Leu Gln Met Asn Ser Leu Lys Ser Glu Asp Thr Ala Val Tyr Tyr Cys
                85                  90                  95
Ala Lys Ala Glu Gly Pro Pro Thr Phe Ser Leu Ile Arg Thr Met Thr
            100                 105                 110
Val Asp Pro Gly Ala Gln Gly Thr Gln Val Thr Val Ser Ser Gly Gly
        115                 120                 125
Gly Gly Ser Gly Gly Gly Gly Ser Gly Gly Gly Gly Ser Gly Gly Gly
    130                 135                 140
Gly Ser Gly Gly Gly Gly Ser Gly Gly Gly Gly Ser Gly Gly Gly Gly
145                 150                 155                 160
Ser Glu Val Gln Leu Val Glu Ser Gly Gly Gly Leu Val Gln Pro Gly
                165                 170                 175
Gly Ser Leu Arg Leu Ser Cys Ala Ala Ser Gly Phe Thr Phe Ser Arg
            180                 185                 190
Tyr Trp Met Tyr Trp Val Arg Gln Ala Pro Gly Lys Gly Leu Glu Trp
        195                 200                 205

```
Val Ser Ala Ile Asn Ser Gly Gly Gly Asp Thr Tyr Tyr Arg Asp Ser
    210                 215                 220
Val Arg Gly Arg Phe Thr Ile Ser Arg Asp Asn Phe Lys Asn Thr Leu
225                 230                 235                 240
Tyr Leu Gln Met Asn Ser Leu Lys Ser Glu Asp Thr Ala Val Tyr Tyr
                245                 250                 255
Cys Ala Lys Ala Glu Gly Pro Pro Thr Phe Ser Leu Ile Arg Thr Met
            260                 265                 270
Thr Val Asp Pro Gly Ala Gln Gly Thr Gln Val Thr Val Ser Ser Gly
        275                 280                 285
Gly Gly Gly Ser Gly Gly Gly Ser Gly Gly Gly Ser Gly Gly Gly Gly
    290                 295                 300
Gly Gly Ser Gly Gly Gly Ser Gly Gly Gly Ser Gly Gly Gly Gly Gly
305                 310                 315                 320
Gly Ser Glu Val Gln Leu Val Glu Ser Gly Gly Gly Leu Val Gln Pro
                325                 330                 335
Gly Gly Ser Leu Arg Leu Ser Cys Ala Ala Ser Gly Phe Thr Phe Ser
            340                 345                 350
Arg Tyr Trp Met Tyr Trp Val Arg Gln Ala Pro Gly Lys Gly Leu Glu
        355                 360                 365
Trp Val Ser Ala Ile Asn Ser Gly Gly Gly Asp Thr Tyr Tyr Arg Asp
    370                 375                 380
Ser Val Arg Gly Arg Phe Thr Ile Ser Arg Asp Asn Phe Lys Asn Thr
385                 390                 395                 400
Leu Tyr Leu Gln Met Asn Ser Leu Lys Ser Glu Asp Thr Ala Val Tyr
                405                 410                 415
Tyr Cys Ala Lys Ala Glu Gly Pro Pro Thr Phe Ser Leu Ile Arg Thr
            420                 425                 430
Met Thr Val Asp Pro Gly Ala Gln Gly Thr Gln Val Thr Val Ser Ser
        435                 440                 445
Gly Gly Gly Gly Ser Gly Gly Gly Ser Gly Gly Gly Gly Ser Gly Gly
    450                 455                 460
Gly Gly Ser Gly Gly Gly Ser Gly Gly Gly Ser Gly Gly Gly Ser Gly
465                 470                 475                 480
Gly Gly Ser Glu Val Gln Leu Val Glu Ser Gly Gly Gly Leu Val Gln
                485                 490                 495
Pro Gly Gly Ser Leu Arg Leu Ser Cys Ala Ala Ser Gly Phe Thr Phe
            500                 505                 510
Ser Arg Tyr Trp Met Tyr Trp Val Arg Gln Ala Pro Gly Lys Gly Leu
        515                 520                 525
Glu Trp Val Ser Ala Ile Asn Ser Gly Gly Gly Asp Thr Tyr Tyr Arg
    530                 535                 540
Asp Ser Val Arg Gly Arg Phe Thr Ile Ser Arg Asp Asn Phe Lys Asn
545                 550                 555                 560
Thr Leu Tyr Leu Gln Met Asn Ser Leu Lys Ser Glu Asp Thr Ala Val
                565                 570                 575
Tyr Tyr Cys Ala Lys Ala Glu Gly Pro Pro Thr Phe Ser Leu Ile Arg
            580                 585                 590
Thr Met Thr Val Asp Pro Gly Ala Gln Gly Thr Gln Val Thr Val Ser
        595                 600                 605
Ser
```

```
<210> SEQ ID NO 16
<211> LENGTH: 770
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 16
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Ser | Leu | Arg | Leu | Ser | Cys | Ala | Ala | Ser | Gly | Phe | Thr | Phe | Ser | Arg | Tyr |
| | | | 20 | | | | | 25 | | | | | 30 | | |
| Trp | Met | Tyr | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Asn | Ser | Gly | Gly | Gly | Asp | Thr | Tyr | Tyr | Arg | Asp | Ser | Val |
| 50 | | | | | 55 | | | | | 60 | | | | | |
| Arg | Gly | Arg | Phe | Thr | Ile | Ser | Arg | Asp | Asn | Phe | Lys | Asn | Thr | Leu | Tyr |
| 65 | | | | | 70 | | | | | 75 | | | | | 80 |
| Leu | Gln | Met | Asn | Ser | Leu | Lys | Ser | Glu | Asp | Thr | Ala | Val | Tyr | Tyr | Cys |
| | | | | 85 | | | | | 90 | | | | | 95 | |
| Ala | Lys | Ala | Glu | Gly | Pro | Pro | Thr | Phe | Ser | Leu | Ile | Arg | Thr | Met | Thr |
| | | | 100 | | | | | 105 | | | | | 110 | | |
| Val | Asp | Pro | Gly | Ala | Gln | Gly | Thr | Gln | Val | Thr | Val | Ser | Ser | Gly | Gly |
| | | 115 | | | | | 120 | | | | | 125 | | | |
| Gly | Gly | Ser | Gly | Gly | Gly | Ser | Gly | Gly | Gly | Ser | Gly | Gly | Gly |
| 130 | | | | | 135 | | | | | 140 | | | | |
| Gly | Ser | Gly | Gly | Gly | Ser | Gly | Gly | Gly | Ser | Gly | Gly | Gly | Gly |
| 145 | | | | | 150 | | | | | 155 | | | | 160 |
| Ser | Glu | Val | Gln | Leu | Val | Glu | Ser | Gly | Gly | Leu | Val | Gln | Pro | Gly |
| | | | | 165 | | | | | 170 | | | | | 175 |
| Gly | Ser | Leu | Arg | Leu | Ser | Cys | Ala | Ala | Ser | Gly | Phe | Thr | Phe | Ser | Arg |
| | | | 180 | | | | | 185 | | | | | 190 | | |
| Tyr | Trp | Met | Tyr | Trp | Val | Arg | Gln | Ala | Pro | Gly | Lys | Gly | Leu | Glu | Trp |
| | | 195 | | | | | 200 | | | | | 205 | | | |
| Val | Ser | Ala | Ile | Asn | Ser | Gly | Gly | Gly | Asp | Thr | Tyr | Tyr | Arg | Asp | Ser |
| | 210 | | | | | 215 | | | | | 220 | | | | |
| Val | Arg | Gly | Arg | Phe | Thr | Ile | Ser | Arg | Asp | Asn | Phe | Lys | Asn | Thr | Leu |
| 225 | | | | | 230 | | | | | 235 | | | | | 240 |
| Tyr | Leu | Gln | Met | Asn | Ser | Leu | Lys | Ser | Glu | Asp | Thr | Ala | Val | Tyr | Tyr |
| | | | | 245 | | | | | 250 | | | | | 255 | |
| Cys | Ala | Lys | Ala | Glu | Gly | Pro | Pro | Thr | Phe | Ser | Leu | Ile | Arg | Thr | Met |
| | | | 260 | | | | | 265 | | | | | 270 | | |
| Thr | Val | Asp | Pro | Gly | Ala | Gln | Gly | Thr | Gln | Val | Thr | Val | Ser | Ser | Gly |
| | | 275 | | | | | 280 | | | | | 285 | | | |
| Gly | Gly | Gly | Ser | Gly | Gly | Gly | Ser | Gly | Gly | Gly | Ser | Gly | Gly |
| | 290 | | | | | 295 | | | | | 300 | | | |
| Gly | Gly | Ser | Gly | Gly | Gly | Ser | Gly | Gly | Gly | Ser | Gly | Gly | Gly |
| 305 | | | | | 310 | | | | | 315 | | | | 320 |
| Gly | Ser | Glu | Val | Gln | Leu | Val | Glu | Ser | Gly | Gly | Leu | Val | Gln | Pro |
| | | | | 325 | | | | | 330 | | | | | 335 |
| Gly | Gly | Ser | Leu | Arg | Leu | Ser | Cys | Ala | Ala | Ser | Gly | Phe | Thr | Phe | Ser |
| | | | 340 | | | | | 345 | | | | | 350 | | |
| Arg | Tyr | Trp | Met | Tyr | Trp | Val | Arg | Gln | Ala | Pro | Gly | Lys | Gly | Leu | Glu |
| | | 355 | | | | | 360 | | | | | 365 | | | |

-continued

Trp Val Ser Ala Ile Asn Ser Gly Gly Gly Asp Thr Tyr Tyr Arg Asp
370                 375                 380

Ser Val Arg Gly Arg Phe Thr Ile Ser Arg Asp Asn Phe Lys Asn Thr
385                 390                 395                 400

Leu Tyr Leu Gln Met Asn Ser Leu Lys Ser Glu Asp Thr Ala Val Tyr
            405                 410                 415

Tyr Cys Ala Lys Ala Glu Gly Pro Pro Thr Phe Ser Leu Ile Arg Thr
            420                 425                 430

Met Thr Val Asp Pro Gly Ala Gln Gly Thr Gln Val Thr Val Ser Ser
            435                 440                 445

Gly Gly Gly Gly Ser Gly Gly Gly Ser Gly Gly Gly Gly Ser Gly
450                 455                 460

Gly Gly Gly Ser Gly Gly Gly Ser Gly Gly Gly Gly Ser Gly Gly
465                 470                 475                 480

Gly Gly Ser Glu Val Gln Leu Val Glu Ser Gly Gly Gly Leu Val Gln
            485                 490                 495

Pro Gly Gly Ser Leu Arg Leu Ser Cys Ala Ala Ser Gly Phe Thr Phe
            500                 505                 510

Ser Arg Tyr Trp Met Tyr Trp Val Arg Gln Ala Pro Gly Lys Gly Leu
            515                 520                 525

Glu Trp Val Ser Ala Ile Asn Ser Gly Gly Gly Asp Thr Tyr Tyr Arg
530                 535                 540

Asp Ser Val Arg Gly Arg Phe Thr Ile Ser Arg Asp Asn Phe Lys Asn
545                 550                 555                 560

Thr Leu Tyr Leu Gln Met Asn Ser Leu Lys Ser Glu Asp Thr Ala Val
            565                 570                 575

Tyr Tyr Cys Ala Lys Ala Glu Gly Pro Pro Thr Phe Ser Leu Ile Arg
            580                 585                 590

Thr Met Thr Val Asp Pro Gly Ala Gln Gly Thr Gln Val Thr Val Ser
            595                 600                 605

Ser Gly Gly Gly Gly Ser Gly Gly Gly Gly Ser Gly Gly Gly Gly Ser
610                 615                 620

Gly Gly Gly Gly Ser Gly Gly Gly Ser Gly Gly Gly Gly Ser Gly
625                 630                 635                 640

Gly Gly Gly Ser Glu Val Gln Leu Val Glu Ser Gly Gly Gly Leu Val
            645                 650                 655

Gln Pro Gly Gly Ser Leu Arg Leu Ser Cys Ala Ala Ser Gly Phe Thr
            660                 665                 670

Phe Ser Arg Tyr Trp Met Tyr Trp Val Arg Gln Ala Pro Gly Lys Gly
            675                 680                 685

Leu Glu Trp Val Ser Ala Ile Asn Ser Gly Gly Gly Asp Thr Tyr Tyr
            690                 695                 700

Arg Asp Ser Val Arg Gly Arg Phe Thr Ile Ser Arg Asp Asn Phe Lys
705                 710                 715                 720

Asn Thr Leu Tyr Leu Gln Met Asn Ser Leu Lys Ser Glu Asp Thr Ala
            725                 730                 735

Val Tyr Tyr Cys Ala Lys Ala Glu Gly Pro Pro Thr Phe Ser Leu Ile
            740                 745                 750

Arg Thr Met Thr Val Asp Pro Gly Ala Gln Gly Thr Gln Val Thr Val
            755                 760                 765

Ser Ser
770

```
<210> SEQ ID NO 17
<211> LENGTH: 436
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 17
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Ser | Ile | Asp | Ser | Ile | Asn |
| | | | 20 | | | | | 25 | | | | | 30 | | |
| Asn | Met | Gly | Trp | Tyr | Arg | Gln | Ala | Pro | Gly | Lys | Gln | Arg | Glu | Leu | Val |
| | | | 35 | | | | | 40 | | | | | 45 | | |
| Ala | Glu | Ile | Thr | Pro | Arg | Gly | Arg | Thr | Asn | Tyr | Ala | Asp | Ser | Glu | Lys |
| | 50 | | | | | 55 | | | | | 60 | | | | |
| Ser | Arg | Phe | Thr | Ile | Ser | Arg | Asp | Asn | Ala | Lys | Arg | Thr | Val | Asn | Leu |
| 65 | | | | | 70 | | | | | 75 | | | | | 80 |
| Gln | Met | Asn | Ser | Leu | Lys | Pro | Glu | Asp | Thr | Ala | Val | Tyr | Tyr | Cys | Asn |
| | | | | 85 | | | | | 90 | | | | | 95 | |
| Ala | Glu | Val | Arg | Glu | Arg | Gly | Thr | Ser | Trp | Tyr | Arg | Pro | Asp | Tyr | Trp |
| | | | 100 | | | | | 105 | | | | | 110 | | |
| Gly | Gln | Gly | Thr | Gln | Val | Thr | Val | Ser | Ser | Gly | Gly | Gly | Gly | Ser | Gly |
| | | | 115 | | | | | 120 | | | | | 125 | | |
| Gly | Gly | Gly | Ser | Gly | Gly | Gly | Ser | Gly | Gly | Gly | Ser | Gly | Gly | Gly | Gly |
| | 130 | | | | | 135 | | | | | 140 | | | | |
| Gly | Gly | Ser | Gly | Gly | Gly | Ser | Gly | Gly | Gly | Ser | Glu | Val | Gln |
| 145 | | | | | 150 | | | | | 155 | | | | | 160 |
| Leu | Val | Glu | Ser | Gly | Gly | Gly | Leu | Val | Gln | Pro | Gly | Gly | Ser | Leu | Arg |
| | | | | 165 | | | | | 170 | | | | | 175 | |
| Leu | Ser | Cys | Ala | Ala | Ser | Gly | Ser | Ile | Asp | Ser | Ile | Asn | Asn | Met | Gly |
| | | | | 180 | | | | | 185 | | | | | 190 | |
| Trp | Tyr | Arg | Gln | Ala | Pro | Gly | Lys | Gln | Arg | Glu | Leu | Val | Ala | Glu | Ile |
| | | | 195 | | | | | 200 | | | | | 205 | | |
| Thr | Pro | Arg | Gly | Arg | Thr | Asn | Tyr | Ala | Asp | Ser | Glu | Lys | Ser | Arg | Phe |
| | 210 | | | | | 215 | | | | | 220 | | | | |
| Thr | Ile | Ser | Arg | Asp | Asn | Ala | Lys | Arg | Thr | Val | Asn | Leu | Gln | Met | Asn |
| 225 | | | | | 230 | | | | | 235 | | | | | 240 |
| Ser | Leu | Lys | Pro | Glu | Asp | Thr | Ala | Val | Tyr | Tyr | Cys | Asn | Ala | Glu | Val |
| | | | | 245 | | | | | 250 | | | | | 255 | |
| Arg | Glu | Arg | Gly | Thr | Ser | Trp | Tyr | Arg | Pro | Asp | Tyr | Trp | Gly | Gln | Gly |
| | | | 260 | | | | | 265 | | | | | 270 | | |
| Thr | Gln | Val | Thr | Val | Ser | Ser | Gly | Gly | Gly | Gly | Ser | Gly | Gly | Gly | Gly |
| | | | 275 | | | | | 280 | | | | | 285 | | |
| Ser | Gly | Gly | Gly | Gly | Ser | Gly | Gly | Gly | Gly | Ser | Gly | Gly | Gly | Gly | Ser |
| | 290 | | | | | 295 | | | | | 300 | | | | |
| Gly | Gly | Gly | Gly | Ser | Gly | Gly | Gly | Ser | Glu | Val | Gln | Leu | Val | Glu |
| 305 | | | | | 310 | | | | | 315 | | | | | 320 |
| Ser | Gly | Gly | Gly | Leu | Val | Gln | Pro | Gly | Gly | Ser | Leu | Arg | Leu | Ser | Cys |
| | | | | 325 | | | | | 330 | | | | | 335 | |
| Ala | Ala | Ser | Gly | Ser | Ile | Asp | Ser | Ile | Asn | Asn | Met | Gly | Trp | Tyr | Arg |
| | | | 340 | | | | | 345 | | | | | 350 | | |
| Gln | Ala | Pro | Gly | Lys | Gln | Arg | Glu | Leu | Val | Ala | Glu | Ile | Thr | Pro | Arg |
| | | | 355 | | | | | 360 | | | | | 365 | | |

```
Gly Arg Thr Asn Tyr Ala Asp Ser Glu Lys Ser Arg Phe Thr Ile Ser
    370                 375                 380

Arg Asp Asn Ala Lys Arg Thr Val Asn Leu Gln Met Asn Ser Leu Lys
385                 390                 395                 400

Pro Glu Asp Thr Ala Val Tyr Tyr Cys Asn Ala Glu Val Arg Glu Arg
                405                 410                 415

Gly Thr Ser Trp Tyr Arg Pro Asp Tyr Trp Gly Gln Gly Thr Gln Val
                420                 425                 430

Thr Val Ser Ser
        435

<210> SEQ ID NO 18
<211> LENGTH: 593
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Asp Ser Ile Asn
            20                  25                  30

Asn Met Gly Trp Tyr Arg Gln Ala Pro Gly Lys Gln Arg Glu Leu Val
        35                  40                  45

Ala Glu Ile Thr Pro Arg Gly Arg Thr Asn Tyr Ala Asp Ser Glu Lys
    50                  55                  60

Ser Arg Phe Thr Ile Ser Arg Asp Asn Ala Lys Arg Thr Val Asn Leu
65                  70                  75                  80

Gln Met Asn Ser Leu Lys Pro Glu Asp Thr Ala Val Tyr Tyr Cys Asn
                85                  90                  95

Ala Glu Val Arg Glu Arg Gly Thr Ser Trp Tyr Arg Pro Asp Tyr Trp
            100                 105                 110

Gly Gln Gly Thr Gln Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Ser Ile Asp Ser Ile Asn Asn Met Gly
            180                 185                 190

Trp Tyr Arg Gln Ala Pro Gly Lys Gln Arg Glu Leu Val Ala Glu Ile
        195                 200                 205

Thr Pro Arg Gly Arg Thr Asn Tyr Ala Asp Ser Glu Lys Ser Arg Phe
    210                 215                 220

Thr Ile Ser Arg Asp Asn Ala Lys Arg Thr Val Asn Leu Gln Met Asn
225                 230                 235                 240

Ser Leu Lys Pro Glu Asp Thr Ala Val Tyr Tyr Cys Asn Ala Glu Val
                245                 250                 255

Arg Glu Arg Gly Thr Ser Trp Tyr Arg Pro Asp Tyr Trp Gly Gln Gly
            260                 265                 270

Thr Gln Val Thr Val Ser Ser Gly Gly Gly Gly Ser Gly Gly Gly Gly
        275                 280                 285
```

-continued

```
Ser Gly Gly Gly Gly Ser Gly Gly Gly Ser Gly Gly Gly Ser
    290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Gly Ser Leu Arg Leu Ser Cys
                325                 330                 335

Ala Ala Ser Gly Ser Ile Asp Ser Ile Asn Asn Met Gly Trp Tyr Arg
                340                 345                 350

Gln Ala Pro Gly Lys Gln Arg Glu Leu Val Ala Glu Ile Thr Pro Arg
                355                 360                 365

Gly Arg Thr Asn Tyr Ala Asp Ser Glu Lys Ser Arg Phe Thr Ile Ser
370                 375                 380

Arg Asp Asn Ala Lys Arg Thr Val Asn Leu Gln Met Asn Ser Leu Lys
385                 390                 395                 400

Pro Glu Asp Thr Ala Val Tyr Tyr Cys Asn Ala Glu Val Arg Glu Arg
                405                 410                 415

Gly Thr Ser Trp Tyr Arg Pro Asp Tyr Trp Gly Gln Gly Thr Gln Val
                420                 425                 430

Thr Val Ser Ser Gly Gly Gly Gly Ser Gly Gly Gly Gly Ser Gly Gly
                435                 440                 445

Gly Gly Ser Gly Gly Gly Gly Ser Gly Gly Gly Ser Gly Gly Gly
450                 455                 460

Gly Ser Gly Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Ser Ile Asp Ser Ile Asn Asn Met Gly Trp Tyr Arg Gln Ala Pro
                500                 505                 510

Gly Lys Gln Arg Glu Leu Val Ala Glu Ile Thr Pro Arg Gly Arg Thr
                515                 520                 525

Asn Tyr Ala Asp Ser Glu Lys Ser Arg Phe Thr Ile Ser Arg Asp Asn
                530                 535                 540

Ala Lys Arg Thr Val Asn Leu Gln Met Asn Ser Leu Lys Pro Glu Asp
545                 550                 555                 560

Thr Ala Val Tyr Tyr Cys Asn Ala Glu Val Arg Glu Arg Gly Thr Ser
                565                 570                 575

Trp Tyr Arg Pro Asp Tyr Trp Gly Gln Gly Thr Gln Val Thr Val Ser
                580                 585                 590

Ser

<210> SEQ ID NO 19
<211> LENGTH: 750
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Asp Ser Ile Asn
                20                  25                  30

Asn Met Gly Trp Tyr Arg Gln Ala Pro Gly Lys Gln Arg Glu Leu Val
            35                  40                  45
```

```
Ala Glu Ile Thr Pro Arg Gly Arg Thr Asn Tyr Ala Asp Ser Glu Lys
         50                  55                  60

Ser Arg Phe Thr Ile Ser Arg Asp Asn Ala Lys Arg Thr Val Asn Leu
 65                  70                  75                  80

Gln Met Asn Ser Leu Lys Pro Glu Asp Thr Ala Val Tyr Tyr Cys Asn
                 85                  90                  95

Ala Glu Val Arg Glu Arg Gly Thr Ser Trp Tyr Arg Pro Asp Tyr Trp
                100                 105                 110

Gly Gln Gly Thr Gln Val Thr Val Ser Ser Gly Gly Gly Gly Ser Gly
                115                 120                 125

Gly Gly Gly Ser Gly Gly Gly Ser Gly Gly Gly Ser Gly
        130                 135                 140

Gly Gly Ser Gly Gly Gly Ser Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Ser Ile Asp Ser Ile Asn Asn Met Gly
                180                 185                 190

Trp Tyr Arg Gln Ala Pro Gly Lys Gln Arg Glu Leu Val Ala Glu Ile
                195                 200                 205

Thr Pro Arg Gly Arg Thr Asn Tyr Ala Asp Ser Glu Lys Ser Arg Phe
            210                 215                 220

Thr Ile Ser Arg Asp Asn Ala Lys Arg Thr Val Asn Leu Gln Met Asn
225                 230                 235                 240

Ser Leu Lys Pro Glu Asp Thr Ala Val Tyr Tyr Cys Asn Ala Glu Val
                245                 250                 255

Arg Glu Arg Gly Thr Ser Trp Tyr Arg Pro Asp Tyr Trp Gly Gln Gly
            260                 265                 270

Thr Gln Val Thr Val Ser Ser Gly Gly Gly Gly Ser Gly Gly Gly Gly
            275                 280                 285

Ser Gly Gly Gly Gly Ser Gly Gly Gly Gly Ser Gly Gly Gly Gly Ser
        290                 295                 300

Gly Gly Gly Gly Ser Gly Gly Gly Gly Ser Glu Val Gln Leu Val Glu
305                 310                 315                 320

Ser Gly Gly Gly Leu Val Gln Pro Gly Gly Ser Leu Arg Leu Ser Cys
                325                 330                 335

Ala Ala Ser Gly Ser Ile Asp Ser Ile Asn Asn Met Gly Trp Tyr Arg
            340                 345                 350

Gln Ala Pro Gly Lys Gln Arg Glu Leu Val Ala Glu Ile Thr Pro Arg
            355                 360                 365

Gly Arg Thr Asn Tyr Ala Asp Ser Glu Lys Ser Arg Phe Thr Ile Ser
            370                 375                 380

Arg Asp Asn Ala Lys Arg Thr Val Asn Leu Gln Met Asn Ser Leu Lys
385                 390                 395                 400

Pro Glu Asp Thr Ala Val Tyr Tyr Cys Asn Ala Glu Val Arg Glu Arg
                405                 410                 415

Gly Thr Ser Trp Tyr Arg Pro Asp Tyr Trp Gly Gln Gly Thr Gln Val
            420                 425                 430

Thr Val Ser Ser Gly Gly Gly Ser Gly Gly Gly Ser Gly Gly
            435                 440                 445

Gly Gly Ser Gly Gly Gly Ser Gly Gly Gly Ser Gly Gly Gly
450                 455                 460
```

```
Gly Ser Gly Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Ser Ile Asp Ser Ile Asn Asn Met Gly Trp Tyr Arg Gln Ala Pro
            500                 505                 510

Gly Lys Gln Arg Glu Leu Val Ala Glu Ile Thr Pro Arg Gly Arg Thr
        515                 520                 525

Asn Tyr Ala Asp Ser Glu Lys Ser Arg Phe Thr Ile Ser Arg Asp Asn
    530                 535                 540

Ala Lys Arg Thr Val Asn Leu Gln Met Asn Ser Leu Lys Pro Glu Asp
545                 550                 555                 560

Thr Ala Val Tyr Tyr Cys Asn Ala Glu Val Arg Glu Arg Gly Thr Ser
                565                 570                 575

Trp Tyr Arg Pro Asp Tyr Trp Gly Gln Gly Thr Gln Val Thr Val Ser
            580                 585                 590

Ser Gly Gly Gly Gly Ser Gly Gly Gly Ser Gly Gly Gly Gly Ser
    595                 600                 605

Gly Gly Gly Gly Ser Gly Gly Gly Ser Gly Gly Gly Ser Gly
    610                 615                 620

Gly Gly Gly Ser Glu Val Gln Leu Val Glu Ser Gly Gly Gly Leu Val
625                 630                 635                 640

Gln Pro Gly Gly Ser Leu Arg Leu Ser Cys Ala Ala Ser Gly Ser Ile
                645                 650                 655

Asp Ser Ile Asn Asn Met Gly Trp Tyr Arg Gln Ala Pro Gly Lys Gln
            660                 665                 670

Arg Glu Leu Val Ala Glu Ile Thr Pro Arg Gly Arg Thr Asn Tyr Ala
        675                 680                 685

Asp Ser Glu Lys Ser Arg Phe Thr Ile Ser Arg Asp Asn Ala Lys Arg
    690                 695                 700

Thr Val Asn Leu Gln Met Asn Ser Leu Lys Pro Glu Asp Thr Ala Val
705                 710                 715                 720

Tyr Tyr Cys Asn Ala Glu Val Arg Glu Arg Gly Thr Ser Trp Tyr Arg
                725                 730                 735

Pro Asp Tyr Trp Gly Gln Gly Thr Gln Val Thr Val Ser Ser
            740                 745                 750

<210> SEQ ID NO 20
<211> LENGTH: 436
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
    50                  55                  60

Gly Arg Phe Thr Ile Ser Arg Asp Asn Ala Lys Asp Thr Met Tyr Leu
65                  70                  75                  80
```

```
Gln Met Asn Ser Leu Lys Pro Glu Asp Thr Ala Val Tyr Phe Cys Asn
                85                  90                  95

Ala Glu Ile Leu Lys Arg Ala Tyr Ile Asp Val Tyr Val Asn Tyr Trp
           100                 105                 110

Gly Gln Gly Thr Gln Val Thr Val Ser Ser Gly Gly Gly Gly Ser Gly
       115                 120                 125

Gly Gly Gly Ser Gly Gly Gly Gly Ser Gly Gly Gly Gly Ser Gly Gly
130                 135                 140

Gly Gly Ser Gly Gly Gly Ser Gly Gly Gly Ser Glu Val Gln
145                 150                 155                 160

Leu Val Glu Ser Gly Gly Leu Val Gln Pro Gly Gly Ser Leu Arg
               165                 170                 175

Leu Ser Cys Ala Ala Ser Gly Thr Phe Asp Lys Ile Asn Asn Met Gly
               180                 185                 190

Trp Tyr Arg Gln Ala Pro Gly Lys Gln Arg Asp Leu Val Ala Gln Ile
           195                 200                 205

Thr Pro Gly Gly Ile Thr Asp Tyr Ala Asp Ser Val Lys Gly Arg Phe
       210                 215                 220

Thr Ile Ser Arg Asp Asn Ala Lys Asp Thr Met Tyr Leu Gln Met Asn
225                 230                 235                 240

Ser Leu Lys Pro Glu Asp Thr Ala Val Tyr Phe Cys Asn Ala Glu Ile
               245                 250                 255

Leu Lys Arg Ala Tyr Ile Asp Val Tyr Val Asn Tyr Trp Gly Gln Gly
               260                 265                 270

Thr Gln Val Thr Val Ser Ser Gly Gly Gly Gly Ser Gly Gly Gly Gly
           275                 280                 285

Ser Gly Gly Gly Gly Ser Gly Gly Gly Gly Ser Gly Gly Gly Gly Ser
290                 295                 300

Gly Gly Gly Ser Gly Gly Gly Ser Glu Val Gln Leu Val Glu
305                 310                 315                 320

Ser Gly Gly Leu Val Gln Pro Gly Gly Ser Leu Arg Leu Ser Cys
               325                 330                 335

Ala Ala Ser Gly Thr Phe Asp Lys Ile Asn Asn Met Gly Trp Tyr Arg
           340                 345                 350

Gln Ala Pro Gly Lys Gln Arg Asp Leu Val Ala Gln Ile Thr Pro Gly
           355                 360                 365

Gly Ile Thr Asp Tyr Ala Asp Ser Val Lys Gly Arg Phe Thr Ile Ser
       370                 375                 380

Arg Asp Asn Ala Lys Asp Thr Met Tyr Leu Gln Met Asn Ser Leu Lys
385                 390                 395                 400

Pro Glu Asp Thr Ala Val Tyr Phe Cys Asn Ala Glu Ile Leu Lys Arg
               405                 410                 415

Ala Tyr Ile Asp Val Tyr Val Asn Tyr Trp Gly Gln Gly Thr Gln Val
           420                 425                 430

Thr Val Ser Ser
       435

<210> SEQ ID NO 21
<211> LENGTH: 593
<212> TYPE: PRT
<213> ORGANISM: Artificial Sequence
<220> FEATURE:
<223> OTHER INFORMATION: Description of Artificial Sequence: Synthetic
      recombinant polypeptide
```

<400> SEQUENCE: 21

| | | | | | | | | | | | | | | |
|---|---|---|---|---|---|---|---|---|---|---|---|---|---|---|
|Glu|Val|Gln|Leu|Val|Glu|Ser|Gly|Gly|Gly|Leu|Val|Gln|Pro|Gly|Gly|
|1| | | |5| | | | |10| | | | |15|
|Ser|Leu|Arg|Leu|Ser|Cys|Ala|Ala|Ser|Gly|Thr|Phe|Asp|Lys|Ile|Asn|
| | | |20| | | | |25| | | | |30| |
|Asn|Met|Gly|Trp|Tyr|Arg|Gln|Ala|Pro|Gly|Lys|Gln|Arg|Asp|Leu|Val|
| | | |35| | | | |40| | | | |45| |
|Ala|Gln|Ile|Thr|Pro|Gly|Gly|Ile|Thr|Asp|Tyr|Ala|Asp|Ser|Val|Lys|
| |50| | | | |55| | | | |60| | | |
|Gly|Arg|Phe|Thr|Ile|Ser|Arg|Asp|Asn|Ala|Lys|Asp|Thr|Met|Tyr|Leu|
|65| | | | |70| | | | |75| | | | |80|
|Gln|Met|Asn|Ser|Leu|Lys|Pro|Glu|Asp|Thr|Ala|Val|Tyr|Phe|Cys|Asn|
| | | | |85| | | | |90| | | | |95| |
|Ala|Glu|Ile|Leu|Lys|Arg|Ala|Tyr|Ile|Asp|Val|Tyr|Val|Asn|Tyr|Trp|
| | | |100| | | | |105| | | | |110| | |
|Gly|Gln|Gly|Thr|Gln|Val|Thr|Val|Ser|Ser|Gly|Gly|Gly|Gly|Ser|Gly|
| | | |115| | | | |120| | | | |125| | |
|Gly|Gly|Gly|Ser|Gly|Gly|Gly|Ser|Gly|Gly|Gly|Ser|Gly|Gly|Gly|Gly|
| | |130| | | | |135| | | | |140| | | |
|Gly|Gly|Ser|Gly|Gly|Gly|Ser|Gly|Gly|Gly|Ser|Glu|Val|Gln|
|145| | | | |150| | | | |155| | | | |160|
|Leu|Val|Glu|Ser|Gly|Gly|Gly|Leu|Val|Gln|Pro|Gly|Gly|Ser|Leu|Arg|
| | | | |165| | | | |170| | | | |175| |
|Leu|Ser|Cys|Ala|Ala|Ser|Gly|Thr|Phe|Asp|Lys|Ile|Asn|Asn|Met|Gly|
| | | |180| | | | |185| | | | |190| | |
|Trp|Tyr|Arg|Gln|Ala|Pro|Gly|Lys|Gln|Arg|Asp|Leu|Val|Ala|Gln|Ile|
| | |195| | | | |200| | | | |205| | | |
|Thr|Pro|Gly|Gly|Ile|Thr|Asp|Tyr|Ala|Asp|Ser|Val|Lys|Gly|Arg|Phe|
| |210| | | | |215| | | | |220| | | | |
|Thr|Ile|Ser|Arg|Asp|Asn|Ala|Lys|Asp|Thr|Met|Tyr|Leu|Gln|Met|Asn|
|225| | | | |230| | | | |235| | | | |240|
|Ser|Leu|Lys|Pro|Glu|Asp|Thr|Ala|Val|Tyr|Phe|Cys|Asn|Ala|Glu|Ile|
| | | | |245| | | | |250| | | | |255| |
|Leu|Lys|Arg|Ala|Tyr|Ile|Asp|Val|Tyr|Val|Asn|Tyr|Trp|Gly|Gln|Gly|
| | | |260| | | | |265| | | | |270| | |
|Thr|Gln|Val|Thr|Val|Ser|Ser|Gly|Gly|Gly|Gly|Ser|Gly|Gly|Gly|Gly|
| | |275| | | | |280| | | | |285| | | |
|Ser|Gly|Gly|Gly|Gly|Ser|Gly|Gly|Gly|Ser|Gly|Gly|Gly|Gly|Ser|
| |290| | | | |295| | | | |300| | | | |
|Gly|Gly|Gly|Gly|Ser|Gly|Gly|Gly|Ser|Glu|Val|Gln|Leu|Val|Glu|
|305| | | | |310| | | | |315| | | | |320|
|Ser|Gly|Gly|Gly|Leu|Val|Gln|Pro|Gly|Gly|Ser|Leu|Arg|Leu|Ser|Cys|
| | | | |325| | | | |330| | | | |335| |
|Ala|Ala|Ser|Gly|Thr|Phe|Asp|Lys|Ile|Asn|Asn|Met|Gly|Trp|Tyr|Arg|
| | | |340| | | | |345| | | | |350| | |
|Gln|Ala|Pro|Gly|Lys|Gln|Arg|Asp|Leu|Val|Ala|Gln|Ile|Thr|Pro|Gly|
| | |355| | | | |360| | | | |365| | | |
|Gly|Ile|Thr|Asp|Tyr|Ala|Asp|Ser|Val|Lys|Gly|Arg|Phe|Thr|Ile|Ser|
| |370| | | | |375| | | | |380| | | | |
|Arg|Asp|Asn|Ala|Lys|Asp|Thr|Met|Tyr|Leu|Gln|Met|Asn|Ser|Leu|Lys|
|385| | | | |390| | | | |395| | | | |400|
|Pro|Glu|Asp|Thr|Ala|Val|Tyr|Phe|Cys|Asn|Ala|Glu|Ile|Leu|Lys|Arg|
| | | | |405| | | | |410| | | | |415| |

```
Ala Tyr Ile Asp Val Tyr Val Asn Tyr Trp Gly Gln Gly Thr Gln Val
            420                 425                 430

Thr Val Ser Ser Gly Gly Gly Gly Ser Gly Gly Gly Ser Gly Gly
        435                 440                 445

Gly Gly Ser Gly Gly Gly Ser Gly Gly Gly Ser Gly Gly Gly
450                 455                 460

Gly Ser Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Thr Phe Asp Lys Ile Asn Asn Met Gly Trp Tyr Arg Gln Ala Pro
            500                 505                 510

Gly Lys Gln Arg Asp Leu Val Ala Gln Ile Thr Pro Gly Gly Ile Thr
            515                 520                 525

Asp Tyr Ala Asp Ser Val Lys Gly Arg Phe Thr Ile Ser Arg Asp Asn
            530                 535                 540

Ala Lys Asp Thr Met Tyr Leu Gln Met Asn Ser Leu Lys Pro Glu Asp
545                 550                 555                 560

Thr Ala Val Tyr Phe Cys Asn Ala Glu Ile Leu Lys Arg Ala Tyr Ile
                565                 570                 575

Asp Val Tyr Val Asn Tyr Trp Gly Gln Gly Thr Gln Val Thr Val Ser
            580                 585                 590

Ser
```

<210> SEQ ID NO 22
<211> LENGTH: 750
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
    50                  55                  60

Gly Arg Phe Thr Ile Ser Arg Asp Asn Ala Lys Asp Thr Met Tyr Leu
65                  70                  75                  80

Gln Met Asn Ser Leu Lys Pro Glu Asp Thr Ala Val Tyr Phe Cys Asn
                85                  90                  95

Ala Glu Ile Leu Lys Arg Ala Tyr Ile Asp Val Tyr Val Asn Tyr Trp
            100                 105                 110

Gly Gln Gly Thr Gln Val Thr Val Ser Ser Gly Gly Gly Ser Gly
        115                 120                 125

Gly Gly Gly Ser Gly Gly Gly Ser Gly Gly Gly Ser Gly Gly
        130                 135                 140

Gly Gly Ser Gly Gly Gly Ser Gly Gly Gly Ser Glu Val Gln
145                 150                 155                 160

Leu Val Glu Ser Gly Gly Gly Leu Val Gln Pro Gly Gly Ser Leu Arg
                165                 170                 175
```

```
Leu Ser Cys Ala Ala Ser Gly Thr Phe Asp Lys Ile Asn Asn Met Gly
            180                 185                 190

Trp Tyr Arg Gln Ala Pro Gly Lys Gln Arg Asp Leu Val Ala Gln Ile
        195                 200                 205

Thr Pro Gly Gly Ile Thr Asp Tyr Ala Asp Ser Val Lys Gly Arg Phe
    210                 215                 220

Thr Ile Ser Arg Asp Asn Ala Lys Asp Thr Met Tyr Leu Gln Met Asn
225                 230                 235                 240

Ser Leu Lys Pro Glu Asp Thr Ala Val Tyr Phe Cys Asn Ala Glu Ile
                245                 250                 255

Leu Lys Arg Ala Tyr Ile Asp Val Tyr Val Asn Tyr Trp Gly Gln Gly
            260                 265                 270

Thr Gln Val Thr Val Ser Ser Gly Gly Gly Gly Ser Gly Gly Gly Gly
        275                 280                 285

Ser Gly Gly Gly Gly Ser Gly Gly Gly Gly Ser Gly Gly Gly Gly Ser
    290                 295                 300

Gly Gly Gly Gly Ser Gly Gly Gly Ser Glu Val Gln Leu Val Glu
305                 310                 315                 320

Ser Gly Gly Gly Leu Val Gln Pro Gly Gly Ser Leu Arg Leu Ser Cys
            325                 330                 335

Ala Ala Ser Gly Thr Phe Asp Lys Ile Asn Asn Met Gly Trp Tyr Arg
            340                 345                 350

Gln Ala Pro Gly Lys Gln Arg Asp Leu Val Ala Gln Ile Thr Pro Gly
        355                 360                 365

Gly Ile Thr Asp Tyr Ala Asp Ser Val Lys Gly Arg Phe Thr Ile Ser
    370                 375                 380

Arg Asp Asn Ala Lys Asp Thr Met Tyr Leu Gln Met Asn Ser Leu Lys
385                 390                 395                 400

Pro Glu Asp Thr Ala Val Tyr Phe Cys Asn Ala Glu Ile Leu Lys Arg
                405                 410                 415

Ala Tyr Ile Asp Val Tyr Val Asn Tyr Trp Gly Gln Gly Thr Gln Val
            420                 425                 430

Thr Val Ser Ser Gly Gly Gly Gly Ser Gly Gly Gly Gly Ser Gly Gly
        435                 440                 445

Gly Gly Ser Gly Gly Gly Gly Ser Gly Gly Gly Gly Ser Gly Gly Gly
    450                 455                 460

Gly Ser Gly Gly Gly Gly Ser Glu Val Gln Leu Val Glu Ser Gly Gly
465                 470                 475                 480

Gly Leu Val Gln Pro Gly Gly Ser Leu Arg Leu Ser Cys Ala Ala Ser
                485                 490                 495

Gly Thr Phe Asp Lys Ile Asn Asn Met Gly Trp Tyr Arg Gln Ala Pro
            500                 505                 510

Gly Lys Gln Arg Asp Leu Val Ala Gln Ile Thr Pro Gly Gly Ile Thr
        515                 520                 525

Asp Tyr Ala Asp Ser Val Lys Gly Arg Phe Thr Ile Ser Arg Asp Asn
    530                 535                 540

Ala Lys Asp Thr Met Tyr Leu Gln Met Asn Ser Leu Lys Pro Glu Asp
545                 550                 555                 560

Thr Ala Val Tyr Phe Cys Asn Ala Glu Ile Leu Lys Arg Ala Tyr Ile
                565                 570                 575

Asp Val Tyr Val Asn Tyr Trp Gly Gln Gly Thr Gln Val Thr Val Ser
            580                 585                 590
```

```
Ser Gly Gly Gly Gly Ser Gly Gly Gly Ser Gly Gly Gly Ser
        595                 600                 605

Gly Gly Gly Gly Ser Gly Gly Gly Ser Gly Gly Gly Ser Gly
        610                 615                 620

Gly Gly Gly Ser Glu Val Gln Leu Val Glu Ser Gly Gly Leu Val
625                 630                 635                 640

Gln Pro Gly Gly Ser Leu Arg Leu Ser Cys Ala Ala Ser Gly Thr Phe
                645                 650                 655

Asp Lys Ile Asn Asn Met Gly Trp Tyr Arg Gln Ala Pro Gly Lys Gln
                660                 665                 670

Arg Asp Leu Val Ala Gln Ile Thr Pro Gly Gly Ile Thr Asp Tyr Ala
                675                 680                 685

Asp Ser Val Lys Gly Arg Phe Thr Ile Ser Arg Asp Asn Ala Lys Asp
                690                 695                 700

Thr Met Tyr Leu Gln Met Asn Ser Leu Lys Pro Glu Asp Thr Ala Val
705                 710                 715                 720

Tyr Phe Cys Asn Ala Glu Ile Leu Lys Arg Ala Tyr Ile Asp Val Tyr
                725                 730                 735

Val Asn Tyr Trp Gly Gln Gly Thr Gln Val Thr Val Ser Ser
                740                 745                 750

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      linker polypeptide

<400> SEQUENCE: 23

Gly Gly Gly Gly Ser Gly Gly Gly Gly Ser Gly Gly Gly Gly Ser Gly
1               5                   10                  15

Gly Gly Ser Gly Gly Gly Ser Gly Gly Gly Ser Gly Gly
            20                  25                  30

Gly Gly Ser
        35

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 24

Gly Gly Gly Gly Ser Gly Gly Gly Gly Ser Gly Gly Gly Gly Ser Gly
1               5                   10                  15

Gly Gly Gly Ser
        20

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 25

Gly Gly Gly Gly Ser Gly Gly Gly Ser
```

```
1               5
```

<210> SEQ ID NO 26
<211> LENGTH: 126
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 26

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Gly Ser Ile
            20                  25                  30

Arg Val Gly Trp Phe Arg Gln Ala Pro Gly Lys Gly Arg Glu Phe Val
        35                  40                  45

Ser Ala Ile Asn Arg Asn Asp Gly Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gly Leu Gln Tyr Asn Arg Ala Ala Asp Arg Val Pro Val Gly
            100                 105                 110

Ala Val Tyr Trp Gly Gln Gly Thr Leu Val Thr Val Ser Ser
        115                 120                 125
```

<210> SEQ ID NO 27
<211> LENGTH: 448
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Gly Ser Ile
            20                  25                  30

Arg Val Gly Trp Phe Arg Gln Ala Pro Gly Lys Gly Arg Glu Phe Val
        35                  40                  45

Ser Ala Ile Asn Arg Asn Asp Gly Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gly Leu Gln Tyr Asn Arg Ala Ala Asp Arg Val Pro Val Gly
            100                 105                 110

Ala Val Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Leu Glu Ser Gly Gly Gly Leu Val Gln Pro Gly
```

Gly Ser Leu Arg Leu Ser Cys Ala Ala Ser Gly Arg Thr Phe Gly Ser
            165                 170                 175

Ile Arg Val Gly Trp Phe Arg Gln Ala Pro Gly Lys Gly Arg Glu Phe
        180                 185                 190

Val Ser Ala Ile Asn Arg Asn Asp Gly Thr Thr Tyr Tyr Ala Asp Ser
    195                 200                 205

Val Lys Gly Arg Phe Thr Ile Ser Arg Asp Asn Ser Lys Asn Thr Val
210                 215                 220

Tyr Leu Gln Met Asn Ser Leu Arg Pro Glu Asp Thr Ala Val Tyr Tyr
225                 230                 235                 240

Cys Ala Ala Gly Leu Gln Tyr Asn Arg Ala Ala Asp Arg Val Pro Val
            245                 250                 255

Gly Ala Val Tyr Trp Gly Gln Gly Thr Leu Val Thr Val Ser Ser Gly
        260                 265                 270

Gly Gly Gly Ser Gly Gly Gly Ser Gly Gly Gly Ser Gly Gly Gly Ser
    275                 280                 285

Gly Gly Ser Gly Gly Gly Ser Gly Gly Gly Ser Gly Gly Gly Ser Gly
290                 295                 300

Gly Ser Glu Val Gln Leu Leu Glu Ser Gly Gly Leu Val Gln Pro Gly
305                 310                 315                 320

Gly Ser Leu Arg Leu Ser Cys Ala Ala Ser Gly Arg Thr Phe Gly Ser
            325                 330                 335

Ser Ile Arg Val Gly Trp Phe Arg Gln Ala Pro Gly Lys Gly Arg Glu
        340                 345                 350

Phe Val Ser Ala Ile Asn Arg Asn Asp Gly Thr Thr Tyr Tyr Ala Asp
    355                 360                 365

Ser Val Lys Gly Arg Phe Thr Ile Ser Arg Asp Asn Ser Lys Asn Thr
370                 375                 380

Val Tyr Leu Gln Met Asn Ser Leu Arg Pro Glu Asp Thr Ala Val Tyr
385                 390                 395                 400

Tyr Cys Ala Ala Gly Leu Gln Tyr Asn Arg Ala Ala Asp Arg Val Pro
            405                 410                 415

Val Gly Ala Val Tyr Trp Gly Gln Gly Thr Leu Val Thr Val Ser Ser
        420                 425                 430

435                 440                 445

<210> SEQ ID NO 28
<211> LENGTH: 609
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Gly Ser Ile
            20                  25                  30

Arg Val Gly Trp Phe Arg Gln Ala Pro Gly Lys Gly Arg Glu Phe Val
        35                  40                  45

Ser Ala Ile Asn Arg Asn Asp Gly Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

```
Leu Gln Met Asn Ser Leu Arg Pro Glu Asp Thr Ala Val Tyr Tyr Cys
                85                  90                  95

Ala Ala Gly Leu Gln Tyr Asn Arg Ala Ala Asp Arg Val Pro Val Gly
            100                 105                 110

Ala Val Tyr Trp Gly Gln Gly Thr Leu Val Thr Val Ser Ser Gly Gly
        115                 120                 125

Gly Gly Ser Gly Gly Gly Gly Ser Gly Gly Gly Ser Gly Gly Gly
    130                 135                 140

Gly Ser Gly Gly Gly Ser Gly Gly Gly Ser Gly Gly Gly Gly
145                 150                 155                 160

Ser Glu Val Gln Leu Leu Glu Ser Gly Gly Leu Val Gln Pro Gly
                165                 170                 175

Gly Ser Leu Arg Leu Ser Cys Ala Ala Ser Gly Arg Thr Phe Gly Ser
        180                 185                 190

Ile Arg Val Gly Trp Phe Arg Gln Ala Pro Gly Lys Gly Arg Glu Phe
    195                 200                 205

Val Ser Ala Ile Asn Arg Asn Asp Gly Thr Thr Tyr Tyr Ala Asp Ser
    210                 215                 220

Val Lys Gly Arg Phe Thr Ile Ser Arg Asp Asn Ser Lys Asn Thr Val
225                 230                 235                 240

Tyr Leu Gln Met Asn Ser Leu Arg Pro Glu Asp Thr Ala Val Tyr Tyr
                245                 250                 255

Cys Ala Ala Gly Leu Gln Tyr Asn Arg Ala Ala Asp Arg Val Pro Val
            260                 265                 270

Gly Ala Val Tyr Trp Gly Gln Gly Thr Leu Val Thr Val Ser Ser Gly
        275                 280                 285

Gly Gly Gly Ser Gly Gly Gly Gly Ser Gly Gly Gly Ser Gly Gly
    290                 295                 300

Gly Gly Ser Gly Gly Gly Ser Gly Gly Gly Ser Gly Gly Gly
305                 310                 315                 320

Gly Ser Glu Val Gln Leu Leu Glu Ser Gly Gly Leu Val Gln Pro
                325                 330                 335

Gly Gly Ser Leu Arg Leu Ser Cys Ala Ala Ser Gly Arg Thr Phe Gly
        340                 345                 350

Ser Ile Arg Val Gly Trp Phe Arg Gln Ala Pro Gly Lys Gly Arg Glu
        355                 360                 365

Phe Val Ser Ala Ile Asn Arg Asn Asp Gly Thr Thr Tyr Tyr Ala Asp
    370                 375                 380

Ser Val Lys Gly Arg Phe Thr Ile Ser Arg Asp Asn Ser Lys Asn Thr
385                 390                 395                 400

Val Tyr Leu Gln Met Asn Ser Leu Arg Pro Glu Asp Thr Ala Val Tyr
                405                 410                 415

Tyr Cys Ala Ala Gly Leu Gln Tyr Asn Arg Ala Ala Asp Arg Val Pro
            420                 425                 430

Val Gly Ala Val Tyr Trp Gly Gln Gly Thr Leu Val Thr Val Ser Ser
        435                 440                 445

Gly Gly Gly Gly Ser Gly Gly Gly Gly Ser Gly Gly Gly Ser Gly
    450                 455                 460

Gly Gly Gly Ser Gly Gly Gly Ser Gly Gly Gly Ser Gly Gly
465                 470                 475                 480

Gly Gly Ser Glu Val Gln Leu Leu Glu Ser Gly Gly Gly Leu Val Gln
                485                 490                 495

Pro Gly Gly Ser Leu Arg Leu Ser Cys Ala Ala Ser Gly Arg Thr Phe
```

```
                        500                 505                 510
Gly Ser Ile Arg Val Gly Trp Phe Arg Gln Ala Pro Gly Lys Gly Arg
            515                 520                 525

Glu Phe Val Ser Ala Ile Asn Arg Asn Asp Gly Thr Thr Tyr Tyr Ala
        530                 535                 540

Asp Ser Val Lys Gly Arg Phe Thr Ile Ser Arg Asp Asn Ser Lys Asn
545                 550                 555                 560

Thr Val Tyr Leu Gln Met Asn Ser Leu Arg Pro Glu Asp Thr Ala Val
                565                 570                 575

Tyr Tyr Cys Ala Ala Gly Leu Gln Tyr Asn Arg Ala Ala Asp Arg Val
            580                 585                 590

Pro Val Gly Ala Val Tyr Trp Gly Gln Gly Thr Leu Val Thr Val Ser
        595                 600                 605

Ser
```

<210> SEQ ID NO 29
<211> LENGTH: 770
<212> TYPE: PRT
<213> ORGANISM: Artificial Sequence
<220> FEATURE:
<223> OTHER INFORMATION: Description of Artificial Sequence: Synthetic
    recombinant polypeptide

<400> SEQUENCE: 29

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Gly Ser Ile
            20                  25                  30

Arg Val Gly Trp Phe Arg Gln Ala Pro Gly Lys Gly Arg Glu Phe Val
        35                  40                  45

Ser Ala Ile Asn Arg Asn Asp Gly Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gly Leu Gln Tyr Asn Arg Ala Ala Asp Arg Val Pro Val Gly
            100                 105                 110

Ala Val Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Leu Glu Ser Gly Gly Gly Leu Val Gln Pro Gly
                165                 170                 175

Gly Ser Leu Arg Leu Ser Cys Ala Ala Ser Gly Arg Thr Phe Gly Ser
            180                 185                 190

Ile Arg Val Gly Trp Phe Arg Gln Ala Pro Gly Lys Gly Arg Glu Phe
        195                 200                 205

Val Ser Ala Ile Asn Arg Asn Asp Gly Thr Thr Tyr Tyr Ala Asp Ser
    210                 215                 220

Val Lys Gly Arg Phe Thr Ile Ser Arg Asp Asn Ser Lys Asn Thr Val
225                 230                 235                 240

Tyr Leu Gln Met Asn Ser Leu Arg Pro Glu Asp Thr Ala Val Tyr Tyr
```

```
                       245                 250                 255
        Cys Ala Ala Gly Leu Gln Tyr Asn Arg Ala Ala Asp Arg Val Pro Val
                    260                 265                 270

Gly Ala Val Tyr Trp Gly Gln Gly Thr Leu Val Thr Val Ser Ser Gly
                    275                 280                 285

Gly Gly Ser Gly Gly Gly Ser Gly Gly Gly Ser Gly Gly
                    290                 295                 300

Gly Gly Ser Gly Gly Gly Ser Gly Gly Gly Ser Gly Gly
        305                 310                 315                 320

Gly Ser Glu Val Gln Leu Leu Glu Ser Gly Gly Gly Leu Val Gln Pro
                        325                 330                 335

Gly Gly Ser Leu Arg Leu Ser Cys Ala Ala Ser Gly Arg Thr Phe Gly
                    340                 345                 350

Ser Ile Arg Val Gly Trp Phe Arg Gln Ala Pro Gly Lys Gly Arg Glu
                    355                 360                 365

Phe Val Ser Ala Ile Asn Arg Asn Asp Gly Thr Thr Tyr Tyr Ala Asp
                    370                 375                 380

Ser Val Lys Gly Arg Phe Thr Ile Ser Arg Asp Asn Ser Lys Asn Thr
        385                 390                 395                 400

Val Tyr Leu Gln Met Asn Ser Leu Arg Pro Glu Asp Thr Ala Val Tyr
                        405                 410                 415

Tyr Cys Ala Ala Gly Leu Gln Tyr Asn Arg Ala Ala Asp Arg Val Pro
                    420                 425                 430

Val Gly Ala Val Tyr Trp Gly Gln Gly Thr Leu Val Thr Val Ser Ser
                    435                 440                 445

Gly Gly Gly Gly Ser Gly Gly Gly Ser Gly Gly Gly Ser Gly
                    450                 455                 460

Gly Gly Gly Ser Gly Gly Gly Ser Gly Gly Gly Ser Gly Gly
        465                 470                 475                 480

Gly Gly Ser Glu Val Gln Leu Leu Glu Ser Gly Gly Gly Leu Val Gln
                        485                 490                 495

Pro Gly Gly Ser Leu Arg Leu Ser Cys Ala Ala Ser Gly Arg Thr Phe
                    500                 505                 510

Gly Ser Ile Arg Val Gly Trp Phe Arg Gln Ala Pro Gly Lys Gly Arg
                    515                 520                 525

Glu Phe Val Ser Ala Ile Asn Arg Asn Asp Gly Thr Thr Tyr Tyr Ala
                    530                 535                 540

Asp Ser Val Lys Gly Arg Phe Thr Ile Ser Arg Asp Asn Ser Lys Asn
        545                 550                 555                 560

Thr Val Tyr Leu Gln Met Asn Ser Leu Arg Pro Glu Asp Thr Ala Val
                        565                 570                 575

Tyr Tyr Cys Ala Ala Gly Leu Gln Tyr Asn Arg Ala Ala Asp Arg Val
                    580                 585                 590

Pro Val Gly Ala Val Tyr Trp Gly Gln Gly Thr Leu Val Thr Val Ser
                    595                 600                 605

Ser Gly Gly Gly Gly Ser Gly Gly Gly Ser Gly Gly Gly Ser
            610                 615                 620

Gly Gly Gly Gly Ser Gly Gly Gly Ser Gly Gly Gly Ser Gly
        625                 630                 635                 640

Gly Gly Ser Glu Val Gln Leu Leu Glu Ser Gly Gly Gly Leu Val
                        645                 650                 655

Gln Pro Gly Gly Ser Leu Arg Leu Ser Cys Ala Ala Ser Gly Arg Thr
                    660                 665                 670
```

```
Phe Gly Ser Ile Arg Val Gly Trp Phe Arg Gln Ala Pro Gly Lys Gly
        675                 680                 685

Arg Glu Phe Val Ser Ala Ile Asn Arg Asn Asp Gly Thr Thr Tyr Tyr
    690                 695                 700

Ala Asp Ser Val Lys Gly Arg Phe Thr Ile Ser Arg Asp Asn Ser Lys
705                 710                 715                 720

Asn Thr Val Tyr Leu Gln Met Asn Ser Leu Arg Pro Glu Asp Thr Ala
                725                 730                 735

Val Tyr Tyr Cys Ala Ala Gly Leu Gln Tyr Asn Arg Ala Ala Asp Arg
            740                 745                 750

Val Pro Val Gly Ala Val Tyr Trp Gly Gln Gly Thr Leu Val Thr Val
        755                 760                 765

Ser Ser
    770

<210> SEQ ID NO 30
<211> LENGTH: 122
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Val Tyr Tyr Cys Asn
                85                  90                  95

Ala Glu Ile Leu Lys Arg Ala Tyr Ile Asp Val Tyr Val Asn Tyr Trp
            100                 105                 110

Gly Gln Gly Thr Leu Val Thr Val Ser Ser
        115                 120

<210> SEQ ID NO 31
<211> LENGTH: 436
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
    50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Pro Glu Asp Thr Ala Val Tyr Tyr Cys Asn
                 85                  90                  95

Ala Glu Ile Leu Lys Arg Ala Tyr Ile Asp Val Tyr Val Asn Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Ser Gly Gly Gly Ser Gly Gly Gly Gly
130                 135                 140

Gly Gly Ser Gly Gly Gly Ser Gly Gly Gly Ser Glu Val Gln Leu Leu
145                 150                 155                 160

Leu Leu Glu Ser Gly Gly Gly Leu Val Gln Pro Gly Gly Ser Leu Arg
                165                 170                 175

Leu Ser Cys Ala Ala Ser Gly Thr Phe Asp Lys Ile Asn Asn Met Gly
            180                 185                 190

Trp Tyr Arg Gln Ala Pro Gly Lys Gln Arg Asp Leu Val Ala Gln Ile
        195                 200                 205

Thr Pro Gly Gly Ile Thr Asp Tyr Ala Asp Ser Val Lys Gly Arg Phe
210                 215                 220

Thr Ile Ser Arg Asp Asn Ser Lys Asn Thr Leu Tyr Leu Gln Met Asn
225                 230                 235                 240

Ser Leu Arg Pro Glu Asp Thr Ala Val Tyr Tyr Cys Asn Ala Glu Ile
                245                 250                 255

Leu Lys Arg Ala Tyr Ile Asp Val Tyr Val Asn Tyr Trp Gly Gln Gly
            260                 265                 270

Thr Leu Val Thr Val Ser Ser Gly Gly Gly Gly Ser Gly Gly Gly Gly
        275                 280                 285

Ser Gly Gly Gly Gly Ser Gly Gly Gly Ser Gly Gly Gly Gly Gly Ser
290                 295                 300

Gly Gly Gly Ser Gly Gly Gly Ser Glu Val Gln Leu Leu Leu Leu Glu
305                 310                 315                 320

Ser Gly Gly Gly Leu Val Gln Pro Gly Gly Ser Leu Arg Leu Ser Cys
                325                 330                 335

Ala Ala Ser Gly Thr Phe Asp Lys Ile Asn Asn Met Gly Trp Tyr Arg
            340                 345                 350

Gln Ala Pro Gly Lys Gln Arg Asp Leu Val Ala Gln Ile Thr Pro Gly
        355                 360                 365

Gly Ile Thr Asp Tyr Ala Asp Ser Val Lys Gly Arg Phe Thr Ile Ser
370                 375                 380

Arg Asp Asn Ser Lys Asn Thr Leu Tyr Leu Gln Met Asn Ser Leu Arg
385                 390                 395                 400

Pro Glu Asp Thr Ala Val Tyr Tyr Cys Asn Ala Glu Ile Leu Lys Arg
                405                 410                 415

Ala Tyr Ile Asp Val Tyr Val Asn Tyr Trp Gly Gln Gly Thr Leu Val
            420                 425                 430

Thr Val Ser Ser
        435

<210> SEQ ID NO 32
<211> LENGTH: 593
<212> TYPE: PRT
<213> ORGANISM: Artificial Sequence
<220> FEATURE:
```

<223> OTHER INFORMATION: Description of Artificial Sequence: Synthetic recombinant polypeptide

<400> SEQUENCE: 32

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Thr | Phe | Asp | Lys | Ile | Asn |
| | | | 20 | | | | | 25 | | | | | 30 | | |

| Asn | Met | Gly | Trp | Tyr | Arg | Gln | Ala | Pro | Gly | Lys | Gln | Arg | Asp | Leu | Val |
| | | 35 | | | | | 40 | | | | | 45 | | | |

| Ala | Gln | Ile | Thr | Pro | Gly | Gly | Ile | Thr | Asp | Tyr | Ala | Asp | Ser | Val | Lys |
| | 50 | | | | | 55 | | | | | 60 | | | | |

| Gly | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |

| Gln | Met | Asn | Ser | Leu | Arg | Pro | Glu | Asp | Thr | Ala | Val | Tyr | Tyr | Cys | Asn |
| | | | | 85 | | | | | 90 | | | | | 95 | |

| Ala | Glu | Ile | Leu | Lys | Arg | Ala | Tyr | Ile | Asp | Val | Tyr | Val | Asn | Tyr | Trp |
| | | | 100 | | | | | 105 | | | | | 110 | | |

| Gly | Gln | Gly | Thr | Leu | Val | Thr | Val | Ser | Ser | Gly | Gly | Gly | Gly | Ser | Gly |
| | | 115 | | | | | 120 | | | | | 125 | | | |

| Gly | Gly | Gly | Ser | Gly | Gly | Gly | Gly | Ser | Gly | Gly | Gly | Ser | Gly | Gly |
| | 130 | | | | | 135 | | | | | 140 | | | | |

| Gly | Gly | Ser | Gly | Gly | Gly | Ser | Gly | Gly | Gly | Ser | Glu | Val | Gln |
| 145 | | | | | 150 | | | | | 155 | | | | | 160 |

| Leu | Leu | Glu | Ser | Gly | Gly | Gly | Leu | Val | Gln | Pro | Gly | Gly | Ser | Leu | Arg |
| | | | | 165 | | | | | 170 | | | | | 175 | |

| Leu | Ser | Cys | Ala | Ala | Ser | Gly | Thr | Phe | Asp | Lys | Ile | Asn | Asn | Met | Gly |
| | | | 180 | | | | | 185 | | | | | 190 | | |

| Trp | Tyr | Arg | Gln | Ala | Pro | Gly | Lys | Gln | Arg | Asp | Leu | Val | Ala | Gln | Ile |
| | | | 195 | | | | | 200 | | | | | 205 | | |

| Thr | Pro | Gly | Gly | Ile | Thr | Asp | Tyr | Ala | Asp | Ser | Val | Lys | Gly | Arg | Phe |
| | 210 | | | | | 215 | | | | | 220 | | | | |

| Thr | Ile | Ser | Arg | Asp | Asn | Ser | Lys | Asn | Thr | Leu | Tyr | Leu | Gln | Met | Asn |
| 225 | | | | | 230 | | | | | 235 | | | | | 240 |

| Ser | Leu | Arg | Pro | Glu | Asp | Thr | Ala | Val | Tyr | Tyr | Cys | Asn | Ala | Glu | Ile |
| | | | | 245 | | | | | 250 | | | | | 255 | |

| Leu | Lys | Arg | Ala | Tyr | Ile | Asp | Val | Tyr | Val | Asn | Tyr | Trp | Gly | Gln | Gly |
| | | | 260 | | | | | 265 | | | | | 270 | | |

| Thr | Leu | Val | Thr | Val | Ser | Ser | Gly | Gly | Gly | Ser | Gly | Gly | Gly | Gly |
| | | 275 | | | | | 280 | | | | | 285 | | | |

| Ser | Gly | Gly | Gly | Gly | Ser | Gly | Gly | Gly | Ser | Gly | Gly | Gly | Gly | Ser |
| | 290 | | | | | 295 | | | | | 300 | | | | |

| Gly | Gly | Gly | Gly | Ser | Gly | Gly | Gly | Ser | Glu | Val | Gln | Leu | Leu | Glu |
| 305 | | | | | 310 | | | | | 315 | | | | | 320 |

| Ser | Gly | Gly | Gly | Leu | Val | Gln | Pro | Gly | Gly | Ser | Leu | Arg | Leu | Ser | Cys |
| | | | | 325 | | | | | 330 | | | | | 335 | |

| Ala | Ala | Ser | Gly | Thr | Phe | Asp | Lys | Ile | Asn | Asn | Met | Gly | Trp | Tyr | Arg |
| | | | 340 | | | | | 345 | | | | | 350 | | |

| Gln | Ala | Pro | Gly | Lys | Gln | Arg | Asp | Leu | Val | Ala | Gln | Ile | Thr | Pro | Gly |
| | | | 355 | | | | | 360 | | | | | 365 | | |

| Gly | Ile | Thr | Asp | Tyr | Ala | Asp | Ser | Val | Lys | Gly | Arg | Phe | Thr | Ile | Ser |
| | | 370 | | | | | 375 | | | | | 380 | | | |

| Arg | Asp | Asn | Ser | Lys | Asn | Thr | Leu | Tyr | Leu | Gln | Met | Asn | Ser | Leu | Arg |
| 385 | | | | | 390 | | | | | 395 | | | | | 400 |

```
Pro Glu Asp Thr Ala Val Tyr Tyr Cys Asn Ala Glu Ile Leu Lys Arg
            405                 410                 415

Ala Tyr Ile Asp Val Tyr Val Asn Tyr Trp Gly Gln Gly Thr Leu Val
            420                 425                 430

Thr Val Ser Ser Gly Gly Gly Gly Ser Gly Gly Gly Gly Ser Gly Gly
            435                 440                 445

Gly Gly Ser Gly Gly Gly Gly Ser Gly Gly Gly Gly Ser Gly Gly Gly
450                 455                 460

Gly Ser Gly Gly Gly Gly Ser Glu Val Gln Leu Leu Glu Ser Gly Gly
465                 470                 475                 480

Gly Leu Val Gln Pro Gly Gly Ser Leu Arg Leu Ser Cys Ala Ala Ser
            485                 490                 495

Gly Thr Phe Asp Lys Ile Asn Asn Met Gly Trp Tyr Arg Gln Ala Pro
            500                 505                 510

Gly Lys Gln Arg Asp Leu Val Ala Gln Ile Thr Pro Gly Gly Ile Thr
            515                 520                 525

Asp Tyr Ala Asp Ser Val Lys Gly Arg Phe Thr Ile Ser Arg Asp Asn
            530                 535                 540

Ser Lys Asn Thr Leu Tyr Leu Gln Met Asn Ser Leu Arg Pro Glu Asp
545                 550                 555                 560

Thr Ala Val Tyr Tyr Cys Asn Ala Glu Ile Leu Lys Arg Ala Tyr Ile
            565                 570                 575

Asp Val Tyr Val Asn Tyr Trp Gly Gln Gly Thr Leu Val Thr Val Ser
            580                 585                 590

Ser
```

<210> SEQ ID NO 33
<211> LENGTH: 750
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
            35                  40                  45

Ala Gln Ile Thr Pro Gly Gly Ile Thr Asp Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Val Tyr Tyr Cys Asn
            85                  90                  95

Ala Glu Ile Leu Lys Arg Ala Tyr Ile Asp Val Tyr Val Asn Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Gly Gly Gly Gly Ser Gly Gly
        130                 135                 140

Gly Gly Ser Gly Gly Gly Gly Ser Gly Gly Gly Gly Ser Glu Val Gln
145                 150                 155                 160
```

```
Leu Leu Glu Ser Gly Gly Leu Val Gln Pro Gly Ser Leu Arg
            165                 170                 175

Leu Ser Cys Ala Ala Ser Gly Thr Phe Asp Lys Ile Asn Asn Met Gly
            180                 185                 190

Trp Tyr Arg Gln Ala Pro Gly Lys Gln Arg Asp Leu Val Ala Gln Ile
            195                 200                 205

Thr Pro Gly Gly Ile Thr Asp Tyr Ala Asp Ser Val Lys Gly Arg Phe
210                 215                 220

Thr Ile Ser Arg Asp Asn Ser Lys Asn Thr Leu Tyr Leu Gln Met Asn
225                 230                 235                 240

Ser Leu Arg Pro Glu Asp Thr Ala Val Tyr Tyr Cys Asn Ala Glu Ile
                245                 250                 255

Leu Lys Arg Ala Tyr Ile Asp Val Tyr Val Asn Tyr Trp Gly Gln Gly
                260                 265                 270

Thr Leu Val Thr Val Ser Ser Gly Gly Gly Gly Ser Gly Gly Gly Gly
            275                 280                 285

Ser Gly Gly Gly Gly Ser Gly Gly Gly Ser Gly Gly Gly Gly Ser
    290                 295                 300

Gly Gly Gly Gly Ser Gly Gly Gly Ser Glu Val Gln Leu Leu Glu
305                 310                 315                 320

Ser Gly Gly Gly Leu Val Gln Pro Gly Ser Leu Arg Leu Ser Cys
                325                 330                 335

Ala Ala Ser Gly Thr Phe Asp Lys Ile Asn Asn Met Gly Trp Tyr Arg
            340                 345                 350

Gln Ala Pro Gly Lys Gln Arg Asp Leu Val Ala Gln Ile Thr Pro Gly
            355                 360                 365

Gly Ile Thr Asp Tyr Ala Asp Ser Val Lys Gly Arg Phe Thr Ile Ser
            370                 375                 380

Arg Asp Asn Ser Lys Asn Thr Leu Tyr Leu Gln Met Asn Ser Leu Arg
385                 390                 395                 400

Pro Glu Asp Thr Ala Val Tyr Tyr Cys Asn Ala Glu Ile Leu Lys Arg
                405                 410                 415

Ala Tyr Ile Asp Val Tyr Val Asn Tyr Trp Gly Gln Gly Thr Leu Val
                420                 425                 430

Thr Val Ser Ser Gly Gly Gly Gly Ser Gly Gly Gly Gly Ser Gly Gly
            435                 440                 445

Gly Gly Ser Gly Gly Gly Gly Ser Gly Gly Gly Gly Ser Gly Gly Gly
    450                 455                 460

Gly Ser Gly Gly Gly Ser Glu Val Gln Leu Leu Glu Ser Gly Gly
465                 470                 475                 480

Gly Leu Val Gln Pro Gly Gly Ser Leu Arg Leu Ser Cys Ala Ala Ser
            485                 490                 495

Gly Thr Phe Asp Lys Ile Asn Asn Met Gly Trp Tyr Arg Gln Ala Pro
            500                 505                 510

Gly Lys Gln Arg Asp Leu Val Ala Gln Ile Thr Pro Gly Gly Ile Thr
            515                 520                 525

Asp Tyr Ala Asp Ser Val Lys Gly Arg Phe Thr Ile Ser Arg Asp Asn
530                 535                 540

Ser Lys Asn Thr Leu Tyr Leu Gln Met Asn Ser Leu Arg Pro Glu Asp
545                 550                 555                 560

Thr Ala Val Tyr Tyr Cys Asn Ala Glu Ile Leu Lys Arg Ala Tyr Ile
                565                 570                 575
```

Asp Val Tyr Val Asn Tyr Trp Gly Gln Gly Thr Leu Val Thr Val Ser
            580                 585                 590

Ser Gly Gly Gly Gly Ser Gly Gly Gly Ser Gly Gly Gly Gly Ser
    595                 600                 605

Gly Gly Gly Gly Ser Gly Gly Gly Ser Gly Gly Gly Ser Gly
610                 615                 620

Gly Gly Gly Ser Glu Val Gln Leu Leu Glu Ser Gly Gly Gly Leu Val
625                 630                 635                 640

Gln Pro Gly Gly Ser Leu Arg Leu Ser Cys Ala Ala Ser Gly Thr Phe
                645                 650                 655

Asp Lys Ile Asn Asn Met Gly Trp Tyr Arg Gln Ala Pro Gly Lys Gln
            660                 665                 670

Arg Asp Leu Val Ala Gln Ile Thr Pro Gly Gly Ile Thr Asp Tyr Ala
        675                 680                 685

Asp Ser Val Lys Gly Arg Phe Thr Ile Ser Arg Asp Asn Ser Lys Asn
    690                 695                 700

Thr Leu Tyr Leu Gln Met Asn Ser Leu Arg Pro Glu Asp Thr Ala Val
705                 710                 715                 720

Tyr Tyr Cys Asn Ala Glu Ile Leu Lys Arg Ala Tyr Ile Asp Val Tyr
                725                 730                 735

Val Asn Tyr Trp Gly Gln Gly Thr Leu Val Thr Val Ser Ser
            740                 745                 750

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 34

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 36

Glu Val Gln Leu Val Glu Ser Gly Gly Gly Ser Val Gln Ala Gly Asp

```
Ser Leu Arg Leu Ser Cys Ala Ala Ser Gly Arg Thr Phe Gly
            20                  25                  30
```

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 37

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Thr Phe Asp Lys
            20                  25                  30
```

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Phe Asp Lys
            20                  25                  30
```

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Asp Ser
            20                  25                  30
```

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 41
<211> LENGTH: 5
<212> TYPE: PRT
<213> ORGANISM: Artificial Sequence
<220> FEATURE:

```
<223> OTHER INFORMATION: Description of Artificial Sequence: Synthetic
      recombinant peptide

<400> SEQUENCE: 41

Asn Tyr Ala Met Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 42

Ser Ile Arg Val Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 43

Ile Asn Asn Met Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 44

Arg Tyr Trp Met Tyr
1               5

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 45

Trp Phe Arg Gln Ala Pro Gly Lys Glu Arg Glu Phe Val Ala
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 46

Trp Phe Arg Gln Ala Pro Gly Lys Gly Arg Glu Phe Val Ser
1               5                   10
```

```
<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 47

Trp Phe Arg Gln Thr Pro Gly Lys Glu Arg Glu Phe Val Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 48

Trp Tyr Arg Gln Ala Pro Gly Lys Gln Arg Asp Leu Val Ala
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 49

Trp Tyr Arg Gln Ala Pro Gly Lys Gln Arg Glu Leu Val Ala
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 50

Trp Val Arg Gln Ala Pro Gly Lys Gly Leu Glu Trp Val Ser
1               5                   10

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 51

Ala Leu Asn Trp Ser Gly Gly Ser Thr Tyr Tyr Val Asp Ser Val Lys
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      recombinant peptide
```

```
<400> SEQUENCE: 52

Ala Ile Asn Arg Asn Asp Gly Thr Thr Tyr Tyr Ala Asp Ser Val Lys
1               5                   10                  15
Gly

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 53

Gln Ile Thr Pro Gly Gly Ile Thr Asp Tyr Ala Asp Ser Val Lys Gly
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 54

Glu Ile Thr Pro Arg Gly Arg Thr Asn Tyr Ala Asp Ser Glu Lys Ser
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 55

Ala Ile Asn Ser Gly Gly Gly Asp Thr Tyr Tyr Arg Asp Ser Val Arg
1               5                   10                  15
Gly

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 56

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 57
```

```
Arg Phe Thr Ile Ser Arg Asp Asn Ser Lys Asn Thr Val Tyr Leu Gln
1               5                   10                  15

Met Asn Ser Leu Arg Pro Glu Asp Thr Ala Val Tyr Tyr Cys Ala Ala
            20                  25                  30
```

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 58

```
Arg Phe Thr Ile Ser Arg Asp Asn Ala Lys Asn Thr Val Tyr Met Gln
1               5                   10                  15

Met Ala Ser Leu Lys Pro Glu Asp Thr Ala Val Tyr Tyr Cys Ala Ala
            20                  25                  30
```

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 59

```
Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Val Tyr Tyr Cys Asn Ala
            20                  25                  30
```

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 60

```
Arg Phe Thr Ile Ser Arg Asp Asn Ala Lys Asp Thr Met Tyr Leu Gln
1               5                   10                  15

Met Asn Ser Leu Lys Pro Glu Asp Thr Ala Val Tyr Phe Cys Asn Ala
            20                  25                  30
```

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic recombinant polypeptide

<400> SEQUENCE: 61

```
Arg Phe Thr Ile Ser Arg Asp Asn Ala Lys Arg Thr Val Asn Leu Gln
1               5                   10                  15

Met Asn Ser Leu Lys Pro Glu Asp Thr Ala Val Tyr Tyr Cys Asn Ala
            20                  25                  30
```

<210> SEQ ID NO 62
<211> LENGTH: 32
<212> TYPE: PRT

```
<213> ORGANISM: Artificial Sequence
<220> FEATURE:
<223> OTHER INFORMATION: Description of Artificial Sequence: Synthetic
      recombinant polypeptide

<400> SEQUENCE: 62

Arg Phe Thr Ile Ser Arg Asp Asn Phe Lys Asn Thr Leu Tyr Leu Gln
1               5                   10                  15

Met Asn Ser Leu Lys Ser Glu Asp Thr Ala Val Tyr Tyr Cys Ala Lys
                20                  25                  30

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 63

Ala Gly Ser Phe Ser Leu Gly Gly Arg Pro Tyr Gly Asp Asp Tyr
1               5                   10                  15

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 64

Gly Leu Gln Tyr Asn Arg Ala Ala Asp Arg Val Pro Val Gly Ala Val
1               5                   10                  15

Tyr

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 65

Gly Leu Gln Tyr Asn Arg Ser Ala Asp Arg Val Pro Val Gly Ala Val
1               5                   10                  15

Tyr

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 66

Glu Ile Leu Lys Arg Ala Tyr Ile Asp Val Tyr Val Asn Tyr
1               5                   10

<210> SEQ ID NO 67
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      recombinant peptide

<400> SEQUENCE: 67

Glu Val Arg Glu Arg Gly Thr Ser Trp Tyr Arg Pro Asp Tyr
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 68

Ala Glu Gly Pro Pro Thr Phe Ser Leu Ile Arg Thr Met Thr Val Asp
1               5                   10                  15

Pro

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 69

Trp Gly Lys Gly Thr Leu Val Thr Val Ser Ser
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 70

Trp Gly Gln Gly Thr Leu Val Thr Val Ser Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 71

Trp Gly Gln Gly Thr Gln Val Thr Val Ser Ser
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 72

Gly Ala Gln Gly Thr Gln Val Thr Val Ser Ser
1               5                   10
```

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggctgagctg ggtggtcctg g                                           21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggctgagttt ggtggtcctg g                                           21

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggtacgtgct gttgaactgt tcc                                         23

<210> SEQ ID NO 76
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
catttgagtt ggcctagccg gccatggcag aggtgcaatt ggtggagtct ggggg       55

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgtaaaacga cggccagt                                               18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caggaaacag ctatgacc                                               18

<210> SEQ ID NO 79
<211> LENGTH: 88
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 79
tcagtaacct ggatcccccg ccaccgctgc ctccaccgcc gctaccccg ccaccgctgc      60 ctccaccgcc tgaggagacg gtgacctg                                        88

<210> SEQ ID NO 80
<211> LENGTH: 84
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 80
aggttactga ggatccggcg gtggaggcag cggaggtggg ggctctggtg gcggggtag      60 cgaggtgcag ctggtggagt ctgg                                            84

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 81

Gly Gly Gly Gly Ser
1               5

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 82

Gly Gly Gly Ser
1

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctgatcaccc aacaagacct ag                                              22

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gcctgagaga gaacagggag a                                                    21

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
caccatggaa caacggggac agaacgcc                                             28

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttaggacatg gcagagtctg cattaccttc                                           30

<210> SEQ ID NO 87
<211> LENGTH: 122
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
    50                  55                  60

Gly Arg Phe Thr Ile Ser Arg Asp Asn Ala Lys Asp Thr Met Tyr Leu
65                  70                  75                  80

Gln Met Asn Ser Leu Lys Pro Glu Asp Thr Ala Val Tyr Phe Cys Asn
                85                  90                  95

Ala Glu Ile Leu Lys Arg Ala Tyr Ile Asp Val Tyr Val Asn Tyr Trp
            100                 105                 110

Gly Gln Gly Thr Gln Val Thr Val Ser Ser
        115                 120

<210> SEQ ID NO 88
<211> LENGTH: 593
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Thr Phe Asp Lys Ile Asn
            20                  25                  30

Asn Met Gly Trp Tyr Arg Gln Ala Pro Gly Lys Gln Arg Asp Leu Val
        35                  40                  45

Ala Gln Ile Thr Pro Gly Gly Ile Thr Asp Tyr Ala Asp Ser Val Lys
50                  55                  60

Gly Arg Phe Thr Ile Ser Arg Asp Asn Ala Lys Asp Thr Met Tyr Leu
65                  70                  75                  80

Gln Met Asn Ser Leu Lys Pro Glu Asp Thr Ala Val Tyr Phe Cys Asn
                85                  90                  95

Ala Glu Ile Leu Lys Arg Ala Tyr Ile Asp Val Tyr Val Asn Tyr Trp
            100                 105                 110

Gly Gln Gly Thr Gln Val Thr Val Ser Ser Gly Gly Gly Gly Ser Gly
        115                 120                 125

Gly Gly Ser Gly Gly Gly Ser Gly Gly Gly Ser Gly Gly
130                 135                 140

Gly Gly Ser Gly Gly Gly Ser Gly Gly Gly Ser Glu Val Gln
145                 150                 155                 160

Leu Leu Glu Ser Gly Gly Leu Val Gln Pro Gly Ser Leu Arg
                165                 170                 175

Leu Ser Cys Ala Ala Ser Gly Thr Phe Asp Lys Ile Asn Asn Met Gly
            180                 185                 190

Trp Tyr Arg Gln Ala Pro Gly Lys Gln Arg Asp Leu Val Ala Gln Ile
        195                 200                 205

Thr Pro Gly Gly Ile Thr Asp Tyr Ala Asp Ser Val Lys Gly Arg Phe
    210                 215                 220

Thr Ile Ser Arg Asp Asn Ala Lys Asp Thr Met Tyr Leu Gln Met Asn
225                 230                 235                 240

Ser Leu Lys Pro Glu Asp Thr Ala Val Tyr Phe Cys Asn Ala Glu Ile
                245                 250                 255

Leu Lys Arg Ala Tyr Ile Asp Val Tyr Val Asn Tyr Trp Gly Gln Gly
            260                 265                 270

Thr Gln Val Thr Val Ser Ser Gly Gly Gly Ser Gly Gly Gly Gly
        275                 280                 285

Ser Gly Gly Gly Ser Gly Gly Gly Ser Gly Gly Gly Ser
290                 295                 300

Gly Gly Gly Ser Gly Gly Gly Ser Glu Val Gln Leu Val Glu
305                 310                 315                 320

Ser Gly Gly Gly Leu Val Gln Pro Gly Ser Leu Arg Leu Ser Cys
                325                 330                 335

Ala Ala Ser Gly Thr Phe Asp Lys Ile Asn Asn Met Gly Trp Tyr Arg
            340                 345                 350

Gln Ala Pro Gly Lys Gln Arg Asp Leu Val Ala Gln Ile Thr Pro Gly
        355                 360                 365

Gly Ile Thr Asp Tyr Ala Asp Ser Val Lys Gly Arg Phe Thr Ile Ser
    370                 375                 380

Arg Asp Asn Ala Lys Asp Thr Met Tyr Leu Gln Met Asn Ser Leu Lys
385                 390                 395                 400

Pro Glu Asp Thr Ala Val Tyr Phe Cys Asn Ala Glu Ile Leu Lys Arg
                405                 410                 415

Ala Tyr Ile Asp Val Tyr Val Asn Tyr Trp Gly Gln Gly Thr Gln Val
            420                 425                 430

-continued

```
Thr Val Ser Ser Gly Gly Gly Ser Gly Gly Gly Ser Gly Gly
            435                 440                 445
Gly Gly Ser Gly Gly Gly Ser Gly Gly Gly Ser Gly Gly Gly
450                 455                 460
Gly Ser Gly Gly Gly Ser Glu Val Gln Leu Leu Glu Ser Gly
465                 470                 475                 480
Gly Leu Val Gln Pro Gly Gly Ser Leu Arg Leu Ser Cys Ala Ala Ser
                485                 490                 495
Gly Thr Phe Asp Lys Ile Asn Asn Met Gly Trp Tyr Arg Gln Ala Pro
            500                 505                 510
Gly Lys Gln Arg Asp Leu Val Ala Gln Ile Thr Pro Gly Gly Ile Thr
            515                 520                 525
Asp Tyr Ala Asp Ser Val Lys Gly Arg Phe Thr Ile Ser Arg Asp Asn
            530                 535                 540
Ala Lys Asp Thr Met Tyr Leu Gln Met Asn Ser Leu Lys Pro Glu Asp
545                 550                 555                 560
Thr Ala Val Tyr Phe Cys Asn Ala Glu Ile Leu Lys Arg Ala Tyr Ile
                565                 570                 575
Asp Val Tyr Val Asn Tyr Trp Gly Gln Gly Thr Gln Val Thr Val Ser
            580                 585                 590
Ser
```

<210> SEQ ID NO 89
<211> LENGTH: 440
<212> TYPE: PRT
<213> ORGANISM: Homo sapiens

<400> SEQUENCE: 89

```
Met Glu Gln Arg Gly Gln Asn Ala Pro Ala Ala Ser Gly Ala Arg Lys
1               5                   10                  15
Arg His Gly Pro Gly Pro Arg Glu Ala Arg Gly Ala Arg Pro Gly Leu
            20                  25                  30
Arg Val Pro Lys Thr Leu Val Leu Val Val Ala Ala Val Leu Leu Leu
        35                  40                  45
Val Ser Ala Glu Ser Ala Leu Ile Thr Gln Gln Asp Leu Ala Pro Gln
    50                  55                  60
Gln Arg Val Ala Pro Gln Gln Lys Arg Ser Ser Pro Ser Glu Gly Leu
65                  70                  75                  80
Cys Pro Pro Gly His His Ile Ser Glu Asp Gly Arg Asp Cys Ile Ser
                85                  90                  95
Cys Lys Tyr Gly Gln Asp Tyr Ser Thr His Trp Asn Asp Leu Leu Phe
            100                 105                 110
Cys Leu Arg Cys Thr Arg Cys Asp Ser Gly Glu Val Glu Leu Ser Pro
        115                 120                 125
Cys Thr Thr Thr Arg Asn Thr Val Cys Gln Cys Glu Glu Gly Thr Phe
    130                 135                 140
Arg Glu Glu Asp Ser Pro Glu Met Cys Arg Lys Cys Arg Thr Gly Cys
145                 150                 155                 160
Pro Arg Gly Met Val Lys Val Gly Asp Cys Thr Pro Trp Ser Asp Ile
                165                 170                 175
Glu Cys Val His Lys Glu Ser Gly Thr Lys His Ser Gly Glu Ala Pro
            180                 185                 190
Ala Val Glu Glu Thr Val Thr Ser Ser Pro Gly Thr Pro Ala Ser Pro
        195                 200                 205
```

```
Cys Ser Leu Ser Gly Ile Ile Ile Gly Val Thr Val Ala Ala Val Val
        210                 215                 220
Leu Ile Val Ala Val Phe Val Cys Lys Ser Leu Leu Trp Lys Lys Val
225                 230                 235                 240
Leu Pro Tyr Leu Lys Gly Ile Cys Ser Gly Gly Gly Asp Pro Glu
                245                 250                 255
Arg Val Asp Arg Ser Ser Gln Arg Pro Gly Ala Glu Asp Asn Val Leu
                260                 265                 270
Asn Glu Ile Val Ser Ile Leu Gln Pro Thr Gln Val Pro Glu Gln Glu
                275                 280                 285
Met Glu Val Gln Glu Pro Ala Glu Pro Thr Gly Val Asn Met Leu Ser
        290                 295                 300
Pro Gly Glu Ser Glu His Leu Leu Glu Pro Ala Glu Ala Glu Arg Ser
305                 310                 315                 320
Gln Arg Arg Arg Leu Leu Val Pro Ala Asn Glu Gly Asp Pro Thr Glu
                325                 330                 335
Thr Leu Arg Gln Cys Phe Asp Asp Phe Ala Asp Leu Val Pro Phe Asp
                340                 345                 350
Ser Trp Glu Pro Leu Met Arg Lys Leu Gly Leu Met Asp Asn Glu Ile
                355                 360                 365
Lys Val Ala Lys Ala Glu Ala Ala Gly His Arg Asp Thr Leu Tyr Thr
370                 375                 380
Met Leu Ile Lys Trp Val Asn Lys Thr Gly Arg Asp Ala Ser Val His
385                 390                 395                 400
Thr Leu Leu Asp Ala Leu Glu Thr Leu Gly Glu Arg Leu Ala Lys Gln
                405                 410                 415
Lys Ile Glu Asp His Leu Leu Ser Ser Gly Lys Phe Met Tyr Leu Glu
                420                 425                 430
Gly Asn Ala Asp Ser Ala Met Ser
                435                 440

<210> SEQ ID NO 90
<211> LENGTH: 109
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 90

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Trp Gly Gln Gly Thr Leu Val Thr Val Ser Ser
                100                 105

<210> SEQ ID NO 91
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      tag peptide

<400> SEQUENCE: 91

Glu Gln Lys Leu Ile Ser Glu Glu Asp Leu Asn
1               5                   10

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 92

His His His His His His
1               5

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic
      tag peptide

<400> SEQUENCE: 93

Ala Ala Ala Glu Gln Lys Leu Ile Ser Glu Glu Asp Leu Asn Gly Ala
1               5                   10                  15

Ala His His His His His His
            20

<210> SEQ ID NO 94
<211> LENGTH: 23
<212> TYPE: PRT
<213> ORGANISM: Artificial Sequence
<220> FEATURE:
<223> OTHER INFORMATION: Description of Artificial Sequence: Synthetic
      tag peptide

<400> SEQUENCE: 94

Gly Ala Ala Glu Gln Lys Leu Ile Ser Glu Glu Asp Leu Asn Gly Ala
1               5                   10                  15

Ala His His His His His His
            20

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      tag peptide

<400> SEQUENCE: 95

Gly Gly Gly Cys
1

<210> SEQ ID NO 96
<211> LENGTH: 378
<212> TYPE: DNA
<213> ORGANISM: Artificial Sequence
```

<220> FEATURE:
<223> OTHER INFORMATION: Description of Artificial Sequence: Synthetic
      recombinant polynucleotide

<400> SEQUENCE: 96

| gaggtgcagc tgctggagtc tggcggcgga ctggtgcagc ctggcggctc cctgagactg | 60 |
| tcctgcgccg cctccggccg gaccttcggc tccatcagag tgggctggtt ccggcaggcc | 120 |
| cctggcaagg gccgggagtt cgtgtccgcc atcaaccgga acgacggcac cacctactac | 180 |
| gccgactccg tgaagggccg gttcaccatc tcccgggaca actccaagaa caccgtgtac | 240 |
| ctgcagatga actccctgcg gcccgaggac accgccgtgt actactgcgc cgctggcctg | 300 |
| cagtacaaca gagccgccga cagagtgcct gtgggcgctg tgtactgggg ccagggcacc | 360 |
| ctggtgaccg tgtcctct | 378 |

<210> SEQ ID NO 97
<211> LENGTH: 1827
<212> TYPE: DNA
<213> ORGANISM: Artificial Sequence
<220> FEATURE:
<223> OTHER INFORMATION: Description of Artificial Sequence: Synthetic
      recombinant polynucleotide

<400> SEQUENCE: 97

| gaggtgcagc tgctggagtc tggcggcgga ctggtgcagc ctggcggctc cctgagactg | 60 |
| tcctgcgccg cctccggccg gaccttcggc tccatcagag tgggctggtt ccggcaggcc | 120 |
| cctggcaagg gccgggagtt cgtgtccgcc atcaaccgga acgacggcac cacctactac | 180 |
| gccgactccg tgaagggccg gttcaccatc tcccgggaca actccaagaa caccgtgtac | 240 |
| ctgcagatga actccctgcg gcccgaggac accgccgtgt actactgcgc cgctggcctg | 300 |
| cagtacaaca gagccgccga cagagtgcct gtgggcgctg tgtactgggg ccagggcacc | 360 |
| ctggtgaccg tgtcctctgg cggcggagga tctggagggg gaggaagcgg cggaggagga | 420 |
| tctggcggcg gaggaagtgg gggcgaggg agtggcggag gtggaagtgg tggaggggc | 480 |
| agcgaggtgc agctgctgga gagcggcgga ggactggtgc agccaggcgg atctctgcgc | 540 |
| ctgagctgcg ccgccagcgg cagaaccttt ggcagcatcc gcgtgggatg gttcagacag | 600 |
| gctcccggaa agggacgcga gtttgtgtct gctatcaatc gcaatgatgg caccacatac | 660 |
| tatgctgata gcgtgaaggg aagattcacc atcagccgcg acaatagcaa gaatacagtg | 720 |
| tatctgcaga tgaatagcct gcgcccagag gatacagctg tgtattactg tgctgccgga | 780 |
| ctgcagtata accgggctgc cgatcgggtg cccgtgggag ccgtgtattg ggacagggga | 840 |
| acactggtga cagtgtcctc tggcggcgga ggatctgggg gtggcggatc tggcggcgga | 900 |
| ggaagcggtg gcgaggatc tggcggcgga ggaagcggag gggaggatc tggcggcgga | 960 |
| ggatctgagg tgcagctgct ggagtccggc ggaggactgg tgcagccagg cggcagcctg | 1020 |
| cggctgtctt gcgccgcttc tggcagaaca ttcggctcta ccgcgtggg ctggtttagg | 1080 |
| caggctccag gcaagggacg cgagttcgtg agcgctatca acagaaacga tggcacaacc | 1140 |
| tattatgctg attctgtgaa gggcaggttt acaatcagca gggataattc taagaatacc | 1200 |
| gtgtacctgc agatgaactc tctgaggcca gaggataccc tgtgtacta ttgcgctgcc | 1260 |
| ggcctgcagt ataatagggc cgctgaccgc gtgccagtgg gcgccgtgta ttggggccag | 1320 |
| ggcacccctgg tgacagtgtc ctctggcgga ggtggcagcg gcgtggcgg atctggcggc | 1380 |
| ggaggaagtg ggggcggagg atctggcggc ggaggaagcg gcggagggg atctggcggc | 1440 |

```
ggaggatctg aggtgcagct gctggagtct ggcggaggac tggtgcagcc tggcggaagc    1500
ctgagactga gctgtgctgc ttctggccgc accttcggaa gcatcagagt gggatggttt    1560
cgccaggctc caggaaaggg ccgggagttc gtctctgcta tcaatagaaa tgacggaaca    1620
acatattacg ccgacagcgt gaagggacgc tttacaatct ctagggataa cagcaagaac    1680
accgtgtatc tgcagatgaa cagcctgcgg cccgaggata ccgccgtgta ttattgtgcc    1740
gctggactgc agtacaatcg ggccgctgat agagtgcctg tgggagccgt gtactggggc    1800
cagggcacac tggtgacagt gtctagc                                       1827

<210> SEQ ID NO 98
<211> LENGTH: 366
<212> TYPE: DNA
<213> ORGANISM: Artificial Sequence
<220> FEATURE:
<223> OTHER INFORMATION: Description of Artificial Sequence: Synthetic
      recombinant polynucleotide

<400> SEQUENCE: 98
gaggtgcagc tgctggagtc tggcggcgga ctggtgcagc tggcggctc cctgagactg      60 tcctgcgccg cctccggcac cttcgacaag atcaacaaca tgggctggta caggcaggcc    120
cctggcaagc agagggacct ggtggcccag atcacccctg gcggcatcac cgactacgcc    180
gactccgtga agggccggtt caccatctcc cgggacaact ccaagaacac cctgtacctg    240
cagatgaact ccctgcggcc cgaggacacc gccgtgtact actgcaacgc cgagatcctg    300
aagcgggcct acatcgacgt gtacgtgaac tactggggcc agggcacccct ggtgaccgtg   360 tcctct                                                               366

<210> SEQ ID NO 99
<211> LENGTH: 1779
<212> TYPE: DNA
<213> ORGANISM: Artificial Sequence
<220> FEATURE:
<223> OTHER INFORMATION: Description of Artificial Sequence: Synthetic
      recombinant polynucleotide

<400> SEQUENCE: 99
gaggtgcagc tgctggagtc tggcggcgga ctggtgcagc tggcggctc cctgagactg      60 tcctgcgccg cctccggcac cttcgacaag atcaacaaca tgggctggta caggcaggcc    120
cctggcaagc agagggacct ggtggcccag atcacccctg gcggcatcac cgactacgcc    180
gactccgtga agggccggtt caccatctcc cgggacaact ccaagaacac cctgtacctg    240
cagatgaact ccctgcggcc cgaggacacc gccgtgtact actgcaacgc cgagatcctg    300
aagcgggcct acatcgacgt gtacgtgaac tactggggcc agggcacccct ggtgaccgtg   360 tcctctggcg gcggaggatc tggaggggga ggaagcggcg gaggaggatc tggcggcgga    420
ggaagtgggg gcggagggag tggcggaggt ggaagtggtg gaggggggcag cgaggtgcag   480 ctgctggaga gcggcggagg actggtgcag ccaggcggat ctctgcgcct gagctgcgcc    540
gccagcggca catttgataa gatcaataat atgggatggt atcgccaggc tccaggcaag    600
cagcgcgatc tggtggctca gatcacacca ggcggaatca cagattatgc cgatagcgtg    660
aagggaagat tcaccatcag ccgcgacaat agcaagaata cactgtatct gcagatgaat    720
agcctgcgcc cagaggatac agctgtgtat tactgtaatg ctgagatcct gaagcgcgct    780
tatatcgatg tgtatgtgaa ttattgggga cagggaacac tggtgacagt gtcctctggc    840
ggcggaggat ctgggggtgg cggatctggc ggcggaggaa gcggtggcgg aggatctggc    900
```

```
ggcggaggaa gcggaggggg aggatctggc ggcggaggat ctgaggtgca gctgctggag   960
tccggcggag gactggtgca gccaggcggc agcctgcggc tgtcttgcgc cgcttctggc  1020
accttcgata agatcaacaa tatgggatgg tacagacagg ctcccggaaa gcagcgggat  1080
ctggtggccc agatcacccc aggcggcatc acagattacg ctgattctgt gaagggcagg  1140
tttacaatca gcagggataa ttctaagaat accctgtacc tgcagatgaa ctctctgagg  1200
ccagaggata ccgctgtgta ctattgtaac gccgagatcc tgaagagggc ttacatcgat  1260
gtgtacgtga attattgggg ccagggcacc ctggtgacag tgtcctctgg cggaggtggc  1320
agcggcggtg gcggatctgg cggcggagga agtggggggcg gaggatctgg cggcggagga  1380
agcggcggag ggggatctgg cggcggagga tctgaggtgc agctgctgga gtctggcgga  1440
ggactggtgc agcctggcgg aagcctgaga ctgagctgtg ctgcttctgg caccttcgac  1500
aagatcaata atatgggctg gtatagacag gccccaggaa agcagaggga cctggtcgct  1560
cagatcacac ccgcggaat caccgactac gctgacagcg tgaagggacg ctttacaatc  1620
tctagggata acagcaagaa caccctgtat ctgcagatga acagcctgcg gcccgaggat  1680
accgccgtgt attattgcaa tgctgagatc ctgaagaggg cctatatcga cgtgtatgtg  1740
aattactggg gccagggcac actggtgaca gtgtcctct                         1779
```

```
<210> SEQ ID NO 100
<211> LENGTH: 188
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 100

Met Val Ser Ala Ile Val Leu Tyr Val Leu Leu Ala Ala Ala Ala His
1               5                  10                  15

Ser Ala Phe Ala Ala Asp Leu Gly Ser Leu Glu Val Leu Phe Gln Ala
            20                  25                  30

Leu Ile Thr Gln Gln Asp Leu Ala Pro Gln Gln Arg Ala Ala Pro Gln
        35                  40                  45

Gln Lys Arg Ser Ser Pro Ser Glu Gly Leu Cys Pro Pro Gly His His
    50                  55                  60

Ile Ser Glu Asp Gly Arg Asp Cys Ile Ser Cys Lys Tyr Gly Gln Asp
65                  70                  75                  80

Tyr Ser Thr His Trp Asn Asp Leu Leu Phe Cys Leu Arg Cys Thr Arg
                85                  90                  95

Cys Asp Ser Gly Glu Val Glu Leu Ser Pro Cys Thr Thr Thr Arg Asn
            100                 105                 110

Thr Val Cys Gln Cys Glu Glu Gly Thr Phe Arg Glu Glu Asp Ser Pro
        115                 120                 125

Glu Met Cys Arg Lys Cys Arg Thr Gly Cys Pro Arg Gly Met Val Lys
    130                 135                 140

Val Gly Asp Cys Thr Pro Trp Ser Asp Ile Glu Cys Val His Lys Glu
145                 150                 155                 160

Ser Ala Ala Ala Leu Glu Val Leu Phe Gln Gly Pro Ser Ser Gly Lys
                165                 170                 175

Leu Gly His His His His His His His His His
            180                 185
```

```
<210> SEQ ID NO 101
<211> LENGTH: 186
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 101

Met Val Ser Ala Ile Val Leu Tyr Val Leu Leu Ala Ala Ala Ala His
1               5                   10                  15

Ser Ala Phe Ala Ala Asp Leu Gly Ser Leu Glu Val Leu Phe Gln Gly
                20                  25                  30

Pro Ser Met Ala Leu Ala Pro Gln Gln Arg Ala Ala Pro Gln Gln Lys
            35                  40                  45

Arg Ser Ser Pro Ser Glu Gly Leu Cys Pro Pro Gly His His Ile Ser
    50                  55                  60

Glu Asp Gly Arg Asp Cys Ile Ser Cys Lys Tyr Gly Gln Asp Tyr Ser
65                  70                  75                  80

Thr His Trp Asn Asp Leu Leu Phe Cys Leu Arg Cys Thr Arg Cys Asp
                85                  90                  95

Ser Gly Glu Val Glu Leu Ser Pro Cys Thr Thr Thr Arg Asn Thr Val
            100                 105                 110

Cys Gln Cys Glu Glu Gly Thr Phe Arg Glu Glu Asp Ser Pro Glu Met
        115                 120                 125

Cys Arg Lys Cys Arg Thr Gly Cys Pro Arg Gly Met Val Lys Val Gly
    130                 135                 140

Asp Cys Thr Pro Trp Ser Asp Ile Glu Cys Val His Lys Glu Ser Ala
145                 150                 155                 160

Ala Ala Leu Glu Val Leu Phe Gln Gly Pro Ser Ser Gly Lys Leu Gly
                165                 170                 175

His His His His His His His His His His
            180                 185

<210> SEQ ID NO 102
<211> LENGTH: 166
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 102

Met Lys Lys Thr Ala Ile Ala Ile Ala Val Ala Leu Ala Gly Leu Ala
1               5                   10                  15

Thr Val Ala Gln Ala Glu Val Gln Leu Leu Glu Ser Gly Gly Gly Leu
                20                  25                  30

Val Gln Pro Gly Gly Ser Leu Arg Leu Ser Cys Ala Ala Ser Gly Thr
            35                  40                  45

Phe Asp Lys Ile Asn Asn Met Gly Trp Tyr Arg Gln Ala Pro Gly Lys
        50                  55                  60

Gln Arg Asp Leu Val Ala Gln Ile Thr Pro Gly Gly Ile Thr Asp Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Pro Glu Asp Thr Ala
            100                 105                 110

Val Tyr Tyr Cys Asn Ala Glu Ile Leu Lys Arg Ala Tyr Ile Asp Val
```

```
                      115                 120                 125
Tyr Val Asn Tyr Trp Gly Gln Gly Thr Leu Val Thr Val Ser Ser Ala
            130                 135                 140
Ala Ala Glu Gln Lys Leu Ile Ser Glu Glu Asp Leu Asn Gly Ala Ala
145                 150                 155                 160
His His His His His His
                165

<210> SEQ ID NO 103
<211> LENGTH: 153
<212> TYPE: PRT
<213> ORGANISM: Artificial Sequence
<220> FEATURE:
<223> OTHER INFORMATION: Description of Artificial Sequence: Synthetic
      recombinant polypeptide

<400> SEQUENCE: 103

Met Lys Lys Thr Ala Ile Ala Ile Ala Val Ala Leu Ala Gly Leu Ala
1               5                   10                  15

Thr Val Ala Gln Ala Glu Val Gln Leu Leu Glu Ser Gly Gly Gly Leu
            20                  25                  30

Val Gln Pro Gly Gly Ser Leu Arg Leu Ser Cys Ala Ala Ser Gly Arg
        35                  40                  45

Thr Phe Gly Ser Ile Arg Val Gly Trp Phe Arg Gln Ala Pro Gly Lys
    50                  55                  60

Gly Arg Glu Phe Val Ser Ala Ile Asn Arg Asn Asp Gly Thr Thr Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Pro Glu Asp Thr
            100                 105                 110

Ala Val Tyr Tyr Cys Ala Ala Gly Leu Gln Tyr Asn Arg Ala Ala Asp
        115                 120                 125

Arg Val Pro Val Gly Ala Val Tyr Trp Gly Gln Gly Thr Leu Val Thr
    130                 135                 140

Val Ser Ser His His His His His His
145                 150

<210> SEQ ID NO 104
<211> LENGTH: 4
<212> TYPE: PRT
<213> ORGANISM: Unknown
<220> FEATURE:
<223> OTHER INFORMATION: Description of Unknown: "GLEW" family peptide
      motif

<400> SEQUENCE: 104

Gly Leu Glu Trp
1

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 105

Gly Gly Gly Gly Ser Gly Gly Gly Ser Gly Gly Gly Gly Ser
1               5                   10                  15
```

```
<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 106

Gly Gly Gly Ser Ser Gly Gly Gly Ser Ser Gly Gly Gly Ser Ser
1               5                   10                  15

<210> SEQ ID NO 107
<211> LENGTH: 4
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 107

Ser Glu Gly Leu
1

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 108

Ile Ser Glu Asp Gly
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 109

Thr His Trp Asn Asp Leu Leu Phe
1               5

<210> SEQ ID NO 110
<211> LENGTH: 4
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 110

Gly Ser Ile Arg
1

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      recombinant peptide
```

```
<400> SEQUENCE: 111

Gly Leu Gln Tyr Asn Arg Ala Ala
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 112

His Ile Ser Glu Asp
1               5

<210> SEQ ID NO 113
<211> LENGTH: 4
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 113

Gln Arg Asp Leu
1

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      recombinant peptide

<400> SEQUENCE: 114

Gln Ile Thr Pro Gly Gly Ile Thr Asp
1               5
```

BIOLOGIC COMPOUNDS DIRECTED AGAINST DEATH RECEPTOR 5

SEQUENCE LISTING

The instant application contains a Sequence Listing which has been submitted electronically in ASCII format and is hereby incorporated by reference in its entirety. Said ASCII copy, created on Nov. 18, 2013, is named PAT054056-US-NP_SL.txt and is 172,423 bytes in size.

BACKGROUND

The tumor necrosis factor (TNF)-related apoptosis-inducing ligand (TRAIL) induces apoptosis in a variety of tumorigenic and transformed cell lines with little or no effect on normal cells. At least five receptors for TRAIL have been identified, of which two, namely DR4 (Death Receptor 4, TRAIL-R1) and DR5 (Death Receptor 5, TRAIL-R2; KILLER or TRICK 2), are capable of transducing an apoptosis signal, whereas the other three (TRAIL-R3, TRAIL-R4 and soluble OPG) serve as decoy receptors to block TRAIL-mediated apoptosis. See e.g., Ozoren and El-Deiry, Sem. Cancer Biol 13: 135 (2003); Yagita et al., Cancer Sci., 95(10): 777 (2004).

TRAIL or Apo2L is a 281 amino-acid cytotoxic ligand found integrated into the cytoplasmic membrane with the C-terminus exposed at the extracellular surface (Type II ligand) of cells. Small quantities of soluble TRAIL ligand can also be detected. TRAIL forms a homo-trimeric molecule that binds its respective receptors, initiating a cascade of signaling events.

The binding of TRAIL ligand to the receptors DR4 or DR5 initiates the extrinsic cell death pathway, resulting in the formation of death-inducing signaling complexes (DISC), which contain the adaptor FADD (Fas-activating DD) and pro-caspase 8 or pro-caspase 10. The interactions at the DISC and the activation of the downstream cascade are similar to FAS, resulting in activation of the NFκB and Jun N-terminal kinase pathways (JNK). See, e.g., Mongkolsapaya et al., Nat. Struct. Biol., 6(11): 1048 (1999); Cha et al., J. Biol. Chem., 275(40): 31171 (2000). TRAIL binding to DR4 or DR5 also results in a BID cleavage (by caspase 8 or 10), activation of mitochondria and hence activation of the intrinsic apoptosis pathway.

The ability of TRAIL ligand to preferentially induce apoptosis of tumor cells, with little or no effect on normal cells, makes it a potentially good candidate for cancer therapy. However, soluble TRAIL has been shown to induce apoptosis of normal human hepatocytes in vitro, highlighting potentially toxicity concerns. See, e.g., Jo et al., Nat Med. 6(5): 564 (2000). A more advantageous target for cancer therapy is DR5. Because DR5 requires multiple receptors to induce apoptosis of normal hepatocytes, the development of agonists against the specific DR5 responsible for induction of apoptosis is predicted to avoid this toxicity against normal cells, while retaining the ability to kill tumor cells.

Peptide and antibody agonists of DR5 have been used to induce apoptosis in cells expressing DR5. See, e.g., Li et al., J. Mol. Biol., 361, 522-536 (2006); Kajiwara et al., Biochim. Biophys. Acta 1699: 131-137 (2004); Yang et al., Cancer Cell, 5, 501-512 (2004). Agonists of DR5 have the potential to be used in cancer therapy against a wide range of cancers. For example, Lexatumumab, a monoclonal antibody against DR5, induces expression of DR5 and promotes apoptosis in a mouse model of renal cell carcinoma. Zhang et al., Cancer Lett. 251(1): 146-57 (2007). Other agonistic monoclonal antibodies against DR5, or single-chain Fv fragment against DR5, and the tumoricidal activity thereof are similarly described, e.g., in Takeda et al., Journal Exp. Medicine, 199, 437-448 (2004); Guo et al., J. Biol. Chem., 280, 41940-41952 (2005); Motoki et al., Clin. Cancer Res 11(8): 3126-35 (2005); and Ichikawa et al., Nature Medicine, 7, 954-960 (2001), Chuntharapai et al., J. Immunol. 166(8): 4891-8 (2001), Shi et al., Cancer Res., 66(24): 11946-11953 (2006).

Various DR5 specific antibodies are being developed for use in the clinic but none are yet approved. It is believed that for DR5 to be activated, multiple cross-linking antibodies are required, and issues remain for sufficient delivery of these antibodies at the site of action to achieve reproducible therapeutic effects. Therefore, a need exists for improved DR5 specific agonists for treatment of associated diseases.

SUMMARY OF THE INVENTION

The present invention relates to one or more "NB agents" comprising amino acid sequences that are directed against Death Receptor 5 (herein referred to as "DR5") as provided herein, as well as to specific compounds or constructs, and in particular proteins and polypeptides, that comprise or essentially consist of one or more such amino acid sequences (also referred to as "compounds", and "polypeptides", respectively) and fragments thereof, plus the nucleic acids that encode such constructs. Monomeric and multimeric variants of the inventive DR5 specific constructs are provided herein. Humanized and humaneered variants of the NB agents are provided. In one embodiment, pharmaceutically relevant NB agents of the invention act as agonists of the TRAIL receptors DR5.

The invention also relates to nucleic acids encoding such amino acid sequences and polypeptides; methods for preparing such amino acid sequences and polypeptides; host cells expressing or capable of expressing such amino acid sequences or polypeptides; compositions, and in particular to pharmaceutical compositions, that comprise such amino acid sequences, polypeptides, nucleic acids and/or host cells; and uses of such amino acid sequences or polypeptides, nucleic acids, host cells and/or compositions, in particular for prophylactic, therapeutic or diagnostic purposes, such as the purposes mentioned herein.

Agonists of the TRAIL receptors DR5 described herein as NB agents have the potential to be used in therapy against a wide range of diseases associated with DR5. These inventive NB agents therefore have utility in the treatment of proliferative diseases including, e.g., cancers such as solid tumors, primary and metastatic cancers such as renal cell carcinoma, and cancers of the lung (e.g., small cell lung cancer "SCLC" and non-small cell lung cancer "NSCLC"), pancreas, hematopoietic malignancy, glioma, astrocytoma, mesothelioma, colorectal cancers, prostate cancer, osteosarcoma, melanoma, lymphoma (including but not limited to Burkitt's Lymphoma), breast cancer, endometrial cancer, liver cancer, gastric cancer, skin cancer, ovarian cancer and squamous cell cancers of any origin (e.g., lung, head and neck, breast, thyroid, cervix, skin, esophageal, etc.), as well as liquid cancers, e.g., such as leukemias (see, e.g., Uno et al., Nature Medicine, 12(6): 693-698 (2006)) including especially a T-cell leukemia such as acute T-cell leukemia (T-ALL), acute B-cell leukemia (B-ALL), chronic myelogenous leukemia (CML), acute myelogenous leukemia (AML), plasma cell myeloma and multiple myeloma (MM). These inventive NB agents also have utility in the treatment of non-cancer indications include inflammatory and autoimmune disease, such as systemic lupus erythematosus, Hashimoto's disease, rheumatoid arthritis, graft-versus-host disease, Sjogren's syndrome, pernicious anemia, Addison disease, scleroderma, Goodpasture's syndrome, Crohn's disease, autoimmune hemolytic anemia; sterility, myasthenia gravis, multiple sclerosis, Basedow's disease; thrombotic throbocytopenia, thrombopenia purpurea, insulin-dependent diabetes mellitus, allergy; asthma; atopic disease; arteriosclerosis; myocarditis; cardiomyopathy; globerula nephritis; and hypoplastic anemia.

The amino acid sequences and polypeptides described herein may be directed against, or be specific to, any DR5. According to one non-limiting aspect, amino acid sequences and polypeptides described herein are directed against DR5. In one embodiment, the NB agents specifically bind to a DR5 extracellular domain.

The polypeptides and compositions of the present invention can generally be used to modulate DR5. In one embodiment, an NB agent will trigger, activate and/or increase or enhance the signaling that is mediated by DR5. In one embodiment, agonism of DR5 by an NB agent will modulate, and in particular trigger or increase the biological mechanisms, responses and effects associated with DR5, their signaling and/or the pathways in which DR5 is involved.

In one embodiment, the compounds, polypeptides and compositions described herein induce, trigger, increase or enhance apoptosis in certain cells or tissues. In one embodiment, the compounds, polypeptides and compositions described herein are capable of binding to DR5 on a cell surface, and in particular of binding to a DR5 in such a way that the signaling mediated by the DR5 is induced, triggered, increased or enhanced. In one embodiment, the polypeptides and compositions described herein may be such that they are capable of binding to a DR5 in such a way that apoptosis is triggered or induced in the cell on which the DR5 is present.

In one embodiment, the NB compounds, (monovalent or multivalent) polypeptides and compositions described herein can bind to the binding site of TRAIL on the DR5. In one embodiment, the NB agents compete with TRAIL for binding to the DR5. In one embodiment, the binding of such compounds and polypeptides to DR5 induces, triggers, increases or enhances the signaling mediated by the DR5, and in particular triggers or induces apoptosis in the cell on which the DR5 is present.

Other aspects, embodiments, advantages and applications of the invention will become clear from the further description herein.

BRIEF DESCRIPTION OF THE FIGURES

(FIG. 6B) 4E6 and 11H6 tetramers and pentamers in Colo205 cells; and (FIG. 6C) 4E6 and 11H6 tetramers and pentamers in H226 cells.

DETAILED DESCRIPTION OF THE INVENTION

Figure 1:
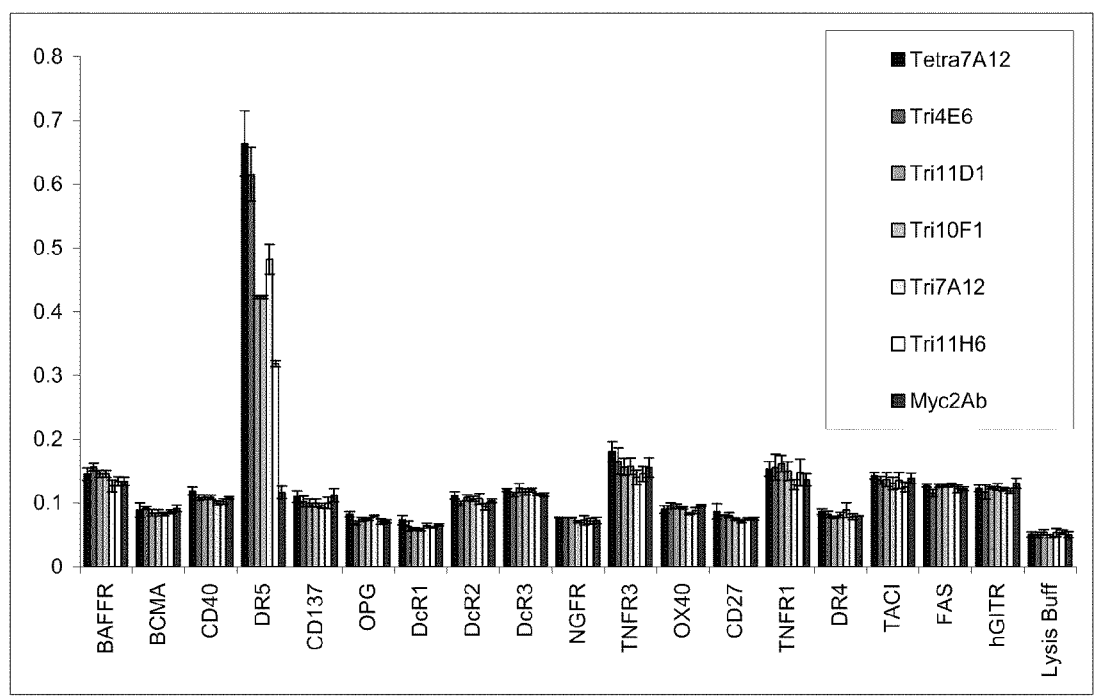
FIG. 1 is a graphic representation of an ELISA experiment showing the binding of multivalent anti-DR5 NB agents against TNF Receptor family members.

The NB agents described herein, namely the compounds, polypeptides (monovalent or multivalent) and compositions, bind to Death Receptor 5 ("DR5"). In one embodiment, the binding of the disclosed compounds and polypeptides to the DR5 induces, triggers, increases or enhances the signaling mediated by the DR5, and in particular triggers or induces apoptosis in the cell on which the DR5 is present.

As used herein a "NB agent" of the invention is defined as a polypeptide containing at least one CDR3 sequence that specifically bind to a DR5 polypeptide and whose binding produces an agonistic effect on DR5 activity, or a nucleotide that encodes such a polypeptide. In one embodiment, NB agents of the invention are a polypeptide having the general structure of a $V_H$ domain. In one embodiment, NB agents of the invention are a polypeptide having the general structure of a $V_{HH}$ domain. In one embodiment, NB agents of the invention are a polypeptide having the general structure of a $V_L$ domain. In one embodiment, NB agents of the invention contain at least one CDR1 and at least one CDR2 sequence in addition to the CDR3 sequence. In one embodiment, NB agents of the invention comprise at least one monovalent polypeptide having the FR1-CDR1-FR2-CDR2-FR3-CDR3-FR4 construction as defined below for Formula 1. In one embodiment, NB agents of the invention are monomeric compositions. In one embodiment, NB agents are multimeric compositions. In one embodiment, NB agents of the invention are monovalent compositions. In one embodiment, NB agents are multivalent compositions. In one embodiment, the framework regions contain residues that are sequence optimized for use in humans. Other aspects of NB agents of the invention are described below.

Whereas the term "NB agent" is used as a general term that is meant to encompass the full scope of the compositions of the invention, the terms "NB sequence" or alternatively "NB construct" are used herein to refer to the specific polypeptide variants disclosed herein as SEQ ID NOS: 1-72, 87-88 and 102-103 and the nucleotides that encode them, including those specifically disclosed herein as SEQ ID NOS: 96-99 and those sequences that encode the same polypeptide sequences as SEQ ID NOs: 96-99 but differ by the degenerate code.

NB Agents of the Invention

In one embodiment, the NB agent is selected from the group of 11D1, 11H6, 10F1, 7A12, and 4E6, or a variant thereof. In one embodiment, the NB agent is a variant whose sequence is optimized for use in humans, e.g., is humanized. In one embodiment humanized NB agents include without limitation the group of 4E6hu and 11H6hu. In one embodiment, the NB agent is a monomeric variant of the listed group, or a variant thereof. In one embodiment, the NB agent is a multimeric variant of the listed group, or a variant thereof. In one embodiment, the multimeric variant of the listed group is monospecific, or a variant thereof. In one embodiment, the multimeric variant of the listed group is multispecific, or a variant thereof. In one embodiment, the multiple epitopes recognized by a multispecific NB agent are various epitopes of the DR5 target, or a variant thereof. In one embodiment, the multiple epitopes recognized by a multispecific NB agent is at least one epitope of the DR5 target and at least one epitope on a target other than the DR5 polypeptide, or a variant thereof.

In one embodiment, the NB agent is selected from one or more of SEQ ID NOs: 1-22, 26-40, 87-88, and 102-103, or SEQ ID NOs: 96-99, or a variant thereof. Specific embodiments of NB agents 11D1, 11H6, 10F1, 7A12, and 4E6, or variants thereof, are as provided below and in Tables 1-4.

Exemplary NB agents of the invention include the following NB polypeptide constructs and variants thereof.

4E6 Family

In one embodiment, the NB agent is 4E6, or a variant thereof. In one embodiment, the 4E6 construct is the monomer of SEQ ID NO: 1, or a variant thereof. In one embodiment, the 4E6 construct is the monomer of SEQ ID NO: 26, or a variant thereof. In one embodiment, the 4E6 construct is a multimer comprising two or more monomers of SEQ ID NO: 1 that are operably linked, or a variant thereof. In one embodiment, the 4E6 construct is a multimer comprising two or more monomers of SEQ ID NO: 26 that are operably linked, or a variant thereof. In one embodiment, the 4E6 construct is a multimer comprising two or more monomers of both SEQ ID NO: 1 and of SEQ ID NO: 26 that are operably linked, or a variant thereof, wherein the monomers may be in any order.

In one embodiment, the 4E6 multimeric construct is a trimer, a tetramer or a pentamer of SEQ ID NO: 1, or a variant thereof. In one embodiment, the 4E6 multimeric construct is a trimer, a tetramer or a pentamer of SEQ ID NO: 26, or a variant thereof. In one embodiment, the 4E6 multimeric construct is a trimer, a tetramer or a pentamer of a combination of both SEQ ID NO: 1 and of SEQ ID NO: 26, or a variant thereof, wherein the monomers may be in any order. In one embodiment, the 4E6 construct is the multimer as provided in any one or more of SEQ ID NOs: 6-8 and 27-29, or a variant thereof. Higher order multimers, such as multimers comprised of 6-10 subunits, are also contemplated.

In one embodiment, the 4E6 construct comprises SEQ ID NO: 64, or a variant thereof. In one embodiment, the 4E6 construct comprises SEQ ID NO: 65, or a variant thereof. In one embodiment, the 4E6 construct comprises a CDR1 sequence of SEQ ID NO: 42, a CDR2 sequence of SEQ ID NO: 52 and a CDR3 sequence of any one or more of SEQ ID NO: 64 and/or SEQ ID NO: 65, or a variant thereof. In one embodiment, the 4E6 construct is a humanized or humaneered sequence, or a variant thereof. In one embodiment, the 4E6 construct is as provided in SEQ ID NO: 28, or a variant thereof. In one embodiment, the 4E6 construct is as provided in SEQ ID NO: 29, or a variant thereof.

In one embodiment, the 4E6 construct comprises SEQ ID NOs: 35, 42, 46, 52, 57, 64 and 70, respectively, or a variant thereof. In one embodiment, the 4E6 construct comprises SEQ ID NOs: 36, 42, 47, 52, 58, 65 and 71, respectively, or a variant thereof.

In one embodiment, the NB construct is a nucleic acid that encodes the 4E6 polypeptide of SEQ ID NO: 1 or variants, multimers or fragments thereof. In one embodiment, the NB construct is a nucleic acid that encodes the 4E6Hu polypeptide of SEQ ID NO: 26 or variants, multimers or fragments thereof. In one embodiment, the NB construct is a nucleic acid that encodes one or more of the CDR regions of the 4E6Hu polypeptide, namely SEQ ID NO: 42, 52 and 64, or variants thereof. In one embodiment, the NB construct is a nucleic acid that encodes one or more of the CDR regions of the 4E6 polypeptide, namely SEQ ID NO: 42, 52 and 65, or variants thereof. In one embodiment, the NB construct is a nucleic acid that encodes the CDR3 region of SEQ ID NO: 64 or variants thereof. In one embodiment, the NB construct is a nucleic acid that encodes the CDR3 region of SEQ ID NO: 65 or variants thereof.

7A12 Family

In one embodiment, the NB agent is 7A12, or a variant thereof. In one embodiment, the 7A12 construct is the monomer of SEQ ID NO: 2, or a variant thereof. In one embodiment, the 7A12 construct is a multimer comprising two or more monomers of SEQ ID NO: 2 that are operably linked, or a variant thereof. In one embodiment, the 7A12 multimeric construct is a trimer, a tetramer or a pentamer of SEQ ID NO: 2, or a variant thereof. In one embodiment, the 7A12 construct is the multimer as provided in any one or more of SEQ ID NOs: 9-11, or a variant thereof. In one embodiment, the 7A12 construct comprises SEQ ID NO: 63. In one embodiment, the 7A12 construct comprises a CDR1 sequence of SEQ ID NO: 41, a CDR2 sequence of SEQ ID NO: 51 and a CDR3 sequence of SEQ ID NO: 63, or a variant thereof. In one embodiment, the 7A12 construct is a humanized or humaneered sequence, or a variant thereof. In one embodiment, the 7A12 construct is as provided in SEQ ID NO: 10, or a variant thereof. In one embodiment, the 7A12 construct is as provided in SEQ ID NO: 11, or a variant thereof. In one embodiment, the 7A12 construct comprises SEQ ID NOs: 34, 41, 45, 51, 56, 63 and 69, respectively, or a variant thereof. Higher order multimers, such as multimers comprised of 6-10 subunits, are also contemplated.

In one embodiment, the NB construct is a nucleic acid that encodes the 7A12 polypeptide of SEQ ID NO: 2 or variants, multimers or fragments thereof. In one embodiment, the NB construct is a nucleic acid that encodes one or more of the CDR regions of SEQ ID NO: 41, 51 and 63, or variants thereof. In one embodiment, the NB construct is a nucleic acid that encodes the CDR3 region of SEQ ID NO: 63 or variants thereof.

10F1 Family

In one embodiment, the NB agent is 10F1, or a variant thereof. In one embodiment, the 10F1 construct is the monomer of SEQ ID NO: 3, or a variant thereof. In one embodiment, the 10F1 construct is a multimer comprising two or more monomers of SEQ ID NO: 3 that are operably linked, or a variant thereof. In one embodiment, the 10F1 multimeric construct is a trimer, a tetramer or a pentamer of SEQ ID NO: 3, or a variant thereof. In one embodiment, the 10F1 construct is the multimer as provided in any one or more of SEQ ID NOs: 12-16, or a variant thereof. In one embodiment, the 10F1 construct comprises SEQ ID NO: 68, or a variant thereof. In one embodiment, the 10F1 construct comprises a CDR1 sequence of SEQ ID NO: 44, a CDR2 sequence of SEQ ID NO: 55 and a CDR3 sequence of SEQ ID NO: 68, or a variant thereof. In one embodiment, the 10F1 construct is a humanized or humaneered sequence, or a variant thereof. In one embodiment, the 10F1 construct comprises SEQ ID NO: 15, or a variant thereof. In one embodiment, the 10F1 construct comprises SEQ ID NO: 16, or a variant thereof. In one embodiment, the 10F1 construct comprises SEQ ID NOs: 40, 44, 50, 55, 62, 68 and 72, respectively, or a variant thereof. Higher order multimers, such as multimers comprised of 6-10 subunits, are also contemplated.

In one embodiment, the NB construct is a nucleic acid that encodes the 10F1 polypeptide of SEQ ID NO: 3 or variants, multimers or fragments thereof. In one embodiment, the NB construct is a nucleic acid that encodes one or more of the CDR regions of SEQ ID NO: 44, 55 and 68, or variants thereof. In one embodiment, the NB construct is a nucleic acid that encodes the CDR3 region of SEQ ID NO: 68 or variants thereof.

11D1 Family

In one embodiment, the NB agent is 11D1, or a variant thereof. In one embodiment, the 11D1 construct is the monomer of SEQ ID NO: 4, or a variant thereof. In one embodiment, the 11D1 construct is a multimer comprising two or more monomers of SEQ ID NO: 4 that are operably linked, or a variant thereof. In one embodiment, the 11D1 multimeric construct is a trimer, a tetramer or a pentamer of SEQ ID NO: 4, or a variant thereof. In one embodiment, the 11D1 construct is the multimer as provided in any one or more of SEQ ID NOs: 17-19, or a variant thereof. In one embodiment, the 11D1 construct comprises SEQ ID NO: 67, or a variant thereof. In one embodiment, the 11D1 construct comprises a CDR1 sequence of SEQ ID NO: 43, a CDR2 sequence of SEQ ID NO: 54 and a CDR3 sequence of SEQ ID NO: 67, or a variant thereof. In one embodiment, the 11D1 construct is a humanized or humaneered sequence, or a variant thereof. In one embodiment, the 11D1 construct comprises SEQ ID NO: 18, or a variant thereof. In one embodiment, the 11D1 construct comprises SEQ ID NO: 19, or a variant thereof. In one embodiment, the 11D1 construct comprises SEQ ID NOs: 39, 43, 49, 54, 61, 67 and 71, respectively, or a variant thereof. Higher order multimers, such as multimers comprised of 6-10 subunits, are also contemplated.

In one embodiment, the NB construct is a nucleic acid that encodes the 11D1 polypeptide of SEQ ID NO: 4 or variants, multimers or fragments thereof. In one embodiment, the NB construct is a nucleic acid that encodes one or more of the CDR regions of SEQ ID NO: 43, 54 and 67, or variants thereof. In one embodiment, the NB construct is a nucleic acid that encodes the CDR3 region of SEQ ID NO: 67 or variants thereof.

11H6 Family

In one embodiment, the NB agent is 11H6, or a variant thereof. In one embodiment, the 11H6 construct is the monomer of SEQ ID NO: 5, or a variant thereof. In one embodiment, the 11H6 construct is the monomer of SEQ ID NO: 30, or a variant thereof. In one embodiment, the 11H6 construct is a multimer comprising two or more monomers of SEQ ID NO: 5 that are operably linked, or a variant thereof. In one embodiment, the 11H6 construct is a multimer comprising two or more monomers of SEQ ID NO: 30 that are operably linked, or a variant thereof. In one embodiment, the 11H6 construct is a multimer comprising two or more monomers of both SEQ ID NO: 5 and of SEQ ID NO: 30 that are operably linked, or a variant thereof (e.g., SEQ ID NO: 88), wherein the monomers may be in any order. Higher order multimers, such as multimers comprised of 6-10 subunits, are also contemplated.

In one embodiment, the 11H6 multimeric construct is a trimer, a tetramer or a pentamer of SEQ ID NO: 5, or a variant thereof. In one embodiment, the 11H6 multimeric construct is a trimer, a tetramer or a pentamer of SEQ ID NO: 30, or a variant thereof. In one embodiment, the 11H6 multimeric construct is a trimer, a tetramer or a pentamer of a combination of both SEQ ID NO: 5 and of SEQ ID NO: 30, or a variant thereof, wherein the monomers may be in any order. In one embodiment, the 11H6 construct is the multimer as provided in any one or more of SEQ ID NOs: 20-22 and 31-33, or a variant thereof.

In one embodiment, the 11H6 construct comprises SEQ ID NO: 66 or 83, or a variant thereof. In one embodiment, the 11H6 construct comprises a CDR1 sequence of SEQ ID NO: 43, a CDR2 sequence of SEQ ID NO: 53 and a CDR3 sequence of any one or more of SEQ ID NO: 66, or a variant thereof. In one embodiment, the 11H6 construct is a humanized or humaneered sequence, or a variant thereof. In one embodiment, the 11H6 construct is as provided in SEQ ID NO: 31, or a variant thereof. In one embodiment, the 11H6 construct is as provided in SEQ ID NO: 32, or a variant thereof. In one embodiment, the 11H6 construct is as provided in SEQ ID NO: 33, or a variant thereof. In one embodiment, the 11H6 construct comprises SEQ ID NOs: 37, 43, 48, 53, 59, 66 and 70, respectively, or a variant thereof. In one embodiment, the 11H6 construct comprises SEQ ID NOs: 38, 43, 48, 53, 60, 66 and 71, respectively, or a variant thereof.

In one embodiment, the NB construct is a nucleic acid that encodes the 11H6 polypeptide of SEQ ID NO: 5 or variants, multimers or fragments thereof. In one embodiment, the NB construct is a nucleic acid that encodes the 11H6Hu polypeptide of SEQ ID NO: 30 or variants, multimers or fragments thereof. In one embodiment, the NB construct is a nucleic acid that encodes one or more of the CDR regions of SEQ ID NO: 43, 53 and 66, or variants thereof. In one embodiment, the NB construct is a nucleic acid that encodes the CDR3 region of SEQ ID NO: 66 or variants thereof.

Other Contemplated Variants of NB Agents

In one embodiment, a NB agent of the invention is a multimeric construct comprising at least two different subunits selected from the group of 11D1, 11H6, 10F1, 7A12, and 4E6, or a variant thereof. In one such embodiment, the particular order of the multimeric constructs comprises alternating subunits. An exemplary construct is provided in SEQ ID NO: 84. Other arrangements of the subunits within a multimeric NB construct are contemplated. A skilled person will generally be able to determine and select suitable substitutions, deletions or insertions, or suitable combinations of thereof, based on the disclosure herein and optionally after a limited degree of routine experimentation, which may e.g., involve introducing a limited number of possible substitutions and determining their influence on the properties of the NB constructs thus obtained.

In addition to the disclosed exemplary NB polypeptides constructs provided herein, the invention encompasses nucleotides that encode any NB agent encompassed within the present invention disclosure, including without limitation: DNA and RNA sequences or variants thereof, in isolation or in recombinant vectors or the like, and/or as coding regions or fragments including especially fragments encoding the CDR3 region of the disclosed NB constructs. In one embodiment, the NB agent is a nucleic acid that encodes the NB construct of any one of the sequences provided in Tables 1-4. In one embodiment, the NB agent is a nucleic acid that encodes the 4E6 construct of any one of SEQ ID NOS: 1-5, 2, 3, 4, 5, 26, 30 and 87. In one embodiment, the NB agent is a nucleic acid that encodes any one of SEQ ID NOS: 41-44, 51-55 and 63-68. In one embodiment, the NB agent is a nucleic acid that encodes any one of SEQ ID NOS: 41-44, 51-55 and 63-68.

Exemplary sequences of the invention are provided below in Tables 1-4. The header term "ID" refers to the given SEQ ID NO. Preferred combinations of FR and CDR sequences for each NB construct are used interchangeably throughout the application.

TABLE 1

Polypeptide sequences of monovalent/monomeric DR5-binding components from initial screen, with SEQ ID NOs.

| Name | Sequences | ID |
|---|---|---|
| 4E6 | evqlvesgggsvqagdslrlscaasgrtfgSIRVGwfrqtpgkerefvaAINRNDGTTYYADSV KGrftisrdnakntvymqmaslkpedtavyycaaGLQYNRSADRVPVGAVYwgqgtqvtvss | 1 |
| 7A12 | evqlvesggglvqaggslrlscaasgrtfsNYAMGwfrqapgkerefvaALNWSGGSTYYVDSV KGrftisrdnakntvylqmnslkpedtavyycaaAGSFSLGGRPYGDDYwgkgtlvtvss | 2 |
| 10F1 | evqlvesggglvqpggslrlscaasgftfsRYWMYwvrqapgkglewvsAINSGGGDTYYRDSV RGrftisrdnfkntlylqmnslksedtavyycakAEGPPTFSLIRTMTVDPgaqgtqvtvss | 3 |
| 11D1 | evqlvesggglvqpggslrlscaasgsidsINNMGwyrqapgkgrelvaEITPRGRTNYADSEK SrftisrdnakrtvnlqmnslkpedtavyycnaEVRERGTSWYRPDYwgqgtqvtvss | 4 |
| 11H6 | evqlvesggglvqpggslrlscaasgtfdkINNMGwyrqapgkqrdlvaQITPGGITDYADSVK GrftisrdnakdtmylqmnslkpedtavyfcnaEILKRAYIDVYVNYwgqgtqvtvss | 5 |
| 11H6a | evqllesggglvqpggslrlscaasgtfdkINNMGwyrqapgkqrdlvaQITPGGITDYADSVK GrftisrdnakdtmylqmnslkpedtavyfcnaEILKRAYIDVYVNYwgqgtqvtvss | 87 |

TABLE 2

Polypeptide sequences of multivalent anti-DR5 NB constructs with optional linker sequences, with SEQ ID NOs.

| Name | Sequence | ID |
|---|---|---|
| 4E6 tri | evqlvesgggsvqagdslrlscaasgrtfgSIRVGwfrqtpgkerefvaAINRNDGTTYYADS VKGrftisrdnakntvymqmaslkpedtavyycaaGLQYNRSADRVPVGAVYwgqgtqvtvss ggggsggggsggggsggggsggggsggggsggggsevqlvesgggsvqagdslrlscaasgrt fgSIRVGwfrqtpgkerefvaAINRNDGTTYYADSVKGrftisrdnakntvymqmaslkpedt avyycaaGLQYNRSADRVPVGAVYwgqgtqvtvssggggsggggsggggsggggsggggsggg gsggggsevqlvesgggsvqagdslrlscaasgrtfgSIRVGwfrqtpgkerefvaAINRNDG TTYYADSVKGrftisrdnakntvymqmaslkpedtavyycaaGLQYNRSADRVPVGAVYwgqg tqvtvss | 6 |
| 4E6 tetra | evqlvesgggsvqagdslrlscaasgrtfgSIRVGwfrqtpgkerefvaAINRNDGTTYYADS VKGrftisrdnakntvymqmaslkpedtavyycaaGLQYNRSADRVPVGAVYwgqgtqvtvss ggggsggggsggggsggggsggggsggggsggggsevqlvesgggsvqagdslrlscaasgrt fgSIRVGwfrqtpgkerefvaAINRNDGTTYYADSVKGrftisrdnakntvymqmaslkpedt avyycaaGLQYNRSADRVPVGAVYwgqgtqvtvssggggsggggsggggsggggsggggsggg gsggggsevqlvesgggsvqagdslrlscaasgrtfgSIRVGwfrqtpgkerefvaAINRNDG TTYYADSVKGrftisrdnakntvymqmaslkpedtavyycaaGLQYNRSADRVPVGAVYwgqg tqvtvssggggsggggsggggsggggsggggsggggsggggsevqlvesgggsvqagdslrls caasgrtfgSIRVGwfrqtpgkerefvaAINRNDGTTYYADSVKGrftisrdnakntvymqma slkpedtavyycaaGLQYNRSADRVPVGAVYwgqgtqvtvss | 7 |
| 4E6 penta | evqlvesgggsvqagdslrlscaasgrtfgSIRVGwfrqtpgkerefvaAINRNDGTTYYADS VKGrftisrdnakntvymqmaslkpedtavyycaaGLQYNRSADRVPVGAVYwgqgtqvtvss ggggsggggsggggsggggsggggsggggsggggsevqlvesgggsvqagdslrlscaasgrt fgSIRVGwfrqtpgkerefvaAINRNDGTTYYADSVKGrftisrdnakntvymqmaslkpedt avyycaaGLQYNRSADRVPVGAVYwgqgtqvtvssggggsggggsggggsggggsggggsggg gsggggsevqlvesgggsvqagdslrlscaasgrtfgSIRVGwfrqtpgkerefvaAINRNDG TTYYADSVKGrftisrdnakntvymqmaslkpedtavyycaaGLQYNRSADRVPVGAVYwgqg tqvtvssggggsggggsggggsggggsggggsggggsggggsevqlvesgggsvqagdslrls caasgrtfgSIRVGwfrqtpgkerefvaAINRNDGTTYYADSVKGrftisrdnakntvymqma slkpedtavyycaaGLQYNRSADRVPVGAVYwgqgtqvtvssggggsggggsggggsggggsg gggsggggsggggsevqlvesgggsvqagdslrlscaasgrtfgSIRVGwfrqtpgkerefva AINRNDGTTYYADSVKGrftisrdnakntvymqmaslkpedtavyycaaGLQYNRSADRVPVG AVYwgqgtqvtvss | 8 |
| 7A12 tri | evqlvesggglvqaggslrlscaasgrtfsNYAMGwfrqapgkerefvaALNWSGGSTYYVDS VKGrftisrdnakntvylqmnslkpedtavyycaaAGSFSLGGRPYGDDYwgkgtivtvssgg ggsggggsggggsggggsggggsggggsggggsevqlvesggglvqaggslrlscaasgrtfs NYAMGwfrqapgkerefvaALNWSGGSTYYVDSVKGrftisrdnakntvylqmnslkpedtav yycaaAGSFSLGGRPYGDDYwgkgtlvtvssggggsggggsggggsggggsggggsggggsgg ggsevqlvesggglvqaggslrlscaasgrtfsNYAMGwfrqapgkerefvaALNWSGGSTYY VDSVKGrftisrdnakntvylqmnslkpedtavyycaaAGSFSLGGRPYGDDYwgkgtivtvs s | 9 |
| 7A12 tetra | evqlvesggglvqaggslrlscaasgrtfsNYAMGwfrqapgkerefvaALNWSGGSTYYVDS VKGrftisrdnakntvylqmnslkpedtavyycaaAGSFSLGGRPYGDDYwgkgtlvtvssgg ggsggggsggggsggggsggggsggggsggggsevqlvesggglvqaggslrlscaasgrtfs NYAMGwfrqapgkerefvaALNWSGGSTYYVDSVKGrftisrdnakntvylqmnslkpedtav | 10 |

TABLE 2-continued

Polypeptide sequences of multivalent anti-DR5 NB constructs with optional linker sequences, with SEQ ID NOs.

| Name | Sequence | ID |
|---|---|---|
| | yycaaAGSFSLGGRPYGDDYwgkgtivtvssggggsggggsggggsggggsggggsggggsgg<br>ggsevqlvesggglvqaggslrlscaasgrtfsNYAMGwfrqapgkerefvaALNWSGGSTYY<br>VDSVKGrftisrdnakntvylqmnslkpedtavyycaaAGSFSLGGRPYGDDYwgkgtivtvs<br>sggggsggggsggggsggggsggggsggggsevqlvesggglvqaggslrlscaasgr<br>tfsNYAMGwfrqapgkerefvaALNWSGGSTYYVDSVKGrftisrdnakntvylqmnslkped<br>tavyycaaAGSFSLGGRPYGDDYwgkgtlvtvss | |
| 7A12<br>penta | evqlvesggglvqaggslrlscaasgrtfsNYAMGwfrqapgkerefvaALNWSGGSTYYVDS<br>VKGrftisrdnakntvylqmnslkpedtavyycaaAGSFSLGGRPYGDDYwgkgtivtvssgg<br>ggsggggsggggsggggsggggsggggsggggsevqlvesggglvqaggslrlscaasgrtfs<br>NYAMGwfrqapgkerefvaALNWSGGSTYYVDSVKGrftisrdnakntvylqmnslkpedtav<br>yycaaAGSFSLGGRPYGDDYwgkgtivtvssggggsggggsggggsggggsggggsggggsgg<br>ggsevqlvesggglvqaggslrlscaasgrtfsNYAMGwfrqapgkerefvaALNWSGGSTYY<br>VDSVKGrftisrdnakntvylqmnslkpedtavyycaaAGSFSLGGRPYGDDYwgkgtlvtvs<br>sggggsggggsggggsggggsggggsggggsggggsevqlvesggglvqaggslrlscaasgr<br>tfsNYAMGwfrqapgkerefvaALNWSGGSTYYVDSVKGrftisrdnakntvylqmnslkped<br>tavyycaaAGSFSLGGRPYGDDYwgkgtlvtvssggggsggggsggggsggggsggggsggggs<br>sggggsevqlvesggglvqaggslrlscaasgrtfsNYAMGwfrqapgkerefvaALNWSGGS<br>TYYVDSVKGrftisrdnakntvylqmnslkpedtavyycaaAGSFSLGGRPYGDDYwgkgtlv<br>tvss | 11 |
| 10F1<br>tri 9 | evqlvesggglvqpggslrlscaasgftfsRYWMYwvrqapgkglewvsAINSGGGDTYYRDS<br>VRGrftisrdnfkntlylqmnslksedtavyycakAEGPPTFSLIRTMTVDPgaqgtqvtvss<br>ggggsggggsevqlvesggglvqpggslrlscaasgftfsRYWMYwvrqapgkglewvsAINSG<br>GGDTYYRDSVRGrftisrdnfkntlylqmnslksedtavyycakAEGPPTFSLIRTMTVDPga<br>qgtqvtvssggggsggggsevqlvesggglvqpggslrlscaasgftfsRYWMYwvrqapgkgl<br>ewvsAINSGGGDTYYRDSVRGrftisrdnfkntlylqmnslksedtavyycakAEGPPTFSLI<br>RTMTVDPgaqgtqvtvss | 12 |
| 10F1<br>tri 20 | evqlvesggglvqpggslrlscaasgftfsRYWMYwvrqapgkglewvsAINSGGGDTYYRDS<br>VRGrftisrdnfkntlylqmnslksedtavyycakAEGPPTFSLIRTMTVDPgaqgtqvtvss<br>ggggsggggsggggsggggsggggsevqlvesggglvqpggslrlscaasgftfsRYWMYwvrqapgk<br>glewvsAINSGGGDTYYRDSVRGrftisrdnfkntlylqmnslksedtavyycakAEGPPTFS<br>LIRTMTVDPgaqgtqvtvssggggsggggsggggsggggsggggsevqlvesggglvqpggslrlsca<br>asgftfsRYWMYwvrqapgkglewvsAINSGGGDTYYRDSVRGrftisrdnfkntlylqmnsl<br>ksedtavyycakAEGPPTFSLIRTMTVDPgaqgtqvtvss | 13 |
| 10F1<br>tri | evqlvesggglvqpggslrlscaasgftfsRYWMYwvrqapgkglewvsAINSGGGDTYYRDS<br>VRGrftisrdnfkntlylqmnslksedtavyycakAEGPPTFSLIRTMTVDPgaqgtqvtvss<br>ggggsggggsggggsggggsggggsggggsggggsevqlvesggglvqpggslrlscaasgft<br>fsRYWMYwvrqapgkglewvsAINSGGGDTYYRDSVRGrftisrdnfkntlylqmnslksedt<br>avyycakAEGPPTFSLIRTMTVDPgaqgtqvtvssggggsggggsggggsggggsggggsgggg<br>gsggggsevqlvesggglvqpggslrlscaasgftfsRYWMYwvrqapgkglewvsAINSGGG<br>DTYYRDSVRGrftisrdnfkntlylqmnslksedtavyycakAEGPPTFSLIRTMTVDPgaqg<br>tqvtvss | 14 |
| 10F1<br>tetra | evqlvesggglvqpggslrlscaasgftfsRYWMYwvrqapgkglewvsAINSGGGDTYYRDS<br>VRGrftisrdnfkntlylqmnslksedtavyycakAEGPPTFSLIRTMTVDPgaqgtqvtvss<br>ggggsggggsggggsggggsggggsggggsggggsevqlvesggglvqpggslrlscaasgft<br>fsRYWMYwvrqapgkglewvsAINSGGGDTYYRDSVRGrftisrdnfkntlylqmnslksedt<br>avyycakAEGPPTFSLIRTMTVDPgaqgtqvtvssggggsggggsggggsggggsggggsgggg<br>gsggggsevqlvesggglvqpggslrlscaasgftfsRYWMYwvrqapgkglewvsAINSGGG<br>DTYYRDSVRGrftisrdnfkntlylqmnslksedtavyycakAEGPPTFSLIRTMTVDPgaqg<br>tqvtvssggggsggggsggggsggggsggggsggggsevqlvesggglvqpggslrls<br>caasgftfsRYWMYwvrqapgkglewvsAINSGGGDTYYRDSVRGrftisrdnfkntlylqmn<br>slksedtavyycakAEGPPTFSLIRTMTVDPgaqgtqvtvss | 15 |
| 10F1<br>penta | evqlvesggglvqpggslrlscaasgftfsRYWMYwvrqapgkglewvsAINSGGGDTYYRDS<br>VRGrftisrdnfkntlylqmnslksedtavyycakAEGPPTFSLIRTMTVDPgaqgtqvtvss<br>ggggsggggsggggsggggsggggsggggsggggsevqlvesggglvqpggslrlscaasgft<br>fsRYWMYwvrqapgkglewvsAINSGGGDTYYRDSVRGrftisrdnfkntlylqmnslksedt<br>avyycakAEGPPTFSLIRTMTVDPgaqgtqvtvssggggsggggsggggsggggsggggsgggg<br>gsggggsevqlvesggglvqpggslrlscaasgftfsRYWMYwvrqapgkglewvsAINSGGG<br>DTYYRDSVRGrftisrdnfkntlylqmnslksedtavyycakAEGPPTFSLIRTMTVDPgaqg<br>tqvtvssggggsggggsggggsggggsggggsggggsggggsevqlvesggglvqpggslrls<br>caasgftfsRYWMYwvrqapgkglewvsAINSGGGDTYYRDSVRGrftisrdnfkntlylqmn<br>slksedtavyycakAEGPPTFSLIRTMTVDPgaqgtqvtvssggggsggggsggggsggggsg<br>gggsggggsggggsevqlvesggglvqpggslrlscaasgftfsRYWMYwvrqapgkglewvs<br>AINSGGGDTYYRDSVRGrftisrdnfkntlylqmnslksedtavyycakAEGPPTFSLIRTMT<br>VDPgaqgtqvtvss | 16 |
| 11D1<br>tri | evqlvesggglvqpggslrlscaasgsidsINNMGwyrqapgkgrelvaEITPRGRTNYADSE<br>KSrftisrdnakrtvnlqmnslkpedtavyycnaEVRERGTSWYRPDYwqgtqvtvssgggg<br>sggggsggggsggggsggggsggggsevqlvesggglvqpggslrlscaasgsidsIN<br>NMGwyrqapgkgrelvaEITPRGRTNYADSEKSrftisrdnakrtvnlqmnslkpedtavyyc | 17 |

TABLE 2-continued

Polypeptide sequences of multivalent anti-DR5 NB constructs with optional linker sequences, with SEQ ID NOs.

| Name | Sequence | ID |
|---|---|---|
| | naEVRERGTSWYRPDYwgqgtqvtvssggggsggggsggggsggggsggggsggggsggggse vqlvesggglvqpggslrlscaasgsidsINNMGwyrqapgkqrelvaEITPRGRTNYADSEK SrftisrdnakrtvnlqmnslkpedtavyycnaEVRERGTSWYRPDYwgqgtqvtvss | |
| 11D1 tetra | evqlvesggglvqpggslrlscaasgsidsINNMGwyrqapgkqrelvaEITPRGRTNYADSE KSrftisrdnakrtvnlqmnslkpedtavyycnaEVRERGTSWYRPDYwgqgtqvtvssgggg sggggsggggsggggsggggsggggsggggsevqlvesggglvqpggslrlscaasgsidsIN NMGwyrqapgkqrelvaEITPRGRTNYADSEKSrftisrdnakrtvnlqmnslkpedtavyyc naEVRERGTSWYRPDYwgqgtqvtvssggggsggggsggggsggggsggggsggggsggggse vqlvesggglvqpggslrlscaasgsidsINNMGwyrqapgkqrelvaEITPRGRTNYADSEK SrftisrdnakrtvnlqmnslkpedtavyycnaEVRERGTSWYRPDYwgqgtqvtvssggggs ggggsggggsggggsggggsggggsggggsevqlvesggglvqpggslrlscaasgsidsINN MGwyrqapgkqrelvaEITPRGRTNYADSEKSrftisrdnakrtvnlqmnslkpedtavyycn aEVRERGTSWYRPDYwgqgtqvtvss | 18 |
| 11D1 penta | evqlvesggglvqpggslrlscaasgsidsINNMGwyrqapgkqrelvaEITPRGRTNYADSE KSrftisrdnakrtvnlqmnslkpedtavyycnaEVRERGTSWYRPDYwgqgtqvtvssgggg sggggsggggsggggsggggsggggsggggsevqlvesggglvqpggslrlscaasgsidsIN NMGwyrqapgkqrelvaEITPRGRTNYADSEKSrftisrdnakrtvnlqmnslkpedtavyyc naEVRERGTSWYRPDYwgqgtqvtvssggggsggggsggggsggggsggggsggggsggggse vqlvesggglvqpggslrlscaasgsidsINNMGwyrqapgkqrelvaEITPRGRTNYADSEK SrftisrdnakrtvnlqmnslkpedtavyycnaEVRERGTSWYRPDYwgqgtqvtvssggggs ggggsggggsggggsggggsggggsggggsevqlvesggglvqpggslrlscaasgsidsINN MGwyrqapgkqrelvaEITPRGRTNYADSEKSrftisrdnakrtvnlqmnslkpedtavyyc aEVRERGTSWYRPDYwgqgtqvtvssggggsggggsggggsggggsggggsggggsggggsev qlvesggglvqpggslrlscaasgsidsINNMGwyrqapgkqrelvaEITPRGRTNYADSEKS rftisrdnakrtvnlqmnslkpedtavyycnaEVRERGTSWYRPDYwgqgtqvtvss | 19 |
| 11H6 tri | evqlvesggglvqpggslrlscaasgtfdkINNMGwyrqapgkqrdlvaQITPGGITDYADSV KGrftisrdnakdtmylqmnslkpedtavyfcnaEILKRAYIDVYVNYwgqgtqvtvssgggg sggggsggggsggggsggggsggggsggggsevqlvesggglvqpggslrlscaasgtfdkIN NMGwyrqapgkqrdlvaQITPGGITDYADSVKGrftisrdnakdtmylqmnslkpedtavyfc naEILKRAYIDVYVNYwgqgtqvtvssggggsggggsggggsggggsggggsggggsggggse vqlvesggglvqpggslrlscaasgtfdkINNMGwyrqapgkqrdlvaQITPGGITDYADSVK GrftisrdnakdtmylqmnslkpedtavyfcnaEILKRAYIDVYVNYwgqgtqvtvss | 20 |
| 11H6 tetra | evqlvesggglvqpggslrlscaasgtfdkINNMGwyrqapgkqrdlvaQITPGGITDYADSV KGrftisrdnakdtmylqmnslkpedtavyfcnaEILKRAYIDVYVNYwgqgtqvtvssgggg sggggsggggsggggsggggsggggsggggsevqlvesggglvqpggslrlscaasgtfdkIN NMGwyrqapgkqrdlvaQITPGGITDYADSVKGrftisrdnakdtmylqmnslkpedtavyfc naEILKRAYIDVYVNYwgqgtqvtvssggggsggggsggggsggggsggggsggggsggggse vqlvesggglvqpggslrlscaasgtfdkINNMGwyrqapgkqrdlvaQITPGGITDYADSVK GrftisrdnakdtmylqmnslkpedtavyfcnaEILKRAYIDVYVNYwgqgtqvtvssggggs ggggsggggsggggsggggsggggsggggsevqlvesggglvqpggslrlscaasgtfdkINN MGwyrqapgkqrdlvaQITPGGITDYADSVKGrftisrdnakdtmylqmnslkpedtavyfcn aEILKRAYIDVYVNYwgqgtqvtvss | 21 |
| 11H6 penta | evqlvesggglvqpggslrlscaasgtfdkINNMGwyrqapgkqrdlvaQITPGGITDYADSV KGrftisrdnakdtmylqmnslkpedtavyfcnaEILKRAYIDVYVNYwgqgtqvtvssgggg sggggsggggsggggsggggsggggsggggsevqlvesggglvqpggslrlscaasgtfdkIN NMGwyrqapgkqrdlvaQITPGGITDYADSVKGrftisrdnakdtmylqmnslkpedtavyfc naEILKRAYIDVYVNYwgqgtqvtvssggggsggggsggggsggggsggggsggggsggggse vqlvesggglvqpggslrlscaasgtfdkINNMGwyrqapgkqrdlvaQITPGGITDYADSVK GrftisrdnakdtmylqmnslkpedtavyfcnaEILKRAYIDVYVNYwgqgtqvtvssggggs ggggsggggsggggsggggsggggsggggsevqlvesggglvqpggslrlscaasgtfdkINN MGwyrqapgkqrdlvaQITPGGITDYADSVKGrftisrdnakdtmylqmnslkpedtavyfcn aEILKRAYIDVYVNYwgqgtqvtvssggggsggggsggggsggggsggggsggggsggggsev qlvesggglvqpggslrlscaasgtfdkINNMGwyrqapgkqrdlvaQITPGGITDYADSVKG rftisrdnakdtmylqmnslkpedtavyfcnaEILKRAYIDVYVNYwgqgtqvtvss | 22 |
| Link 1 | ggggsggggsggggsggggsggggsggggsggggs | 23 |
| Link 2 | ggggsggggsggggsggggs | 24 |
| Link 3 | ggggsgggs | 25 |
| Link 4 | GGGGS | 81 |
| Link 5 | GGGS | 82 |
| 11H6a tetra2 | evqlvesggglvqpggslrlscaasgtfdkINNMGwyrqapgkqrdlvaQITPGGITDYADSV KGrftisrdnakdtmylqmnslkpedtavyfcnaEILKRAYIDVYVNYwgqgtqvtvssgggg sggggsggggsggggsggggsggggsggggsevqllesggglvqpggslrlscaasgtfdkIN NMGwyrqapgkqrdlvaQITPGGITDYADSVKGrftisrdnakdtmylqmnslkpedtavyfc naEILKRAYIDVYVNYwgqgtqvtvssggggsggggsggggsggggsggggsggggsggggse | 88 |

TABLE 2-continued

Polypeptide sequences of multivalent anti-DR5 NB constructs with optional linker sequences, with SEQ ID NOs.

| Name | Sequence | ID |
|---|---|---|
| | vqlvesggglvqpggslrlscaasgtfdkINNMGwyrqapgkqrdlvaQITPGGITDYADSVK GrftisrdnakdtmylqmnslkpedtavyfcnaEILKRAYIDVYVNYwgqgtqvtvssggggs ggggsggggsggggsggggsggggsggggsevqllesggglvqpggslrlscaasgtfdkINN MGwyrqapgkqrdlvaQITPGGITDYADSVKGrftisrdnakdtmylqmnslkpedtavyfcn aEILKRAYIDVYVNYwgqgtqvtvss | |
| Tag1 | EQKLISEEDLN | 91 |
| Tag2 | HHHHHH | 92 |
| Tag3 | AAAEQKLISEEDLNGAAHHHHHH | 93 |
| Tag4 | GAAEQKLISEEDLNGAAHHHHHH | 94 |
| Tag5 | GGGC | 95 |

TABLE 3

Human Optimized Nucleotide (NT) and Polypeptide (AA) Sequences

| Name | Sequence | ID: |
|---|---|---|
| 4E6 hu (AA) | evqllesggglvqpggslrlscaasgrtfgSIRVGwfrqapgkgrefvsAINRNDGTTYYADS VKGrftisrdnskntvylqmnslrpedtavyycaaGLQYNRAADRVPVGAVYwgqgtivtvss | 26 |
| 4E6 hu trimer (AA) | EVQLLESGGGLVQPGGSLRLSCAASGRTFGSIRVGWFRQAPGKGREFVSAINRNDGTTYYADS VKGRFTISRDNSKNTVYLQMNSLRPEDTAVYYCAAGLQYNRAADRVPVGAVYWGQGTLVTVSS GGGGSGGGGSGGGGSGGGGSGGGGSGGGGSEVQLLESGGGLVQPGGSLRLSCAASGRT FGSIRVGWFRQAPGKGREFVSAINRNDGTTYYADSVKGRFTISRDNSKNTVYLQMNSLRPEDT AVYYCAAGLQYNRAADRVPVGAVYWGQGTLVTVSSGGGGSGGGGSGGGGSGGGGSGGGGSGGGG GSGGGGSEVQLLESGGGLVQPGGSLRLSCAASGRTFGSIRVGWFRQAPGKGREFVSAINRNDG TTYYADSVKGRFTISRDNSKNTVYLQMNSLRPEDTAVYYCAAGLQYNRAADRVPVGAVYWGQG TLVTVSS | 27 |
| 4E6 hu tetramer (AA) | EVQLLESGGGLVQPGGSLRLSCAASGRTFGSIRVGWFRQAPGKGREFVSAINRNDGTTYYADS VKGRFTISRDNSKNTVYLQMNSLRPEDTAVYYCAAGLQYNRAADRVPVGAVYWGQGTLVTVSS GGGGSGGGGSGGGGSGGGGSGGGGSGGGGSEVQLLESGGGLVQPGGSLRLSCAASGRT FGSIRVGWFRQAPGKGREFVSAINRNDGTTYYADSVKGRFTISRDNSKNTVYLQMNSLRPEDT AVYYCAAGLQYNRAADRVPVGAVYWGQGTLVTVSSGGGGSGGGGSGGGGSGGGGSGGGGSGGGG GSGGGGSEVQLLESGGGLVQPGGSLRLSCAASGRTFGSIRVGWFRQAPGKGREFVSAINRNDG TTYYADSVKGRFTISRDNSKNTVYLQMNSLRPEDTAVYYCAAGLQYNRAADRVPVGAVYWGQG TLVTVSSGGGGSGGGGSGGGGSGGGGSGGGGSGGGGSEVQLLESGGGLVQPGGSLRLS CAASGRTFGSIRVGWFRQAPGKGREFVSAINRNDGTTYYADSVKGRFTISRDNSKNTVYLQMN SLRPEDTAVYYCAAGLQYNRAADRVPVGAVYWGQGTLVTVSS | 28 |
| 4E6 hu pentamer (AA) | EVQLLESGGGLVQPGGSLRLSCAASGRTFGSIRVGWFRQAPGKGREFVSAINRNDGTTYYADS VKGRFTISRDNSKNTVYLQMNSLRPEDTAVYYCAAGLQYNRAADRVPVGAVYWGQGTLVTVSS GGGGSGGGGSGGGGSGGGGSGGGGSGGGGSEVQLLESGGGLVQPGGSLRLSCAASGRT FGSIRVGWFRQAPGKGREFVSAINRNDGTTYYADSVKGRFTISRDNSKNTVYLQMNSLRPEDT AVYYCAAGLQYNRAADRVPVGAVYWGQGTLVTVSSGGGGSGGGGSGGGGSGGGGSGGGGSGGGG GSGGGGSEVQLLESGGGLVQPGGSLRLSCAASGRTFGSIRVGWFRQAPGKGREFVSAINRNDG TTYYADSVKGRFTISRDNSKNTVYLQMNSLRPEDTAVYYCAAGLQYNRAADRVPVGAVYWGQG TLVTVSSGGGGSGGGGSGGGGSGGGGSGGGGSGGGGSEVQLLESGGGLVQPGGSLRLS CAASGRTFGSIRVGWFRQAPGKGREFVSAINRNDGTTYYADSVKGRFTISRDNSKNTVYLQMN SLRPEDTAVYYCAAGLQYNRAADRVPVGAVYWGQGTLVTVSSGGGGSGGGGSGGGGSGGGGS GGGGSGGGGSEVQLLESGGGLVQPGGSLRLSCAASGRTFGSIRVGWFRQAPGKGREFVS AINRNDGTTYYADSVKGRFTISRDNSKNTVYLQMNSLRPEDTAVYYCAAGLQYNRAADRVPVG AVYWGQGTLVTVSS | 29 |
| 4E6 hu Monomer (NT) | gaggtgcagctgctggagtctggcggcggactggtgcagcctggcggctccctgagactgtcctgcgccg cctccggccggaccttcggctccatcagagtgggctggttccggcaggcccctggcaagggccgggagtt cgtgtccgccatcaaccggaacgacggcaccacctactacgccgactcgtgaagggccggttcaccatc tcccgggacaactccaagaacaccgtgtacctgcagatgaactccctgcggcccgaggacaccgccgtgt actactgcgccgctggcctgcagtacaacagagccgccgacagagtgcctgtgggcgctgtgtactgggg ccagggcaccctggtgaccgtgtcctct | 96 |
| 4E6 hu Monomer (NT) | gaggtgcagctgctggagtctggcggcggactggtgcagcctggcggctccctgagactgtcctgcgccg cctccggccggaccttcggctccatcagagtgggctggttccggcaggcccctggcaagggccgggagtt cgtgtccgccatcaaccggaacgacggcaccacctactacgccgactcgtgaagggccggttcaccatc tcccgggacaactccaagaacaccgtgtacctgcagatgaactccctgcggcccgaggacaccgccgtgt actactgcgccgctggcctgcagtacaacagagccgccgacagagtgcctgtgggcgctgtgtactgggg ccagggcaccctggtgaccgtgtcctctggcggcggaggatctggaggggggaggaagcggcggaggagga | 97 |

TABLE 3-continued

Human Optimized Nucleotide (NT) and Polypeptide (AA) Sequences

| Name | Sequence | ID: |
|---|---|---|
|  | tctggcggcggaggaagtgggggcggagggagtggcggaggtggaagtggtggaggggcagcgaggtgc<br>agctgctggagagcggcggaggactggtgcagccaggcggatctctgcgcctgagctgcgccgccagcgg<br>cagaacctttggcagcatccgcgtgggatggttcagacaggctcccggaaagggacgcgagtttgtgtct<br>gctatcaatcgcaatgatggcaccacatactatgctgatagcgtgaagggaagattcaccatcagccgcg<br>acaatagcaagaatacagtgtatctgcagatgaatagcctgcgcccagaggatacagctgtgtattactg<br>tgctgccgactgcagtataaccgggctgccgatcgggtgccgtgggagccgtgtattggggacaggga<br>acactggtgacagtgtcctctggcggcggaggatctgggggtggcggatctggcggcggaggaagcggtg<br>gcggaggatctggcggcggaggaagcggaggggggaggatctggcggcggaggatctgaggtgcagctgct<br>ggagtccggcggaggactggtgcagccaggcggcagcctgcgcctgtcttgcgccgcttctggcagaaca<br>ttcggctctatccgcgtgggctggtttaggcaggctccaggcaagggacgcgagttcgtgagcgctatca<br>acagaaacgatggcacaacctattatgctgattctgtgaagggcaggtttacaatcagcagggataattc<br>taagaataccgtgtacctgcagatgaactctctgaggccagaggataccgctgtgtactattgcgctgcc<br>ggcctgcagtataatagggccgctgaccgcgtgccagtgggccgtgtattgggcagggcaccctgg<br>tgacagtgtcctctggcggaggtggcagcggcggtggcggatctggcggcggaggaagtgggggcggagg<br>atctggcggcggaggaagcggcggaggggggatctggcggcggaggatctgaggtgcagctgctggagtct<br>ggcggaggactggtgcagcctggcggaagcctgagactgagctgtgctgcttctggccgcaccttcggaa<br>gcatcagagtgggatggtttcgccaggctccaggaaagggccgggatcttcgtctctctgctatcaataaa<br>tgacgaacaacatattacgccgacagcgtgaagggacgctttacaatctctagggataacagcaagaac<br>accgtgtatctgcagatgaacagcctgcggcccgaggataccgccgtgtattattgtgccgctggactgc<br>agtacaatcgggccgctgatagagtgcctgtgggagccgtgtactgggccagggcacactggtgacagt<br>gtctagc |  |
| 11H6 hu<br>(AA) | evqllesggglvqpggslrlscaasgtfdkINNMGwyrqapgkgrdlvaQITPGGITDYADSV<br>KGrftisrdnskntlylqmnslrpedtavyycnaEILKRAYIDVYVNYwgqgtlvtvss | 30 |
| 11H6 hu<br>trimer<br>(AA) | EVQLLESGGGLVQPGGSLRLSCAASGTFDKINNMGWYRQAPGKQRDLVAQITPGGITDYADSV<br>KGRFTISRDNSKNTLYLQMNSLRPEDTAVYYCNAEILKRAYIDVYVNYWGQGTLVTVSSGGGG<br>SGGGGSGGGGSGGGGSGGGGSGGGGSGGGGSEVQLLESGGGLVQPGGSLRLSCAASGTFDKIN<br>NMGWYRQAPGKQRDLVAQITPGGITDYADSVKGRFTISRDNSKNTLYLQMNSLRPEDTAVYYC<br>NAEILKRAYIDVYVNYWGQGTLVTVSSGGGGSGGGGSGGGGSGGGGSGGGGSGGGGSGGGGSE<br>VQLLESGGGLVQPGGSLRLSCAASGTFDKINNMGWYRQAPGKQRDLVAQITPGGITDYADSVK<br>GRFTISRDNSKNTLYLQMNSLRPEDTAVYYCNAEILKRAYIDVYVNYWGQGTLVTVSS | 31 |
| 11H6 hu<br>tetramer<br>(AA) | EVQLLESGGGLVQPGGSLRLSCAASGTFDKINNMGWYRQAPGKQRDLVAQITPGGITDYADSV<br>KGRFTISRDNSKNTLYLQMNSLRPEDTAVYYCNAEILKRAYIDVYVNYWGQGTLVTVSSGGGG<br>SGGGGSGGGGSGGGGSGGGGSGGGGSGGGGSEVQLLESGGGLVQPGGSLRLSCAASGTFDKIN<br>NMGWYRQAPGKQRDLVAQITPGGITDYADSVKGRFTISRDNSKNTLYLQMNSLRPEDTAVYYC<br>NAEILKRAYIDVYVNYWGQGTLVTVSSGGGGSGGGGSGGGGSGGGGSGGGGSGGGGSGGGGSE<br>VQLLESGGGLVQPGGSLRLSCAASGTFDKINNMGWYRQAPGKQRDLVAQITPGGITDYADSVK<br>GRFTISRDNSKNTLYLQMNSLRPEDTAVYYCNAEILKRAYIDVYVNYWGQGTLVTVSSGGGGS<br>GGGGSGGGGSGGGGSGGGGSGGGGSGGGGSEVQLLESGGGLVQPGGSLRLSCAASGTFDKINN<br>MGWYRQAPGKQRDLVAQITPGGITDYADSVKGRFTISRDNSKNTLYLQMNSLRPEDTAVYYCN<br>AEILKRAYIDVYVNYWGQGTLVTVSS | 32 |
| 11H6 hu<br>pentamer<br>(AA) | EVQLLESGGGLVQPGGSLRLSCAASGTFDKINNMGWYRQAPGKQRDLVAQITPGGITDYADSV<br>KGRFTISRDNSKNTLYLQMNSLRPEDTAVYYCNAEILKRAYIDVYVNYWGQGTLVTVSSGGGG<br>SGGGGSGGGGSGGGGSGGGGSGGGGSGGGGSEVQLLESGGGLVQPGGSLRLSCAASGTFDKIN<br>NMGWYRQAPGKQRDLVAQITPGGITDYADSVKGRFTISRDNSKNTLYLQMNSLRPEDTAVYYC<br>NAEILKRAYIDVYVNYWGQGTLVTVSSGGGGSGGGGSGGGGSGGGGSGGGGSGGGGSGGGGSE<br>VQLLESGGGLVQPGGSLRLSCAASGTFDKINNMGWYRQAPGKQRDLVAQITPGGITDYADSVK<br>GRFTISRDNSKNTLYLQMNSLRPEDTAVYYCNAEILKRAYIDVYVNYWGQGTLVTVSSGGGGS<br>GGGGSGGGGSGGGGSGGGGSGGGGSGGGGSEVQLLESGGGLVQPGGSLRLSCAASGTFDKINN<br>MGWYRQAPGKQRDLVAQITPGGITDYADSVKGRFTISRDNSKNTLYLQMNSLRPEDTAVYYCN<br>AEILKRAYIDVYVNYWGQGTLVTVSSGGGGSGGGGSGGGGSGGGGSGGGGSGGGGSGGGGSEV<br>QLLESGGGLVQPGGSLRLSCAASGTFDKINNMGWYRQAPGKQRDLVAQITPGGITDYADSVKG<br>RFTISRDNSKNTLYLQMNSLRPEDTAVYYCNAEILKRAYIDVYVNYWGQGTLVTVSS | 33 |
| 11H6 hu<br>monomer<br>(NT) | gaggtgcagctgctggagtctggcggcggactggtgcagcctggcggctccctgagactgtcctgcgccg<br>cctccggcaccttcgacaagatcaacaacatgggctggtacaggcaggcccctggcaagcagagggaccct<br>ggtggcccagatcaccctggcggcatcaccgactacgcgactccgtgaagggccggttcaccatctcc<br>cgggacaactccaagaacaccctgtacctgcagatgaactccctgcggcccgaggacaccgccgtgtact<br>actgcaacgccgagatcctgaagcgggcctacatcgacgtgtacgtgaactactggggccagggcaccct<br>ggtgaccgtgtcctct | 98 |
| 11H6 hu<br>tetramer<br>(NT) | gaggtgcagctgctggagtctggcggcggactggtgcagcctggcggctccctgagactgtcctgcgccg<br>cctccggcaccttcgacaagatcaacaacatgggctggtacaggcaggcccctggcaagcagagggacct<br>ggtggcccagatcaccctggcggcatcaccgactacgcgactccgtgaagggccggttcaccatctcc<br>cgggacaactccaagaacaccctgtacctgcagatgaactccctgcggcccgaggacaccgccgtgtact<br>actgcaacgccgagatcctgaagcgggcctacatcgacgtgtacgtgaactactggggccagggcaccct<br>ggtgaccgtgtcctctggcggcggaggatctgggggggaggaagcggcggaggaggatctggcggcgga<br>ggaagtgggggcggagggagtggcggaggtggaagtggtggaggggcagcgaggtgcagctgctggaga<br>gcggcggaggactggtgcagccaggcggatctctgcgcctgagctgcgccgccagcggcacatttgataa<br>gatcaataatatgggatggtatcgccaggctccaggcaagcagcgcgatctggtggctcagatcacacca<br>ggcggaatcacagattatgccgatagcgtgaagggaagattcaccatcagccgcgacaatagcaagaata<br>cactgtatctgcagatgaatagcctgcgcccagaggatacagctgtgtattactgtaatgctgagatcct<br>gaagcgcgcttatatcgatgtgtatgtgaattattggggacagggaacactggtgacagtgtcctctggc |  99 |

TABLE 3-continued

Human Optimized Nucleotide (NT) and Polypeptide (AA) Sequences

| Name | Sequence | ID: |
|------|----------|-----|
| | ggcggaggatctgggggtggcggatctggcggcggaggaagcggtggcggaggatctggcggcggaggaa | |
| | gcggagggggaggatctggcggcggaggatctgaggtgcagctgctggagtccggcggaggactggtgca | |
| | gccaggcggcagcctgcggctgtcttgcgccgcttctggcaccttcgataagatcaacaatatgggatgg | |
| | tacagacaggctcccggaaagcagcgggatctggtggcccagatcaccccaggcggcatcacagattacg | |
| | ctgattctgtgaagggcaggtttacaatcagcagggataattctaagaatacccctgtacctgcagatgaa | |
| | ctctctgaggccagaggataccgctgtgtactattgtaacgccgagatcctgaagagggcttacatcgat | |
| | gtgtacgtgaattattggggccagggcacctggtgacagtgtcctctggcggaggtggcagcggcggtg | |
| | gcggatctggcggcggaggaagtgggggcggaggatctggcggcggaggaagcggcggagggggatctgg | |
| | cggcggaggatctgaggtgcagctgctggcggaggactggtgcagcctggcggaagcctgaga | |
| | ctgagctgtgctgcttctggcaccttcgacaagatcaataatatgggctggtatagacaggccccaggaa | |
| | agcagagggacctggtcgctcagatcacaccggcggaatcaccgactacgctgacagcgtgaagggacg | |
| | ctttacaatctctagggataacagcaagaacaccctgtatctgcagatgaacagcctgcggcccgaggat | |
| | accgccgtgtattattgcaatgctgagatcctgaagagggcctatatcgacgtgtatgtgaattactggg | |
| | gccagggcacactggtgacagtgtcctct | |

TABLE 4

Sequences for CDRs and frameworks, plus preferred combinations as provided in for formula I, namely FR1-CDR1-FR2-CDR2-FR3-CDR3-FR4

| Clone | FR1 | ID | CDR1 | ID | FR2 | ID |
|-------|-----|----|------|----|-----|-----|
| 7A12 | evqlvesggglvqaggslrlscaasgrtfs | 34 | NYAMG | 41 | wfrqapgkerefva | 45 |
| 4E6hu | evqllesggglvqpggslrlscaasgrtfg | 35 | SIRVG | 42 | wfrqapgkgrefvs | 46 |
| 4E6 | evqlvesgggsvqagdslrlscaasgrtfg | 36 | SIRVG | 42 | wfrqtpgkerefva | 47 |
| 11H6 hu | evqllesggglvqpggslrlscaasgtfdk | 37 | INNMG | 43 | wyrqapgkqrdlva | 48 |
| 11H6 | evqlvesggglvqpggslrlscaasgtfdk | 38 | INNMG | 43 | wyrqapgkqrdlva | 48 |
| 11D1 | evqlvesggglvqpggslrlscaasgsids | 39 | INNMG | 43 | wyrqapgkqrelva | 49 |
| 10F1 | evqlvesggglvqpggslrlscaasgftfs | 40 | RYWMY | 44 | wvrqapgkglewvs | 50 |

| Clone | CDR2 | ID | FR3 | ID |
|-------|------|----|-----|-----|
| 7A12 | ALNWSGGSTYYVDSVKG | 51 | rftisrdnakntvylqmnslkpedtavyycaa | 56 |
| 4E6 hu | AINRNDGTTYYADSVKG | 52 | rftisrdnskntvylqmnslrpedtavyycaa | 57 |
| 4E6 | AINRNDGTTYYADSVKG | 52 | rftisrdnakntvymqmaslkpedtavyycaa | 58 |
| 11H6 hu | QITPGGITDYADSVKG | 53 | rftisrdnskntlylqmnslrpedtavyycna | 59 |
| 11H6 | QITPGGITDYADSVKG | 53 | rftisrdnakdtmylqmnslkpedtavyfcna | 60 |
| 11D1 | EITPRGRTNYADSEKS | 54 | rftisrdnakrtvnlqmnslkpedtavyycna | 61 |
| 10F1 | AINSGGGDTYYRDSVRG | 55 | rftisrdnfkntlylqmnslksedtavyycak | 62 |

| Clone | CDR3 | ID | FR4 | ID |
|-------|------|----|-----|-----|
| 7A12 | AGSFSLGGRPYGDDY | 63 | wgkgtlvtvss | 69 |
| 4E6 hu | GLQYNRAADRVPVGAVY | 64 | wgqgtlvtvss | 70 |
| 4E6 | GLQYNRSADRVPVGAVY | 65 | wgqgtqvtvss | 71 |
| 11H6 hu | EILKRAYIDVYVNY | 66 | wgqgtlvtvss | 70 |
| 11H6 | EILKRAYIDVYVNY | 66 | wgqgtqvtvss | 71 |
| 11D1 | EVRERGTSWYRPDY | 67 | wgqgtqvtvss | 71 |
| 10F1 | AEGPPTFSLIRTMTVDP | 68 | gaqgtqvtvss | 72 |

Further Aspects of the NB Agents of the Invention are Provided Below.

The compounds, (monovalent or multivalent) polypeptides and compositions described herein may be such that they bind DR5 but not to the binding site of TRAIL on the DR5, and/or may be such that they do not compete with TRAIL for binding to the DR5. Such compounds and polypeptides may be such that their binding to the DR5 induces, triggers, increases or enhances the signaling mediated by the DR5, and in particular triggers or induces apoptosis in the cell on which the DR5 is present. Such compounds and polypeptides may also be such that they increase or enhance the signaling that is mediated by TRAIL and the DR5 upon binding of TRAIL to its receptor. According to this aspect, binding of both TRAIL as well as the compounds/polypeptides described herein to the same receptor may lead to a synergistic effect on such signaling.

In one specific aspect, the compounds and polypeptides described herein are multimeric compounds and polypeptides (as described herein) directed against DR5. In particular, the compounds and polypeptides described herein may be multimeric polypeptides that are capable of multimerizing DR5 on a cell membrane and as such are capable of inducing, triggering, increasing or enhancing the signaling mediated by the DR5, and more in particular of triggering or inducing apoptosis in the cell on which the DR5 is present. In one embodiment, such monomeric or multimeric compounds or polypeptides disclosed herein may bind DR5 at or near the binding site of TRAIL on the DR5, and/or may compete with TRAIL for binding to DR5. In one embodiment, they do not bind to the binding site for TRAIL on the DR5, essentially do not hinder or prevent binding of TRAIL to the DR5, and/or do not compete with TRAIL for binding to the DR5, and even be such that they increase or enhance the signaling that is mediated by TRAIL and the DR5 upon binding of TRAIL to its receptor (which may again result in a synergistic effect upon the signaling mediated by the DR5). In one embodiment, the amino acid sequence contains a portion derived from naturally occurring TRAIL ligand, i.e., it comprises a segment made up of a natural TRAIL ligand polypeptide or any TRAIL-receptor binding fragment of such TRAIL-ligand.

The polypeptides and compositions of the present invention can be used for the prevention and treatment of diseases and disorders associated with DR5. Specifically, "diseases and disorders associated with DR5" are defined as those that can be prevented and/or treated, respectively, by suitably administering to a subject in need thereof (i.e., having the disease or disorder or at least one symptom thereof and/or at risk of attracting or developing the disease or disorder) of either a polypeptide or composition of the invention (and in particular, of a pharmaceutically active amount thereof) and/or of a known active principle active against DR5 or a biological pathway or mechanism in which DR5 is involved (and in particular, of a pharmaceutically active amount thereof), which results in the modulation, i.e., agonism or antagonism, of DR5-mediated signaling. As listed below, diseases and disorders treatable by the induction of apoptosis in the cell or tissue targeted in the disease are particularly included herein as being associated with DR5.

Diseases and disorders associated with DR5 may in particular be diseases and disorders that can be treated by triggering, initiating, increasing or enhancing the signaling, mechanisms, responses and effects in which a DR5 is involved (in other words, by effecting an agonistic effect on a DR5 or on DR5 mediated signaling). More in particular, diseases and disorders associated with DR5 may be diseases and disorders that can be treated by triggering, initiating, increasing or enhancing cell apoptosis in one or more cells or tissues in the subject to be treated.

In one embodiment, the NB agents of the invention are agonists of the TRAIL receptors DR5, having the potential to be used in therapy against a wide range of diseases associated with DR5. Examples of diseases and disorders associated with DR5 will be clear to the skilled person based on the disclosure herein. In one embodiment, inventive NB agents have utility in the treatment of proliferative diseases including, e.g., cancers such as solid tumors, primary and metastatic cancers such as renal cell carcinoma, and cancers of the lung (e.g., small cell lung cancer "SCLC" and non-small cell lung cancer "NSCLC"), pancreas, hematopoietic malignancy, glioma, astrocytoma, mesothelioma, colorectal cancers, prostate cancer, osteosarcoma, melanoma, lymphoma (including but not limited to Burkitt's Lymphoma), breast cancer, endometrial cancer, liver cancer, gastric cancer, skin cancer, ovarian cancer and squamous cell cancers of any origin (e.g., lung, head and neck, breast, thyroid, cervix, skin, esophageal, etc.), as well as liquid cancers, e.g., such as leukemias including especially a T-cell leukemia such as acute T-cell leukemia (T-ALL), acute B-cell leukemia (B-ALL), chronic myelogenous leukemia (CML), acute myelogenous leukemia (AML), plasma cell myeloma and multiple myeloma (MM). In one embodiment, the inventive NB agents have utility in the treatment of non-cancer indications including, but not limited to, e.g., inflammatory and autoimmune diseases, such as systemic lupus erythematosus, Hashimoto's disease, rheumatoid arthritis, graft-versus-host disease, Sjogren's syndrome, pernicious anemia, Addison disease, scleroderma, Goodpasture's syndrome, Crohn's disease, autoimmune hemolytic anemia, sterility, myasthenia gravis, multiple sclerosis, Basedow's disease, thrombotic throbocytopenia, thrombopenia purpurea, insulin-dependent diabetes mellitus, allergy; asthma, atopic disease; arteriosclerosis; myocarditis; cardiomyopathy; globerula nephritis; and hypoplastic anemia.

Thus, without being limited thereto, the amino acid sequences and polypeptides of the invention can, e.g., be used to prevent and/or to treat all diseases and disorders that are currently being prevented or treated with active principles that can modulate DR5-mediated signaling, such as those mentioned herein and in the art references cited. In one embodiment the polypeptides of the invention can be used to prevent and/or to treat all diseases and disorders for which treatment with such active principles is currently being developed, has been proposed, or will be proposed or developed in future. In one embodiment, it is envisaged that, because of their favorable properties as further described herein, the polypeptides herein may be used for the prevention and treatment of other diseases and disorders than those for which these known active principles are being used or will be proposed or developed; and/or that the polypeptides of the present invention may provide new methods and regimens for treating the diseases and disorders described herein.

Other applications and uses of the amino acid sequences and polypeptides of the invention will become clear to the skilled person from the further disclosure herein.

In one embodiment, the invention provides pharmacologically active agents, as well as compositions comprising the same (whether or not complete polypeptides as described herein, and/or fragments and/or multimeric variants of said polypeptides or fragment, all of which are broadly referred to herein as "inventive compositions"), that can be used in the diagnosis, prevention and/or treatment of diseases and disorders associated with DR5 and of the further diseases and disorders mentioned herein; and to provide methods for the diagnosis, prevention and/or treatment of such diseases and disorders that involve the administration and/or use of such agents and compositions.

In one embodiment the invention provides such pharmacologically active agents, compositions and/or methods that have certain advantages compared to the agents, compositions and/or methods that are currently used and/or known in the art. These advantages will become clear from the further description below.

In one embodiment, the invention provides amino acid sequences that are directed against DR5, in particular against DR5 from a warm-blooded animal, more in particular against DR5 from a mammal, and especially against human DR5; and to provide proteins and polypeptides comprising or essentially consisting of at least one such amino acid sequence.

In one embodiment the invention provides such amino acid sequences and such proteins and/or polypeptides that are suitable for prophylactic, therapeutic and/or diagnostic use in a warm-blooded animal, and in particular in a mammal, and especially in a human being.

In one embodiment the invention provides such amino acid sequences and such proteins and/or polypeptides that can be used for the prevention, treatment, alleviation and/or diagnosis of one or more diseases, disorders or conditions associated with DR5 and/or mediated by DR5 (such as the diseases, disorders and conditions mentioned herein) in a warm-blooded animal, in particular in a mammal, and more in particular in a human being.

In one embodiment the invention provides such inventive compositions that for use in the preparation of pharmaceutical or veterinary compositions for the prevention and/or treatment of one or more diseases, disorders or conditions associated with and/or mediated by DR5 (such as the diseases, disorders and conditions mentioned herein) in a warm-blooded animal, in particular in a mammal, and more in particular in a human being.

In one embodiment, the invention provides inventive compositions that are directed against and/or can specifically bind to DR5; as well as compounds and constructs, and in particular proteins and polypeptides, that comprise at least one such amino acid sequence. More specifically, the invention provides amino acid sequences that can specifically bind to DR5 cell surface receptor as e.g., defined with the accession number "BAA33723" to be found at e.g. the NCBI protein database. In particular, the invention provides amino acid sequences that can specifically bind to DR5 cell surface receptor as e.g. defined with the accession number "BAA33723" to be found at e.g. the NCBI protein database and that does not bind to at least another TRAIL-receptor, such as TRAIL-R3 and TRAIL-R4. A short from splice variant of human DR5 is also known (GenBank entry NP_671716).

In one embodiment, the invention provides amino acid sequences that can bind to DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, in the pharmaceutically acceptable range as provided herein; as well as compounds and constructs, and in particular proteins and polypeptides, that comprise at least one such amino acid sequence.

In one embodiment, inventive compositions are such that they:

a) bind to DR5 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles); and/or b) bind to DR5 with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$; and/or c) bind to DR5 with a $k_{off}$-rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

In one embodiment, an inventive composition, whether monovalent or multivalent, binds to DR5 with an affinity less than 100 nM, and/or less than 10 nM, and/or less than 1 nM, such as less than 500 pM. In one embodiment, the inventive composition is a tetravalent composition. In one embodiment, the inventive composition is a pentavalent composition.

In one embodiment, an inventive composition, whether monovalent or multivalent, will specifically induce apoptosis in various cancer cell types (e.g., at least one type) with an $IC_{50}$ less than 100 nM, preferably less than 10 nM, more preferably less than 1 nM, such as less than 500 pM. In one embodiment, a multivalent amino acid sequence of the invention is at least 10 fold more potent in tumor cell line than in normal (non-tumor) cell line, or at least 100 fold more potent than in normal (non-tumor) cell line, as measured, e.g., in non-tumor cell lines mentioned in the experimental part, e.g. Huvec, IMR-90 and ARPE-19. See examples and Table 13.

For binding to DR5, an inventive composition will usually contain within its amino acid sequence one or more amino acid residues or one or more stretches of amino acid residues (i.e., with each "stretch" comprising two or more amino acid residues that are adjacent to each other or in close proximity to each other, i.e., in the primary (linear) or tertiary (conformational) structure of the amino acid sequence) via which the amino acid sequence of the invention can bind to DR5, which amino acid residues or stretches of amino acid residues thus form the "site" for binding to DR5 (also referred to herein as the "antigen binding site" or "epitope"). Epitope mapping experiments are provided herein in the Examples.

In one embodiment the inventive compositions provided herein are in essentially isolated form, or form part of a protein or polypeptide of the invention that may comprise or essentially consist of one or more amino acid sequences herein disclosed. In one embodiment the inventive compositions may further comprise one or more additional amino acid sequences. In one embodiment, such additional sequences are linked via one or more suitable linkers. Without limitation, the inventive compositions may be used as a binding unit in such a protein or polypeptide. Such inventive compositions may contain one or more further amino acid sequences that can serve as an additional binding unit (i.e., against one or more other targets than DR5), so as to provide a monovalent, multivalent or multispecific polypeptide of the invention, respectively. Such a protein or polypeptide may also be in essentially isolated form.

In one embodiment the inventive compositions essentially consist of a single amino acid chain that is not linked via disulphide bridges to any other amino acid sequence or chain (but that may or may not contain one or more intramolecular disulphide bridges) or pharmaceutically relevant composition. As an example of an intramolecular disulfide bridge, it is known that camelid $V_{HH}$ constructs may sometimes contain a disulphide bridge between CDR3 and CDR1 or FR2. In one embodiment, inventive compositions may be linked to each other and/or to other amino acid sequences (e.g. via disulphide bridges) to provide alternative peptide constructs (for example Fab' fragments, F(ab')$_2$ fragments, ScFv constructs, "diabodies" and other multivalent and/or multispecific constructs. See review by Holliger and Hudson, Nat Biotechnol. 2005 September; 23(9): 1126-36). Examples of pharmaceutically relevant compositions include drugs that treat a disease, or compositions that increase half life, target specific tissues, and/or kill the target cell.

In one embodiment the inventive compositions essentially consist of a single amino acid chain that is linked via at least one intermolecular disulphide bridge to any other amino acid sequence or chain (either of which may or may not contain one or more intramolecular disulphide bridges) or pharmaceutically relevant composition.

In one embodiment, when an inventive composition is intended for administration to a subject (for example for therapeutic and/or diagnostic purposes as described herein), it is either an amino acid sequence that does not occur naturally in said subject; or, when it does occur naturally in said subject, is in essentially isolated form.

In one embodiment for pharmaceutical use, the disclosed amino acid sequences of the invention (as well as compounds, constructs and polypeptides comprising the same) are directed against human DR5. In one embodiment for veterinary purposes, such disclosed compositions are directed against DR5 from the species to be treated. In one embodiment for veterinary purposes, such disclosed compositions are cross-reactive with DR5 from the species to be treated.

In one embodiment, an inventive amino acid sequence has at least one binding site for binding against DR5, and may contain one or more further binding sites for binding against other epitopes, antigens, proteins or targets.

The efficacy of the amino acid sequences and polypeptides of the invention, and of compositions comprising the same, can be tested using any suitable in vitro assay, cell-based assay, in vivo assay and/or animal model known per se, or any combination thereof, depending on the specific disease or disorder involved. These may, e.g., be assays or models for measuring the influence of the amino acid sequences or compounds described herein on apoptosis, on the proliferation of tumor cells, and/or on the growth of tumors in an animal model for such a tumor. Suitable assays and animal models will be clear to the skilled person, and, e.g., include assays and animal models used in the experimental part below and in the art references cited herein. Examples are binding assays such as ELISA, FACS or surface plasmon resonance methodology; functional in vitro assays such as in vitro cell survival assay with a panel of tumor and normal cell lines, in vitro efficacy assay with Jurkat cell survival detection; functional in vivo assays such as single dose in vivo study combined with a caspase 3/7 activation read out providing various efficacy, PK and PD data.

In one embodiment according to the invention, amino acid sequences and polypeptides that are directed against DR5 from a first species of warm-blooded animal may or may not show cross-reactivity with DR5 from one or more other species of warm-blooded animal. For example, amino acid sequences and polypeptides directed against human DR5 may or may not show cross reactivity with DR5 from one or more other species of primates (such as, without limitation, monkeys from the genus *Macaca* (such as, and in particular, cynomologus monkeys (*Macaca fascicularis*, a.k.a., "cyno") and/or rhesus monkeys (*Macaca mulatta*)) and baboon (*Papio ursinus*)) and/or with DR5 from one or more species of animals that are often used in animal models for diseases (for example mouse, rat, rabbit, pig or dog), and in particular in animal models for diseases and disorders associated with DR5 (such as the species and animal models mentioned herein).

In this respect, it will be clear to the skilled person that such cross-reactivity, when present, may have advantages from a drug development point of view, since it allows the amino acid sequences and polypeptides against human DR5 to be tested in such disease models. Various inventive constructs provided herein show specific cross-reactivity with cyno DR5.

In one embodiment, amino acid sequences and polypeptides of the invention that are cross-reactive with DR5 from multiple species of mammal will usually be advantageous for use in veterinary applications, since it will allow the same amino acid sequence or polypeptide to be used across multiple species. Thus, in one embodiment amino acid sequences and polypeptides directed against DR5 from one species of animal (such as amino acid sequences and polypeptides against human DR5) can be used in the treatment of another species of animal, as long as the use of the amino acid sequences and/or polypeptides provide the desired effects in the species to be treated.

The present invention is in its broadest sense also not particularly limited to or defined by a specific antigenic determinant, epitope, part, domain, subunit or confirmation (where applicable) of DR5 against which the amino acid sequences and polypeptides of the invention are directed. However, in one embodiment the inventive amino acid sequences and polypeptides are directed against the extracellular domain of the DR5. In one non-limiting aspect, the inventive amino acid sequences and polypeptides are directed against the DR5-binding domain of DR5, and are as further defined herein. In one embodiment, a monovalent or multivalent amino acid sequence and polypeptides of the invention compete with the natural ligand of the DR5 in a competitive binding assay as described in the experimental part. In one embodiment, a monovalent or multivalent amino acid sequence and polypeptides of the invention binds synergistically with the natural ligand of the DR5 in a competitive binding assay.

In one embodiment of the invention, where applicable, an amino acid sequence of the invention can bind to two or more antigenic determinants, epitopes, parts, domains, subunits or confirmations of DR5. In such a case, the antigenic determinants, epitopes, parts, domains or subunits of DR5 to which the amino acid sequences and/or polypeptides of the invention bind may be essentially the same (for example, if DR5 contains repeated structural motifs or occurs in a multimeric form) or may be different (and in the latter case, the amino acid sequences and polypeptides of the invention may bind to such different antigenic determinants, epitopes, parts, domains, subunits of DR5 with an affinity and/or specificity which may be the same or different). Also, e.g., when DR5 exists in an activated conformation and in an inactive conformation, the amino acid sequences and polypeptides of the invention may bind to either one of these confirmation, or may bind to both these confirmations (i.e., with an affinity and/or specificity which may be the same or different). Also, e.g., the amino acid sequences and polypeptides of the invention may bind to a conformation of DR5 in which it is bound to a pertinent ligand, may bind to a conformation of DR5 in which it not bound to a pertinent ligand, or may bind to both such conformations (again with an affinity and/or specificity which may be the same or different).

It is also expected that the amino acid sequences and polypeptides of the invention will generally bind to all naturally occurring or synthetic analogs, variants, mutants, alleles, parts and fragments of DR5; or at least to those analogs, variants, mutants, alleles, parts and fragments of DR5 that contain one or more antigenic determinants or epitopes that are essentially the same as the antigenic determinant(s) or epitope(s) to which the amino acid sequences and polypeptides of the invention bind in DR5 (e.g. in wild-type DR5). Again, in such a case, the amino acid sequences and polypeptides of the invention may bind to such analogs, variants, mutants, alleles, parts and fragments with an affinity and/or specificity that are the same as, or that are different from (i.e., higher than or lower than), the affinity and specificity with which the amino acid sequences of the invention bind to (wild-type) DR5. Also included within the inventive scope is that the amino acid sequences and polypeptides of the invention bind to some analogs, variants, mutants, alleles, parts and fragments of DR5, but not to others.

In general, when DR5 exists in a monomeric form and in one or more multimeric forms, it is within the scope of the invention that the amino acid sequences and polypeptides of the invention only bind to DR5 in monomeric form, only bind to DR5 in multimeric form, or bind to both the monomeric and the multimeric form. Again, in such a case, the amino acid sequences and polypeptides of the invention may bind to the monomeric form with an affinity and/or specificity that are the same as, or that are different from (i.e., higher than or lower than), the affinity and specificity with which the amino acid sequences of the invention bind to the multimeric form.

Also, when DR5 can associate with other proteins or polypeptides to form protein complexes (e.g. with multiple subunits), it is within the scope of the invention that the amino acid sequences and polypeptides of the invention bind to DR5 in its non-associated state, bind to DR5 in its associated state, or bind to both. In all these cases, the amino acid sequences and polypeptides of the invention may bind to such multimers or associated protein complexes with an affinity and/or specificity that may be the same as or different from (i.e., higher than or lower than) the affinity and/or specificity with which the amino acid sequences and polypeptides of the invention bind to DR5 in its monomeric and non-associated state.

In one embodiment, as will be clear to the skilled person, inventive compositions that contain two or more amino acid sequences directed against DR5 may bind with higher avidity to DR5 than the corresponding monomeric amino acid sequence(s). For example, and without limitation, proteins or polypeptides that contain two, three, four, five, six, eight, ten or more operably linked monomeric units of amino acid sequences directed against the same or different epitopes of DR5 may (and usually will) bind with higher avidity than each of the different monomers, and proteins or polypeptides that contain two, three, four or more amino acid sequences directed against DR5 may (and usually will) bind also with higher avidity to a multimer of DR5. In one embodiment, the inventive composition is a single polypeptide chain made of four monomers directed against DR5 connected by amino acid linkers. In one embodiment, the inventive composition is a single polypeptide chain made of five monomers directed against DR5 connected by amino acid linkers.

Generally, amino acid sequences and polypeptides of the invention will at least bind to those forms of DR5 (including monomeric, multimeric and associated forms) that are the most relevant from a biological and/or therapeutic point of view, as will be clear to the skilled person.

It is within the scope of the invention to use compositions comprising parts, fragments, analogs, mutants, variants, alleles and/or derivatives of the amino acid sequences and polypeptides of the invention, and/or to use proteins or polypeptides comprising or essentially consisting of one or more of such compositions as long as these are suitable for the uses envisaged herein. In one embodiment such compositions will contain (at least part of) a functional antigen-binding site for binding against DR5. In one embodiment such compositions will be capable of specific binding to DR5. In one embodiment such compositions will be capable of binding to DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as provided herein. Some non-limiting examples of such compositions will become clear from the further description herein. Additional fragments or polypeptides of the invention may also be provided by suitably combining (i.e., by linking or genetic fusion) one or more (smaller) compositions as described herein.

In one non-limiting aspect of the invention, analogs, mutants, variants, alleles, and/or derivatives of the polypeptides of the invention have an increased half-life in serum (as further described herein) compared to the amino acid sequence from which they have been derived. For example, an amino acid sequence of the invention may be linked (chemically or otherwise) to one or more groups or moieties that extend the half-life (such as PEG), so as to provide a derivative of an amino acid sequence of the invention with increased half-life.

In one specific, but non-limiting aspect, the amino acid sequence of the invention may be an amino acid sequence that comprises an immunoglobulin fold or may be an amino acid sequence that, under suitable conditions (such as physiological conditions) is capable of forming an immunoglobulin fold (i.e., by folding). Reference is made inter alia to the review by Halaby et al., J. (1999) Protein Eng. 12, 563-71. In one embodiment, when properly folded so as to form an immunoglobulin fold, such an amino acid sequence is capable of specific binding to DR5. In one further embodiment, such a construct is capable of binding to DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as provided herein. In one embodiment, parts, fragments, analogs, mutants, variants, alleles and/or derivatives of such amino acid sequences are such that they comprise an immunoglobulin fold or are capable for forming, under suitable conditions, an immunoglobulin fold.

In particular, but without limitation, the amino acid sequences of the invention may be amino acid sequences that essentially consist of four framework regions (FR1, FR2, FR3 and FR4 respectively) and three interspersed complementarity determining regions (CDR1, CDR2 and CDR3 respectively); or any suitable fragment of such an amino acid sequence (which will then usually contain at least some of the amino acid residues that form at least one of the CDR's, as further described herein). In one embodiment these regions are arranged as shown in formula I:

FR1-CDR1-FR2-CDR2-FR3-CDR3-FR4  (formula I)

The amino acid sequences of the invention may in particular be an immunoglobulin sequence or a suitable fragment thereof, and more in particular be an immunoglobulin variable domain sequence or a suitable fragment thereof, such as light chain variable domain sequence (e.g. a $V_L$ sequence) or a suitable fragment thereof; or a heavy chain variable domain sequence (e.g. a $V_H$ sequence) or a suitable fragment thereof. When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence that is derived from a so-called "heavy chain antibody".

It should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the amino acid sequences of the invention may contain naturally occurring amino acid sequences (from any suitable species) or synthetic or semi-synthetic amino acid sequences. In a specific but non-limiting aspect of the invention, the amino acid sequence is a naturally occurring immunoglobulin sequence (from any suitable species) or a synthetic or semi-synthetic immunoglobulin sequence, including but not limited to "humanized" immunoglobulin sequences (e.g., such as partially or fully humanized mouse, rabbit or monkey immunoglobulin sequences (or immunoglobulin sequences of any other mammalian species contemplated by one skilled in the art), and in particular partially or fully humanized camelid $V_{HH}$ sequences or fragments thereof), "camelized" immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the above. Reference is, e.g., made to standard handbooks, as well as to the further description and art references mentioned herein.

Similarly, the nucleotide sequences of the invention may be naturally occurring nucleotide sequences or synthetic or semi-synthetic sequences, and may, e.g., be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

The amino acid sequence of the invention may in particular be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a camelid antibody (and including but not limited to a $V_{HH}$ sequence or variants thereof); other single variable domains, or any suitable fragment of any one thereof. For a general description of (single) domain antibodies, reference is also made to the art references cited above, as well as to EP 0 368 684. For the term "dAb's", reference is, e.g., made to Ward et al. (Nature 1989 Oct. 12; 341 (6242): 544-6), to Holt et al., Trends Biotechnol., 2003, 21(11): 484-490; as well as to, e.g., WO 06/030220, WO 06/003388 and other published patent applications of Domantis Ltd. In one embodiment of the invention, single domain antibodies or single variable domains can be derived from certain species of shark (for example, the so-called "IgNAR domains", see e.g., WO 05/18629).

In particular, the amino acid sequence of the invention may be a camelid heavy chain variable domain construct (e.g., a $V_{HH}$ or variables thereof, including variables optimized for use as a human therapeutic, e.g., as defined in, e.g., WO 2008/020079) or a suitable fragment or variant thereof. In one embodiment, the amino acid sequence is a NANOBODY® or a construct thereof. Note that NANOBODY™, NANOBODIES™ and NANOCLONE™ are registered trademarks of Ablynx N.V. Specific heavy chain variable domain constructs directed against DR5, whether or not "humanized" or otherwise altered or optimized, will be referred to herein as a "NB Sequence" of the invention.

As used herein, the phrase "sequence optimized", or alternatively sequences that are "altered or optimized" is defined to refer to the replacement of residues of a NB agent, especially in the framework region, to reduce the occurrence of an immunogenic response to the NB agent by the subject to which it is administered. In the case where the subject is a human, the phrase includes any technique known in the art to humanize the sequence.

In one embodiment, NB agents are so-called "$V_H3$ class" (i.e., a NB construct with a high degree of sequence homology to human germline sequences of the $V_H3$ class such as DP-47, DP-51 or DP-29). In one embodiment, this $V_H3$ class of NB constructs comprise the framework regions of this invention. However, the invention in its broadest sense generally covers any type of NB agents directed against DR5. For example, in one embodiment, the invention also covers the NB constructs belonging to the so-called "$V_H4$ class" (i.e., NB constructs with a high degree of sequence homology to human germline sequences of the $V_H4$ class such as DP-78). See e.g., WO 07/118,670.

In one embodiment, NB constructs (in particular fully humanized and partially humanized constructs) are characterized by the presence of one or more "Hallmark residues" in one or more of the framework sequences. In one embodiment, the framework sequences present in the NB constructs of the invention may be such that the amino acid sequence is a variant of a camelid $V_{HH}$ construct. Some non-limiting examples of (suitable combinations of) such framework sequences and alternative Hallmark residues appear, e.g., in WO 2008/020079, pages 65-98, which pages are incorporated by reference in their entirety. Other humanized or partially humanized residues known in the art are also contemplated as encompassed within the invention.

Generally, a $V_H$ or a $V_{HH}$ construct can be defined as an amino acid sequence with the (general) structure of formula I, in which FR1 to FR4 refer to framework regions 1 to 4, respectively, and in which CDR1 to CDR3 refer to the complementarity determining regions 1 to 3, respectively.

In one embodiment an inventive composition may be a NB construct with an amino acid sequence with the (general) structure of formula I in which one or more of the amino acid residues at positions 11, 37, 44, 45, 47, 83, 84, 103, 104 and 108 according to the Kabat numbering are chosen from the Hallmark residues mentioned in Table A-3 in WO 2008/020079 and in which said amino acid sequence has at least 80%, 85%, 90%, 95%, 98%, 99% or 100% amino acid identity with at least one of the framework amino acid sequences of SEQ ID NO's: 1 to 22 in WO 2008/020079, in which for the purposes of determining the degree of amino acid identity, the amino acid residues that form the CDR sequences (indicated with X in the sequences) are disregarded.

In the NB agents of the invention, including without limitation the various formats or scaffolds, the CDR sequences are generally as provided in Tables 1-3 and especially as specifically designated by SEQ ID NO in Table 4. In particular, CDR1 may be any one of SEQ ID NOs: 41 to 44; CDR2 may be any one of SEQ ID NOs: 51 to 55; and CDR3 may be any one of SEQ ID NOs: 63 to 68.

Thus, in one embodiment the invention relates to such $V_H$ constructs that can bind to and/or are directed against DR5, to suitable fragments thereof, as well as to polypeptides that comprise or essentially consist of one or more of such $V_H$ constructs and/or suitable fragments.

In general, SEQ ID NOs: 1-22, 26-40, 87-88, and 102-103 provide the amino acid sequences of a number of NB Agents that have been raised against DR5 (see Tables 1-4). SEQ ID NOs: 96-99 provide specific nucleic acid sequences that encode specific NB Agents as provided herein.

In some embodiments, inventive compositions are NB agents, e.g., as shown in Tables 1 through 4, that can bind to and/or are directed against to DR5 and that have at least 90% amino acid identity with at least one of the amino acid sequences of SEQ ID NOs: 1-22, 26-40, 87-88 and 102-103, in which for the purposes of determining the degree of amino acid identity, the amino acid residues that form the CDR sequences are disregarded and in which one or more of the amino acid residues at positions 11, 37, 44, 45, 47, 83, 84, 103, 104 and 108 according to the Kabat numbering are Hallmark residues.

In various embodiments and as provided in Table 4, the NB constructs comprise framework 1 sequences of SEQ ID NO's: 34 to 40), framework 2 sequences of SEQ ID NO's: 45 to 50, framework 3 sequences of SEQ ID NO's: 56 to 62 and framework 4 sequences of SEQ ID NO's: 69 to 72. In one embodiment, amino acid residues at positions 1 to 4 and 27 to 30 of the framework 1 sequences of NB constructs of SEQ ID NO's: 1-22, 26-40, 87-88 and 102-103 are disregarded for determining the degree of amino acid identity.

In one embodiment, inventive NB agents and compositions may be derived in any suitable manner and from any suitable source, and may, e.g., be naturally occurring $V_{HH}$ sequences (i.e., from a suitable species of Camelid) or synthetic or semi-synthetic amino acid sequences, including but not limited to "humanized" NB agents, "camelized" immunoglobulin sequences (and in particular camelized heavy chain variable domain sequences), as well as NB agents that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an inventive composition comprises a $V_{HH}$ sequence, said composition may be suitably humanized, as described herein, so as to provide one or more further (partially or fully) humanized composition of the invention. In one embodiment, when an inventive composition comprises a synthetic or semi-synthetic sequence (such as a partially humanized sequence), said composition may optionally be further suitably humanized, e.g., again either partially or fully humanized.

In one embodiment, humanized compositions are amino acid sequences that have at least one amino acid residue present (and in particular, in at least one of the framework residues) that is and/or that corresponds to a humanizing substitution. In such a non-limiting embodiment, humanizing substitutions (and suitable combinations thereof) will be clear to the skilled person based on the disclosure herein. In one embodiment, potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence in any manner known per se. In one embodiment, the resulting humanized $V_{HH}$ sequences are tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an inventive composition of the invention may be partially humanized or fully humanized.

In one embodiment, humanized compositions herein are humanized variants of the compositions of SEQ ID NOs: 1-22, 26-40, 87-88, and 102-103 and of SEQ ID NOS: 96-99. In one embodiment, humanized NB constructs are as provided in Table 3.

Thus, some other preferred compositions of the invention are compositions which can bind (as further defined herein) to DR5 and which (a) are a humanized variant of one of the amino acid sequences of SEQ ID NO's: 1-22, 26-40, 87-88, and 102-103; and/or (b) have at least 90% amino acid identity with at least one of the amino acid sequences of SEQ ID NO's: 1-22, 26-40, 87-88, and 102-103. In one embodiment, for the purposes of determining the degree of amino acid identity, the amino acid residues that form the CDR sequences are disregarded.

In one embodiment, one or more of the amino acid residues at positions 11, 37, 44, 45, 47, 83, 84, 103, 104 and 108 according to the Kabat numbering are chosen from the Hallmark residues mentioned in Table A-3 in WO 2008/020079.

In one embodiment, the invention provides a number of stretches of amino acid residues (i.e., small peptides) that are particularly suited for binding to DR5. These stretches of amino acid residues may be present in, and/or may be incorporated into, an amino acid sequence of the invention, in particular in such a way that they form (part of) the antigen binding site of an amino acid sequence of the invention. As these stretches of amino acid residues are first generated as CDR sequences of heavy chain antibodies or $V_{HH}$ sequences that are raised against DR5 (or may be based on and/or derived from such CDR sequences, as further described herein), they will also generally be referred to herein as "CDR sequences" (i.e., as CDR1 sequences, CDR2 sequences and CDR3 sequences, respectively). It should however be noted that the invention in its broadest sense is not limited to a specific structural role or function that these stretches of amino acid residues may have in an amino acid sequence of the invention, as long as these stretches of amino acid residues allow the amino acid sequence of the invention to bind to DR5. Thus, generally, the invention in its broadest sense comprises any amino acid sequence that is capable of binding to DR5 and that comprises one or more CDR sequences as described herein, and in particular a suitable combination of two or more such CDR sequences, that are suitably linked to each other via one or more further amino acid sequences, such that the entire amino acid sequence forms a binding domain and/or binding unit that is capable of binding to DR5. It should however also be noted that the presence of only one such CDR sequence in an amino acid sequence of the invention may by itself already be sufficient to provide an amino acid sequence of the invention that is capable of binding to DR5; reference is, e.g., again made to the so-called "Expedite fragments" described in WO 03/050531.

In one embodiment, the amino acid sequence of the invention may be an amino acid sequence that comprises at least one amino acid sequence that is chosen from the group consisting of the CDR1 sequences, CDR2 sequences and CDR3 sequences that are described herein (or any suitable combination thereof). In particular, an amino acid sequence of the invention may be an amino acid sequence that comprises at least one antigen binding site, wherein said antigen binding site comprises at least one amino acid sequence that is chosen from the group consisting of the CDR1 sequences, CDR2 sequences and CDR3 sequences that are described herein (or any suitable combination thereof).

In one embodiment, the amino acid sequence of the invention may be any amino acid sequence that comprises at least one stretch of amino acid residues, in which said stretch of amino acid residues has an amino acid sequence that corresponds to the sequence of at least one of the CDR sequences described herein. Such an amino acid sequence may or may not comprise an immunoglobulin fold. For example, and without limitation, such an amino acid sequence may be a suitable fragment of an immunoglobulin sequence that comprises at least one such CDR sequence, but that is not large enough to form a (complete) immunoglobulin fold (reference is, e.g., again made to the "Expedite fragments" described in WO 03/050531). Alternatively, such an amino acid sequence may be a suitable "protein scaffold" that comprises least one stretch of amino acid residues that corresponds to such a CDR sequence (i.e., as part of its antigen binding site). Suitable scaffolds for presenting amino acid sequences will be clear to the skilled person, and, e.g., comprise, without limitation, to binding scaffolds based on or derived from immunoglobulins (i.e., other than the immunoglobulin sequences already described herein), protein scaffolds derived from protein A domains (e.g., such as AFFIBODIES™) tendamistat, fibronectin, including fibronectin type III domain, lipocalin, CTLA-4, T-cell receptors, designed ankyrin repeats, avimers and PDZ domains (Binz et al., Nat. Biotech 2005, Vol. 23: 1257), and binding moieties based on DNA or RNA including but not limited to DNA or RNA aptamers (Ulrich et al., Comb Chem. High Throughput Screen 2006 9(8): 619-32).

In one embodiment, any amino acid sequence herein that comprises one or more of these CDR sequences can specifically bind to DR5. In one embodiment it can bind to DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value) as provided herein.

In one embodiment, an inventive composition herein may be any amino acid sequence that comprises at least one antigen binding site, wherein said antigen binding site comprises at least two amino acid sequences that are chosen from the group consisting of the CDR1 sequences described herein, the CDR2 sequences described herein and the CDR3 sequences described herein, such that (1) when the first amino acid sequence is chosen from the CDR1 sequences described herein, the second amino acid sequence is chosen from the CDR2 sequences described herein or the CDR3 sequences described herein; (2) when the first amino acid sequence is chosen from the CDR2 sequences described herein, the second amino acid sequence is chosen from the CDR1 sequences described herein or the CDR3 sequences described herein; or (3) when the first amino acid sequence is chosen from the CDR3 sequences described herein, the second amino acid sequence is chosen from the CDR1 sequences described herein or the CDR3 sequences described herein.

In one embodiment, an inventive composition herein may be amino acid sequences that comprise at least one antigen binding site, wherein said antigen binding site comprises at least three amino acid sequences that are chosen from the group consisting of the CDR1 sequences described herein, the CDR2 sequences described herein and the CDR3 sequences described herein, such that the first amino acid sequence is chosen from the CDR1 sequences described herein, the second amino acid sequence is chosen from the CDR2 sequences described herein, and the third amino acid sequence is chosen from the CDR3 sequences described herein. Preferred combinations of CDR1, CDR2 and CDR3 sequences will become clear from the further description herein. As will be clear to the skilled person, such an amino acid sequence is preferably an immunoglobulin sequence (as further described herein), but it may, e.g., also be any other amino acid sequence that comprises a suitable scaffold for presenting said CDR sequences.

In one embodiment, an inventive composition herein relates to an amino acid sequence directed against DR5, and in particular against DR5 as provided in public databases such as the e.g. NCBI protein database accession number BAA33723, wherein the amino acid sequence comprises one or more stretches of amino acid residues chosen from the group consisting of:

(a) the amino acid sequences of SEQ ID NO's: 41 to 44;

(b) amino acid sequences that have at least 90% amino acid identity with at least one of the amino acid sequences of SEQ ID NO's: 41 to 44;

(c) amino acid sequences that have 3, 2, or 1 amino acid difference with at least one of the amino acid sequences of SEQ ID NO's: 41 to 44;

(d) amino acid sequences of SEQ ID NO's: 51 to 55;

(e) amino acid sequences that have at least 90% amino acid identity with at least one of the amino acid sequences of SEQ ID NO's: 51 to 55;

(f) amino acid sequences that have 3, 2, or 1 amino acid difference with at least one of the amino acid sequences of SEQ ID NO's: 51 to 55;

(g) the amino acid sequences of SEQ ID NO's: 63 to 68;

(h) amino acid sequences that have at least 90% amino acid identity with at least one of the amino acid sequences of SEQ ID NO's: 63 to 68;

(i) amino acid sequences that have 3, 2, or 1 amino acid difference with at least one of the amino acid sequences of SEQ ID NO's: 63 to 68;

or any suitable combination thereof.

When an amino acid sequence of the invention contains one or more amino acid sequences according to b) and/or c):

(1) any amino acid substitution in such an amino acid sequence according to b) and/or c) is preferably, and compared to the corresponding amino acid sequence according to a), a conservative amino acid substitution; and/or (2) the amino acid sequence according to b) and/or c) preferably only contains amino acid substitutions, and no amino acid deletions or insertions, compared to the corresponding amino acid sequence according to a); and/or (3) the amino acid sequence according to b) and/or c) may be an amino acid sequence that is derived from an amino acid sequence according to a) by means of affinity maturation using one or more techniques of affinity maturation known per se.

Similarly, when an amino acid sequence of the invention contains one or more amino acid sequences according to e) and/or f):

(1) any amino acid substitution in such an amino acid sequence according to e) and/or f) is preferably, and compared to the corresponding amino acid sequence according to d), a conservative amino acid substitution; and/or (2) the amino acid sequence according to e) and/or f) preferably only contains amino acid substitutions, and no amino acid deletions or insertions, compared to the corresponding amino acid sequence according to d); and/or (3) the amino acid sequence according to e) and/or f) may be an amino acid sequence that is derived from an amino acid sequence according to d) by means of affinity maturation using one or more techniques of affinity maturation known per se.

Also, similarly, when an amino acid sequence of the invention contains one or more amino acid sequences according to h) and/or i):

(1) any amino acid substitution in such an amino acid sequence according to h) and/or i) is preferably, and compared to the corresponding amino acid sequence according to g), a conservative amino acid substitution; and/or (2) the amino acid sequence according to h) and/or i) preferably only contains amino acid substitutions, and no amino acid deletions or insertions, compared to the corresponding amino acid sequence according to g); and/or (3) the amino acid sequence according to h) and/or i) may be an amino acid sequence that is derived from an amino acid sequence according to g) by means of affinity maturation using one or more techniques of affinity maturation known per se.

It should be understood that the last preceding paragraphs also generally apply to any amino acid sequences of the invention that comprise one or more amino acid sequences according to a), b), c), d), e), f), g), h) or i), respectively.

In this specific aspect, the amino acid sequence preferably comprises one or more stretches of amino acid residues chosen from the group consisting of:

(i) the amino acid sequences of SEQ ID NO's: 41 to 44;

(ii) the amino acid sequences of SEQ ID NO's: 51 to 55; and (iii) the amino acid sequences of SEQ ID NO's: 63 to 68; or any suitable combination thereof.

Also, preferably, in such an amino acid sequence, at least one of said stretches of amino acid residues forms part of the antigen binding site for binding against DR5.

In one non-limiting aspect, the invention relates to an amino acid sequence directed against DR5, that comprises two or more stretches of amino acid residues chosen from the group consisting of:

a) the amino acid sequences of SEQ ID NO's: 41 to 44;
b) amino acid sequences that have at least 90% amino acid identity with at least one of the amino acid sequences of SEQ ID NO's: 41 to 44;
c) amino acid sequences that have 3, 2, or 1 amino acid difference with at least one of the amino acid sequences of SEQ ID NO's: 41 to 44;
d) the amino acid sequences of SEQ ID NO's: 51 to 55;
e) amino acid sequences that have at least 90% amino acid identity with at least one of the amino acid sequences of SEQ ID NO's: 51 to 55;
f) amino acid sequences that have 3, 2, or 1 amino acid difference with at least one of the amino acid sequences of SEQ ID NO's: 51 to 55;
g) the amino acid sequences of SEQ ID NO's: 63 to 68;
h) amino acid sequences that have at least 90% amino acid identity with at least one of the amino acid sequences of SEQ ID NO's: 63 to 68;
i) amino acid sequences that have 3, 2, or 1 amino acid difference with at least one of the amino acid sequences of SEQ ID NO's: 63 to 68;
such that (1) when the first stretch of amino acid residues corresponds to one of the amino acid sequences according to a), b) or c), the second stretch of amino acid residues corresponds to one of the amino acid sequences according to d), e), f), g), h) or i); (2) when the first stretch of amino acid residues corresponds to one of the amino acid sequences according to d), e) or f), the second stretch of amino acid residues corresponds to one of the amino acid sequences according to a), b), c), g), h) or i); or (3) when the first stretch of amino acid residues corresponds to one of the amino acid sequences according to g), h) or i), the second stretch of amino acid residues corresponds to one of the amino acid sequences according to a), b), c), d), e) or f).

In this specific aspect, the amino acid sequence preferably comprises two or more stretches of amino acid residues chosen from the group consisting of:

(i) the amino acid sequences of SEQ ID NO's: 41 to 44;

(ii) the amino acid sequences of SEQ ID NO's: 51 to 55; and (iii) the amino acid sequences of SEQ ID NO's: 63 to 68; such that, (1) when the first stretch of amino acid residues corresponds to one of the amino acid sequences of SEQ ID NO's: 41 to 44, the second stretch of amino acid residues corresponds to one of the amino acid sequences of SEQ ID NO's: 51 to 55 or of SEQ ID NO's: 63 to 68; (2) when the first stretch of amino acid residues corresponds to one of the amino acid sequences of SEQ ID NO's: 51 to 55, the second stretch of amino acid residues corresponds to one of the amino acid sequences of SEQ ID NO's: 41 to 44 or of SEQ ID NO's: 63 to 68; or (3) when the first stretch of amino acid residues corresponds to one of the amino acid sequences of SEQ ID NO's: 63 to 68, the second stretch of amino acid residues corresponds to one of the amino acid sequences of SEQ ID NO's: 41 to 44 or of SEQ ID NO's: 51 to 55.

Also, in such an amino acid sequence, the at least two stretches of amino acid residues again preferably form part of the antigen binding site for binding against DR5.

In one embodiment, in particular as it relates to the preceding paragraphs, the invention related to an amino acid comprising two or more amino acid sequences according to a), b), c), d), e), f), g), h) or i), respectively. In one embodiment, the amino acid sequence is a dimeric variant of a NB agent. In one embodiment, the monomers that comprise the dimer are operably linked in a single reading frame. In one embodiment, the linker sequence joining the monomers is a multimer of the sequence GGGGS (SEQ ID NO: 81) or GGGS (SEQ ID NO: 82), or a combination of both, or is selected from a linker sequences provided herein as SEQ ID NOs: 44, 45 or 46, or as known in the art.

In one embodiment, in particular as it relates to the preceding paragraphs, the invention related to an amino acid comprising three or more amino acid sequences according to a), b), c), d), e), f), g), h) or i), respectively. In one embodiment, the amino acid sequence is a trimeric variant of a NB agent. In one embodiment, the monomers that comprise the trimer are operably linked in a single reading frame. In one embodiment, the linker sequence joining the monomers is a multimer of the sequence GGGGS (SEQ ID NO: 81) or GGGS (SEQ ID NO: 82), or a combination of both, or is selected from a linker sequences provided herein as SEQ ID NOs: 44, 45 or 46, or as known in the art.

In one embodiment, in particular as it relates to the preceding paragraphs, the invention related to an amino acid comprising four or more amino acid sequences according to a), b), c), d), e), f), g), h) or i), respectively. In one embodiment, the amino acid sequence is a tetrameric variant of a NB agent. In one embodiment, the monomers that comprise the tetramer are operably linked in a single reading frame. In one embodiment, the linker sequence joining the monomers is a multimer of the sequence GGGGS (SEQ ID NO: 81) or GGGS (SEQ ID NO: 82), or a combination of both, or is selected from a linker sequences provided herein as SEQ ID NOs: 44, 45 or 46, or as known in the art.

In one embodiment, in particular as it relates to the preceding paragraphs, the invention related to an amino acid comprising five or more amino acid sequences according to a), b), c), d), e), f), g), h) or i), respectively. In one embodiment, the amino acid sequence is a pentameric variant of a NB agent. In one embodiment, the monomers that comprise the pentamer are operably linked in a single reading frame. In one embodiment, the linker sequence joining the monomers is a multimer of the sequence GGGGS (SEQ ID NO: 81) or GGGS (SEQ ID NO: 82), or a combination of both, or is selected from a linker sequences provided herein as SEQ ID NOs: 44, 45 or 46, or as known in the art.

In one embodiment, in particular as it relates to the preceding paragraphs, the invention related to an amino acid comprising six or more amino acid sequences according to a), b), c), d), e), f), g), h) or i), respectively. In one embodiment, the amino acid sequence is a hexameric variant of a NB agent. In one embodiment, the monomers that comprise the hexamer are operably linked in a single reading frame. In one embodiment, the linker sequence joining the monomers is a multimer of the sequence GGGGS (SEQ ID NO: 81) or GGGS (SEQ ID NO: 82), or a combination of both, or is selected from a linker sequences provided herein as SEQ ID NOs: 44, 45 or 46, or as known in the art.

In one embodiment, in particular as it relates to the preceding paragraphs, the invention related to an amino acid comprising two, three, four, five six, seven, eight, nine, ten or more amino acid sequences according to a), b), c), d), e), f), g), h) or i), respectively. In one embodiment, the amino acid sequence is a multimeric variant of a NB agent. In one embodiment, monomers that comprise the multimer are operably linked in a single reading frame. In one embodiment, the linker sequence joining the monomers is selected from at least one of the sequence GGGGS (SEQ ID NO: 81) or GGGS (SEQ ID NO: 82), or a combination of both, or is selected from a linker sequences provided herein as SEQ ID NOs: 44, 45 or 46, or as known to one skilled in the art.

Preferably, in such amino acid sequences the CDR sequences have at least 70% amino acid identity, preferably at least 90% amino acid identity, more preferably at least 90% amino acid identity, such as at least 95% amino acid identity or more or even essentially 100% amino acid identity with the CDR sequences of at least one of the amino acid sequences of SEQ ID NO's: 1-22, 26-40, 87-88, and 102-103. This degree of amino acid identity can, e.g., be determined by determining the degree of amino acid identity (in a manner described herein) between said amino acid sequence and one or more of the sequences of SEQ ID NO's: 1-22, 26-40, 87-88, and 102-103, in which the amino acid residues that form the framework regions are disregarded. Also, such amino acid sequences can be humanized or modified as further described herein.

Also, such amino acid sequences are preferably such that they can specifically bind to DR5; and more in particular bind to DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as provided herein.

In one non-limiting aspect, the invention relates to an amino acid sequence that essentially consists of four framework regions (FR1 to FR4, respectively) and three complementarity determining regions (CDR1 to CDR3, respectively), in which the CDR sequences of said amino acid sequence have at least 70% amino acid identity, preferably at least 90% amino acid identity, more preferably at least 90% amino acid identity, such as at least 95% amino acid identity or more, at least 98% amino acid identity or more, at least 99% amino acid identity or more, or even essentially 100% amino acid identity with the CDR sequences of at least one of the amino acid sequences of SEQ ID NO's: 1-22, 26-40, 87-88, and 102-103. This degree of amino acid identity can, e.g., be determined by determining the degree of amino acid identity (in a manner described herein) between said amino acid sequence and one or more of the sequences of SEQ ID NO's: 1-22, 26-40, 87-88, and 102-103, in which the amino acid residues that form the framework regions are disregarded. Such amino acid sequences of the invention can be as further modified as described herein.

In such an amino acid sequence of the invention, the framework sequences may be any suitable framework sequences, and examples of suitable framework sequences will be clear to the skilled person, e.g., on the basis the standard handbooks and the further disclosure and art references mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$ sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional VH sequences that have been camelized.

The framework sequences are preferably such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a NB agent (including but not limited to $V_H$ and/or $V_{HH}$ sequence). Again, suitable framework sequences will be clear to the skilled person, e.g., on the basis the standard handbooks and the further disclosure and art references mentioned herein.

In one embodiment, as generally described herein for the amino acid sequences of the invention, it is possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived). Such fragments may also again be such that they comprise or can form an immunoglobulin fold, or alternatively be such that they do not comprise or cannot form an immunoglobulin fold.

In one aspect, such a fragment comprises a single CDR sequence as described herein (and in particular a CDR3 sequence), that is flanked on each side by (part of) a framework sequence (and in particular, part of the framework sequence(s) that, in the immunoglobulin sequence from which the fragment is derived, are adjacent to said CDR sequence. For example, a CDR3 sequence may be preceded by (part of) a FR3 sequence and followed by (part of) a FR4 sequence). Such a fragment may also contain a disulphide bridge, and in particular a disulphide bridge that links the two framework regions that precede and follow the CDR sequence, respectively (for the purpose of forming such a disulphide bridge, cysteine residues that naturally occur in said framework regions may be used, or alternatively cysteine residues may be synthetically added to or introduced into said framework regions). In one embodiment, such a construct is an Expedite fragment. For a further description of these "Expedite fragments", reference is again made to WO 03/050531, as well as to the US provisional application of Ablynx N.V. entitled "Peptides capable of binding to serum proteins" of Ablynx N.V. (inventors: Revets et al.) filed on Dec. 5, 2006.

In one aspect, the invention relates to a NB agent, and in particular a protein or polypeptide that comprises or essentially consists of one or more amino acid sequences of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence of the invention (and/or to the compound or construct in which it is present) and may or may not modify the properties of the amino acid sequence of the invention.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb's", amino acid sequences that are suitable for use as a dAb, or camelid $V_{HH}$ constructs.

In one embodiment, such groups, residues, moieties or binding units may e.g., be chemical groups, residues, moieties, which may or may not by themselves be biologically and/or pharmacologically active. For example, and without limitation, such groups may be linked to the one or more amino acid sequences of the invention so as to provide a "derivative" of an amino acid sequence or polypeptide of the invention, as further described herein.

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are amino acid sequences.

In the compounds or constructs described above, the one or more amino acid sequences of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion protein or fusion polypeptide. The amino acid sequences of such linkers may be as provided herein, or may be one known to a person skilled in the art.

The compounds or polypeptides of the invention can generally be prepared by a method which comprises at least one step of suitably linking the one or more amino acid sequences of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, e.g., on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted amino acid sequences form a further aspect of the invention.

According to one preferred aspect, a compound of the invention is a multivalent polypeptide that contains two or more (preferably three or more, four or more, five or more, six or more, eight or more, and/or ten or more) amino acid sequences directed against the DR5 (e.g. amino acid sequences as provided herein), optionally linked via one or more suitable linkers (which may be as further described herein) or via a cross-linking technique or covalent bond created in a manner known to one skilled in the art. In one or more alternative embodiments, the multivalent polypeptide contains an optional subunit that binds to a target other than DR5.

In particular, a compound of the invention may be such a multivalent polypeptide which is capable of inducing, triggering, increasing or enhancing the signaling mediated by the DR5, and more in particular of triggering or inducing apoptosis in the cell on which the DR5 is present. In one embodiment, the multivalent polypeptide consists of three monomeric DR5 binding units that are operably linked, thereby creating a trimeric polypeptide. In one embodiment, the multivalent polypeptide consists of four monomeric DR5 binding units that are operably linked, thereby creating a tetrameric polypeptide. In one embodiment, the multivalent polypeptide consists of five monomeric DR5 binding units that are operably linked, thereby creating a pentameric polypeptide. In one embodiment, the multivalent polypeptide consists of six monomeric DR5 binding units that are operably linked, thereby creating a hexameric polypeptide. In one embodiment, the multivalent polypeptide consists of seven, eight, nine, ten or more monomeric DR5 binding units that are operably linked, thereby creating additional variants of a multimeric protein.

As already mentioned herein, such multimeric polypeptide may be further such that it can bind to the binding site of TRAIL on the DR5, and/or such that they can compete with TRAIL for binding to the DR5.

The multivalent polypeptide may also be such that it does not bind to the binding site for TRAIL on the DR5, and/or essentially does not prevent or inhibit the binding of TRAIL to the DR5, and/or does not compete with TRAIL for binding to the DR5, and/or even be such that they increase or enhance the signaling that is mediated by TRAIL and the DR5 upon binding of TRAIL to its receptor (which may again result in a synergistic effect upon the signaling mediated by the DR5). In one embodiment, said multivalent polypeptide binds to DR5 with a higher affinity than a monovalent composition.

In the multivalent polypeptides of the invention, the amino acid sequences of the invention that form the binding units may each be directed against the same epitope on the DR5 receptor, e.g., an epitope of DR5, or against different epitopes on the DR5.

In one specific aspect of the invention, a compound of the invention or a polypeptide of the invention may have an increased half-life, compared to the corresponding amino acid sequence of the invention. Some non-limiting examples of such compounds and polypeptides will become clear to the skilled person based on the further disclosure herein, and e.g., comprise amino acid sequences or polypeptides of the invention that have been chemically modified to increase the half-life thereof (for example, by means of pegylation); amino acid sequences of the invention that comprise at least one additional binding site for binding to a serum protein (such as serum albumin); or polypeptides of the invention that comprise at least one amino acid sequence of the invention that is linked to at least one moiety (and in particular at least one amino acid sequence) that increases the half-life of the amino acid sequence of the invention. Examples of polypeptides of the invention that comprise such half-life extending moieties or amino acid sequences will become clear to the skilled person based on the further disclosure herein; and, e.g., include, without limitation, polypeptides in which the one or more amino acid sequences of the invention are suitable linked to one or more serum proteins or fragments thereof (such as (human) serum albumin or suitable fragments thereof) or to one or more binding units that can bind to serum proteins (such as, e.g., domain antibodies, amino acid sequences that are suitable for use as a domain antibody, single domain antibodies, amino acid sequences that are suitable for use as a single domain antibody, (dAb's), amino acid sequences that are suitable for use as a dAb, or NANOBODIES™ that can bind to serum proteins such as serum albumin (such as human serum albumin), serum immunoglobulins such as IgG, or transferrine; reference is made to the further description and references mentioned herein); polypeptides in which an amino acid sequence of the invention is linked to an Fc portion (such as a human Fc) or a suitable part or fragment thereof; or polypeptides in which the one or more amino acid sequences of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006.

Generally, the compounds or polypeptides of the invention with increased half-life preferably have a half-life that is at least 1.5 times, preferably at least 2 times, such as at least 5 times, e.g., at least 10 times or more than 20 times, greater than the half-life of the corresponding amino acid sequence of the invention per se. For example, the compounds or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention relates to a nucleic acid that encodes an amino acid sequence of the invention or a polypeptide of the invention (or a suitable fragment thereof). Such a nucleic acid will also be referred to herein as a "nucleic acid of the invention" and may, e.g., be in the form of a genetic construct, e.g., a CDR fragment or in a vector, as further described herein. In one embodiment, the nucleic acid sequences of the invention encode the NB constructs of any one or more polypeptide disclosed in any one or more of Tables 1 through 4. In one embodiment, the nucleic acid sequence of the invention encodes any one or more construct provided in SEQ ID NOs: 1-72, 81-82 and 87-92. In one embodiment, the nucleic acid sequences of the invention are codon optimized for expression in the host cell or host organism of interest. In one embodiment, the codon optimization is for expression in a mammalian cell. In one embodiment, the codon optimization is for expression in a yeast cell. In one embodiment, the codon optimization is for expression in *E. coli*.

In another aspect, the invention relates to a host or host cell that expresses (or that under suitable circumstances is capable of expressing) an amino acid sequence of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention, at least one polypeptide of the invention (or a suitable fragment thereof), at least one compound of the invention and/or at least one nucleic acid of the invention, and optionally one or more further components of such compositions known per se, i.e., depending on the intended use of the composition. Such a product or composition may, e.g., be a pharmaceutical composition (as described herein), a veterinary composition or a product or composition for diagnostic use (as also described herein). Some non-limiting examples of such products or compositions are provided herein.

In one embodiment the invention relates to the use of a NB construct, or of a composition comprising the same, in methods or compositions for modulating DR5, either in vitro (e.g. in an in vitro or cellular assay) or in vivo (e.g. in an a single cell or in a multicellular organism, and in particular in a mammal, and more in particular in a human being, such as in a human being that is at risk of or suffers from a diseases and disorders associated with DR5).

The invention also relates to methods for modulating DR5, either in vitro (e.g. in an in vitro or cellular assay) or in vivo (e.g. in an a single cell or multicellular organism, and in particular in a mammal, and more in particular in a human being, such as in a human being that is at risk of or suffers from a diseases and disorders associated with DR5), which method comprises at least the step of contacting DR5 with at least one amino acid sequence, NB construct of the invention, or with a composition comprising the same, in a manner and in an amount suitable to modulate DR5, with at least one amino acid sequence, NB construct of the invention.

The invention also relates to the use of an one amino acid sequence, NB construct of the invention in the preparation of a composition (such as, without limitation, a pharmaceutical composition or preparation as further described herein) for modulating DR5, either in vitro (e.g. in an in vitro or cellular assay) or in vivo (e.g. in an a single cell or multicellular organism, and in particular in a mammal, and more in particular in a human being, such as in a human being that is at risk of or suffers from a diseases and disorders associated with DR5).

In the context of the present invention, "modulating" or "to modulate" generally means either reducing or completely inhibiting the activity of, or alternatively increasing the activity of, DR5, as measured using a suitable in vitro, cellular or in vivo assay (such as those mentioned herein). In particular, "modulating" or "to modulate" may mean either reducing or completely inhibiting the activity of, or alternatively increasing the activity of DR5, as measured using a suitable in vitro, cellular or in vivo assay (such as those mentioned herein), by at least 1%, preferably at least 5%, such as at least 10% or at least 25%, e.g., by at least 50%, at least 60%, at least 70%, at least 80%, or at least 90% or more, compared to activity of DR5 in the same assay under the same conditions but without the presence of the NB construct of the invention. In a main embodiment, DR5 activity, especially including DR5-mediated signaling, requires the formation of a trimer of DR5 on the cell surface. In one embodiment, a NB construct herein acts to modulate DR5 activity by promoting the formation of a DR5 homotrimer and thereby increasing the DR5-mediated initiation of apoptosis, e.g., via the extrinsic cell death pathway.

As will be clear to the skilled person, "modulating" may also involve effecting a change (which may either be an increase or a decrease) in affinity, avidity, specificity and/or selectivity of DR5 for one or more of its targets, ligands or substrates; and/or effecting a change (which may either be an increase or a decrease) in the sensitivity of DR5 for one or more conditions in the medium or surroundings in which DR5 is present (such as pH, ion strength, the presence of co-factors, etc.), compared to the same conditions but without the presence of the amino acid sequence, NB construct of the invention. As will be clear to the skilled person, this may again be determined in any suitable manner and/or using any suitable assay known per se, such as the assays described herein or in the art references cited herein.

"Modulating" may also mean effecting a change (i.e., an activity as an agonist or as an antagonist, respectively) with respect to one or more biological or physiological mechanisms, effects, responses, functions, pathways or activities in which DR5 (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, such as the assays described herein or in the art references cited herein. In particular, an action as an agonist or antagonist may be such that an intended biological or physiological activity is increased or decreased, respectively, by at least 1%, preferably at least 5%, such as at least 10% or at least 25%, e.g., by at least 50%, at least 60%, at least 70%, at least 80%, or at least 90% or more, compared to the biological or physiological activity in the same assay under the same conditions but without the presence of the NB construct of the invention.

Modulating may, e.g., involve reducing or inhibiting the binding of DR5 to one of its substrates or ligands and/or competing with a natural ligand, substrate for binding to DR5. Modulating may also involve activating DR5 or the mechanism or pathway in which it is involved. Modulating may be reversible or irreversible, but for pharmaceutical and pharmacological purposes will usually be in a reversible manner.

The invention further relates to methods for preparing or generating the amino acid sequences, polypeptides, nucleic acids, host cells, products and compositions described herein. Some preferred but non-limiting examples of such methods will become clear from the further description herein.

Generally, these methods may comprise the steps of:

a) providing a set, collection or library of amino acid sequences;

b) screening said set, collection or library of amino acid sequences for amino acid sequences that can bind to and/or have affinity for DR5; and c) isolating the amino acid sequence(s) that bind to and/or have affinity for DR5.

In such a method, the set, collection or library of amino acid sequences may be any suitable set, collection or library of amino acid sequences. For example, the set, collection or library of amino acid sequences may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of amino acid sequences may be a set, collection or library of heavy chain variable domains (such as $V_H$ domains or $V_{HH}$ domains) or of light chain variable domains. For example, the set, collection or library of amino acid sequences may be a set, collection or library of domain antibodies or single domain antibodies, or may be a set, collection or library of amino acid sequences that are capable of functioning as a domain antibody or single domain antibody.

In a preferred aspect of this method, the set, collection or library of amino acid sequences may be an immune set, collection or library of immunoglobulin sequences, e.g., derived from a mammal that has been suitably immunized with DR5 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, e.g., on the basis of the further disclosure herein. Reference is also made to the review by Hoogenboom in Nature Biotechnology, 23(9): 1105-1116 (2005).

In another aspect, the method for generating amino acid sequences comprises at least the steps of:

a) providing a collection or sample of cells expressing amino acid sequences;

b) screening said collection or sample of cells for cells that express an amino acid sequence that can bind to and/or have affinity for DR5; and c) either (1) isolating said amino acid sequence; or (2) isolating from said cell a nucleic acid sequence that encodes said amino acid sequence, followed by expressing said amino acid sequence.

For example, when the desired amino acid sequence is an immunoglobulin sequence, the collection or sample of cells may, e.g., be a collection or sample of B-cells. Also, in this method, the sample of cells may be derived from a mammal that has been suitably immunized with DR5 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is, e.g., made to EP 0 542 810, WO 05/19824, WO 04/051268 and WO 04/106377. The screening of step b) is preferably performed using a flow cytometry technique such as FACS. For this, reference is, e.g., made to Lieby et al., Blood, 97(12), 3820 (2001).

In another aspect, the method for generating an amino acid sequence directed against DR5 may comprise at least the steps of:

a) providing a set, collection or library of nucleic acid sequences encoding amino acid sequences;

b) screening said set, collection or library of nucleic acid sequences for nucleic acid sequences that encode an amino acid sequence that can bind to and/or has affinity for DR5; and c) isolating said nucleic acid sequence, followed by expressing said amino acid sequence.

In such a method, the set, collection or library of nucleic acid sequences encoding amino acid sequences may, e.g., be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

Also, in such a method, the set, collection or library of nucleic acid sequences may encode a set, collection or library of heavy chain variable domains (such as $V_H$ domains or $V_{HH}$ domains) or of light chain variable domains. In one example, the set, collection or library of nucleic acid sequences encode a set, collection or library of domain antibodies or single domain antibodies, or a set, collection or library of amino acid sequences that are capable of functioning as a domain antibody or single domain antibody.

In one aspect of this method, the set, collection or library of amino acid sequences may be an immune set, collection or library of nucleic acid sequences, e.g., derived from a mammal that has been suitably immunized with DR5 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The set, collection or library of nucleic acid sequences may, e.g., encode an immune set, collection or library of heavy chain variable domains or of light chain variable domains. In one specific aspect, the set, collection or library of nucleotide sequences may encode a set, collection or library of $V_{HH}$ sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, e.g., on the basis of the further disclosure herein. Reference is also made to the review by Hoogenboom in Nature Biotechnology, 23(9): 1105-1116 (2005).

The invention also relates to amino acid sequences that are obtained by the above methods, or alternatively by a method that comprises one of the above methods and in addition at least the steps of determining the nucleotide sequence or amino acid sequence of said immunoglobulin sequence; and of expressing or synthesizing said amino acid sequence in a known manner, such as by expression in a suitable host cell or host organism or by chemical synthesis.

Also, following the steps above, one or more amino acid sequences of the invention may be suitably humanized (or alternatively camelized); and/or the amino acid sequence(s) thus obtained may be linked to each other or to one or more other suitable amino acid sequences (optionally via one or more suitable linkers) so as to provide a polypeptide of the invention. Also, a nucleic acid sequence encoding an amino acid sequence of the invention may be suitably humanized (or alternatively camelized) and suitably expressed; and/or one or more nucleic acid sequences encoding an amino acid sequence of the invention may be linked to each other or to one or more nucleic acid sequences that encode other suitable amino acid sequences (optionally via nucleotide sequences that encode one or more suitable linkers), after which the nucleotide sequence thus obtained may be suitably expressed so as to provide a polypeptide of the invention.

The invention further relates to applications and uses of the amino acid sequences, compounds, constructs, polypeptides, nucleic acids, host cells, products and compositions described herein, as well as to methods for the prevention and/or treatment for diseases and disorders associated with DR5. Some preferred but non-limiting applications and uses will become clear from the further description herein.

In one embodiment, the invention relates to the amino acid sequences, compounds, constructs, polypeptides, nucleic acids, host cells, products and compositions described herein for use in therapy of a disease or disorder.

In one embodiment, the invention relates to one or more of the amino acid sequences, compounds, constructs, polypeptides, nucleic acids, host cells, products and compositions described herein for use in therapy of a subject at risk for or suffering from a disease or disorder that can be prevented or treated by administering, to the subject in need thereof, a pharmaceutically effective amount of an amino acid sequence, compound, construct or polypeptide as described herein as an NB agent or NB construct.

In one embodiment, the invention relates to the amino acid sequences, compounds, constructs, polypeptides, nucleic acids, host cells, products and compositions described herein for use in therapy of diseases and disorders associated with DR5.

Other aspects, embodiments, advantages and applications of the invention will become clear from the further description herein, in which the invention is described and discussed in more detail.

In certain embodiments, inventive $V_{HH}$ variants of the NB agents generally offer certain advantages (outlined herein) compared to "dAb's" or similar (single) domain antibodies or immunoglobulin sequences, which advantages are also provided by the inventive compositions of the invention. However, it will be clear to the skilled person that the more general aspects of the teaching below can also be applied (either directly or analogously) to other amino acid sequences of the invention.

DEFINITIONS

In the present description, examples and claims, the following definitions are generally applied, unless indicated otherwise. As used below and throughout the text, the use of a term or phrase in the singular is meant to incorporate the meaning of the plural, and vice versa, unless noted otherwise or apparent through context.

Unless indicated or defined otherwise, all terms used have their usual meaning in the art, which will be clear to the skilled person. Reference is made, e.g., to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10 Ed. Blackwell Publishing, UK (2001); and Janeway et al., "Immunobiology" (6th Ed.), Garland Science Publishing/Churchill Livingstone, New York (2005), as well as to the general background art cited herein. Additional references include, e.g., the following reviews: Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

Unless indicated otherwise, it is believed that all methods, steps, techniques and manipulations that are not specifically described in detail can be performed and have been performed in a manner known per se, and will be clear to the skilled person. Reference is again made, e.g., to the standard handbooks and the general background art mentioned herein and to the further references cited therein. Amino acid residues will be indicated according to the standard three-letter or one-letter amino acid code as provided by the IUPAC Code Tables.

Unless indicated otherwise, the term "immunoglobulin sequence", whether used herein to refer to a heavy chain antibody or to a conventional four-chain antibody, is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "sequence" as used herein (for example in terms like "immunoglobulin sequence", "antibody sequence", "variable domain sequence", "sdAb sequence", "$V_H$ sequence", "$V_{HH}$ sequence" or "protein sequence"), is generally used to include both the relevant amino acid sequence as well as nucleic acid sequences or nucleotide sequences encoding the same, unless the context requires a more limited interpretation.

Unless indicated otherwise, the terms "nucleotide sequence" and "nucleic acid" generally is used interchangeably to refer to a polymer of deoxyribonucleic acids (DNA) or ribonucleic acids (RNA), unless the context requires a more limited interpretation.

For the purposes of comparing two or more nucleotide sequences, the percentage of "sequence identity" between a first nucleotide sequence and a second nucleotide sequence may be calculated or determined, e.g., by taking the number of nucleotides in the first nucleotide sequence that are identical to the nucleotides at the corresponding positions in the second nucleotide sequence, dividing that number by the total number of nucleotides in the first nucleotide sequence and then multiplying by 100%. Each deletion, insertion, substitution or addition of a nucleotide in the second nucleotide sequence—when compared to the first nucleotide sequence—is considered as a difference at a single nucleotide position. One skilled in the art may also use a suitable computer algorithm or technique such as, e.g., NCBI Blast v2.0, using standard settings.

With regard to framework 1 (FR1), it should be clear to the skilled person that, for determining the degree of amino acid identity, the amino acid residues on positions 1 to 4 and 27 to 30 are preferably disregarded.

In one embodiment, in determining the degree of sequence identity between two amino acid sequences, the skilled person may take into account so-called "conservative" amino acid substitutions. Conservative substitutions are known in that art and are substitutions in which one amino acid is substituted by another amino acid residue within the same group that have a common property. Conserved amino acid groups and their common properties are as follows: (a) small aliphatic, nonpolar or slightly polar residues, including Ala, Ser, Thr, Pro and Gly; (b) polar, negatively charged residues and their (uncharged) amides, including Asp, Asn, Glu and Gln; (c) polar, positively charged residues, including His, Arg and Lys; (d) large aliphatic, nonpolar residues, including Met, Leu, He, Val and Cys; and (e) aromatic residues, including Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 1981, and Goldman et al., Ann. Rev. Biophys. Chem. 15: 321-353, 1986. Information on the primary, secondary and tertiary structure of camelid $V_{HH}$ constructs is given in the general background art cited above, and the crystal structure of such a $V_{HH}$ construct from a llama is, e.g., given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the art cited above.

Amino acid sequences and nucleic acid sequences are said to be "exactly the same" if they have 100% sequence identity over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

When a nucleotide sequence or amino acid sequence is said to "comprise" another nucleotide sequence or amino acid sequence, respectively, or to "essentially consist of another nucleotide sequence or amino acid sequence, this generally means that the first mentioned nucleotide sequence or amino acid sequence has within its sequence a stretch of nucleotides or amino acid residues, respectively, that has the same nucleotide sequence or amino acid sequence, respectively, as the latter sequence, irrespective of how the first mentioned sequence has actually been generated or obtained (which may, e.g., be by any suitable method described herein).

The term "in essentially isolated form" for a nucleic acid or amino acid sequence is separated from at least one other component with which it is usually associated in a source or medium, compared to its native biological source and/or the reaction medium or cultivation medium from which it has been obtained. The "at least one other component" may be another nucleic acid, another protein/polypeptide, another biological component or macromolecule or at least one contaminant, impurity or minor component. In one embodiment, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis.

The terms "domain" and "binding domain" as used herein generally refers to a globular region of an antibody chain, and in particular to a globular region of a heavy chain antibody, or to a polypeptide that essentially consists of such a globular region. Usually, such a domain will comprise peptide loops (for example 3 or 4 peptide loops) stabilized, e.g., as a sheet or by disulfide bonds.

The terms "antigenic determinant" and "epitope", which may also be used interchangeably herein, refers to the epitope on the antigen recognized by the antigen-binding molecule (such as a NB construct of the invention) and more in particular by the antigen-binding site of said molecule.

An amino acid sequence (such as a NB construct of the invention, a $V_{HH}$ or $V_H$ construct, an antibody, or generally an antigen binding protein or polypeptide or a fragment thereof) that can (specifically) bind to, that has affinity for, and/or that has specificity for a particular antigenic determinant, epitope, antigen or protein (or for at least one part, fragment or epitope thereof) is said to be "against" or "directed against" said antigenic determinant, epitope, antigen or protein.

The term "specificity" as mentioned therein refers to the number of different types of antigens or antigenic determinants to which a particular antigen-binding molecule or antigen-binding protein (such as a NB construct of the invention) molecule can bind. The specificity of an antigen-binding protein can be determined based on affinity and/or avidity. Typically, antigen-binding proteins (such as the NB construct of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ M$^{-1}$) liters/mol is generally considered to indicate non-specific binding. Preferably, a NB construct of the invention will bind to its desired antigen with an affinity less than 500 nM, preferably less than 200 nM, more preferably less than 10 nM, such as less than 500 pM. "Specific binding" of an antigen-binding protein to an antigen or antigenic determinant can be determined in any suitable manner known per se, including, e.g., Scatchard analysis and/or competitive binding assays, such as radioimmunoassays (RIA), enzyme immunoassays (EIA) and sandwich competition assays, and the different variants thereof known per se in the art; as well as the other techniques mentioned herein.

"Affinity", represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person, affinity can be determined in a manner known per se, depending on the specific antigen of interest.

"Avidity" is the measure of the strength of binding between an antigen-binding molecule (such as a NB construct of the invention) and the pertinent antigen. Avidity is related to both the affinity between an antigenic determinant and its antigen binding site on the antigen-binding molecule and the number of pertinent binding sites present on the antigen-binding molecule.

The dissociation constant may be the actual or apparent dissociation constant. Methods for determining the dissociation constant are known in the art.

The phrase "specifically binds" or "selectively binds," when used in the context of describing the interaction between an antigen (e.g., a protein) and an NB construct, or functional fragment thereof, e.g., having the disclosed CDRs in the framework of an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the NB construct, antibodies or binding agents with a particular binding specificity bind to a particular antigen at least two times the background and do not substantially bind in a significant amount to other antigens present in the sample. In one embodiment, under designated immunoassay conditions, the NB construct, antibody or binding agents with a particular binding specificity bind to a particular antigen at least ten (10) times the background and do not substantially bind in a significant amount to other antigens present in the sample. Specific binding to an NB construct, antibody or binding agent under such conditions may require the NB construct, antibody or binding agent to have been selected for its specificity for a particular protein. As desired or appropriate, this selection may be achieved by subtracting out NB constructs or antibodies that cross-react with, e.g., DR5 molecules from other species (e.g., mouse or rat) or other polypeptides that are Death Receptor family members or subtypes. Alternatively, in some embodiments, NB constructs, antibodies or antibody fragments are selected that cross-react with certain desired molecules.

A variety of immunoassay formats may be used to select NB constructs that are specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity) and can likewise be used for NB construct binding analysis. Typically a specific or selective binding reaction will produce a signal at least twice over the background signal and more typically at least than 10 to 100 times over the background. In addition to the affinity constant ($K_A$) described herein, an DR5-binding NB construct of the invention typically also has a dissociation rate constant ($K_D$) ($k_{off}/k_{on}$) of less than $5 \times 10^{-2}$M, less than $10^{-2}$M, less than $5 \times 10^{-3}$M, less than $10^{-3}$M, less than $5 \times 10^{-4}$M, less than $10^{-4}$M, less than $5 \times 10^{-5}$M, less than $10^{-5}$M, less than $5 \times 10^{-6}$M, less than $10^{-6}$M, less than $5 \times 10^{-7}$M, less than $10^{-7}$M, less than $5 \times 10^{-8}$M, less than $10^{-8}$M, less than $5 \times 10^{-9}$M, less than $10^{-9}$M, less than $5 \times 10^{-10}$M less than $10^{-10}$M less than $5 \times 10^{-11}$M, less than $10^{-11}$M, less than $5 \times 10^{-12}$M less than $10^{-12}$M, less than $5 \times 10^{-13}$M, less than $10^{-13}$M, less than $5 \times 10^{-14}$M, less than $10^{-14}$M, less than $5 \times 10^{-15}$M, or less than $10^{-15}$M or lower, and binds to DR5 with an affinity that is at least two-fold greater than its affinity for binding to a non-specific antigen (e.g., human serum albumin "HSA").

The half-life of an amino acid sequence, compound or polypeptide of the invention generally refers to the time taken for the serum concentration of the construct to be reduced by 50%, in vivo, e.g., due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art. Half-life can be expressed using parameters such as the $t_{1/2}$-alpha, $t_{1/2}$-beta and the area under the curve (AUC). See the Experimental Part below, plus standard handbooks, such as Kenneth et al., Chemical Stability of Pharmaceuticals: A Handbook for Pharmacists, and Peters et al., Pharmacokinetic analysis: A Practical Approach (1996); Gibaldi & Perron, "Pharmacokinetics", published by Marcel Dekker, 2nd Rev. edition (1982). The terms "increase in half-life" or "increased half-life" refer to an increase in the $t_{1/2}$-beta, either with or without an increase in the $t_{1/2}$-alpha and/or the AUC or both.

"Diseases and disorders associated with DR5" are as defined above and throughout the specification. While not being limited by theory, the mechanism of action of DR5 in such diseases and/or disorders is believed to be as provided. Nonlimiting examples of contemplated diseases and disorders associated with DR5 are as provided and throughout the specification, and others may become apparent to one skilled in the art based upon the teachings provided herein.

In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, e.g., by at least 50%, at least 60%, at least 70%, at least 80%, or at least 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

In one embodiment, "modulating" may also mean effecting a change (i.e., an activity as a neutralizing agent, as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. As will be clear to the skilled person, such an action as a neutralizing agent, as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, e.g., by at least 50%, at least 60%, at least 70%, at least 80%, or at least 90% or more, compared to the biological or physiological activity in the same assay under the same conditions but without the presence of the construct of the invention.

Modulating may involve, e.g., allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may also involve, e.g., effecting a change in respect of the folding or confirmation of the target or antigen, or in respect of the ability of the target or antigen to fold, to change its confirmation (for example, upon binding of a ligand), to associate with other (sub)units, or to disassociate. Modulating may involve, e.g., effecting a change in the ability of the target or antigen to transport other compounds or to serve as a channel for other compounds (such as ions).

Modulating may be reversible or irreversible, but for pharmaceutical and pharmacological purposes will usually be in a reversible manner.

In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerization (such as homomerization or heteromerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signaling, biological mechanism or biological effect in which the target or antigen is involved) is modulated.

An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10,000 times or more better than the affinity with which said amino acid sequence or polypeptide binds to the second target or polypeptide. For example, the first antigen may bind to the target or antigen with a $K_D$ value that is at least 10 times less, e.g., at least 100 times less, and preferably at least 1000 times less, such as 10,000 times less or even a greater fold difference, than the $K_D$ with which said amino acid sequence or polypeptide binds to the second target or polypeptide. In one embodiment, when an amino acid sequence or polypeptide is "specific for" a first target or antigen compared to a second target or antigen, it is directed against said first target or antigen, but not directed against said second target or antigen.

The terms "cross-block", "cross-blocked" and "cross-blocking" are used interchangeably herein to mean the ability of an amino acid sequence or other binding agents (such as a polypeptide of the invention) to interfere with the binding of other amino acid sequences or binding agents of the invention to a given target. The extend to which an amino acid sequence or other binding agents of the invention is able to interfere with the binding of another to DR5, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between amino acid sequence or another binding agents in terms of their binding to the target.

A suitable assay for determining whether an amino acid sequence or other binding agent cross-blocks or is capable of cross-blocking according to the invention is an exemplary Biacore assay or an exemplary ELISA assay.

An amino acid sequence is said to be "cross-reactive" for two different antigens or antigenic determinants (such as serum albumin from two different species of mammal, such as human serum albumin and cyno serum albumin) if it is specific for both these different antigens or antigenic determinants.

By binding that is "essentially independent of the pH" is generally meant herein that the association constant ($K_A$) of the amino acid sequence with respect to the serum protein (such as serum albumin) at the pH value(s) that occur in a cell of an animal or human body (as further described herein) is at least 5%, such as at least 10%, preferably at least 25%, more preferably at least 50%, even more preferably at least 60%, such as even more preferably at least 70%, such as at least 80% or at least 90% or more (or even more than 100%, such as more than 110%, more than 120% or even 130% or more, or even more than 150%, or even more than 200%) of the association constant ($K_A$) of the amino acid sequence with respect to the same serum protein at the pH value(s) that occur outside said cell. Alternatively, by binding that is "essentially independent of the pH" is generally meant herein that the $k_{off}$ rate (measured by Biacore—see e.g. Experiment 2) of the amino acid sequence with respect to the serum protein (such as serum albumin) at the pH value(s) that occur in a cell of an animal or human body (as e.g. further described herein, e.g. pH around 5.5, e.g. 5.3 to 5.7) is at least 5%, such as at least 10%, preferably at least 25%, more preferably at least 50%, even more preferably at least 60%, such as even more preferably at least 70%, such as at least 80% or at least 90% or more (or even more than 100%, such as more than 110%, more than 120% or even 130% or more, or even more than 150%, or even more than 200%) of the $k_{off}$ rate of the amino acid sequence with respect to the same serum protein at the pH value(s) that occur outside said cell, e.g. pH 7.2 to 7.4. By "the pH value(s) that occur in a cell of an animal or human body" is meant the pH value(s) that may occur inside a cell, and in particular inside a cell that is involved in the recycling of the serum protein. In particular, by "the pH value(s) that occur in a cell of an animal or human body" is meant the pH value(s) that may occur inside a (sub)cellular compartment or vesicle that is involved in recycling of the serum protein (e.g. as a result of pinocytosis, endocytosis, transcytosis, exocytosis and phagocytosis or a similar mechanism of uptake or internalization into said cell), such as an endosome, lysosome or pinosome.

As further described herein, the total number of amino acid residues in a NB construct can be in the region of 110-120, is preferably 112-115, and is most preferably 113. It should however be noted that parts, fragments, analogs or derivatives (as further described herein) of a NB construct are not particularly limited as to their length and/or size, as long as such parts, fragments, analogs or derivatives meet the further requirements outlined herein, and are optionally suitable for the purposes herein.

As mentioned herein "preferred" (or "more preferred", "even more preferred", etc.) apply to specific NB compounds or variants thereof, or their uses, for a variety of embodiments described herein, or for particular embodiments if so described.

The amino acid residues of a NB construct are numbered according to the general numbering for $V_H$ domains as given by Kabat et al. "Sequence of proteins of immunological interest", US Public Health Services, NIH Bethesda, Md., Publication No. 91, as applied to $V_{HH}$ domains from Camelids in the article of Riechmann and Muyldermans, J. Immunol. Methods 2000 Jun. 23; 240 (1-2): 185-195 (see, e.g., FIG. 2 of this publication). Accordingly, in general a FR1 of a NB construct comprises the amino acid residues at positions 1-30, a CDR1 of a NB construct comprises the amino acid residues at positions 31-35, a FR2 of a NB construct comprises the amino acids at positions 36-49, a CDR2 of a NB construct comprises the amino acid residues at positions 50-65, a FR3 of a NB construct comprises the amino acid residues at positions 66-94, a CDR3 of a NB construct comprises the amino acid residues at positions 95-102, and a FR4 of a NB construct comprises the amino acid residues at positions 103-113. However, it is well known in the art for $V_H$ domains and for $V_{HH}$ domains that the total number of amino acid residues in each of the CDR's may vary and therefore may not correspond to the total number of amino acid residues indicated by the Kabat numbering. By way of example, for an inventive NB construct described herein, the amino acid residues and their position in the NB construct for their particular FR1, CDR1, FR2, CDR2, FR3, CDR3 and FR4 are as provided in Table 4 herein. Other methods such as Chothia (Al-Lazikani et al., (1997) JMB 273, 927-948 ("Chothia" numbering scheme)) may be used to define alternative versions of the particular CDRs, and crystalographic determination of contact points and interaction sites may further inform one skilled in the art as to the extent of each particular CDR and/or FR region.

The Figures, Sequence Listing and the Experimental Part/Examples are given to further illustrate the invention and should not be interpreted or construed as limiting the scope of the invention and/or of the appended claims in any way, except if explicitly indicated otherwise herein.

For a general description of heavy chain antibodies and the variable domains thereof, reference is inter alia made to the art references cited herein.

In accordance with the terminology used in the art, the variable domains present in naturally occurring heavy chain antibodies will also be referred to as "$V_{HH}$ domains", in order to distinguish them from the heavy chain variable domains that are present in conventional 4-chain antibodies (which will be referred to herein as "$V_H$ domains") and from the light chain variable domains that are present in conventional 4-chain antibodies (which will be referred to herein as "$V_L$ domains"). In general, $V_{HH}$ domains have been "designed" by nature to functionally bind to an antigen without the presence of, and without any interaction with, a light chain variable domain.

As mentioned in the art references cited above, $V_{HH}$ domains have a number of unique structural characteristics and functional properties. These make isolated $V_{HH}$ domains (as well as inventive compositions based thereon that share these structural characteristics and functional properties with the naturally occurring $V_{HH}$ domains) and proteins containing the same highly advantageous for use as functional antigen-binding domains or proteins. In particular, and without being limited thereto, $V_{HH}$ domains and inventive compositions can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in, e.g., conventional antibody fragments such as Fab fragments; in ScFv's fragments, which consist of a $V_H$ domain covalently linked to a $V_L$ domain).

Because of these unique properties, the use of $V_{HH}$ domains, and of inventive NB agents and compositions based thereon, as single antigen-binding proteins or as antigen-binding domains (i.e., as part of a larger protein or polypeptide) offers a number of significant advantages over the use of conventional $V_H$ and $V_L$ domains, ScFv's or conventional antibody fragments (such as Fab- or F(ab)$_2$-fragments). Advantages of a camelid $V_{HH}$ variant of a NB construct are e.g., only a single domain is required to bind an antigen with high affinity and with high selectivity, so there is no need to manufacture or combine multiple separate domains nor is there a need to assure that these two domains are present in the right spacial conformation and configuration; $V_{HH}$ domains can be expressed from a single transcript and require no post-translational folding or modifications; $V_{HH}$ domains can easily be engineered into multivalent and multispecific formats (as further discussed herein); $V_{HH}$ domains are highly soluble and do not have a tendency to aggregate; $V_{HH}$ domains are highly stable to heat, pH, proteases and other denaturing agents or conditions; $V_{HH}$ domains are easy and relatively cheap to prepare and to scale up for production; $V_{HH}$ domains are relatively small (monomers are approximately 15 kDa, or 10 times smaller than a conventional IgG) compared to conventional 4-chain antibodies and antigen-binding fragments thereof, and therefore show high(er) penetration into tissues (including but not limited to solid tumors and other dense tissues) than such conventional 4-chain antibodies and antigen-binding fragments thereof; $V_{HH}$ domains can show so-called cavity-binding properties (inter alia due to their extended CDR3 loop, compared to conventional $V_H$ domains) and can therefore also access targets and epitopes not accessible to conventional 4-chain antibodies and antigen-binding fragments thereof.

NB Constructs Against DR5

In a specific and preferred aspect, the invention provides NB agents against DR5, and in particular NB agents against DR5 from a warm-blooded animal, and more in particular NB agents against DR5 from a mammal, and especially NB agents against human DR5, such as provided in public databases, e.g. in NCBI Protein database accession number BAA33723 (SEQ ID NO: 89); as well as proteins and/or polypeptides comprising at least one such NB agent.

In particular, the invention provides NB agents against DR5, and proteins and/or polypeptides comprising the same, that have improved therapeutic and/or pharmacological properties and/or other advantageous properties (such as, e.g., improved ease of preparation and/or reduced costs of goods), compared to conventional antibodies against DR5, or fragments thereof, compared to constructs that could be based on such conventional antibodies or antibody fragments (such as $F_{ab}$' fragments, $F_{(ab')2}$ fragments, ScFv constructs, "diabodies" and other multispecific constructs (see, e.g., the review by Holliger and Hudson, Nat Biotechnol. 2005 September; 23(9): 1126-36)), and also compared to the so-called "dAb's" or similar (single) domain antibodies that may be derived from variable domains of conventional antibodies.

In one embodiment and as generally described herein for the therapeutically useful amino acid sequences of the invention, the NB agents and variants thereof of the invention are in essentially isolated form, or form part of a protein or polypeptide of the invention that may comprise or essentially consist of one or more NB agents of the invention. In one embodiment, the NB agent variant may further comprise one or more additional amino acid sequences. In one embodiment, the one or more additional amino acid sequences are linked via one or more suitable linkers. In one embodiment, and without limitation, the one or more amino acid sequences of the invention may be used as a binding unit in such a protein or polypeptide, which may optionally contain one or more further amino acid sequences that can serve as a binding unit (i.e., against one or more other targets than DR5), so as to provide a monovalent, multivalent or multispecific polypeptide of the invention, respectively. In one embodiment, such a protein or polypeptide may comprise or essentially consist of one or more NB agents of the invention and optionally one or more (other) polypeptide domains or epitope binding compositions (i.e., directed against other targets than DR5), all optionally linked via one or more suitable linkers, so as to provide a monovalent, multivalent or multispecific NB agent, respectively.

In one embodiment, the binding site for binding against DR5 is formed by the CDR sequences. In one embodiment, an inventive composition may, in addition to the at least one binding site for binding against DR5, contain one or more further binding sites for binding against other antigens, proteins or targets. For methods and positions for introducing such second binding sites, reference is, e.g., made to Keck and Huston, Biophysical Journal, 71, October 1996, 2002-2011; EP 0 640 130; WO 06/07260 and the U.S. provisional application by Ablynx N.V. entitled "Immunoglobulin domains with multiple binding sites" filed on Nov. 27, 2006.

In one embodiment when the inventive amino acid sequences (or a polypeptide of the invention comprising the same) is intended for administration to a subject (for example for therapeutic and/or diagnostic purposes as described herein), it is directed against human DR5. In one embodiment for veterinary purposes, the inventive composition is directed against DR5 from the species to be treated. The inventive compositions herein may or may not be cross-reactive (i.e., active against DR5 from two or more species of mammal, such as against human DR5 and DR5 from at least one of the species of mammal mentioned herein). In one embodiment, a NB construct of the invention can specifically bind to DR5 but does not bind to DR-4, TRAIL-R3 or TRAIL-R4.

In one embodiment, the compositions of the invention is generally directed against any antigenic determinant, epitope, part, domain, subunit or confirmation (where applicable) of DR5. In one embodiment, the inventive NB agents are directed against the extracellular domain portion of DR5.

In one specific embodiment, inventive compositions herein compete with the natural ligand of DR5 in a competitive binding assay. In one embodiment, an inventive NB agent competes with TRAIL for binding to DR5. In one embodiment, an inventive composition of the invention does not compete with TRAIL—for binding to DR5. In one embodiment, an inventive NB agent synergizes with TRAIL for binding to DR5.

In one non-limiting embodiment, the amino acid sequence and structure of an inventive composition are comprised of four framework regions or "FR's" (or sometimes also referred to as "FW's"), which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDRs", which are referred to in the art as "Complementarity Determining Region 1" or "CDR1"; as "Complementarity Determining Region 2" or "CDR2"; and as "Complementarity Determining Region 3" or "CDR3", respectively. In one embodiment, the framework sequences and CDRs (and combinations thereof) are those present in the NB constructs of the invention as described herein and especially in Table 4. Other suitable CDR sequences can be obtained by the methods described herein.

In one non-limiting embodiment, the CDR sequences of the invention are such that:
a) the NB constructs can bind to DR5 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles); and/or such that
b) the NB constructs can bind to DR5 with a $k_{on}$-rate of between $10^2 \, M^{-1} \, s^{-1}$ to about $10^7 \, M^{-1} \, s^{-1}$, preferably between $10^3 \, M^{-1} \, s^{-1}$ and $10^7 \, M^{-1} \, s^{-1}$, more preferably between $10^4 \, M^{-1} \, s^{-1}$ and $10^7 \, M^{-1} \, s^{-1}$, such as between $10^5 \, M^{-1} \, s^{-1}$ and $10^7 \, M^{-1} \, s^{-1}$; and/or such that
c) the NB constructs can bind to DR5 with a $k_{off}$ rate between 1 s$^{-1}$ ($t_{1/2}$=0.69 s) and $10^{-6}$ s$^{-1}$ (providing a near irreversible complex with a $t_{1/2}$ of multiple days), preferably between $10^{-2}$ s$^{-1}$ and $10^{-6}$ s$^{-1}$, more preferably between $10^{-3}$ s$^{-1}$ and $10^{-6}$ s$^{-1}$, such as between $10^{-4}$ s$^{-1}$ and $10^{-6}$ s$^{-1}$.

In one embodiment, the CDR sequences herein are such that: a monovalent composition of the invention (or a polypeptide that contains only one NB construct of the invention) will bind to DR5 with an affinity less than 100 nM, preferably less than 10 nM, more preferably less than 1 nM, such as less than 500 pM.

The affinity of the NB agents of the invention against DR5 can be determined in a manner known per se, e.g., using the general techniques for measuring $K_D$, $K_A$, $k_{off}$ or $k_{on}$ mentioned herein, as well as some of the specific assays described herein.

In one non-limiting aspect, the invention relates to a NB agent against DR5, which consists of four framework regions (FR1 to FR4 respectively) and three complementarity determining regions (CDR1 to CDR3 respectively). In one embodiment, the NB agent is a NB construct in which:

CDR1 is chosen from the group consisting of:
a) the amino acid sequences of SEQ ID NO's: 41 to 44;
b) amino acid sequences that have at least 90% amino acid identity with at least one of the amino acid sequences of SEQ ID NO's: 41 to 44;
c) amino acid sequences that have 3, 2, or 1 amino acid difference with at least one of the amino acid sequences of SEQ ID NO's: 41 to 44;
and/or
CDR2 is chosen from the group consisting of:
a) the amino acid sequences of SEQ ID NO's: 51 to 55;
b) amino acid sequences that have at least 90% amino acid identity with at least one of the amino acid sequences of SEQ ID NO's: 51 to 55;
c) amino acid sequences that have 3, 2, or 1 amino acid difference with at least one of the amino acid sequences of SEQ ID NO's: 51 to 55;
and/or
CDR3 is chosen from the group consisting of:
a) the amino acid sequences of SEQ ID NO's: 63 to 68;
b) amino acid sequences that have at least 90% amino acid identity with at least one of the amino acid sequences of SEQ ID NO's: 63 to 68
c) amino acid sequences that have 3, 2, or 1 amino acid difference with at least one of the amino acid sequences of SEQ ID NO's: 63 to 68;
or any suitable fragment of such an amino acid sequence.

Of the NB agents of the invention, NB construct comprising one or more of the CDR's explicitly listed above are particularly preferred; NB construct comprising two or more of the CDR's explicitly listed above are more particularly preferred; and NB construct comprising three of the CDR's explicitly listed above are most particularly preferred.

Some particularly preferred, but non-limiting combinations of CDR sequences, as well as preferred combinations of CDR sequences and framework sequences, are mentioned in Table 4 below, which lists the CDR sequences and framework sequences that are present in a number of preferred (but non-limiting) NB construct of the invention. As will be clear to the skilled person, a combination of CDR1, CDR2 and CDR3 sequences that occur in the same clone (i.e., CDR1, CDR2 and CDR3 sequences that are mentioned on the same line in Table 4, and especially as provided in SEQ ID NOS: 1-22, 26-40, 87-88, and 102-103) will usually be preferred (although the invention in its broadest sense is not limited thereto, and also comprises other suitable combinations of the CDR sequences mentioned in Table 4). Also, a combination of CDR sequences and framework sequences that occur in the same clone (i.e., CDR sequences and framework sequences that are mentioned on the same line in Table 4, and especially as provided in context within SEQ ID NOS: 1-22, 26-40, 87-88, and 102-103)) will usually be preferred (although the invention in its broadest sense is not limited thereto, and also comprises other suitable combinations of the CDR sequences and framework sequences mentioned in Table 4, as well as combinations of such CDR sequences and other suitable framework sequences.

In one embodiment, in the NB constructs that comprise the combinations of CDR's mentioned in Table 4, each CDR can be replaced by a CDR chosen from the group consisting of amino acid sequences that have at least 80%, preferably at least 90%, more preferably at least 95%, even more preferably at least 99% sequence identity with the mentioned CDR's.

Thus, in the NB constructs of the invention, at least one of the CDR1, CDR2 and CDR3 sequences present is suitably chosen from the group consisting of the CDR1, CDR2 and CDR3 sequences, respectively, listed in Table 4; or from the group of CDR1, CDR2 and CDR3 sequences, respectively, that have at least 80%, preferably at least 90%, more preferably at least 95%, even more preferably at least 99% "sequence identity" with at least one of the CDR1, CDR2 and CDR3 sequences, respectively, listed in Table 4; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table 4.

In this context, by "suitably chosen" is meant that, as applicable, a CDR1 sequence is chosen from suitable CDR1 sequences (i.e., as defined herein), a CDR2 sequence is chosen from suitable CDR2 sequences (i.e., as defined herein), and a CDR3 sequence is chosen from suitable CDR3 sequence (i.e., as defined herein), respectively. In one embodiment, the CDR sequences are chosen such that the NB constructs of the invention bind to DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value that is as provided herein.

In one embodiment of the NB constructs of the invention, at least the CDR3 sequence present is suitably chosen from the group consisting of the CDR3 sequences listed in Table 4 or from the group of CDR3 sequences that have at least 80%, preferably at least 90%, more preferably at least 95%, even more preferably at least 99% sequence identity with at least one of the CDR3 sequences listed in Table 4; and/or from the group consisting of the CDR3 sequences that have 3, or have 2 or have only 1 amino acid difference(s) with at least one of the CDR3 sequences listed in Table 4.

In one embodiment of the NB constructs of the invention, at least two of the CDR1, CDR2 and CDR3 sequences present are suitably chosen from the group consisting of the CDR1, CDR2 and CDR3 sequences, respectively, listed in Table 4 or from the group consisting of CDR1, CDR2 and CDR3 sequences, respectively, that have at least 80%, and/or at least 90%, and/or at least 95%, and/or at least 99% sequence identity with at least one of the CDR1, CDR2 and CDR3 sequences, respectively, listed in Table 4; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table 4.

In one embodiment of the NB constructs of the invention, at least the CDR3 sequence present is suitably chosen from the group consisting of the CDR3 sequences listed in Table 4 or from the group of CDR3 sequences that have at least 80%, and/or at least 90%, and/or at least 95%, and/or at least 99% sequence identity with at least one of the CDR3 sequences listed in Table 4, respectively; and at least one of the CDR1 and CDR2 sequences present is suitably chosen from the group consisting of the CDR1 and CDR2 sequences, respectively, listed in Table 4 or from the group of CDR1 and CDR2 sequences, respectively, that have at least 80%, and/or at least 90%, and/or at least 95%, and/or at least 99% sequence identity with at least one of the CDR1 and CDR2 sequences, respectively, listed in Table 4; and/or from the group consisting of the CDR1 and CDR2 sequences, respectively, that have 3, 2 or only 1 amino acid difference(s) with at least one of the CDR1 and CDR2 sequences, respectively, listed in Table 4.

In one embodiment of the NB constructs of the invention, all three CDR1, CDR2 and CDR3 sequences present are suitably chosen from the group consisting of the CDR1, CDR2 and CDR3 sequences, respectively, listed in Table 4.

In one embodiment, the combinations of CDR's listed in Table 4 (i.e., those mentioned for the same construct in Table 4) are preferred. Thus, in one aspect, when a CDR in a NB construct of the invention is a CDR sequence mentioned in Table 4 or is suitably chosen from the group of CDR sequences that have at least 80%, preferably at least 90%, more preferably at least 95%, even more preferably at least 99% sequence identity with a CDR sequence listed in Table 4; and/or from the group consisting of CDR sequences that have 3, 2 or only 1 amino acid difference(s) with a CDR sequence listed in Table 4, that at least one and preferably both of the other CDR's are suitably chosen from the CDR sequences that belong to the same combination in Table 4 (i.e., mentioned on the same line in Table 4) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table 4.

In one embodiment of a NB construct of the invention, the CDR1, CDR2 and CDR3 sequences present are suitably chosen from one of the combinations of CDR1, CDR2 and CDR3 sequences, respectively, listed in Table 4.

According to one non-limiting aspect of a NB construct of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In one non-limiting aspect, the invention relates to a NB construct in which the CDR sequences have more than 80%, preferably more than 90%, more preferably more than 95%, such as at least 99% or more sequence identity with the CDR sequences of at least one of the amino acid sequences of SEQ ID NO's: 1-22, 26-40, 87-88, and 102-103.

Generally, NB agents with the above CDR sequences may be as further described herein. In one embodiment the NB agents have framework sequences that are also as further described herein. Thus, e.g., and as mentioned herein, such NB agents may be naturally occurring single domain antibodies (from any suitable species), naturally occurring $V_{HH}$ sequences (i.e., from a suitable species of Camelid) or synthetic or semi-synthetic amino acid sequences or NB agents, including but not limited to partially humanized NB constructs or $V_{HH}$ sequences, fully humanized NB constructs or $V_{HH}$ sequences, camelized heavy chain variable domain sequences, as well as NB agents that have been obtained by the techniques mentioned herein.

Thus, in one non-limiting aspect, the invention relates to a humanized NB agent, which consists of four framework regions (FR1 to FR4 respectively) and three complementarity determining regions (CDR1 to CDR3 respectively), in which CDR1 to CDR3 are as defined herein and in which said humanized NB agent comprises at least one humanizing substitution, and in particular at least one humanizing substitution in at least one of its framework sequences.

In another preferred, but non-limiting aspect, the invention relates to a NB agent in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 1-22, 26-40, 87-88, and 102-103. This degree of amino acid identity can, e.g., be determined by determining the degree of amino acid identity (in a manner described herein) between said NB agent and one or more of the sequences of SEQ ID NO's: 1-22, 26-40, 87-88, and 102-103, in which the amino acid residues that form the framework regions are disregarded. Such NB agents can be as further described herein.

In one non-limiting aspect, the invention relates to an NB agent, including but not limited to a NB construct, with an amino acid sequence that is chosen from the group consisting of SEQ ID NO's: 1-22, 26-40, 87-88, and 102-103 or from the group consisting of from amino acid sequences that have more than 80%, preferably more than 90%, more preferably more than 95%, such as at least 99% or more sequence identity with at least one of the amino acid sequences of SEQ ID NO's: 1-22, 26-40, 87-88, and 102-103.

Another non-limiting aspect of the invention relates to humanized or further humanized variants of the NB constructs of SEQ ID NO's: 1-22, 26-40, 87-88, and 102-103 that comprise, compared to the corresponding native sequence, at least one humanizing substitution, and in particular at least one humanizing substitution in at least one of its framework sequences.

Monovalent and Multivalent Binding Polypeptides

The invention further relates to a compound that comprises or essentially consists of one or more polypeptides of the invention against DR5, and more specifically against human DR5, and optionally comprises one or more other groups, residues, moieties or binding units, wherein said compound is capable of enhancing apoptosis. In one embodiment, some NB agents of the invention are proteins that comprise at least three, four, five or more monovalent binding polypeptides against the DR5 receptor, such as NB agents of the invention directed against the DR5. As mentioned herein, in such multivalent polypeptides of the invention, each monovalent binding polypeptide, such as a NB construct, may be directed against the same epitope on the DR5, or against different epitopes on the DR5. Some non-limiting examples of such NB polypeptides of the invention are given in SEQ ID NO's: 1-22, 26-40, 87-88, and 102-103.

Generally, proteins or polypeptides that comprise or essentially consist of a single binding polypeptide (such as a single DR5 binding subunit of a NB agent of the invention) will be referred to herein as "monovalent" proteins or polypeptides or as "monovalent constructs". Proteins and polypeptides that comprise or essentially consist of two or more binding polypeptides (such as at least two joined NB agents of the invention or at least one NB agent of the invention and at least one other NB agent or polypeptide construct) will be referred to herein as "multivalent" proteins or polypeptides or as "multivalent constructs", and these may provide certain advantages compared to the corresponding monovalent binding polypeptides of the invention. Particular non-limiting examples of such multivalent constructs are as provided herein.

Specific examples of multivalent NB agent include a dimer or divalent construct comprising two polypeptide subunits, a trimer or trivalent NB agent comprising three polypeptide subunits, a tetramer or tetravalent NB agent comprising four polypeptide subunits, a pentamer or pentavalent NB agent comprising five polypeptide subunits, a hexamer or hexavalent NB agent comprising six polypeptide subunits, or additional multimeric variants thereof.

In one non-limiting aspect, a trimeric NB agent of the invention comprises or essentially consists of three monovalent polypeptide subunits of the invention. In one embodiment, the trimeric NB agent comprises three identical DR5 binding monovalent polypeptide subunits of the invention, in which case the NB agent is a trimer that is multivalent but monospecific. In one embodiment a trimeric NB agent comprises or essentially consists of a first and/or second DR5 binding subunit and a second or third subunit, respectively, that is optionally a subunit that binds specifically to a different epitope (either on DR5 or on another target), e.g., in which case the NB agent is a trimer that is multivalent and multispecific.

In one non-limiting embodiment, a NB agent comprises or essentially consists of at least four monovalent DR5 binding polypeptide subunits of the invention. Such a tetrameric NB agent of the invention may be monospecific or may be converted to a multispecific construct by optionally joining additional subunits that bind specifically to the same or a different DR5 epitope from the first and/or to a target other than DR5.

In one non-limiting embodiment, a NB agent comprises or essentially consists of at least five monovalent DR5 binding polypeptide subunits of the invention. Such a pentameric NB agent of the invention may be monospecific or may be converted to a multispecific construct by optionally joining additional subunits that bind specifically to a different DR5 epitope from the first and/or to a target other than DR5.

In one non-limiting embodiment, a NB agent comprises or essentially consists of six, eight or ten monovalent DR5 binding polypeptide subunits of the invention. Such a multimeric NB agent of the invention may be monospecific or may be converted to a multispecific construct by optionally joining additional subunits that bind specifically to a different DR5 epitope from the first and/or to a target other than DR5.

In one embodiment, such multimeric NB agents, whether monospecific or multispecific, provide certain advantages compared to a protein or polypeptide comprising or essentially consisting of a monomeric NB agent of the invention, In one embodiment, advantages include, but are not limited to, a much improved avidity for DR5, e.g., for human DR5. Some specific, but non-limiting examples of multimeric NB agents are the NB constructs of SEQ ID NO's: 6 to 22, 27-29, 31-33 and 88.

In one non-limiting aspect, a polypeptide of the invention comprises or essentially consists of at least one NB agent of the invention, optionally one or more further NB agents, and at least one other amino acid sequence (such as a protein or polypeptide) that confers at least one desired property to the NB agent of the invention and/or to the resulting fusion protein. Again, such fusion proteins may provide certain advantages compared to the corresponding monovalent NB agent of the invention. Some non-limiting examples of such amino acid sequences and of such fusion constructs will become clear from the further description herein.

In one embodiment, it is possible to combine two or more of the above aspects, e.g., to provide a trivalent bispecific construct comprising two NB agents of the invention and one other NB agent, and optionally one or more other amino acid sequences. Further non-limiting examples of such constructs, as well as some constructs that are particularly preferred within the context of the present invention, will become clear from the further description herein.

In the above constructs, the one or more binding polypeptides against DR5 and/or other amino acid sequences may be operably linked to each other and/or suitably linked to each other via one or more linker sequences. Some suitable but non-limiting examples of such linkers will become clear from the further description herein.

In one specific aspect, the multivalent compound of the invention comprises at least three, four, five or more monovalent binding polypeptides (i.e., subunits) and has an $IC_{50}$ less than 100 nM, preferably less than 10 nM, more preferably less than 1 nM, even more preferably less than 100 pM, e.g., below 10 pM as measured, e.g., in Colo205 or Jurkat cell survival assay. Other cancer cell lines can be used for determining $IC_{50}$, e.g., such as mentioned in the Examples. Furthermore, possible cancer cell lines that may be used in cell survival assays include, but are not limited to, e.g., Jurkat, Molt4, Colo205, BxPC3, T24, Panc-1, M30, H226, H2122, H2052, and MiaPaCa-2.

In one embodiment, the multivalent compound of the invention are at least 10 fold, preferably at least 100 fold more potent in a tumor cell line than in a non-tumor cell line and measured in a cell survival assay such as Colo205 or Jurkat cell survival assay.

In one specific aspect of the invention, a NB agent of the invention or a compound, construct or polypeptide of the invention comprising at least one NB agent of the invention may have an increased half-life, compared to the corresponding amino acid sequence of the invention. Some non-limiting examples of such NB agents, compounds and polypeptides will become clear to the skilled person based on the further disclosure herein, and, e.g., comprise NB agent sequences or polypeptides of the invention that have been chemically modified to increase the half-life thereof (for example, by means of pegylation); amino acid sequences of the invention that comprise at least one additional binding site for binding to a serum protein (such as serum albumin. or polypeptides of the invention that comprise at least one NB agent of the invention that is linked to at least one moiety (and in particular at least one amino acid sequence) that increases the half-life of the NB agent of the invention. Examples of polypeptides of the invention that comprise such half-life extending moieties or amino acid sequences will become clear to the skilled person based on the further disclosure herein; and, e.g., include, without limitation, polypeptides in which the one or more NB agents of the invention are suitable linked to one or more serum proteins or fragments thereof (such as serum albumin or suitable fragments thereof) or to one or more binding units that can bind to serum proteins (such as, e.g., NB agents, camelid $V_{HH}$ constructs or (single) domain antibodies that can bind to serum proteins such as serum albumin, serum immunoglobulins such as IgG, or transferrine); polypeptides in which a NB agent of the invention is linked to an Fc portion (such as a human Fc) or a suitable part or fragment thereof; or polypeptides in which the one or more NB agents of the invention are suitable linked to one or more small proteins or peptides that can bind to serum proteins (such as, without limitation, the proteins and peptides described in WO 91/01743, WO 01/45746, WO 02/076489 and to WO 2006/122787, WO 2008/028977, WO 2008/043821, WO 2008/068280 and WO 2009/127691 filed by Ablynx N.V.

Again, as will be clear to the skilled person, such NB agents may contain one or more additional groups, residues, moieties or binding units, such as one or more further amino acid sequences and in particular one or more additional NB agents (i.e., not directed against DR5), so as to provide a di-, tri- or higher multispecific NB agent construct.

Generally, the NB agents of the invention (or compounds, constructs or polypeptides comprising the same) with increased half-life preferably have a half-life that is at least 1.5 times, preferably at least 2 times, such as at least 5 times, e.g., at least 10 times or more than 20 times, greater than the half-life of the corresponding amino acid sequence of the invention per se. For example, the NB agents, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such NB agents, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another one aspect of the invention, a polypeptide of the invention comprises one or more (such as two or preferably one) NB agents of the invention linked (optionally via one or more suitable linker sequences) to one or more (such as two and preferably one) amino acid sequences that allow the resulting polypeptide of the invention to cross the blood brain barrier. In particular, said one or more amino acid sequences that allow the resulting polypeptides of the invention to cross the blood brain barrier may be one or more (such as two and preferably one) NANOBODIES™, such as the NANOBODIES™ described in WO 02/057445, of which FC44 (SEQ ID NO: 189 of WO 06/040153) and FC5 (SEQ ID NO: 190 of WO 06/040154) are particular examples.

In one embodiment, polypeptides comprising one or more NB agents of the invention are such that they:

a) bind to DR5 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

b) bind to DR5 with a $k_{on}$-rate of between $10^2$ M$^{-1}$ s$^{-1}$ to about $10^7$ M$^{-1}$ s$^{-1}$, preferably between $10^3$ M$^{-1}$ s$^{-1}$ and $10^7$ M$^{-1}$ s$^{-1}$, more preferably between $10^4$ M$^{-1}$ s$^{-1}$ and $10^7$ M$^{-1}$ s$^{-1}$, such as between $10^5$ M$^{-1}$ s$^{-1}$ and $10^7$ M$^{-1}$ s$^{-1}$;

and/or such that they:

c) bind to DR5 with a $k_{off}$-rate between 1 s$^{-1}$ ($t_{1/2}$=0.69 s) and $10^{-6}$ s$^{-1}$ (providing a near irreversible complex with a $t_{1/2}$ of multiple days), preferably between $10^{-2}$ s$^{-1}$ and $10^{-6}$ s$^{-1}$, more preferably between $10^{-3}$ s$^{-1}$ and $10^{-6}$ s$^{-1}$, such as between $10^{-4}$ s$^{-1}$ and $10^{-6}$ s$^{-1}$.

In one embodiment, a polypeptide that contains only one amino acid sequence of the invention is such that it will bind to DR5 with an affinity less than 500 nM, preferably less than 200 nM, more preferably less than 10 nM, such as less than 500 pM. In this respect, it will be clear to the skilled person that a polypeptide that contains two or more NB agents of the invention may bind to DR5 with an increased avidity, compared to a polypeptide that contains only one amino acid sequence of the invention.

Other polypeptides according to this preferred aspect of the invention may, e.g., be chosen from the group consisting of amino acid sequences that have more than 80%, preferably more than 90%, more preferably more than 95%, such as at least 99% or more "sequence identity" with one or more of the amino acid sequences of SEQ ID NO's: 1-22, 26-40 and 87-88, in which the NB agents comprised within said amino acid sequences are preferably as further defined herein.

Nucleic Acids, Host Cells and Method for Generating NB Constructs of the Invention Another aspect of this invention relates to a nucleic acid that encodes a NB agent of the invention or a polypeptide of the invention comprising the same. Again, as generally described herein for the nucleic acids of the invention, such a nucleic acid may be in the form of a genetic construct, as provided herein.

In another aspect, the invention relates to host or host cell that expresses or that is capable of expressing a NB agent of the invention and/or a polypeptide of the invention comprising the same; and/or that contains a nucleic acid of the invention. Some preferred but non-limiting examples of such hosts or host cells will become clear from the further description herein.

Another aspect of the invention relates to a product or composition containing or comprising at least one NB agent of the invention, at least one polypeptide of the invention and/or at least one nucleic acid of the invention, and optionally one or more further components of such compositions known per se, i.e., depending on the intended use of the composition. Such a product or composition may, e.g., be a pharmaceutical composition (as described herein), a veterinary composition or a product or composition for diagnostic use (as also described herein). Some preferred but non-limiting examples of such products or compositions will become clear from the further description herein.

The invention further relates to methods for preparing or generating the NB agents, polypeptides, nucleic acids, host cells, products and compositions described herein. Some preferred but non-limiting examples of such methods will become clear from the further description herein.

The invention further relates to applications and uses of the NB agents, polypeptides, nucleic acids, host cells, products and compositions described herein, as well as to methods for the prevention and/or treatment for diseases and disorders associated with DR5. Particular non-limiting applications and uses will become clear from the further description herein.

Other aspects, embodiments, advantages and applications of the invention will also become clear from the further description hereinbelow.

Generally, it should be noted that the term "NB agent" as used herein in its broadest sense is not limited to a specific biological source or to a specific method of preparation. For example, as will be discussed in more detail below, the NB agents of the invention can generally be obtained by any of the techniques (1) to (8) mentioned on pages 61 and 62 of WO 08/020,079, or any other suitable technique known per se. One preferred class of NB agents corresponds to the $V_{HH}$ or $V_H$ domains of naturally occurring heavy chain antibodies directed against DR5. As further described herein, $V_{HH}$ sequences can generally be generated or obtained by suitably immunizing a species of Camelid with DR5 (i.e., so as to raise an immune response and/or heavy chain antibodies directed against DR5), by obtaining a suitable biological sample from said Camelid (such as a blood sample, serum sample or sample of B-cells), and by generating $V_{HH}$ sequences directed against DR5, starting from said sample, using any suitable technique known per se. Such techniques will be clear to the skilled person and/or are further described herein.

Alternatively, such naturally occurring $V_{HH}$ domains against DR5, can be obtained from naïve libraries of Camelid $V_{HH}$ sequences, e.g., by screening such a library using DR5, or at least one part, fragment, antigenic determinant or epitope thereof using one or more screening techniques known per se. Such libraries and techniques are, e.g., described in WO 99/37681, WO 01/90190, WO 03/025020 and WO 03/035694. Alternatively, improved synthetic or semi-synthetic libraries derived from naïve $V_{HH}$ libraries may be used, such as $V_{HH}$ libraries obtained from naïve $V_{HH}$ libraries by techniques such as random mutagenesis and/or CDR shuffling, as, e.g., described in WO 00/43507.

Thus, in another aspect, the invention relates to a method for generating NB agents that are directed against DR5. In one aspect, said method at least comprises the steps of:

a) providing a set, collection or library of NB agent sequences;

b) screening said set, collection or library of NB agent sequences for NB agent sequences that can bind to and/or have affinity for DR5; and c) isolating the amino acid sequence(s) that can bind to and/or have affinity for DR5.

In such a method, the set, collection or library of NB agent sequences may be a naïve set, collection or library of NB agent sequences; a synthetic or semi-synthetic set, collection or library of NB agent sequences; and/or a set, collection or library of NB agent sequences that have been subjected to affinity maturation.

In a particular aspect of this method, the set, collection or library of NB agent sequences may be an immune set, collection or library of NB agent sequences, and in particular an immune set, collection or library of $V_{HH}$ sequences, that have been derived from a species of Camelid that has been suitably immunized with DR5 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of $V_{HH}$ sequences may be displayed on a phage, phagemid, ribosome or suitable micro-organism (such as yeast), such as to facilitate screening. Suitable methods, techniques and host organisms for displaying and screening (a set, collection or library of) sequences will be clear to the person skilled in the art, e.g., on the basis of the further disclosure herein. Reference is also made to WO 03/054016 and to the review by Hoogenboom in Nature Biotechnology, 23, 9, 1105-1116 (2005).

In one embodiment, the method for generating $V_{HH}$ sequences comprises at least the steps of:

a) providing a collection or sample of cells derived from a species of Camelid that express immunoglobulin sequences;

b) screening said collection or sample of cells for (1) cells that express an immunoglobulin sequence that can bind to and/or have affinity for DR5; and (2) cells that express heavy chain antibodies, in which substeps (1) and (2) can be performed essentially as a single screening step or in any suitable order as two separate screening steps, so as to provide at least one cell that expresses a heavy chain antibody that can bind to and/or has affinity for DR5;

and c) either (1) isolating from said cell the $V_{HH}$ sequence present in said heavy chain antibody; or (2) isolating from said cell a nucleic acid sequence that encodes the $V_{HH}$ sequence present in said heavy chain antibody, followed by expressing said $V_{HH}$ domain.

In the method according to this aspect, the collection or sample of cells may, e.g., be a collection or sample of B-cells. Also, in this method, the sample of cells may be derived from a Camelid that has been suitably immunized with DR5 or a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is, e.g., made to EP 0 542 810, WO 05/19824, WO 04/051268 and WO 04/106377. The screening of step b) is preferably performed using a flow cytometry technique such as FACS. For this, reference is, e.g., made to Lieby et al., Blood, Vol. 97, No. 12, 3820. See, e.g., the so-called "Nanoclone™" technique described in International application WO 06/079372 by Ablynx N.V.

In another aspect, the method for generating an amino acid sequence directed against DR5 may comprise at least the steps of:

a) providing a set, collection or library of nucleic acid sequences encoding heavy chain antibodies or $V_{HH}$ sequences;

b) screening said set, collection or library of nucleic acid sequences for nucleic acid sequences that encode a heavy chain antibody or a $V_{HH}$ sequence that can bind to and/or has affinity for DR5; and c) isolating said nucleic acid sequence, followed by expressing the $V_{HH}$ sequence present in said heavy chain antibody or by expressing said NB construct sequence, respectively.

In such a method, the set, collection or library of nucleic acid sequences encoding heavy chain antibodies or $V_{HH}$ sequences may, e.g., be a set, collection or library of nucleic acid sequences encoding a naïve set, collection or library of heavy chain antibodies or $V_{HH}$ sequences; a set, collection or library of nucleic acid sequences encoding a synthetic or semi-synthetic set, collection or library of $V_{HH}$ sequences; and/or a set, collection or library of nucleic acid sequences encoding a set, collection or library of $V_{HH}$ sequences that have been subjected to affinity maturation.

In one embodiment of this method, the set, collection or library of amino acid sequences may be an immune set, collection or library of nucleic acid sequences encoding heavy chain antibodies or $V_{HH}$ sequences derived from a Camelid that has been suitably immunized with DR5 or with a suitable antigenic determinant based thereon or derived therefrom, such as an antigenic part, fragment, region, domain, loop or other epitope thereof. In one aspect, said antigenic determinant may be an extracellular part, region, domain, loop or other extracellular epitope(s).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, e.g., on the basis of the further disclosure herein. Reference is also made to WO 03/054016 and to Hoogenboom in Nature Biotechnology, 23, 9, 1105-1116 (2005).

In one embodiment, the screening step of the methods described herein can also be performed as a selection step. Accordingly the term "screening" as used in the present description can comprise selection, screening or any suitable combination of selection and/or screening techniques. Also, when a set, collection or library of sequences is used, it may contain any suitable number of sequences, such as 1, 2, 3 or about 5, 10, 50, 100, 500, 1000, 5000, $10^4$, $10^5$, $10^6$, $10^7$, $10^8$ or more sequences.

In one embodiment, one or more or all of the sequences in the above set, collection or library of amino acid sequences may be obtained or defined by rational, or semi-empirical approaches such as computer modeling techniques or biostatics or data mining techniques.

Furthermore, such a set, collection or library can comprise one, two or more sequences that are variants from one another (e.g. with designed point mutations or with randomized positions), compromise multiple sequences derived from a diverse set of naturally diversified sequences (e.g. an immune library)), or any other source of diverse sequences (as described, e.g., in Hoogenboom et al, Nat Biotechnol 23: 1105, 2005 and Binz et al, Nat Biotechnol 2005, 23: 1247). Such set, collection or library of sequences can be displayed on the surface of a phage particle, a ribosome, a bacterium, a yeast cell, a mammalian cell, and linked to the nucleotide sequence encoding the amino acid sequence within these carriers. This makes such set, collection or library amenable to selection procedures to isolate the desired amino acid sequences of the invention. More generally, when a sequence is displayed on a suitable host or host cell, it is also possible (and customary) to first isolate from said host or host cell a nucleotide sequence that encodes the desired sequence, and then to obtain the desired sequence by suitably expressing said nucleotide sequence in a suitable host organism. Again, this can be performed in any suitable manner known per se, as will be clear to the skilled person.

Yet another technique for obtaining $V_{HH}$ sequences, $V_H$ sequences, or some other variant of NB agent sequences directed against DR5 involves suitably immunizing a transgenic mammal that is capable of expressing heavy chain antibodies (i.e., so as to raise an immune response and/or heavy chain antibodies directed against DR5), obtaining a suitable biological sample from said transgenic mammal that contains (nucleic acid sequences encoding) said sequences (such as a blood sample, serum sample or sample of B-cells), and then generating NB agent sequences directed against DR5, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssen's et al., Proc. Natl. Acad. Sci. USA. 2006 Oct. 10; 103(41): 15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as, e.g., synthetic or semi-synthetic (single) variable domains.

In one embodiment the invention relates to the NB agent sequences that are obtained by the above methods, or alternatively by a method that comprises the one of the above methods and in addition at least the steps of determining the nucleotide sequence or amino acid sequence of said NB agent sequence; and of expressing or synthesizing said NB agent sequence in a manner known per se, such as by expression in a suitable host cell or host organism or by chemical synthesis.

In one embodiment the invention provides a class of NB agents that comprises camelid $V_{HH}$ constructs with an amino acid sequence that corresponds to the amino acid sequence of a naturally occurring llama $V_{HH}$ domain, but that has been "humanized", i.e., by replacing one or more amino acid residues in the amino acid sequence of said naturally occurring $V_{HH}$ sequence (and in particular in the framework sequences, but also optionally in one or more CDR) by one or more of the amino acid residues that occur at the corresponding position(s) in a $V_H$ domain from a conventional four-chain antibody from a human being, e.g. as indicated above, and e.g., as further described on, and using the techniques mentioned on, page 63 of WO 08/020,079. In one embodiment the invention provides a class of NB agents that comprises an amino acid sequence that corresponds to the amino acid sequence of a naturally occurring $V_H$ domain, but that has been "camelized", i.e., by replacing one or more amino acid residues in the amino acid sequence of a naturally occurring $V_H$ domain from a conventional four-chain antibody by one or more of the amino acid residues that occur at the corresponding position(s) in $V_{HH}$ domain of a heavy chain antibody, e.g., as further described on, and using the techniques mentioned on, page 63 of WO 08/020,079.

Other suitable methods and techniques for obtaining the NB agents of the invention (including polypeptides and/or nucleic acids encoding the same), starting from naturally occurring $V_H$ sequences or $V_{HH}$ sequences, will be clear to the skilled person, and may, e.g., include the techniques that are mentioned on page 64 of WO 08/020,079.

As mentioned herein, NB agents may in particular be characterized by the presence of one or more "Hallmark residues" (as described in WO 2008/020079, pages 65-98) in one or more of the framework sequences.

In one embodiment NB agents may, e.g., be $V_{HH}$ sequences or may be humanized or further humanized NB constructs. When the NB agent sequences are $V_{HH}$ sequences, they may be suitably humanized. When the NB agents are partially humanized NB constructs, they may optionally be further suitably humanized. In the above NB agents, one or more of the further Hallmark residues are preferably as described (for example, when they are $V_{HH}$ sequences or partially or fully humanized NB constructs).

The NB agents herein may, e.g., be $V_{HH}$ sequences or may be humanized or humaneered. When the above NB agents sequences are $V_{HH}$ sequences, they may be suitably humanized, as provided herein. When the NB agents are partially humanized, they may optionally be further suitably humanized, as described herein. One nonlimiting and exemplary method of humanization is provided in the examples, but other methods known in the art may be contemplated.

In one embodiment of the above NB agents, one or more of the (further) Hallmark residues are as described herein (for example, when they are camelid $V_{HH}$ sequences or partially or fully humanized $V_{HH}$ constructs).

In one non-limiting aspect, the invention relates to a NB agents as described above, in which the CDR sequences have at least 70% amino acid identity, preferably at least 80% amino acid identity, more preferably at least 90% amino acid identity, such as at least 95% amino acid identity or more or even essentially 100% amino acid identity with the CDR sequences of at least one of the amino acid sequences of SEQ ID NO's: 1-22, 26-40, 87-88, and 102-103. This degree of amino acid identity can, e.g., be determined by determining the degree of amino acid identity (in a manner described herein) between said NB agents and one or more of the sequences of SEQ ID NO's: 1-22, 26-40, 87-88, and 102-103, in which the amino acid residues that form the framework regions are disregarded. Such NB agents can be modified as further described herein.

As already mentioned herein, another preferred but non-limiting aspect of the invention relates to a NB agent with an amino acid sequence that is chosen from the group consisting of SEQ ID NO's: 1-22, 26-40, 87-88, and 102-103 or from the group consisting of from amino acid sequences that have more than 80%, preferably more than 90%, more preferably more than 95%, such as at least 99% or more sequence identity with at least one of the amino acid sequences of SEQ ID NO's: 1-22, 26-40, 87-88, and 102-103.

In particular embodiments of the above NB agents:
i) any amino acid substitution (when it is not a humanizing substitution as defined herein) is preferably, and compared to the corresponding amino acid sequence of SEQ ID NO's: 1-22, 26-40 and 87-88, a conservative amino acid substitution;

and/or:
ii) its amino acid sequence preferably contains either only amino acid substitutions, or otherwise preferably no more than 5, preferably no more than 3, and more preferably only 1 or 2 amino acid deletions or insertions, compared to the corresponding amino acid sequence of SEQ ID NO's: 1-22, 26-40 and 87-88;

and/or
iii) the CDR's may be CDR's that are derived by means of affinity maturation, e.g., starting from the CDR's of to the corresponding amino acid sequence of SEQ ID NO's: 1-22, 26-40 and 87-88.

Preferably, the CDR sequences and FR sequences in the NB agents of the invention are such that the NB agents of the invention (and polypeptides comprising the same):
a) bind to a DR5, e.g., human DR5, with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:
b) bind to a DR5, e.g., human DR5, with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$;

and/or such that they:
c) bind to a DR5, e.g., human DR5, with a $k_{off}$ rate between $1$ $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

In one embodiment, CDR sequences and FR sequences present in the NB agents of the invention are such that the NB agents of the invention will bind to a DR5, e.g., human DR5, with an affinity less than 500 nM, preferably less than 200 nM, more preferably less than 10 nM, such as less than 500 pM.

In one non-limiting aspect of the invention, a NB agent may be as provided herein, but with the proviso that it has at least "one amino acid difference" in at least one of the framework regions compared to the corresponding framework region of a naturally occurring human $V_H$ domain, and in particular compared to the corresponding framework region of DP-47. More specifically, according to one non-limiting aspect of the invention, a NB agent may be as provided herein, but with the proviso that it has at least "one amino acid difference" at least one of the Hallmark residues (including those at positions 108, 103 and/or 45) compared to the corresponding framework region of a naturally occurring human $V_H$ domain, and in particular compared to the corresponding framework region of DP-47. Usually, a NB agent will have at least one such amino acid difference with a naturally occurring $V_H$ domain in at least one of FR2 and/or FR4, and in particular at least one of the Hallmark residues in FR2 and/or FR4 (again, including those at positions 108, 103 and/or 45).

In one embodiment, a humanized NB agent of the invention may be as provided herein, but with the proviso that it has at least "one amino acid difference" in at least one of the framework regions compared to the corresponding framework region of a naturally occurring $V_{HH}$ domain. More specifically, according to one non-limiting aspect of the invention, a humanized NB agent may be as provided herein, but with the proviso that it has at least "one amino acid difference" at least one of the Hallmark residues (including those at positions 108, 103 and/or 45) compared to the corresponding framework region of a naturally occurring $V_{HH}$ domain. Usually, a humanized NB agent will have at least one such amino acid difference with a naturally occurring $V_{HH}$ domain in at least one of FR2 and/or FR4, and in particular at least one of the Hallmark residues in FR2 and/or FR4 (again, including those at positions 108, 103 and/or 45).

As will be clear from the disclosure herein, it is within the scope of the invention to use natural or synthetic analogs, mutants, variants, alleles, homologs and orthologs (herein collectively referred to as "analogs") of the NB agents of the invention as provided herein, and in particular analogs of the NB constructs of SEQ ID NO's 1-22, 26-40, 87-88, and 102-103 and of SEQ ID NOS: 96-99. Thus, according to one aspect of the invention, the term "NB agents of the invention" and the term "NB constructs of the invention" in its broadest sense also covers such analogs.

Generally, in such analogs, one or more amino acid residues may have been replaced, deleted and/or added, compared to the NB agents of the invention as provided herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanizing substitutions as described herein).

By means of non-limiting examples, a substitution may, e.g., be a conservative substitution (as described herein) and/or an amino acid residue may be replaced by another amino acid residue that naturally occurs at the same position in another $V_{HH}$ domain (see e.g., WO 2008/020079 for non-limiting examples of such substitutions), although the invention is generally not limited thereto. Thus, any one or more substitutions, deletions or insertions, or any combination thereof, that either improve the properties of the NB agents of the invention or that at least do not detract too much from the desired properties or from the balance or combination of desired properties of the NB agents of the invention (i.e., to the extent that the NB agent is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may, e.g., involve introducing a limited number of possible substitutions and determining their influence on the properties of the NB agents thus obtained.

In one aspect, depending on the host organism used to express the NB agent (i.e., a polynucleotide or polypeptide of the invention), such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), e.g., to allow site-specific pegylation (again as described herein).

As provided in WO 2008/020079 regarding possible amino acid substitutions and as presented above, some amino acid residues in the framework regions are more conserved than others. In one aspect, although the invention in its broadest sense is not limited thereto, any substitutions, deletions or insertions are preferably made at positions that are less conserved. In one nonlimiting aspect, amino acid substitutions are preferred over amino acid deletions or insertions.

In one nonlimiting aspect, the analogs are such that they can bind to DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as provided herein for the NB agents of the invention.

In one nonlimiting aspect, the analogs are such that they retain the favorable properties of the NB agents, as described herein.

In one embodiment, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference, with one of the NB constructs of SEQ ID NOs: 1-22, 26-40, 87-88, and 102-103.

In a nonlimiting aspect, the framework sequences and CDR's of the analogs will have (a) a Q at position 108; and/or (b) a charged amino acid or a cysteine residue at position 45 and preferably an E at position 44, and more preferably E at position 44 and R at position 45; and/or (c) P, R or S at position 103.

In one nonlimiting aspect, one class of analogs of the NB agents of the invention comprise NB agents that have been humanized (i.e., compared to the sequence of a naturally occurring NB agents of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, e.g., from the Tables herein, from the possible humanizing substitutions mentioned in the background art cited herein, and/or from a comparison between the sequence of a NB agent and the sequence of a naturally occurring human $V_H$ domain.

In one nonlimiting aspect, the humanizing substitutions are chosen such that the resulting humanized NB agents still retain the favorable properties of NB agents as provided herein, and further such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may, e.g., involve introducing a limited number of possible humanizing substitutions and determining their influence on the properties of the NB agents thus obtained.

In one nonlimiting aspect, as a result of humanization, the NB agents of the invention may become more "human-like", while still retaining the favorable properties of the NB agents of the invention as described herein. As a result, such humanized NB agents may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_{HH}$ domains on the other hand.

The NB agents of the invention may be suitably humanized at any framework residue(s), such as at one or more Hallmark residues or at one or more other framework residues (i.e., non-Hallmark residues) or any suitable combination thereof. One preferred humanizing substitution for NB agents of the "P,R,S-103 group" or the "KERE group" is Q108 into L108. NB agents of the "GLEW class" ("GLEW" is disclosed as SEQ ID NO: 104) may also be humanized by a Q108 into L108 substitution, provided at least one of the other Hallmark residues contains a camelid (camelizing) substitution. For example, as mentioned herein, one particularly preferred class of humanized NB agents has GLEW (SEQ ID NO: 104) or a GLEW-like sequence ("GLEW" is disclosed as SEQ ID NO: 104) at positions 44-47; P, R or S (and in particular R) at position 103, and an L at position 108.

The humanized and other analogs, and nucleic acid sequences encoding the same, can be provided in any manner known per se, e.g., using one or more of the techniques mentioned on pages 103 and 104 of WO 08/020,079.

In one nonlimiting aspect, one class of analogs of the NB agents of the invention comprise NB agents that have been humanized (i.e., compared to the sequence of a naturally occurring NB agent of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, e.g., from the Tables herein, from the possible humanizing substitutions mentioned in the background art cited herein, and/or from a comparison between the sequence of a NB agent and the sequence of a naturally occurring human $V_H$ domain.

In one nonlimiting aspect, the humanizing substitutions are chosen such that the resulting humanized NB agents still retain the favorable properties of NB agents as provided herein, and more preferably such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may, e.g., involve introducing a limited number of possible humanizing substitutions and determining their influence on the properties of the NB agents thus obtained.

Generally, as a result of humanization, the NB agents of the invention may become more "human-like", while still retaining the favorable properties of the NB agents of the invention as described herein. As a result, such humanized NB agents may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_{HH}$ domains on the other hand.

The NB agents of the invention may be suitably humanized at any framework residue(s), such as at one or more Hallmark residues (as defined in WO 2008/020079) or at one or more other framework residues (i.e., non-Hallmark residues) or any suitable combination thereof.

The humanized and other analogs, and nucleic acid sequences encoding the same, can be provided in any manner known per se. For example, the analogs can be obtained by providing a nucleic acid that encodes a naturally occurring $V_{HH}$ domain, changing the codons for the one or more amino acid residues that are to be substituted into the codons for the corresponding desired amino acid residues (e.g. by site-directed mutagenesis or by PCR using suitable mismatch primers), expressing the nucleic acid/nucleotide sequence thus obtained in a suitable host or expression system; and optionally isolating and/or purifying the analog thus obtained to provide said analog in essentially isolated form (e.g. as further described herein).

This can generally be performed using methods and techniques known per se, which will be clear to the skilled person, e.g., from the handbooks and references cited herein, the background art cited herein and/or from the further description herein. Alternatively, a nucleic acid encoding the desired analog can be synthesized in a manner known per se (for example using an automated apparatus for synthesizing nucleic acid sequences with a predefined amino acid sequence) and can then be expressed as described herein. Yet another technique may involve combining one or more naturally occurring and/or synthetic nucleic acid sequences each encoding a part of the desired analog, and then expressing the combined nucleic acid sequence as described herein. Also, the analogs can be provided using chemical synthesis of the pertinent amino acid sequence using techniques for peptide synthesis known per se, such as those mentioned herein.

In this respect, it will be also be clear to the skilled person that the NB agents of the invention (including their analogs) can be designed and/or prepared starting from human $V_H$ sequences (i.e., amino acid sequences or the corresponding nucleotide sequences), such as, e.g., from human $V_H3$ sequences such as DP-47, DP-51 or DP-29, i.e., by introducing one or more camelizing substitutions (i.e., changing one or more amino acid residues in the amino acid sequence of said human $V_H$ domain into the amino acid residues that occur at the corresponding position in a $V_{HH}$ domain), so as to provide the sequence of a NB agent of the invention and/or so as to confer the favorable properties of a NB agent to the sequence thus obtained. Again, this can generally be performed using the various methods and techniques referred to in the previous paragraph, using an amino acid sequence and/or nucleotide sequence for a human $V_H$ domain as a starting point.

As mentioned there, it will be clear to the skilled person that the NB agents of the invention (including their analogs) can be designed and/or prepared starting from human $V_H$ sequences (i.e., amino acid sequences or the corresponding nucleotide sequences), such as, e.g., from human $V_H3$ sequences such as DP-47, DP-51 or DP-29, i.e., by introducing one or more camelizing substitutions (i.e., changing one or more amino acid residues in the amino acid sequence of said human $V_H$ domain into the amino acid residues that occur at the corresponding position in a $V_{HH}$ domain), so as to provide the sequence of a NB agent of the invention and/or so as to confer the favorable properties of a NB agents to the sequence thus obtained. Again, this can generally be performed using the various methods and techniques referred to in the previous paragraph, using an amino acid sequence and/or nucleotide sequence for a human $V_H$ domain as a starting point.

Some non-limiting camelizing substitutions can be derived from WO 2008/020079. It will be clear that camelizing substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelizing substitutions that already confer at least some the desired properties, and then to introduce further camelizing substitutions that either further improve said properties and/or confer additional favorable properties. Again, the skilled person will generally be able to determine and select suitable camelizing substitutions or suitable combinations of camelizing substitutions, based on the disclosure herein and optionally after a limited degree of routine experimentation, which may, e.g., involve introducing a limited number of possible camelizing substitutions and determining whether the favorable properties of NB agents are obtained or improved (i.e., compared to the original $V_H$ domain).

In one nonlimiting aspect, such camelizing substitutions are such that the resulting an amino acid sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelizing substitutions. In one nonlimiting aspect, the camelizing substitutions are such that they result in a NB agent of the invention and/or in an analog thereof, such as in a humanized analog and/or preferably in an analog that is as provided in the preceding paragraphs.

As will also be clear from the disclosure herein, it is also within the scope of the invention to use parts or fragments, or combinations of two or more parts or fragments, of the NB agents of the invention as provided herein, and in particular parts or fragments of the NB agents of SEQ ID NO's: 1-22, 26-40, 87-88, and 102-103 and of SEQ ID NOS: 96-99. Thus, according to one aspect of the invention, the term "NB agents of the invention" in its broadest sense also covers such parts or fragments.

Generally, such parts or fragments of the NB agents of the invention (including analogs thereof) have amino acid sequences in which, compared to the amino acid sequence of the corresponding full length NB agent of the invention (or analog thereof), one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to a DR5, e.g., human DR5 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as provided herein for the NB agents of the invention.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length NB agent of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e., CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting aspect, such a part or fragment comprises at least CDR3, such as FR3, CDR3 and FR4 of the corresponding full length NB agent of the invention, i.e., as, e.g., described in the International application WO 03/050531 (Lasters et al.).

As already mentioned herein, it is also possible to combine two or more of such parts or fragments (i.e., from the same or different NB agents of the invention), i.e., to provide an analog and/or to provide further parts or fragments of a NB agent of the invention. It is, e.g., also possible to combine one or more parts or fragments of a NB agent of the invention with one or more parts or fragments of a human $V_H$ domain.

According to one aspect, the parts or fragments have a degree of sequence identity of at least 50%, at least 60%, at least 70%, at least 80%, and/or at least 90%, 95% or 99% or more with one of the NB agents of SEQ ID NOs 1-22, 26-40, 87-88, and 102-103, and with SEQ ID NOs: 96-99.

The parts and fragments, and nucleic acid sequences encoding the same, can be provided and optionally combined in any manner known per se. For example, such parts or fragments can be obtained by inserting a stop codon in a nucleic acid that encodes a full-sized NB agent of the invention, and then expressing the nucleic acid thus obtained in a manner known per se (e.g. as described herein). Alternatively, nucleic acids encoding such parts or fragments can be obtained by suitably restricting a nucleic acid that encodes a full-sized NB agent of the invention or by synthesizing such a nucleic acid in a manner known per se. Parts or fragments may also be provided using techniques for peptide synthesis known per se.

The invention in its broadest sense also comprises derivatives of the NB agents of the invention. Such derivatives can generally be obtained by modification, and in particular by chemical and/or biological (e.g. enzymatic) modification, of the NB agents of the invention and/or of one or more of the amino acid residues that form the NB agents of the invention.

Examples of such modifications, as well as examples of amino acid residues within the NB agent sequence that can be modified in such a manner (i.e., either on the polypeptide backbone but preferably on a side chain), methods and techniques that can be used to introduce such modifications and the potential uses and advantages of such modifications will be clear to the skilled person.

In one nonlimiting aspect, such a modification involves the introduction (e.g. by covalent linking or in an other suitable manner) of one or more functional groups, residues or moieties into or onto the NB agent of the invention, and in particular of one or more functional groups, residues or moieties that confer one or more desired properties or functionalities to the NB agent of the invention. Example of such functional groups will be clear to the skilled person.

In one nonlimiting aspect, such modification comprise the introduction (e.g. by covalent binding or in any other suitable manner) of one or more functional groups that increase the half-life, the solubility and/or the absorption of the NB agent of the invention, that reduce the immunogenicity and/or the toxicity of the NB agent of the invention, that eliminate or attenuate any undesirable side effects of the NB agent of the invention, and/or that confer other advantageous properties to and/or reduce the undesired properties of the NB agents and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is, e.g., made to Remington's Pharmaceutical Sciences, 16th ed., Mack Publishing Co., Easton, Pa. (1980). Such functional groups may, e.g., be linked directly (for example covalently) to a NB agent of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethylene glycol) (PEG) or derivatives thereof (such as methoxypoly(ethylene glycol) or mPEG). Generally, any suitable form of pegylation can be used, such as the pegylation used in the art for antibodies and antibody fragments (including but not limited to (single) domain antibodies and ScFv's); See, e.g., Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, e.g., from Nektar Therapeutics, USA.

In one embodiment, site-directed pegylation is used, in particular via a cysteine-residue (see, e.g., Yang et al., Protein Engineering, 16, 10, 761-770 (2003). In various embodiments, for this purpose, PEG is attached to a cysteine residue that naturally occurs in a NB agent of the invention. A NB agent of the invention may be modified so as to suitably introduce one or more cysteine residues for attachment of PEG, or an amino acid sequence comprising one or more cysteine residues for attachment of PEG may be fused to the N- and/or C-terminus of a NB agent of the invention, all using techniques of protein engineering known per se to the skilled person.

In one embodiment, for the NB agents and proteins of the invention, a PEG is used with a molecular weight of more than 5000, such as more than 10,000 and less than 200,000, such as less than 100,000;, e.g., in the range of 20,000-80,000.

In one embodiment, modification comprises N-linked or O-linked glycosylation, usually as part of co-translational and/or post-translational modification, depending on the host cell used for expressing the NB agent or polypeptide of the invention.

In one embodiment, modification may comprise the introduction of one or more detectable labels or other signal-generating groups or moieties, depending on the intended use of the labeled NB agent. Suitable labels and techniques for attaching, using and detecting them will be clear to the skilled person, and, e.g., include, but are not limited to, the fluorescent labels, phosphorescent labels, chemiluminescent labels, bioluminescent labels, radio-isotopes, metals, metal chelates, metallic cations, chromophores and enzymes, such as those mentioned on page 109 of WO 08/020,079. Other suitable labels will be clear to the skilled person, and, e.g., include moieties that can be detected using NMR or ESR spectroscopy.

Such labeled NB agents and polypeptides of the invention may, e.g., be used for in vitro, in vivo or in situ assays (including immunoassays known per se such as ELISA, RIA, EIA and other "sandwich assays", etc.) as well as in vivo diagnostic and imaging purposes, depending on the choice of the specific label.

In one embodiment, modification may involve the introduction of a chelating group, e.g., to chelate one of the metals or metallic cations referred to above. Suitable chelating groups, e.g., include, without limitation, diethyl-enetriamine-pentaacetic acid (DTPA) or ethylenediaminetetraacetic acid (EDTA).

In one embodiment, modification may comprise the introduction of a functional group that is one part of a specific binding pair, such as the biotin-(strept)avidin binding pair. Such a functional group may be used to link the NB agent of the invention to another protein, polypeptide or chemical compound that is bound to the other half of the binding pair, i.e., through formation of the binding pair. For example, a NB agent of the invention may be conjugated to biotin, and linked to another protein, polypeptide, compound or carrier conjugated to avidin or streptavidin. For example, such a conjugated NB agent may be used as a reporter, e.g., in a diagnostic system where a detectable signal-producing agent is conjugated to avidin or streptavidin. Such binding pairs may, e.g., also be used to bind the NB agent of the invention to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the inventive NB agent.

For some applications, in particular for those applications in which it is intended to kill a cell that expresses the target against which the NB agents of the invention are directed (e.g. in the treatment of cancer), or to reduce or slow the growth and/or proliferation of such a cell, the NB agents of the invention may also be linked to a toxin or to a (cyto)toxic residue or moiety. Examples of toxic moieties, compounds or residues which can be linked to a NB agent of the invention to provide —, e.g.,—a cytotoxic compound will be clear to the skilled person and can, e.g., be found in the art references cited above and/or in the further description herein. One example is the so-called ADEPT™ technology described in WO 03/055527.

Other potential chemical and enzymatic modifications will be clear to the skilled person and are within the scope of the invention. Such modifications may also be introduced for research purposes (e.g. to study function-activity relationships). Reference is, e.g., made to Lundblad and Bradshaw, Biotechnol. Appl. Biochem., 26, 143-151 (1997).

In one nonlimiting aspect, the derivatives are such that they bind to a DR5, e.g., human DR5, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as provided herein for the NB agents of the invention.

As mentioned herein, the invention also relates to proteins or polypeptides that essentially consist of or comprise at least one NB agent of the invention. By "essentially consist of" is meant that the amino acid sequence of the polypeptide of the invention either is exactly the same as the amino acid sequence of a NB agent of the invention or corresponds to the amino acid sequence of a NB agent of the invention which has a limited number of amino acid residues, such as 1-20 amino acid residues, e.g., 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence of the NB agent.

Said amino acid residues may or may not change, alter or otherwise appreciably influence the (biological) properties of the NB agent, and may or may not add further functionality to the NB agent. For example, such amino acid residues:

a) can comprise an N-terminal Met residue, e.g., as result of expression in a heterologous host cell or host organism; or b) may form a signal sequence or leader sequence that directs secretion of the NB agent from a host cell upon synthesis. Suitable secretory leader peptides will be clear to the skilled person, and may be as further described herein. Usually, such a leader sequence will be linked to the N-terminus of the NB agent, although the invention in its broadest sense is not limited thereto; or c) may form a sequence or signal that allows the NB agent to be directed towards and/or to penetrate or enter into specific organs, tissues, cells, or parts or compartments of cells, and/or that allows the NB agent to penetrate or cross a biological barrier such as a cell membrane, a cell layer such as a layer of epithelial cells, a tumor including solid tumors, or the blood-brain-barrier. Examples of such amino acid sequences will be clear to the skilled person and include those mentioned in paragraph c) on page 112 of WO 08/020,079; or d) may form a "tag", e.g., an amino acid sequence or residue that allows or facilitates the purification of the NB agent, e.g., using affinity techniques directed against said sequence or residue. Thereafter, said sequence or residue may be removed (e.g. by chemical or enzymatic cleavage) to provide the NB agent sequence (for this purpose, the tag may optionally be linked to the NB agent sequence via a cleavable linker sequence or contain a cleavable motif). Some non-limiting examples of such residues are one or more of each of a cMyc tag (SEQ ID NO: 91), multiple histidine residues such as the Hisx6 tag (SEQ ID NO: 92), or a combination of a cMyc tag and the Hisx6 tag (SEQ ID NO: 93 or SEQ ID NO: 94) ("Hisx6" is disclosed as SEQ ID NO: 92) PEGylation substrate tag (SEQ ID NO: 95), glutathione residues and other myc-tag (see, e.g., SEQ ID NO: 31 of WO 06/12282); or e) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the NB agents of the invention.

According to one aspect, a polypeptide of the invention comprises a NB agent of the invention that is fused at its amino terminal end, at its carboxy terminal end, or both at its amino terminal end and at its carboxy terminal end, to at least one further amino acid sequence, i.e., so as to provide a fusion protein comprising said NB agent of the invention and the one or more further amino acid sequences. Such a fusion is referred to herein as a "NB agent fusion".

The one or more further amino acid sequence may be any suitable and/or desired amino acid sequences. The further amino acid sequences may or may not change, alter or otherwise influence the (biological) properties of the NB agent, and may or may not add further functionality to the NB agent or the polypeptide of the invention. Preferably, the further amino acid sequence is such that it confers one or more desired properties or functionalities to the NB agent or the polypeptide of the invention.

For example, the further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the NB agent of the invention is directed, or a different protein, polypeptide, antigen, antigenic determinant or epitope).

Example of such amino acid sequences will be clear to the skilled person, and may generally comprise all amino acid sequences that are used in peptide fusions based on conventional antibodies and fragments thereof (including but not limited to ScFv's and single domain antibodies). Reference is, e.g., made to the review by Holliger and Hudson, Nature Biotechnology, 23, 9, 1126-1136 (2005).

In one nonlimiting aspect, such an amino acid sequence is an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the NB agent of the invention per se. Some non-limiting examples of such amino acid sequences are serum proteins, such as human serum albumin (see, e.g., WO 00/27435) or haptenic molecules (for example haptens that are recognized by circulating antibodies, see, e.g., WO 98/22141).

In particular, it has been described in the art that linking fragments of immunoglobulins (such as $V_H$ domains) to serum albumin or to fragments thereof can be used to increase the half-life. Reference is made, e.g., to WO 00/27435 and WO 01/077137. According to the invention, a NB agent of the invention is preferably either directly linked to serum albumin (or to a suitable fragment thereof) or via a suitable linker, and in particular via a suitable peptide linked so that the polypeptide of the invention can be expressed as a genetic fusion (protein). According to one specific aspect, the NB agent of the invention may be linked to a fragment of serum albumin that at least comprises the domain III of serum albumin or part thereof. Reference is, e.g., made to WO 07/112,940 of Ablynx N.V.

Alternatively, the further amino acid sequence may provide a second binding site or binding unit that is directed against a serum protein (such as, e.g., human serum albumin or another serum protein such as IgG), so as to provide increased half-life in serum. Such amino acid sequences, e.g., include the NB agent described below, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, and to WO 2006/122787, WO 2008/028977, WO 2008/043821, WO 2008/068280 and WO 2009/127691 by Ablynx N.V.

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see, e.g., WO 06/0122787) and/or amino acid sequences that are capable of binding to amino acid residues on serum albumin that do not form part of domain III of serum albumin (see again, e.g., WO 06/0122787); amino acid sequences that have or can provide an increased half-life (see, e.g., WO 08/028,977 by Ablynx N.V); amino acid sequences against human serum albumin that are cross-reactive with serum albumin from at least one species of mammal, and in particular with at least one species of primate (such as, without limitation, monkeys from the genus *Macaca* (such as, and in particular, cynomologus monkeys, a.k.a. "cyno" (*Macaca fascicularis*) and/or rhesus monkeys (*Macaca mulatta*)) and baboon (*Papio ursinus*), reference is again made to the U.S. provisional application 60/843, 349); amino acid sequences that can bind to serum albumin in a pH independent manner (see, e.g., the U.S. provisional application 60/850,774 by Ablynx N.V. entitled "Amino acid sequences that bind to serum proteins in a manner that is essentially independent of the pH, compounds comprising the same, and uses thereof", filed on Oct. 11, 2006) and/or amino acid sequences that are conditional binders (see, e.g., the U.S. provisional application 60/850,775 by Ablynx N.V. entitled "Amino acid sequences that bind to a desired molecule in a conditional manner", filed on Oct. 11, 2006) and to WO 2006/122787, WO 2008/028977, WO 2008/043821, WO 2008/068280 and WO 2009/127691.

According to another aspect, the one or more further amino acid sequences may comprise one or more parts, fragments or domains of conventional four-chain antibodies (and in particular human antibodies) and/or of heavy chain antibodies. For example, although usually less preferred, a NB agent of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

The at least one NB agent may be linked to one or more (preferably human) $C_H1$, $C_H2$ and/or $C_H3$ domains, optionally via a linker sequence. For instance, a NB agent linked to a suitable $C_H1$ domain could be used—together with suitable light chains—to generate antibody fragments/structures analogous to conventional Fab fragments or $F(ab')_2$ fragments, but in which one or (in case of an $F(ab')_2$ fragment) one or both of the conventional $V_H$ domains have been replaced by a NB agent of the invention. Also, two NB agents could be linked to a $C_H3$ domain (optionally via a linker) to provide a construct with increased half-life in vivo.

In one aspect of the invention, one or more NB agents of the invention are linked to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, e.g., from IgG, from IgE or from another human Ig. For example, WO 94/04678 describes heavy chain antibodies comprising a Camelid $V_{HH}$ domain or a humanized derivative thereof, in which the Camelidae $C_H2$ and/or $C_H3$ domain have been replaced by human $C_H2$ and $C_H3$ domains, so as to provide an immunoglobulin that consists of two heavy chains each comprising a $V_{HH}$ and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the NB agents of the invention so as to provide an effector function will be clear to the skilled person, and may be chosen on the basis of the desired effector function(s). Reference is, e.g., made to WO 04/058820, WO 99/42077 and WO 05/017148, as well as the review by Holliger and Hudson, supra. Coupling of a NB agent of the invention to an Fc portion may also lead to an increased half-life, compared to the corresponding NB agent of the invention. For some applications, the use of an Fc portion and/or of constant domains (i.e., $C_H2$ and/or $C_H3$ domains) that confer increased half-life without any biologically significant effector function may also be suitable or even preferred. Other suitable constructs comprising one or more NB agents and one or more constant domains with increased half-life in vivo will be clear to the skilled person, and may, e.g., comprise two NB agents linked to a $C_H3$ domain, optionally via a linker sequence. Generally, any fusion protein or derivatives with increased half-life will preferably have a molecular weight of more than 50 kD, the cut-off value for renal absorption.

The further amino acid sequences may also form a signal sequence or leader sequence that directs secretion of the NB agent or the polypeptide of the invention from a host cell upon synthesis (for example to provide a pre-, pro- or prepro-form of the polypeptide of the invention, depending on the host cell used to express the polypeptide of the invention).

In one aspect, a further amino acid sequence forms a sequence or signal that allows the NB agent or polypeptide of the invention to be directed towards and/or to penetrate or enter into specific organs, tissues, cells, or parts or compartments of cells, and/or that allows the NB agent or polypeptide of the invention to penetrate or cross a biological barrier such as a cell membrane, a cell layer such as a layer of epithelial cells, a tumor including solid tumors, or the blood-brain-barrier. Suitable examples of such amino acid sequences will be clear to the skilled person, and, e.g., include, but are not limited to, those mentioned on page 118 of WO 08/020,079. For some applications, in particular for those applications in which it is intended to kill a cell that expresses the target against which the NB agents of the invention are directed (e.g. in the treatment of cancer), or to reduce or slow the growth and/or proliferation of such a cell, the NB agents of the invention may also be linked to a (cyto)toxic protein or polypeptide. Examples of such toxic proteins and polypeptides which can be linked to a NB agent of the invention to provide —, e.g.,—a cytotoxic polypeptide of the invention will be clear to the skilled person and can, e.g., be found in the art references cited above and/or in the further description herein. One example is the so-called ADEPT™ technology described in WO 03/055527.

In one non-limiting aspect, said one or more further amino acid sequences comprise at least one further NB agent, so as to provide a polypeptide of the invention that comprises at least two, such as three, four, five or more NB agents, in which said NB agents may optionally be linked via one or more linker sequences. Polypeptides of the invention that comprise one, two or more $V_{HH}$ constructs, e.g., as described on pages 119 and 120 of WO 08/020,079, and at least one NB agent of the invention, will also be referred to herein as "multivalent" polypeptides of the invention, and the NB agent(s) present in such polypeptides will also be referred to herein as being in a "multivalent format".

Polypeptides of that contain at least two NB agents, in which at least one NB agent is directed against a first antigen (i.e., against DR5,) and at least one NB agent is directed against a second antigen (i.e., different from DR5), will also be referred to as "multispecific" polypeptides of the invention, and the NB agent present in such polypeptides will also be referred to herein as being in a "multispecific format". Thus, e.g., a "bispecific" polypeptide of the invention is a polypeptide that comprises at least one NB agent directed against a first antigen (i.e., DR5), more preferably three, four, five or more NB agents directed against DR5 and at least one further NB agent directed against a second antigen (i.e., different from DR5), whereas a "trispecific" polypeptide of the invention is a polypeptide that comprises at least one NB agent directed against a first antigen (i.e., one epitope of DR5), at least one further NB agent directed against a second antigen (i.e., a different epitope from DR5 or an antigen different from TRAIIL-receptor,) and at least one further NB agent directed against a third antigen (i.e., different from both DR5 and the second antigen); etc.

Accordingly, in its simplest form, a bispecific polypeptide of the invention is a bivalent polypeptide of the invention, comprising a first NB agent directed against DR5, and a second NB agent directed against a second antigen, in which said first and second NB agent may optionally be linked via a linker sequence; whereas a trispecific polypeptide of the invention in its simplest form is a trivalent polypeptide of the invention, comprising a first NB agent directed against DR5, a second NB agent directed against a second antigen and a third NB agent directed against a third antigen, in which said first, second and third NB agent may optionally be linked via one or more, and in particular one and more, in particular two, linker sequences.

As will be clear from the description herein, the invention is not limited the above, in the sense that a multispecific polypeptide of the invention may comprise at least one or more NB agents against DR5, and any number of NB agents directed against one or more antigens different from DR5.

When reference is made to a specific multivalent or multispecific polypeptide of the invention, it should be noted that this encompasses any order or arrangements of the relevant NB agents, unless explicitly indicated otherwise.

Furthermore, it is within the scope of the invention that the polypeptides of the invention contain two or more NB agents and one or more further amino acid sequences (as mentioned herein).

For multivalent and multispecific polypeptides containing one or more $V_{HH}$ domains and their preparation, reference is also made to Conrath et al., J. Biol. Chem., Vol. 276, 10. 7346-7350, 2001; Muyldermans, Reviews in Molecular Biotechnology 74 (2001), 277-302; as well as to, e.g., WO 96/34103 and WO 99/23221. Some other examples of some specific multispecific and/or multivalent polypeptide of the invention can be found in the applications by Ablynx N.V. referred to herein.

One non-limiting example of a multispecific polypeptide of the invention comprises at least one NB agent of the invention and at least one NB agent that provides for an increased half-life. Such NB agents may, e.g., be NB agents that are directed against a serum protein, and in particular a human serum protein, such as human serum albumin, thyroxine-binding protein, (human) transferrin, fibrinogen, an immunoglobulin such as IgG, IgE or IgM, or against one of the serum proteins listed in WO 04/003019. Of these, NB agents that can bind to serum albumin (and in particular human serum albumin) or to IgG (and in particular human IgG, see, e.g., NANOBODY™ VH-1 described in the review by Muyldermans, supra) are particularly preferred (although, e.g., for experiments in mice or primates, NB agents against or cross-reactive with mouse serum albumin (MSA) or serum albumin from said primate, respectively, can be used. However, for pharmaceutical use, NB agents against human serum albumin or human IgG will usually be preferred). NB agents that provide for increased half-life and that can be used in the polypeptides of the invention include the NB agents directed against serum albumin that are described in WO 04/041865, in WO 06/122787 and in the further patent applications by Ablynx N.V., such as those mentioned herein.

For example, the some preferred NB agents that provide for increased half-life for use in the present invention include NANOBODIES™ that can bind to amino acid residues on (human) serum albumin that are not involved in binding of serum albumin to FcRn (see, e.g., WO 06/0122787); NANOBODIES™ that are capable of binding to amino acid residues on serum albumin that do not form part of domain III of serum albumin (see, e.g., WO 06/0122787); NANOBODIES™ that have or can provide an increased half-life (see, e.g., the U.S. provisional application 60/843,349 by Ablynx N.V mentioned herein); NANOBODIES™ against human serum albumin that are cross-reactive with serum albumin from at least one species of mammal, and in particular with at least one species of primate (such as, without limitation, monkeys from the genus *Macaca* (such as, and in particular, cynomologus monkeys (*Macaca fascicularis*) and/or rhesus monkeys (*Macaca mulatta*)) and baboon (*Papio ursinus*)) (see, e.g., the U.S. provisional application 60/843,349 by Ablynx N.V); NANOBODIES™ that can bind to serum albumin in a pH independent manner (see, e.g., the U.S. provisional application 60/850,774 by Ablynx N.V. mentioned herein) and/or NANOBODIES™ that are conditional binders (see, e.g., the U.S. provisional application 60/850,775 by Ablynx N.V.).

Some particularly preferred NANOBODIES™ that provide for increased half-life and that can be used in the polypeptides of the invention include the NANOBODIES™ ALB-1 to ALB-10 disclosed in WO 06/122787 (see Tables II and III therein) of which ALB-8 (SEQ ID NO: 62 in WO 06/122787) is particularly preferred.

According to a specific, but non-limiting aspect of the invention, the polypeptides of the invention contain, besides the one or more NB agents of the invention, at least one NB agent against human serum albumin.

In one embodiment, any polypeptides of the invention with increased half-life that contain one or more NB agents of the invention, and any derivatives of NB agents of the invention or of such polypeptides that have an increased half-life, have a half-life that is at least 1.5 times, and/or at least 2 times, and/or at least 5 times, e.g., at least 10 times or more than 20 times, greater than the half-life of the corresponding NB agent of the invention per se. For example, such a derivative or polypeptides with increased half-life may have a half-life that is increased with more than 1 hours, and/or more than 2 hours, and/or more than 6 hours, such as more than 12 hours, or even more than 24, 48 or 72 hours, compared to the corresponding NB agent of the invention per se.

In one non-limiting aspect of the invention, such derivatives or polypeptides exhibit a serum half-life in human of at least about 12 hours, and/or at least 24 hours, and/or at least 48 hours, and/or at least 72 hours or more. For example, such derivatives or polypeptides may have a half-life of at least 5 days (such as about 5 to 10 days), and/or at least 9 days (such as about 9 to 14 days), and/or at least about 10 days (such as about 10 to 15 days), and/or at least about 11 days (such as about 11 to 16 days), and/or at least about 12 days (such as about 12 to 18 days or more), and/or more than 14 days (such as about 14 to 19 days).

According to one aspect of the invention, such polypeptides are capable of binding to one or more molecules that can increase the half-life of the polypeptide in vivo.

Such polypeptides of the invention are stabilized in vivo and their half-life increased by binding to molecules that resist degradation and/or clearance or sequestration. Typically, such molecules are naturally occurring proteins which themselves have a long half-life in vivo.

Another non-limiting example of a multispecific polypeptide of the invention comprises at least one NB agent of the invention and at least one NB agent that directs the polypeptide of the invention towards, and/or that allows the polypeptide of the invention to penetrate or to enter into specific organs, tissues, cells, or parts or compartments of cells, and/or that allows the NB agent to penetrate or cross a biological barrier such as a cell membrane, a cell layer such as a layer of epithelial cells, a tumor including solid tumors, or the blood-brain-barrier. Examples of such NB agents include NB agents that are directed towards specific cell-surface proteins, markers or epitopes of the desired organ, tissue or cell (for example cell-surface markers associated with tumor cells), and the single-domain brain targeting antibody fragments described in WO 02/057445 and WO 06/040153, of which FC44 (SEQ ID NO: 189 of WO 06/040153) and FC5 (SEQ ID NO: 190 of WO 06/040154) are preferred examples.

Linkers

In the polypeptides or compounds of the invention, the one or more binding polypeptides against DR5, such as NB agents and the one or more polypeptides may be directly linked to each other (as, e.g., described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as, e.g., linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each NB agent by itself forms a complete antigen-binding site).

For example, a linker may be a suitable amino acid sequence, and in particular amino acid sequences of between 1 and 50, e.g., between 5 and 50, preferably between 1 and 35, such as between 1 and 10 amino acid residues. Some preferred examples of such amino acid sequences include gly-ser linkers, e.g., of the type $(gly_x ser_y)_z$, such as (for example $(gly_4 ser)_3$ (SEQ ID NO: 105) or $(gly_3 ser_2)_3$ (SEQ ID NO: 106), as described in WO 99/42077 and the GS30, GS15, GS9 and GS7 linkers described in the applications by Ablynx mentioned herein (see, e.g., WO 06/040153 and WO 06/122825), as well as hinge-like regions, such as the hinge regions of naturally occurring heavy chain antibodies or similar sequences (e.g., such as described in WO 94/04678).

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. Nonlimiting examples include, e.g., poly(ethylene glycol) moieties, e.g., such as those used to link antibody domains. See, e.g., WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for DR5, or for one or more of the other antigens. Based on the disclosure herein, the skilled person will be able to determine the optimal linker(s) for use in a specific polypeptide of the invention, optionally after some limited routine experiments.

In one embodiment, in multivalent polypeptides of the invention that comprise, e.g., NB agents directed against a multimeric antigen (such as a multimeric receptor or other protein), the length and flexibility of the linker may be such that it allows each NB agent of the invention present in the polypeptide to bind to the antigenic determinant on each of the subunits of the multimer. Similarly, in a multispecific polypeptide of the invention that comprises NB agents directed against two or more different antigenic determinants on the same antigen (for example against different epitopes of an antigen and/or against different subunits of a multimeric receptor, channel or protein), the length and flexibility of the linker may be such that it allows each NB agent to bind to its intended antigenic determinant. Again, based on the disclosure herein, the skilled person will be able to determine the optimal linker(s) for use in a specific polypeptide of the invention, optionally after some limited routine experiments.

It is within the scope of the invention that the linker(s) used confer one or more other favorable properties or functionality to the polypeptides of the invention, and/or provide one or more sites for the formation of derivatives and/or for the attachment of functional groups (e.g. as described herein for the derivatives of the NB agents of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three or more NB agents, it is possible to link them by use of a linker with three or more "arms", with each "arm" being linked to a NB agent, so as to provide a "star-shaped" construct. It is also possible, although usually less preferred, to use circular constructs.

The invention further comprises derivatives of the polypeptides of the invention, which may be essentially analogous to the derivatives of the NB agents of the invention, i.e., as described herein.

The invention also comprises proteins or polypeptides that "essentially consist" of a polypeptide of the invention (in which the wording "essentially consist of" has essentially the same meaning as indicated hereinabove).

According to one aspect of the invention, the polypeptide of the invention is in essentially isolated form, as defined herein.

Method of Manufacturing the NB Agents of the Invention

The amino acid sequences, NB agents, polypeptides, compounds and nucleic acids of the invention can be prepared in a manner known per se, as will be clear to the skilled person from the further description herein. For example, the NB agents and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, NB agents, polypeptides and nucleic acids include the methods and techniques described herein.

As will be clear to the skilled person, one particularly useful method for preparing an amino acid sequence, NB agent and/or a polypeptide of the invention generally comprises the steps of:
 a) the expression, in a suitable host cell or host organism (also referred to herein as a "host of the invention") or in another suitable expression system of a nucleic acid that encodes said amino acid sequence, NB agent or polypeptide of the invention (also referred to herein as a "nucleic acid of the invention"), optionally followed by:
 b) isolating and/or purifying the amino acid sequence, NB agent or polypeptide of the invention thus obtained.

In particular, such a method may comprise the steps of:
 a) cultivating and/or maintaining a host of the invention under conditions that are such that said host of the invention expresses and/or produces at least one amino acid sequence, NB agent and/or polypeptide of the invention; optionally followed by:
 b) isolating and/or purifying the amino acid sequence, NB agent or polypeptide of the invention thus obtained.

A nucleic acid of the invention can be in the form of single or double stranded DNA or RNA. In one embodiment, a polynucleotide NB agent is in the form of double stranded DNA. For example, the nucleotide NB sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated form, as defined herein.

The nucleic acid of the invention may be in the form of, be present in and/or be part of a vector, such as, e.g., a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring $V_{HH}$ domains can, e.g., be subjected to site-directed mutagenesis, so at to provide a nucleic acid of the invention encoding said analog. As will be clear to the skilled person, to prepare a nucleic acid of the invention, including several nucleotide sequences, e.g., at least one nucleotide sequence encoding a NB agent and, e.g., nucleic acids encoding one or more linkers, such sequences can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using, e.g., a sequence of a naturally occurring form of DR5 as a template. These and other techniques will be clear to the skilled person, and reference is again made to the standard handbooks, such as Sambrook et al. and Ausubel et al., mentioned herein, as well as the Examples below.

The nucleic acid of the invention may be in the form of, be present in and/or be part of a genetic construct, as will be clear to the person skilled in the art and, e.g., as described on pages 131-134 of WO 08/020,079. Such genetic constructs generally comprise at least one nucleic acid of the invention that is optionally linked to one or more elements of genetic constructs known per se, such as, e.g., one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA. The genetic constructs of the invention may be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as, e.g., a plasmid, cosmid, YAC, a viral vector or transposon. In particular, the vector may be an expression vector, i.e., a vector that can provide for expression in vitro and/or in vivo (e.g. in a suitable host cell, host organism and/or expression system).

The nucleic acid of the invention may be in the form of, be present in and/or be part of a genetic construct. Such genetic constructs generally comprise at least one nucleic acid of the invention that is optionally linked to one or more elements of genetic constructs known per se, such as, e.g., one or more suitable regulatory elements (such as a suitable promoter(s), enhancer(s), terminator(s), etc.) and the further elements of genetic constructs referred to herein. Other suitable genetic constructs known in the art are contemplated as being within the scope of the invention, including e.g., those described on pages 131-134 of WO 08/020,079. Such genetic constructs comprising at least one nucleic acid of the invention will also be referred to herein as "genetic constructs of the invention".

In one non-limiting embodiment, a genetic construct of the invention comprises a) at least one nucleic acid of the invention; wherein said polynucleotide NB agent is operably connected to b) one or more regulatory elements, such as a promoter and optionally a suitable terminator; and optionally c) one or more further elements of genetic constructs known per se.

In one embodiment, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of said promotor). Generally, when two nucleotide sequences are operably linked, they will be in the same orientation and usually also in the same reading frame. They will usually be essentially contiguous, although this may not be required. The phrases "operably connected" and "operably linked" are used in the alternative.

The terms "regulatory element", "promoter", "terminator" and "operably connected" have their usual meaning in the art. The "further elements" present in the genetic constructs may be, e.g., a 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

In one embodiment, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein). Some particularly preferred promoters include, but are not limited to, promoters known per se for the expression in the host cells mentioned herein; and in particular promoters for the expression in the bacterial cells.

The nucleic acids of the invention and/or the genetic constructs of the invention may be used to transform a host cell or host organism, i.e., for expression and/or production of the amino acid sequence, NB agent or polypeptide of the invention. Suitable hosts or host cells will be clear to the skilled person, and may, e.g., be any suitable fungal, prokaryotic or eukaryotic cell or cell line or any suitable fungal, prokaryotic or eukaryotic organism, e.g., those described on pages 134 and 135 of WO 08/020,079; as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to, e.g., WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The NB amino acid sequences and polypeptides of the invention can be introduced and expressed in one or more cells, tissues or organs of a multicellular organism, e.g., for prophylactic and/or therapeutic purposes (e.g., as a gene therapy), as further described on pages 135 and 136 of in WO 08/020,079 and in the further references cited in WO 08/020,079.

For expression of the NB agents in a cell, they may be expressed as so-called "intrabodies", as, e.g., described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino NB acid sequences and polypeptides of the invention can, e.g., also be produced in the milk of transgenic mammals, e.g., in the milk of rabbits, cows, goats or sheep (see, e.g., U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or tubers (for example in tobacco, maize, soybean or alfalfa) or in, e.g., pupae of the silkworm *Bombix mori*.

Furthermore, the NB amino acid sequences and polypeptides of the invention can be expressed and/or produced in cell-free expression systems, and suitable examples of such systems will be clear to the skilled person. Some non-limiting examples include expression in the wheat germ system; in rabbit reticulocyte lysates; or in the *E. coli* Zubay system.

As mentioned herein, one of the advantages of the use of NB agents expressed from plasmids or vectors is that the polypeptides based thereon can be prepared through expression in a suitable bacterial system, and suitable bacterial expression systems, vectors, host cells, regulatory elements, etc., will be clear to the skilled person, e.g., from the references cited above. It should however be noted that the invention in its broadest sense is not limited to expression in bacterial systems.

In one embodiment, codon usage for a polynucleotide sequence of the invention is optimization by referring to the frequency of codon usage of the particular host cell/host organism. The resulting nucleotide sequence is a "codon optimized" NB nucleotide sequence. Codon optimized NB sequences may be made for expression in prokaryotic or eukaryotic host cells/host organisms. Particular examples include the expression systems provided herein.

In one embodiment of the invention an expression system (either in vivo or in vitro), e.g., such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of NB agents or NB agent-containing protein therapeutics include strains of *E. coli, Pichia pastoris, S. cerevisiae* that are suitable for large scale expression/production/fermentation, and in particular for large scale pharmaceutical (i.e., GMP grade) expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned herein.

The choice of the specific expression system would depend in part on the requirement for certain post-translational modifications, more specifically glycosylation. The production of a NB agent-containing recombinant protein for which glycosylation is desired or required would necessitate the use of mammalian expression hosts that have the ability to glycosylate the expressed protein. In this respect, it will be clear to the skilled person that the glycosylation pattern obtained (i.e., the kind, number and position of residues attached) will depend on the cell or cell line that is used for the expression. Preferably, either a human cell or cell line is used (i.e., leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, NB agent or polypeptide to be obtained.

Thus, according to one non-limiting aspect of the invention, the amino acid sequence, NB agent or polypeptide of the invention is glycosylated. According to another non-limiting aspect of the invention, the amino acid sequence, NB agent or polypeptide of the invention is non-glycosylated.

According to one preferred, but non-limiting aspect of the invention, the amino acid sequence, NB agent or polypeptide of the invention is produced in a bacterial cell, in particular a bacterial cell suitable for large scale pharmaceutical production, such as cells of the strains mentioned herein.

According to another preferred, but non-limiting aspect of the invention, the amino acid sequence, NB agent or polypeptide of the invention is produced in a yeast cell, in particular a yeast cell suitable for large scale pharmaceutical production, such as cells of the species mentioned herein.

According to yet another preferred, but non-limiting aspect of the invention, the amino acid sequence, NB agent or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, NB agents and the polypeptides of the invention, the NB amino acid sequences and polypeptides of the invention can be produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. Thus, according to one non-limiting aspect of the invention, the amino acid sequence, NB agent or polypeptide of the invention is an amino acid sequence, NB agent or polypeptide that has been produced intracellularly and that has been isolated from the host cell, and in particular from a bacterial cell or from an inclusion body in a bacterial cell. According to another non-limiting aspect of the invention, the amino acid sequence, NB agent or polypeptide of the invention is an amino acid sequence, NB agent or polypeptide that has been produced extracellularly, and that has been isolated from the medium in which the host cell is cultivated.

A more complete discussion of expression systems is provided, e.g., on pages 138 and 139 of WO 08/020,079. Included are a non-limiting list of promoters for use with these host cells, e.g., including those mentioned on pages 139 and 140 of WO 08/020,079. Also included are a non-limiting list of secretory sequences for use with these host cells, e.g., including those mentioned on page 140 of WO 08/020,079.

Suitable techniques for transforming a host or host cell of the invention will be clear to the skilled person and may depend on the intended host cell/host organism and the genetic construct used. Reference is again made to the handbooks and patent applications mentioned herein.

It will also be clear to the skilled person that the amino acid sequence, NB agent or polypeptide of the invention may (first) be generated in an immature form (as mentioned herein), which may then be subjected to post-translational modification, depending on the host cell/host organism used. Also, the amino acid sequence, NB agent or polypeptide of the invention may be glycosylated, again depending on the host cell/host organism used.

The amino acid sequence, NB agent or polypeptide of the invention may then be isolated from the host cell/host organism and/or from the medium in which said host cell or host organism is cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, NB agent or polypeptide of the invention) and/or preparative immunological techniques (i.e., using antibodies against the amino acid sequence to be isolated).

Pharmaceutical Preparation or Compositions

Generally, for pharmaceutical use, the polypeptides of the invention may be formulated as a pharmaceutical preparation or composition comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one amino acid of the invention, at least one NB agent of the invention or at least one polypeptide of the invention and at least one suitable carrier, diluent or excipient (i.e., suitable for pharmaceutical use), and optionally one or more further active substances.

Generally, the NB amino acid sequences and polypeptides of the invention can be formulated and administered in any suitable manner known per se. Reference is, e.g., made to the general background art cited above (and in particular to WO 04/041862, WO 04/041863, WO 04/041865, WO 04/041867 and WO 08/020,079) as well as to the standard handbooks, such as Remington's Pharmaceutical Sciences, 18$^{th}$ Ed., Mack Publishing Company, USA (1990), Remington, the Science and Practice of Pharmacy, 21th Edition, Lippincott Williams and Wilkins (2005); or the Handbook of Therapeutic Antibodies (S. Dubel, Ed.), Wiley, Weinheim, 2007 (see, e.g., pages 252-255).

The NB amino acid sequences and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and, e.g., include preparations suitable for parenteral administration (for example intravenous, intraperitoneal, subcutaneous, intramuscular, intraluminal, intra-arterial or intrathecal administration) or for topical (i.e., transdermal or intradermal) administration.

Preparations for parenteral administration may, e.g., be sterile solutions, suspensions, dispersions or emulsions that are suitable for infusion or injection. Suitable carriers or diluents for such preparations, e.g., include, without limitation, those mentioned on page 143 of WO 08/020,079. In one embodiment, the preparation is an aqueous solution or suspension.

The NB amino acid sequences and polypeptides of the invention can be administered using gene therapy methods of delivery. See, e.g., U.S. Pat. No. 5,399,346, which is incorporated by reference for its gene therapy delivery methods. Using a gene therapy method of delivery, primary cells transfected with the gene encoding an amino acid sequence, NB agent or polypeptide of the invention can additionally be transfected with tissue specific promoters to target specific organs, tissue, grafts, tumors, or cells and can additionally be transfected with signal and stabilization sequences for subcellularly localized expression.

Thus, the NB amino acid sequences and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the NB amino acid sequences and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, NB agent or polypeptide of the invention. Their percentage in the compositions and preparations may, of course, be varied and may conveniently be between about 2 to about 60% of the weight of a given unit dosage form. The amount of the amino acid sequence, NB agent or polypeptide of the invention in such therapeutically useful compositions is such that an effective dosage level will be obtained.

The tablets, troches, pills, capsules, and the like may also contain binders, excipients, disintegrating agents, lubricants and sweetening or flavoring agents, e.g., those mentioned on pages 143-144 of WO 08/020,079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the NB amino acid sequences and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the NB amino acid sequences and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The NB amino acid sequences and polypeptides of the invention may also be administered intravenously or intraperitoneally by infusion or injection. Particular examples are as further described on pages 144 and 145 of WO 08/020,079.

For topical administration, the NB amino acid sequences and polypeptides of the invention may be applied in pure form, i.e., when they are liquids. However, it will generally be desirable to administer them to the skin as compositions or formulations, in combination with a dermatologically acceptable carrier, which may be a solid or a liquid. Particular examples are as further described on page 145 of WO 08/020, 079.

Generally, the concentration of the NB amino acid sequences and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the NB amino acid sequences and polypeptides of the invention required for use in treatment will vary not only with the particular amino acid sequence, NB agent or polypeptide selected but also with the route of administration, the nature of the condition being treated and the age and condition of the patient and will be ultimately at the discretion of the attendant physician or clinician. Also the dosage of the NB amino acid sequences and polypeptides of the invention varies depending on the target cell, tumor, tissue, graft, or organ.

The desired dose may conveniently be presented in a single dose or as divided doses administered at appropriate intervals, e.g., as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one diseases and disorders associated with DR5, said method comprising administering, to a subject in need thereof, a pharmaceutically active amount of an amino acid sequence of the invention, of a NB agent of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with DR5, with its biological or pharmacological activity, and/or with the biological pathways or signaling in which DR5 is involved, said method comprising administering, to a subject in need thereof, a pharmaceutically active amount of an amino acid sequence of the invention, of a NB agent of the invention, of a polypeptide of the invention, and/or of a pharmaceutical composition comprising the same. In one embodiment, the invention relates to a method for the prevention and/or treatment of at least one disease or disorder that can be treated by modulating DR5, its biological or pharmacological activity, and/or the biological pathways or signaling in which DR5 are involved, said method comprising administering, to a subject in need thereof, a pharmaceutically active amount of an amino acid sequence of the invention, of a NB agent of the invention, of a polypeptide of the invention, and/or of a pharmaceutical composition comprising the same. In one embodiment, said pharmaceutically effective amount may be an amount that is sufficient to modulate DR5, its biological or pharmacological activity, and/or the biological pathways or signaling in which DR5 is involved; and/or an amount that provides a level of the amino acid sequence of the invention, of a NB agent of the invention, of a polypeptide of the invention in the circulation that is sufficient to modulate DR5, its biological or pharmacological activity, and/or the biological pathways or signaling in which DR5 is involved.

In one embodiment the invention relates to a method for the prevention and/or treatment of at least one disease or disorder that can be prevented and/or treated by administering a NB amino acid sequence or polypeptide of the invention, or a NB nucleotide construct of the invention encoding the same, and/or of a pharmaceutical composition comprising the same, to a patient. In one embodiment, the method comprises administering a pharmaceutically active amount of a NB amino acid sequence or polypeptide of the invention, or a NB nucleotide construct of the invention encoding the same, and/or of a pharmaceutical composition comprising the same to a subject in need thereof.

In one embodiment the invention relates to a method for the prevention and/or treatment of at least one disease or disorder that can be prevented and/or treated by enhancing cell apoptosis in specific cells or in a specific tissue of a subject to be treated (and in particular, by enhancing cell apoptosis in cancer cells or in a tumor present in the subject to be treated), said method comprising administering a pharmaceutically active amount of a NB amino acid sequence or polypeptide of the invention, or a NB nucleotide construct of the invention encoding the same, and/or of a pharmaceutical composition comprising the same, to a subject in need thereof.

In one embodiment, the invention relates to a method for the prevention and/or treatment of at least one disease or disorder chosen from the group consisting of the diseases and disorders listed herein, said method comprising administering, to a subject in need thereof, a NB amino acid sequence or polypeptide of the invention, or a NB nucleotide construct of the invention encoding the same, and/or of a pharmaceutical composition comprising the same.

In one embodiment, the invention relates to a method for immunotherapy, and in particular for passive immunotherapy, which method comprises administering, to a subject suffering from or at risk of the diseases and disorders mentioned herein, a pharmaceutically active amount of a NB amino acid sequence or polypeptide of the invention, or a NB nucleotide construct of the invention encoding the same, and/or of a pharmaceutical composition comprising the same.

In the above methods, the amino acid sequences, NB agents and/or polypeptides of the invention and/or the compositions comprising the same can be administered in any suitable manner, depending on the specific pharmaceutical formulation or composition to be used. Thus, the amino acid sequences, NB agents and/or polypeptides of the invention and/or the compositions comprising the same can, e.g., be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The amino acid sequences, NB agents and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, NB agent or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, NB agents and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific amino acid sequence, NB agent and polypeptide of the invention to be used, the specific route of administration and the specific pharmaceutical formulation or composition used, the NB amino acid sequences and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, e.g., on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

In one embodiment, a single contiguous amino acid sequence, NB agent or polypeptide of the invention will be used, whether the translated sequences contains a single domain or multiple monovalent or multivalent domains. In one embodiment two or more amino acid sequences, NB agents and/or polypeptides of the invention are provided in combination.

The NB agents, amino acid sequences and polypeptides of the invention may be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgment.

In particular, the NB amino acid sequences and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician, and generally include the cytostatic active principles usually applied for the treatment of the tumor to be treated.

Specific contemplated combinations for use with the NB agents of the invention include, but are not limited to, e.g., taxol; gemcitobine; cisplatin; cIAP inhibitors (such as inhibitors to cIAP1, cIAP2 and/or XIAP); MEK inhibitors including but not limited to, e.g., U0126, PD0325901; bRaf inhibitors including but not limited to, e.g., RAF265; and mTOR inhibitors including but not limited to, e.g., RAD001. Specific combinations are provided herein and in the Examples.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, NB agent or polypeptide of the invention in the preparation of a pharmaceutical composition for prevention and/or treatment of at least one diseases and disorders associated with DR5; and/or for use in one or more of the methods of treatment mentioned herein.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases and disorders mentioned herein.

The invention relates to the use of a NB amino acid sequence or polypeptide of the invention, or a NB nucleotide encoding the same, in the preparation of a pharmaceutical composition for the prevention and/or treatment of at least one disease or disorder that can be prevented and/or treated by administering a NB amino acid sequence or polypeptide of the invention, or a NB nucleotide encoding the same, and/or a pharmaceutical composition of the same to a patient.

More in particular, the invention relates to the use of a NB amino acid sequence or polypeptide of the invention, or a NB nucleotide encoding the same, in the preparation of a pharmaceutical composition for the prevention and/or treatment of diseases and disorders associated with DR5, and in particular for the prevention and treatment of one or more of the diseases and disorders listed herein.

Again, in such a pharmaceutical composition, the one or more NB amino acid sequence or polypeptide of the invention, or NB nucleotide encoding the same, and/or a pharmaceutical composition of the same, may also be suitably combined with one or more other active principles, such as those mentioned herein.

In one embodiment, although the use of the exemplary NB agents of the invention is much preferred, it will be clear that on the basis of the description herein, the skilled person will be able to design and/or generate, in an analogous manner, other amino acid sequences and in particular (single) domain antibodies against DR5, as well as polypeptides comprising such (single) domain antibodies, and/or nucleotides that encode them.

For example, it will be clear to the skilled person that it may be possible to "graft" one or more of the CDR's mentioned herein for the NB agents of the invention onto such (single) domain antibodies or other protein scaffolds, including but not limited to human scaffolds or non-immunoglobulin scaffolds. Suitable scaffolds and techniques for such CDR grafting will be clear to the skilled person and are well known in the art, see, e.g., those mentioned in WO 08/020,079. For example, techniques known per se for grafting mouse or rat CDR's onto human frameworks and scaffolds can be used in an analogous manner to provide chimeric proteins comprising one or more of the CDR's of the NB agents of the invention and one or more human framework regions or sequences.

It should also be noted that, when the NB agents of the inventions contain one or more other CDR sequences than the preferred CDR sequences mentioned herein, these CDR sequences can be obtained in any manner known per se, e.g., using one or more of the techniques described in WO 08/020,079.

Further uses of the amino acid sequences, NB agent s, polypeptides, nucleic acids, genetic constructs and hosts and host cells of the invention will be clear to the skilled person based on the disclosure herein. For example, and without limitation, the amino acid sequences of the invention can be linked to a suitable carrier or solid support so as to provide a medium than can be used in a manner known per se to purify DR5 from compositions and preparations comprising the same. Derivatives of the amino acid sequences of the invention that comprise a suitable detectable label can also be used as markers to determine (qualitatively or quantitatively) the presence of DR5 in a composition or preparation or as a marker to selectively detect the presence of DR5 on the surface of a cell or tissue (for example, in combination with suitable cell sorting techniques).

The invention will now be further described by means of the following non-limiting experimental part.

1. Example I

1.1. Human and Cyno DR5 Cloning and Protein Preparation 1.1.1. Cloning of Human Long Form DR5 Extracellular Domain (ECD) and Cyno Long and Short Form DR5 ECD The human long form DR5 ECD (aa55-213) is cloned by RT-PCR. Total RNA are isolated from Jurkat and Raji cells by Qiagen's RNeasy mini Kit (Cat No. 74104). cDNA is made by the SuperScript II First Strand Synthesis System (Invitrogen, Cat: 11904-018) then are amplified by High Fidelity Platinum Taq DNA Polymerase (Invitrogen, Cat no. 11304-011) using standard protocol: 94° C. for 2 min followed by 30 cycles of 95° C./30 seconds, 55° C./30 seconds, 72° C./60 seconds and a final incubation at 72° C. for 7 min. The forward and reverse primers used for PCR are: 5'-CTGAT-CACCC AACAAGACCT AG-3' (SEQ ID NO: 83) and 5'-GCCTGAGAGA GAACAGGGAG A-3' (SEQ ID NO: 84) respectively. The resulting 476 by fragment is then ligated into E. coli expression vector pBAD/Thio-TOPO (Invitrogen, Cat No. K370-01). Positive clones are identified by PCR and confirmed by DNA sequencing.

The full length cyno DR5 gene is originally cloned from cynomolgus liver cDNA (BioChain Institute, Inc. USA) by PR-PCR. The forward (5'-CACCATGGAA CAACGGG-GAC AGAACGCC-3') (SEQ ID NO: 85) and reverse (5'-TTAGGACATG GCAGAGTCTG CATTACCTTC-3') (SEQ ID NO: 86) primers are designed based on the human DR5 nucleotide sequence, including the start (ATG) and stop (TAA) codons respectively. High Fidelity Platinum Taq DNA Polymerase (Invitrogen, Cat no. 11304-011) is used for PCR and the resulting fragments are ligated into the pcDNA3.1 directional TOPO vector. The positive colonies are identified by DNA sequencing. Similar to human DR5 gene, two splicing alternatives of cyno DR5 gene are identified. One has the long form ECD, and the other has the short form ECD.

Both cyno long (aa55-213) and short (aa55-174) form of DR5 ECD are further cloned into pBAD/Thio-TOPO vector (Invitrogen, Cat No. K370-01). Positive clones are identified by PCR and are confirmed by DNA sequencing.

1.1.2. Establishment of CHO Cell Lines Expressing Cell Surface Cyno DR5

Chinese Hamster Ovary cells (CHO-K1) are transfected at 90-95% confluency using FuGENE6 (Roche Applied Sciences) and 1 µg pcDNA3.1-cynoDR5 expression vector. Transfected cells are selected by 500 µg/ml Geneticin (G418) and are subcloned by cell sorting.

1.1.3. Expression and Purification of Thioredoxin-DR5ECD-his6 "his6" is Disclosed as SEQ ID NO: 92) Fusion from E. coli For expression of DR5 ECD, pBAD/Thio-DR5ECD is transformed into E. coli strain TOP10 (Invitrogen, Cat No. C4040-03). A single colony is used to inoculate 100 ml LB containing 100 µg/ml ampicillin. This culture is incubated overnight at 37° C. with shaking at 225 rpm. Three liters of LB/ampicillin are inoculated with 30 ml of the overnight culture and shaken at 37° C. till the $OD_{600}$ reaches 0.5. The culture is then induced with 0.02% arabinose for 3 hours at 37° C. The bacterial pellet is resuspended in 2 l lysis buffer (PBS with 0.3M NaCl, 0.4% Triton X-100 and 10 mM imidazole) containing protease inhibitors (Roche, Cat No. 1836153). Lysate is sonicated two times for 60 seconds followed by centrifugation at 20,000×g for 20 min. Soluble Hisx6 tagged ("Hisx6" is disclosed as SEQ ID NO: 92) DR5 ECD is purified by nickel chelate affinity chromatography. Soluble Hisx6 tagged ("Hisx6" is disclosed as SEQ ID NO: 92) DR5 ECD is created by inserting the sequence encoding the polypeptide tag of SEQ ID NO: 91 or 92 at the 3' end of the reading frame of the DR5 construct, wherein the tag is expressed at the C-terminal end of the polypeptide. Clarified lysate is passed over 6 ml of Ni-NTA Agarose (Qiagen, Cat No. 30210) equilibrated with lysis buffer. The column is washed with 20 ml of lysis buffer followed by 15 ml of PBS containing 50 mM imidazole and 0.1% Triton X-100. DR5 ECD protein is then eluted with 10 ml PBS containing 100 mM imidazole and 0.1% Triton X-100 followed by the same buffer containing 250 mM imidazole. Fractions are checked on 4-12% NuPAGE Bis-Tris gel (Invitrogen, Cat No. NP0329BOX). Positive fractions containing the DR5 ECD protein are pooled, concentrated and stored at −20° C.

After nickel chelate affinity chromatography, the protein is further purified by size exclusion chromatography done on Amersham AKTA explorer with software program Unicorn. The column is HiPrep 26/60 Sephacryl S-200 HR with bed volume of 320 ml (Amersham, Cat No. 17-1195-01). The standard parameters are used according to manufacture's recommendations. Briefly, 1×PBS buffer (pH7.2) flew through the column at 0.5 ml/min, and 0.5 ml/fraction is collected at 4° C.

The last step of purification is ion exchange chromatography. The anion-exchanger Mono Q 5/50 GL column (Amersham, Cat No. 17-5166-01) is used with gradient elution at flow rate 1 ml/min, and 0.5 ml/fraction is collected at 4° C.

1.1.4. Expression and Purification of DR5ECD-Fc Fusion Protein from HEK293 Cells Both human and cyno, long form and short form DR5 ECD are cloned into pRS5a-IgG expression vector containing a CMV promoter and a human IgG1 Fc gene fragment. Positive clones are identified by PCR and confirmed by DNA sequencing. HEK293 cells are transient transfected with Lipofectamine 2000 (Gibco, lot no. 11317078). The medium containing DR5ECD-Fc fusion protein is collected seven days post transfection. The concentrated supernatant is adjusted to pH 7.2, clarified by filtration and loaded onto a 5 ml Protein A-Sepharose FF column at 0.5 ml/min. After baseline washing with PBS, pH 7.3, bound material is eluted with 50 mM Citrate/140 mM NaCl, pH 2.7, neutralized and sterile filtered.

1.2. Immunizations

Three llamas are immunized with human DR5 antigen. One llama (106) is immunized with the short (133 residues) recombinant human DR5 (Peprotech, Rocky Hill N.J., catalog #310-19). Two other llamas are immunized with full ectodomain human DR5-thioredoxin fusion. The llamas receives seven weekly doses, injected intramuscularly of 50-100 microgram of antigen (with Stimune (Cedi Diagnostics, Lelystad NL) as an adjuvant), followed by an additional 50 microgram dose two weeks later. Immune blood samples are taken at day 47 and 88 after the start of the immunizations as well as lymph node tissues at day 88.

1.3. Library Constructions cDNA samples are made from total RNA preparations of the immune blood and lymph node samples. Nucleotide sequences encoding DR5 NB constructs are amplified from the cDNA samples of the three llamas immunized with human DR5 in a one-step RT-PCR reaction using primers ABL051 (SEQ ID NO: 73), ABL052 (SEQ ID NO: 74) and ABL003 (SEQ ID NO: 75). Primer sequences are shown in Table 5. The 700 by amplicons amplified from the IgG2 and IgG3 cDNA's in the sample are isolated from gel and subsequently used as template in a nested PCR reaction using the ABL050-MfeI primer (SEQ ID NO: 76) containing SfiI and MfeI restriction sites and the ABL003 primer. The PCR products are subsequently digested with SfiI and BstEII (naturally occurring in FR4 of $V_{HH}$ genes) and ligated into the corresponding restriction sites of phagemid vector pAX50 to obtain a library after electroporation in *Escherichia coli* TG-1. pAX50 is an expression vector derived from pUC119 which contained the LacZ promoter, a coliphage pill protein coding sequence, a resistance gene for ampicillin or carbenicillin, a multicloning site and the gen3 leader sequence. In frame with the NB construct coding sequence, the vector coded for a C-terminal c-myc tag and a (His)6 tag (SEQ ID NO: 92). The phagemid vector allows for production of phage particles, expressing the individual DR5 NB constructs as a fusion protein with the gene3 product.

TABLE 5

| Primer and linker sequences, with SEQ ID NO | | |
|---|---|---|
| Name | Sequences (5' to 3') | ID |
| ABL051 | GGCTGAGCTG GGTGGTCCTG G | 73 |
| ABL052 | GGCTGAGTTT GGTGGTCCTG G | 74 |
| ABL003 | GGTACGTGCT GTTGAACTGT TCC | 75 |
| ABL050-MfeI | CATTTGAGTT GGCCTAGCCG GCCATGGCAG AGGTGCAATT GGTGGAGTCT GGGGG | 76 |
| M13Fwd | TGTAAAACGA CGGCCAGT | 77 |
| M13Rev | CAGGAAACAG CTATGACC | 78 |
| Rev_30GlySer | TCAGTAACCT GGATCCCCCG CCACCGCTGC CTCCACCGCC GCTACCCCG CCACCGCTGC CTCCACCGCC TGAGGAGACG GTGACCTG | 79 |
| For_GlySer35 | AGGTTACTGA GGATCCGGCG GTGGAGGCAG CGGAGGTGGG GGCTCTGGTG GCGGGGGTAG CGAGGTGCAG CTGGTGGAGT CTGG | 80 |
| DR5 ECD For | CTGATCACCC AACAAGACCT AG | 83 |
| DR5 ECD Rev | GCCTGAGAGA GAACAGGGAG A | 84 |
| DR5 cyno For | CACCATGGAA CAACGGGGAC AGAACGCC | 85 |
| DR5 cyno Rev | TTAGGACATG GCAGAGTCTG CATTACCTTC | 86 |

1.4. Selections

Different concentrations between 0 and 1 microgram/ml short (182 amino acids) human DR5-Fc fusion protein (R&D Systems, Minneapolis Minn., catalogue #631-T2/CF), full-ectodomain human DR5-Fc fusion protein ((human DR5 amino acids 56 to 213 fused with human IgG1 Fc) and biotinylated short (133 residues) recombinant human DR5 (Peprotech, Rocky Hill N.J., catalog #310-19) are immobilized on plates and streptavidin-coated plates, respectively. Blocking is done using PBS supplemented with 1% casein. Phages prepared from the three above mentioned pAX50 libraries are added and incubated for 30 minutes (in PBS supplemented with 0.1% casein and 0.1% tween20). Unbound phages are washed away (with PBS supplemented with 0.05% tween20); bound phages are eluted by addition of trypsin (1 mg/ml in PBS) and 30 min incubation at 37° C. Eluted phages are allowed to infect exponentially growing TG-1 cells that are then plated on ampicillin containing LB agar plates. Phages prepared from selected outputs are used as inputs in a second selection round on full-length human DR5-Fc fusion protein (human DR5 amino acids 56 to 213 fused with human IgG1 Fc) and biotinylated short (133 residues) recombinant human DR5 (Peprotech, Rocky Hill N.J., catalog #310-19) as described above.

Plasmid DNA of the round 1 and 2 selection outputs is prepared, digested with SfiI and BstEII, and the DNA fragments encoding anti-DR5 NB constructs are ligated into pAX51 vector and transformed into TG-1 competent cells. pAX50 is an expression vector derived from pUC119 which contained the LacZ promoter, a resistance gene for ampicillin or carbenicillin, a multicloning site and the gen3 leader sequence. In frame with the NB construct coding sequence, the vector coded for a C-terminal c-myc tag and a (His)6 tag (SEQ ID NO: 92). Carbenicillin resistant clones are analyzed for the presence of insert and sequences of positive clones are verified. TG-1 cells containing the DR5 NB constructs of interest are grown in TB medium supplemented with carbenicillin and induced by addition of IPTG for expression. The expression is allowed to continue for 4 hours at 37° C. After centrifugation, cell pellets are frozen overnight, then resuspended for 1 hour at 4° C. in PBS ($\frac{1}{10}^{th}$ of culture volume), again followed by centrifugation. The resulting supernatant is used as periplasmic extract.

1.5. Screening

Periplasmic extracts (as described above) are analyzed for DR5 binding by ELISA. 10-fold dilutions of periplasmic extracts are added to plates coated with short (133 residues) recombinant human DR5 (Peprotech, Rocky Hill N.J., catalog #310-19) or cynomolgus DR5-Fc fusion protein (cyno DR5 amino acids 56 to 213 fused with human IgG1 Fc) amino acids 56 to 213, IgG1 NVTS) and incubated for 2 hours (in PBS supplemented with 0.1% casein and 0.1% tween20). Unbound periplasmic extracts are washed away (PBS supplemented with 0.05% tween20) and bound NB constructs are detected using mouse anti-myc (Roche, Basel CH, catalogue #11667149001) followed by rabbit anti-mouse-alkaline phosphatase (Sigma, St. Louis Mo., catalogue # A-1902).

In another set of experiments, cell lines expressing human DR5 (Colo205) or cynomolgus DR5 (CHO-K1 cells transfected with an expression vector carrying the full length cynoDR5 gene downstream of a CMV promoter) are exposed to the periplasmic extracts (resuspended in PBS supplemented with 10% fetal calf serum). Binding of NB constructs to cell-bound DR5 is detected using mouse anti-myc (monoclonal antibody, clone 9E10 ATCC (Teddington, UK) number CRL-1729), is produced in mice as ascites and purified in-house using standard affinity chromatography) followed by anti-mouse IgG-phytoerythrin (Jackson ImmunoResearch Laboratories, West Grove, Pa., catalogue #115-115-164). Dead cells are counterstained with TO-PRO-3 (Molecular Probes, Carlsbad Calif., catalogue # T3605). Results are shown in Table 6.

TABLE 6

Binding of monomeric NB constructs to DR5 by ELISA ($ABS_{405\,nm}$)

| NB Construct | Human | Cyno |
|---|---|---|
| 10F1 | 0.754 | 0.124 |
| 11D1 | 0.540 | 0.213 |
| 11H6 | 0.552 | 0.133 |
| 4E6 | 0.838 | 0.313 |
| 7A12 | 0.812 | 0.341 |

Binding of NB constructs to DR5 is evaluated by surface plasmon resonance on a Biacore 3000 instrument. Specificity of binding is analyzed by allowing dilutions of the periplasmic extracts to pass over a CM5 sensor chip coated with 270 RU short (133 residues) recombinant human DR5 (Peprotech, Rocky Hill N.J., catalog #310-19). The dissociation phases are analyzed and corresponding off-rates ($k_{off}$) are given in Table 7 and Table 8. Table 7 shows results for the binding of monomeric NB constructs to cell-bound DR5 by FACS (mean count fluorescence). Table 8 shows results for off-rates as determined by Surface Plasmon Resonance. Sequences are provided in Tables 1-4.

TABLE 7

Binding of monomeric NB constructs to cell-bound DR5 by FACS

| NB construct | Human | Cyno |
|---|---|---|
| 10F1 | 125 | 1626 |
| 11D1 | 919 | 417 |
| 11H6 | 723 | 292 |
| 4E6 | 972 | 2868 |
| 7A12 | 1097 | 24516 |

TABLE 8

Off-rates (1/s) as determined by Surface Plasmon Resonance

| NB construct | $k_{off}$ (1/s) |
|---|---|
| 10F1 | $2.34 \times 10^{-03}$ |
| 11D1 | $4.44 \times 10^{-04}$ |
| 11H6 | $2.12 \times 10^{-03}$ |
| 4E6 | $9.54 \times 10^{-05}$ |
| 7A12 | $1.90 \times 10^{-04}$ |

2. Example II

2.1. Trimerization

DNA fragments encoding anti-DR5 NB constructs are digested with MfeI and BstEII and cloned into pAX73, pAX74 and pAX75 vectors in frame with linker sequences. These are transformed into TG-1 competent cells and kanamycin resistant clones are analyzed for the presence of insert and sequence verified. The resulting constructs are digested with SfiI, BpuAI and NotI and the NB construct containing fragments are then cloned through a four-point ligation into SfiI-NotI digested pAX51 vector. Positive carbenicillin resistant clones, i.e., those encoding trivalent CMYC-HIS6-tagged NB construct constructs ("HIS6" is disclosed as SEQ ID NO: 92) (each NB construct building block fused to the next by a linker sequence), are again sequence verified. pAX73, pAX74, pAX75 and pAX83 are pUC-derived cloning vectors that contain a resistance gene for kanamycin or neomycin, multicloning sites and in frame with the NB construct coding sequence, these vectors encode GlySer linker sequences.

2.2. Tetramerization

DNA fragments encoding anti-DR5 NB constructs are amplified by means of PCR using M13Rev (SEQ ID NO: 78) and Rev__30GlySer (SEQ ID NO: 79) or For_GlySer35 (SEQ ID NO: 80) and M13Fwd (SEQ ID NO: 77) respectively. Both Rev__30GlySer and For_GlySer35 encode linker sequences (primer sequences in Table 5). The PCR products are digested with MfeI, BamHI and BstEII and both fragments are jointly cloned through a three-point ligation in pAX75 and in pAX83, in frame with vector encoded linker sequences. These are transformed into TG-1 competent cells and kanamycin resistant clones are analyzed for the presence of bivalent NB construct insert and sequence verified. Positive bivalent clones are then digested with SfiI, BpuAI and NotI and the NB construct containing fragments are then cloned into SfiI-NotI digested pAX51 vector. Positive carbenicillin resistant clones, encoding tetravalent NB construct constructs, each NB construct building block fused to the next by a linker sequence, are again sequence verified.

2.3. Pentamerization

Synthetic genes encoding the fourth GlySer linker sequence and the fifth NB building block are ordered from GENEART AG (Regensburg, Germany). These fragments are then digested with HgaI and NotI and ligated into BstEII-NotI digested tetravalent NB constructs.

2.4. Small Scale Expression

TG-1 cells containing the multivalent anti-DR5 NB constructs of interest are grown in baffled shaker flasks containing TB medium plus 100 µg/ml Carbenicillin and induced by addition of 1 mM IPTG for expression. The expression is allowed to continue for 4 hours at 37° C. After collecting the cells, periplasmic extracts are prepared and the HIS6-tagged NB constructs ("HIS6" disclosed as SEQ ID NO: 92) are purified by immobilized metal affinity chromatography (His-Trap FF Crude, GE Healthcare) followed by gel filtration chromatography (Superdex 75 HR16/10, GE Healthcare) in PBS.

3. Example III

3.1. Binding on Biacore

Biacore CM5 sensor chips are coated with short (182 amino acids) human DR5-Fc fusion protein (R&D Systems, Minneapolis Minn., catalogue #631-T2/CF) or cynomolgus DR5-Fc fusion protein (amino acids 56 to 213, IgG1 NVTS). Different concentrations (1 to 100 nM) of monovalent and multivalent anti-DR5 NB constructs are then floated over the chips for a kinetic analysis of the binding interaction. All multivalent anti-DR5 NB constructs bind to human and cynomolgus DR5 (Table 9).

TABLE 9

Affinities (M) of anti-DR5 NB constructs as determined by surface plasmon resonance

| | Human DR5 | | | Cynomolgus DR5 | | |
|---|---|---|---|---|---|---|
| Clone | Mono | Tri | Tetra | Mono | Tri | Tetra |
| 11D1 | $1.0 \times 10^{-9}$ | $<3.0 \times 10^{-11}$ | ND | $2.2 \times 10^{-7}$ | $<2.0 \times 10^{-10}$ | ND |
| 7A12 | $7.3 \times 10^{-9}$ | $<3.0 \times 10^{-12}$ | ND | $7.1 \times 10^{-9}$ | $<3.0 \times 10^{-11}$ | ND |
| 10F1 | $4.2 \times 10^{-9}$ | $<5.0 \times 10^{-11}$ | $3.9 \times 10^{-12}$ | $1.4 \times 10^{-7}$ | $<6.0 \times 10^{-10}$ | $2.2 \times 10^{-11}$ |
| 11H6 | $6.7 \times 10^{-9}$ | $<2.0 \times 10^{-10}$ | ND | $9.2 \times 10^{-6}$ | $<3.0 \times 10^{-10}$ | ND |
| 4E6 | $1.7 \times 10^{-10}$ | $<5.0 \times 10^{-11}$ | ND | $1.6 \times 10^{-8}$ | $<9.0 \times 10^{-11}$ | ND |

ND: Not determined;
BDL: below detection limit

3.2. Binding on FACS

In another set of experiments, cell lines expressing human (Colo205) or cynomolgus (CHO-K1 cells transfected with an expression vector carrying the full length cynoDR5 gene downstream of a CMV promoter) DR5 are exposed to 1 nM of multivalent anti-DR5 NB constructs (resuspended in PBS supplemented with 10% fetal calf serum). Binding of NB constructs to cell-bound DR5 is detected using mouse anti-myc (monoclonal antibody, clone 9E10 ATCC (Teddington, UK) number CRL-1729, is produced in mice as ascites and purified in-house using standard affinity chromatography) followed by anti-mouse IgG-phytoerythrin (Jackson ImmunoResearch Laboratories, West Grove, Pa., catalogue #115-115-164). Dead cells are counterstained with TO-PRO-3 (Molecular Probes, Carlsbad Calif., catalogue # T3605). All multivalent NB constructs bind specifically to cell bound human and cynomolgus DR5. Binding of the NB agents to each of the short form and the long form of DR5 is roughly equivalent for each, suggesting that all epitopes are held in common between the two forms In another experiment, apparent binding constants are estimated from saturation binding experiments on FACS (as described above) of 10 to 0.005 nM tetravalent anti-DR5 NB constructs to cell bound human and cynomolgus DR5. Apparent binding constants are calculated using GraphPad Prism 5 (GrafPad Software, San Diego, Calif.).

3.3. DR5-Specificity

A group of TNF receptor superfamily members are selected for testing the DR5 specificity (Table 10). The extracellular domain of members of the TNF receptor superfamily are cloned into pBadThioTopo and transformed into E. coli strain TOP10 (Invitrogen #C4040-03). The protein is expressed according to the protocol of manufacturer. The cell lysates are collected for ELISA screening. 25 µL of 20% BSA is added per 10 mL of lysate. His capture plates (Sigma

S-5688) are coated with 100 μL of lysate and incubated 1 hour at room temperature. The remaining solution is aspirated and wells are washed three times with PBS+0.05% Tween (PBST). The primary antibodies are diluted as follows in Blocking Buffer (PBS containing 10% FBS); LBY135 (positive control, anti-DR5 antibody, Novartis AG) is diluted to 0.24 mg/mL and rabbit anti-V5 (Abcam #Ab9116-100) is diluted 1:5000. 100 μL of diluted primary antibody is added per well. Assay plates are incubated at room temperature for one hour and then washed three times with PBST. The secondary antibodies (goat anti-rabbit IgG-HRP) (Jackson Immunoresearch Laboratories #111-035-046) for wells incubated with V5, and goat anti-human IgG-HRP (Jackson Immunoresearch Laboratories #109-035-098) for wells incubated with LBY135) are diluted 1:5000 in PBS containing 5% FBS and 0.025% Tween. 100 μL of secondary antibody is added to appropriate wells. After incubation at room temperature for 1 hr, the plates are washed three times with PBST. 100 μL of Sure Blue (KPL #52-00-03) is added and once the color had developed, the plates are read at an absorbance of 650 nm.

TABLE 10

TNF receptor superfamily members

| TNFR number | TNFR name | Accession Number | ECD |
|---|---|---|---|
| TNFRSF1A | TNFR1 | NM001065 | Leu34-Thr211 |
| TNFRSF1B | TNFR2 | M32315 | Thr27-Leu241 |
| TNFRSF3 | TNFR3 | L04270 | Pro30-Thr224 |
| TNFRSF4 | OX40 | X75962 | Gly33-Gly212 |
| TNFRSF5 | CD40 | X60592 | Val18-Leu192 |
| TNFRSF6 | FAS | M67454 | Ser20-Gly175 |
| TNFRSF6B | DcR3 | AF104419 | Val27-Ala176 |
| TNFRSF7 | CD27 | M63928 | Thr21-Ser187 |
| TNFRSF9 | CD137 | L12964 | Glu19-Ile188 |
| TNFRSF10C | DcR1 | AF012536 | Thr27-Leu241 |
| TNFRSF10D | DcR2 | AF029761 | Thr57-Thr198 |
| TNFRSF11B | OPG | U94332 | Lys17-Ile197 |
| TNFRSF13 | BCMA | NM001192 | Met1-Thr56 |
| TNFRSF13B | TACI | NM012452 | Met2-Val161 |
| TNFRSF13C | BAFFR | NM052945 | Met1-Gly64 |
| TNFRSF16 | NGFR | M14764 | Lys29-Ile233 |

All NB constructs specifically bind to DR5, but not to other TRAIL and TNF receptor family members. See, e.g., FIG. 1.

3.4. Biacore Epitope Mapping

Biacore off-rate screening (Table 8) on short (133 residues) recombinant human DR5 (Peprotech, Rocky Hill N.J., catalog #310-19) revealed that all anti-DR5 NB constructs bind to the extracellular domain of DR5 but not to the 29 residue alternatively spliced region (amino acid residues 185 to 231).

In another experiment, Biacore CM5 sensor chips are coated with monovalent anti-DR5 NB constructs (230 to 520 RU). Then, 500 nM of short (133 residues) recombinant human DR5 (Peprotech, Rocky Hill N.J., catalog #310-19) is floated over the chips until saturation is reached. At this point, 50 nM human TRAIL (R&D Systems, Minneapolis Minn., catalogue #375-TEC/CF) is floated over the chips and the increase in binding signal is used to categorize the NB constructs in different epitope classes compared to the TRAIL epitope (Table 11).

TABLE 11

Epitope mapping of anti-DR5 NB constructs compared to TRAIL

| NB construct | Result |
|---|---|
| 11D1 | No TRAIL blocking |
| 4E6 | Partial TRAIL blocking |
| 10F1 | TRAIL blocking |
| 11H6 | No TRAIL blocking |
| 7A12 | TRAIL blocking |

3.5. In Vitro Cell Survival

Cells are maintained in logarithmic growth phase prior to the experiments. On the day of the assay, cells are transferred to 96-well plates (Corning Inc., Lowell, Mass., Cat#3917) at 5,000-20,000 cells per well, then series diluted anti-DR5 NB constructs are added at 50 μl/well. After incubation for 24 to 72 hours, the relative number of surviving cells are quantified using a luciferase-based ATP quantification Kit (Cell Titer Glo, Promega, Madison, Wis. Cat#G7571) and read on a luminescence plate reader (Fluoroskan Ascent FL, Thermo Electron, Waltham, Mass.).

A panel of trivalent anti-DR5 NB constructs is screened in a cell survival assay with Colo205 cells. All trivalent constructs induced apoptosis on Colo205 (see Table 12) in contrast to their monovalent counterparts (data not shown) that are not biologically active in this assay. A tetravalent construct of an irrelevant (non-DR5 binding) NB construct did not induce apoptosis.

TABLE 12

In vitro potency ($IC_{50}$ (M)) of trivalent anti-DR5 NB constructs on Colo205

| NB construct | $IC_{50}$ (M) |
|---|---|
| 10F1 tri | $4.07 \times 10^{-11}$ |
| 11D1 tri | $1.11 \times 10^{-10}$ |
| 11H6 tri | $4.58 \times 10^{-11}$ |
| 4E6 tri | $3.79 \times 10^{-11}$ |
| 7A12 tri | $1.20 \times 10^{-10}$ |

In another experiment (Table 13), selected trivalent anti-DR5 NB constructs are screened in cell survival assays against a panel of tumor and normal cell lines.

TABLE 13

In vitro potency ($IC_{50}$ (M)) of trivalent anti-DR5 NB constructs

| | 4E6 tri | 11D1 tri | 10F1 tri | 7A12 tri | 11H6 tri |
|---|---|---|---|---|---|
| Jurkat | 20 | 20 | 20 | 20 | 20 |
| Molt4 | 20 | 20 | 20 | 20 | 20 |
| A549 | 20 | 20 | 20 | 20 | 20 |
| H226 | $2.0 \times 10^{-11}$ | $3.0 \times 10^{-11}$ | $2.0 \times 10^{-11}$ | $3.0 \times 10^{-11}$ | 20 |

TABLE 13-continued

In vitro potency (IC$_{50}$ (M)) of trivalent anti-DR5 NB constructs

| | 4E6 tri | 11D1 tri | 10F1 tri | 7A12 tri | 11H6 tri |
|---|---|---|---|---|---|
| H2052 | $6.0 \times 10^{-12}$ | $1.5 \times 10^{-11}$ | $1.3 \times 10^{-11}$ | $6.4 \times 10^{-11}$ | $3.6 \times 10^{-10}$ |
| H2122 | $2.0 \times 10^{-12}$ | $4.0 \times 10^{-12}$ | $3.0 \times 10^{-12}$ | $8.0 \times 10^{-12}$ | $1.2 \times 10^{-11}$ |
| M30 | 20 | 20 | 20 | 20 | 20 |
| Panc-1 | 20 | 20 | 20 | 20 | 20 |
| MiaPaCa-2 | $2.3 \times 10^{-11}$ | 20 | 20 | 20 | 20 |
| ARPE-19 | 20 | 20 | 20 | 20 | 20 |
| IMR-90 | 20 | 20 | 20 | 20 | 20 |
| Huvec | 20 | 20 | 20 | 20 | 20 |

20: IC$_{50}$ 20 nM

In another experiment (Table 14), selected tetravalent anti-DR5 NB constructs are screened in cell survival assays against a panel of tumor and normal cell lines.

TABLE 14

In vitro potency (IC$_{50}$ (M)) of tetravalent anti-DR5 NB constructs

| | 4E6 tetra | 11D1 tetra | 10F1 tetra | 7A12 tetra | 11H6 tetra |
|---|---|---|---|---|---|
| Colo205 | $8.0 \times 10^{-13}$ | $8.1 \times 10^{-12}$ | $2.0 \times 10^{-12}$ | $6.6 \times 10^{-12}$ | $3.7 \times 10^{-12}$ |
| Jurkat | $6.0 \times 10^{-13}$ | $3.5 \times 10^{-11}$ | $3.0 \times 10^{-12}$ | $3.7 \times 10^{-11}$ | $9.1 \times 10^{-12}$ |
| Molt4 | $<1.0 \times 10^{-13}$ | $1.5 \times 10^{-11}$ | $2.0 \times 10^{-12}$ | 20 | $8.0 \times 10^{-13}$ |
| A549 | $3.3 \times 10^{-10}$ | 20 | 20 | 20 | 20 |
| H2122 | $8.0 \times 10^{-13}$ | $8.0 \times 10^{-12}$ | $1.0 \times 10^{-12}$ | $3.6 \times 10^{-12}$ | $2.8 \times 10^{-12}$ |
| H226 | $1.0 \times 10^{-11}$ | $8.9 \times 10^{-11}$ | $2.4 \times 10^{-11}$ | 20 | $1.1 \times 10^{-10}$ |
| H2052 | $8.0 \times 10^{-13}$ | $2.5 \times 10^{-11}$ | $4.0 \times 10^{-12}$ | $3.3 \times 10^{-11}$ | $1.5 \times 10^{-11}$ |
| M30 | 20 | 20 | 20 | 20 | 20 |
| Panc-1 | $3.0 \times 10^{-12}$ | 20 | $9.0 \times 10^{-12}$ | 20 | $2.2 \times 10^{-10}$ |
| MiaPaCa-2 | $1.8 \times 10^{-12}$ | $1.9 \times 10^{-11}$ | $2.8 \times 10^{-11}$ | $4.1 \times 10^{-11}$ | $1.1 \times 10^{-11}$ |
| BxPC-3 | $1.9 \times 10^{-12}$ | $4.1 \times 10^{-11}$ | $3.0 \times 10^{-12}$ | $2.3 \times 10^{-11}$ | $2.7 \times 10^{-11}$ |
| Malme-3 | 20 | 20 | 20 | 20 | 20 |
| WI-38 | 20 | 20 | 20 | 20 | 20 |
| ARPE-19 | 20 | 20 | 20 | 20 | 20 |
| 184A1 | 20 | 20 | 20 | 20 | 20 |
| Huvec | 20 | 20 | 20 | 20 | 20 |
| HAAE-1 | 20 | 20 | 20 | 20 | 20 |

20: IC$_{50}$ 20 nM

Figure 6A:
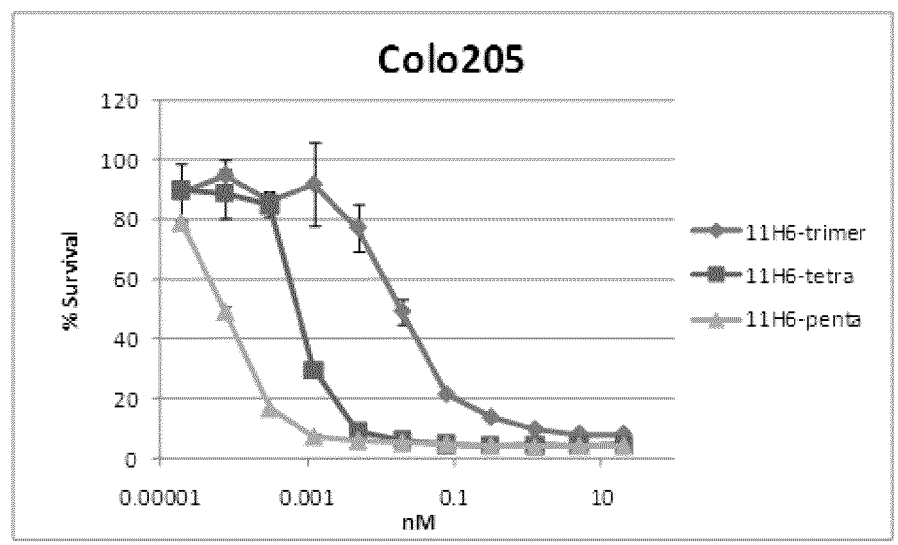
FIGS. 6A, 6B and 6C are graphic representations showing that an increased number of subunits in a NB construct corresponds with an improved efficacy and potency for (FIG. 6A) 11H6 trimers, tetramers and pentamers in Colo205 cells.
Figure 6B:
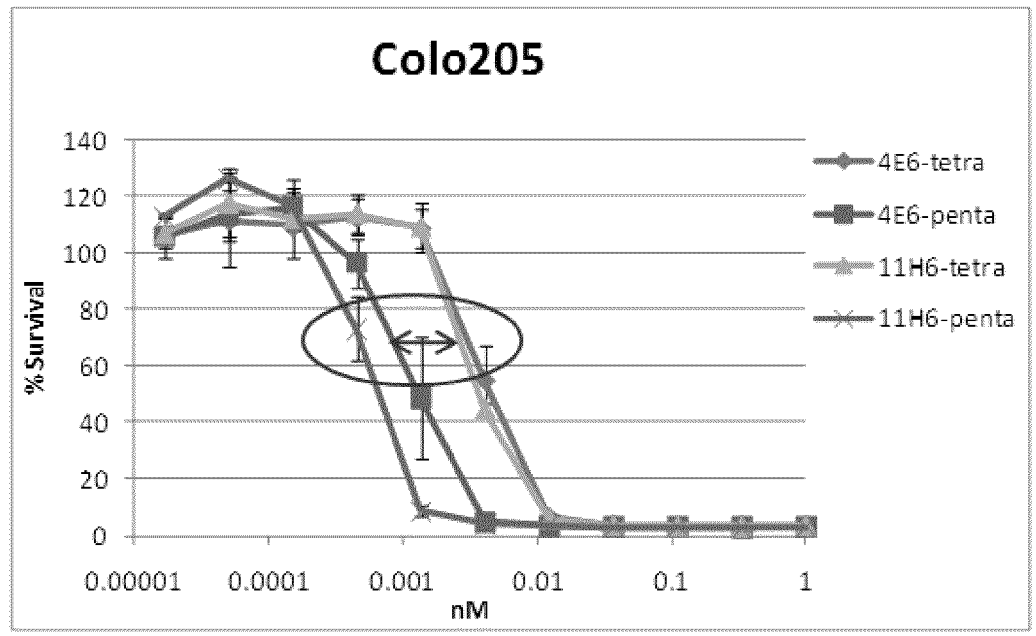
Figure 6C:
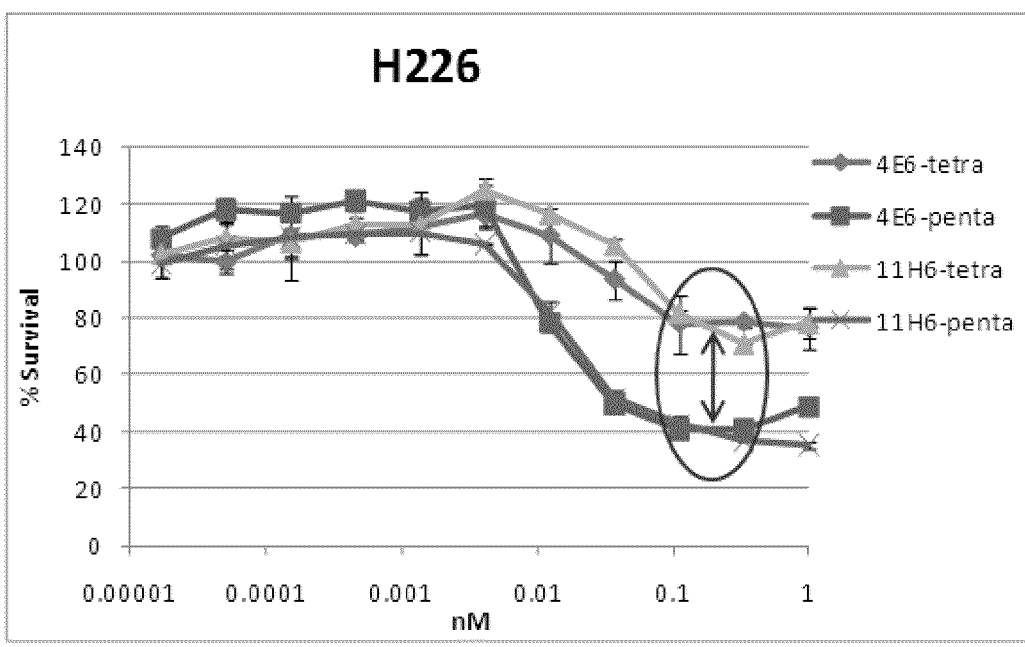

Graphic representations showing that increasing the hierarchy of multimers results in increased efficacy and potency is shown in FIGS. 6A, 6B and 6C, wherein trimeric, tetrameric and pentameric 11H6 and 4E6 NB constructs have increasing potency, respectively, against treated Colo205 and H226 tumor cells in vitro.

The multivalent anti-DR5 NB constructs display apoptosis-inducing activity on tumor cell lines but not on normal (healthy) cell lines. The general trend is that increased apoptosis-inducing activity is seen with an increased number of subunits in a multimeric NB composition. Increasing from tetrameric to pentameric forms of the NB provides evidence of further increase in potency in cell death assays, as exemplified by lowering the IC50 or increasing the maximum cell death achieved depending on the cell line.

3.6. Cross-Linking

In another experiment, multivalent NB constructs (10 micrograms) that contain a cMYC tag are cross-linked through their CMYC-tag with 1.5 µg up to 150 micrograms of mouse anti-myc (monoclonal antibody, clone 9E10 ATCC (Teddington, UK) number CRL-1729) is produced in mice as ascites and purified in-house using standard affinity chromatography) during a 30 minute incubation at room temperature. The cross-linked NB constructs are then evaluated in in vitro cell survival assays. Increased cross-linking correlated with improved potency and efficacy (see Tables 15-16). Table 15 provides in vitro potency (1050 (M)) of trivalent anti-DR5 NB constructs cross-linked with different amounts of antibody on Jurkat cells. Table 16 provides in vitro efficacy (% dead cells) of tetravalent anti-DR5 NB constructs cross-linked with different amounts of antibody on Jurkat cells. The general trend is that more cells are killed with increased amounts of cross-linking of the tagged NB multimers.

TABLE 15

In vitro potency (IC$_{50}$ (M)) of cross-linked trivalent anti-DR5 NB constructs

| Jurkat cells | Weight ratio (µg/µg) | IC$_{50}$ (M) |
|---|---|---|
| 11D1 tri | 0 | No apoptosis observed |
| 11D1 tri | 0.15 | $1.1 \times 10^{-8}$ |
| 11D1 tri | 15.0 | $7.3 \times 10^{-10}$ |

Ratio: Weight ratio of cross-linking antibody/tetravalent anti-DR5 NB constructs

TABLE 16

In vitro efficacy (% dead cells) of cross-linked tetravalent anti-DR5 NB constructs

| Jurkat cells | Weight ratio (µg/µg) | Efficacy (% dead cells) |
|---|---|---|
| 11D1 tetra | 0 | 48 |
| 11D1 tetra | 0.15 | 48 |
| 11D1 tetra | 0.75 | 60 |
| 11D1 tetra | 1.5 | 63 |

TABLE 16-continued

In vitro efficacy (% dead cells) of cross-linked tetravalent anti-DR5 NB constructs

| Jurkat cells | Weight ratio (µg/µg) | Efficacy (% dead cells) |
|---|---|---|
| 11D1 tetra | 7.5 | 88 |
| 11D1 tetra | 15.0 | 93 |

Ratio: Weight ratio of cross-linking antibody/tetravalent anti-DR5 NB constructs

3.7. Serum Stability

3.7.1. NB Constructs and DR5 Binding in ELISA

NB constructs are pre-incubated with 100% fresh human serum at 37° C. for 24 hours. Flat bottom 96-well ELISA plates (Costar, Cambridge, Mass., Catalog No. 3590) are coated overnight at 4° C. with 50 µl DR5-Fc fusion protein (DR5 amino acids 56 to 213) at 1 µg/ml in PBS. The plates are then blocked with 300 µl 2% BSA (Gibco, Grand Island, N.Y., Cat#11018-025) in PBS for one hour and washed three times. NB construct samples are serially diluted in the PBS buffer containing 10% human serum, then added in ELISA plates and incubated for one hour at room temperature. After wash, 1:5000 HRP conjugated anti-myc polyclonal antibody (Invitrogen: 460709) or 1:7000 rabbit anti-$V_{HH}$ antibody followed by 1:15000 HRP conjugated anti-rabbit IgG (Jackson ImmunoResearch Laboratories, Inc. West Grove, Pa., Cat#115-035-072) is added in plates. After a final set of washes, 100 µl/well of TMB Microwell peroxidase substrate (BioFX, Owings Mills, Md., Catalog No. TBNP-1000-01) is added and incubated at room temperature for 10 minutes. The reaction is stopped with 100 µl Stop Reagent (BioFX, Owings Mills, Md., Cat#LSTP-0100-01). Colorimetric detection of the product is done at 450 nm in SpectraMax M5 microplate reader (Molecular Devices, Sunnyvale, Calif.). Data is analyzed with SoftMax Pro software (Molecular Devices, Sunnyvale, Calif.) according to its user's manual.

Human serum shows little interference with NB construct trimers or tetramers binding to DR5, detected by either anti-Myc or anti-NB construct-antibody.

3.7.2. NB Construct Function in Cell Survival Assay

Cell survival assays are also performed in presence and absence of about 10-15% human serum albumin. Tetravalent anti-DR5 NB constructs maintain their in vitro potency compared to control assays in the presence of 10% fetal calf serum.

4. Example IV

4.1. Single Dose In Vivo Trivalent Anti-DR5 NB Constructs

Outbred athymic (nu/nu) female mice (Harlan Sprague Dawley, Indianapolis, Ind.) are anesthetized and implanted s.c. into the right axillary (lateral) region of each animal with $1\times10^6$ Colo205 cells. Tumors are allowed to grow until the size of 200 mm$^3$ before the dosing is initiated. NB construct is formulated as a solution in PBS and administered single dose at 200 ug/mouse by a bolus i.v. injection. Tumor samples are collected from groups of animals (one group per time point, 3 animals per group) at 1 h, 2 h, 4 h and 8 h.

Part of the tissue samples are used for immunohistochemical (IHC) staining of Caspase3. The tissues are immediately put into 10% neutral buffered formalin (NBF, Fisher Scientific, Pittsburgh, Pa., Catalog No. SF100-20), processed and embedded into paraffin blocks. Sections of 4.0 µm are cut on to SUPERFROST™ Plus charged slides (Fisher Scientific, Catalog No. 12-550-15). The sections are deparaffinized in xylene (5 minutes×2) and hydrated in a graded series of alcohols (100% alcohol for 5 minutes, 95% alcohol for 2 minutes, 70% alcohol for 2 minutes, and de-ionized water for 5 minutes). The hydrated sections underwent antigen retrieval which is conducted by microwaving the slides in citric acid buffer (0.01M, pH 6.0, BioGenex, San Ramon, Calif., Catalog No. HK080-9K) for 10 minutes. The slides are placed onto the staining racks of the autostainer (Dako Cytomation) after they are washed with de-ionized water for 5 minutes. The following steps are done with the Dako automated system at room temperature. Between each steps, the slides are rinsed with the rinse buffer (OptiMax Wash Buffer, Biogenex, Catalog No. HK583-5K) three times. Endogenous peroxidase is blocked by incubation of the slides with hydrogen peroxide (Dako, Catalog No. S2001) for 10 minutes. The nonspecific antigen reaction is blocked by the Block Serum (Dako, Catalog No. X0909) for 10 minutes. The slides are incubated with the cleaved Caspase3 rabbit polyclonal antibody (Cell Signaling Technology, Beverly, Mass., Catalog No. 9661) for 60 minutes, then rinsed and exposed to the peroxidase conjugated antibody (DAKO Envision system, Catalog No. K4003) for 30 minutes. For detection, DAB (3,3'-diaminobenzidine) solution (Dako Cytomation, Catalog No. K3468) is applied for 2 minutes. Immunostained slides are lightly counterstained with Harris Hematoxylin (SurgiPath, Catalog No. 01560), dehydrated through a series of increasing alcohol concentrations (70%, 95% and 100% alcohol, each for 1 minute) and xylene (5 minutes×2), and mounted with a coversliper (Leica).

The slides are scanned into the digitized slide database using the Aperio system (Aperio Technologies, Inc. Vista, Calif.) and image analysis is done by using the optimized Positive Pixel Counting Algorithm from Aperio. The whole sections excluding necrotic areas and host tissue portion "marked out" by using the tools provided by the imaging system are used for image analysis. All multivalent anti-DR5 NB constructs induce Caspase3 activation.

Part of the tissue samples are mixed with T-per buffer (Pierce, Rockford, Ill., Catalog No. 78510) then immediately homogenized in the tissue lyser (Qiagen, Catalog No. 85210). The supernatant of tissue lysate is collected and its protein concentration is determined using a standard BCA assay (Pierce, Catalog No. 1856210). The tissue lysates are used in the following assays to check NB construct and antibody concentration plus Caspase3 activity in tumor.

NB construct concentration is determined in ELISA. The ELISA plates (Nunc, Rochester N.Y., Catalog No. 439454) are coated overnight at 4° C. with 100 µl human DR5-Fc fusion protein (DR5 amino acids 56 to 213) at 1 µg/ml in PBS, then blocked with 1% BSA (Gibco, Catalog No. 11018-025) in PBS for 1 hour at room temperature and then washed three times. The serially diluted serum or tissue lysate samples are transferred into ELISA plates along and incubated 1.5 hours at room temperature. Following three washes, 1/22500 diluted anti-$V_{HH}$ is added to the ELISA plates, and incubated for one hour at room temperature. The plates are washed three more times and then incubated for one hour with 100 µl/well of 1/20000 diluted HRP-goat-anti-rabbit (Pierce, Catalog No. 31462). After a final set of washes, 100 µl/well of TMB Microwell peroxidase substrate (BioFX, Owings Mills, Md., Catalog No. TMBW-0100-01) is added for 10 minutes and the reaction is then stopped with 100 µl stop solution (BioFX, Catalog No. LSTP-1000-01). Colorimetric detection of the product is done at 450 nm in SpectraMax M5 microplate reader (Molecular Devices, Sunnyvale, Calif.). Data is analyzed in 4-parameter model with SoftMax Pro software (Molecular Devices, Sunnyvale, Calif.) according to its user's manual. All NB constructs show quick clearance in serum and in tumor tissue, and fast tissue penetration.

Caspase 3/7 activity in tumor tissue lysate is evaluated by Caspase glo assay (Promega Catalog no. G8092) according to its user's manual. Luminescence is read using the SpectraMax M5 microplate reader (Molecular Devices, Sunnyvale, Calif.). Consistent with IHC results, all NB constructs activate Caspase 3 within 8 hours.

4.2. Single Dose In Vivo Tetravalent Anti-DR5 NB Constructs

Outbred athymic (nu/nu) female mice (Harlan Sprague Dawley, Indianapolis, Ind.) are anesthetized and implanted s.c. into the right axillary (lateral) region of each animal with $1 \times 10^6$ Colo205 cells. Tumors are allowed to grow until the size of 200 mm$^3$ before the dosing is initiated. NB construct is formulated as a solution in PBS and administered single dose at 200 ug/mouse by a bolus i.v. injection. Serum and tumor tissue are collected from groups of animals (one group per time point, 3 animals per group) at the following time points: 0.25 h, 0.5 h, 1 h, 2 h, 4 h, 8 h, 24 h, and 48 h. The tumor tissue sample is mixed with T-per buffer (Pierce, Rockford, Ill., Catalog No. 78510) then immediately homogenized in the tissue lyser (Qiagen, Catalog No. 85210). The supernatant of tissue lysate is collected and its protein concentration is determined using a standard BCA assay (Pierce, Catalog No. 1856210).

NB construct concentration in serum and tissue lysate is determined in ELISA as described above. Mean serum concentration-time profiles are subjected to a two-compartmental pharmacokinetic analysis using model 7 within WinNonlin Professional Software Version 5.1 (Pharsight Corporation, Mountain View Calif., USA). For each NB construct the concentration-time profile is fit using iterative reweighting 1/y·y, where y is the predicted concentration. The mean residence time (MRT, Table 17) off the different NB constructs ranged from 2.6 to 13.5 hr. The Volume of distribution (Vss) of the different NB constructs is 2-35 times larger than the plasma volume of a 20 g mouse ($\approx$1.5 ml), indicating extensive distribution outside the vascular space. The overall clearance rate of the different NB constructs is at least 5 times less than the murine glomerular filtration rate ($\approx$15 ml/hr), hence, all tetravalent constructs are highly effective in reducing significantly the urinary filtration and subsequent excretion at the level of the kidney.

TABLE 17

PK-parameters of tetravalent anti-DR5 NB constructs

| Parameter | 10F1 tetra | 11D1 tetra | 11H6 tetra | 4E6 tetra | 7A12 tetra |
| --- | --- | --- | --- | --- | --- |
| $C_{(0)}$ (μg/ml) | 114 | 336 | 163 | 25.2 | 71.7 |
| $V_{ss}$ (mL) | 12.5 | 5.63 | 2.83 | 56.8 | 12.2 |
| $V_1$ (mL) | 1.76 | 0.595 | 1.22 | 7.95 | 2.79 |
| $V_2$ (mL) | 10.7 | 5.04 | 1.61 | 48.8 | 9.43 |
| CL (mL/hr) | 2.85 | 2.11 | 0.211 | 4.2 | 1.42 |
| $CL_d$ (mL/hr) | 1.29 | 0.453 | 0.387 | 2.89 | 1.59 |
| $t_{1/2\alpha}$ (hr) | 0.3 | 0.161 | 1.04 | 0.756 | 0.589 |
| $t_{1/2\beta}$ (hr) | 8.49 | 9.41 | 11.1 | 20.3 | 9.46 |
| MRT (hr) | 4.38 | 2.68 | 13.4 | 13.5 | 8.57 |
| $AUC_{inf}$ (μg * hr/ml) | 70.2 | 95 | 947 | 47.6 | 140 |

Figure 2:
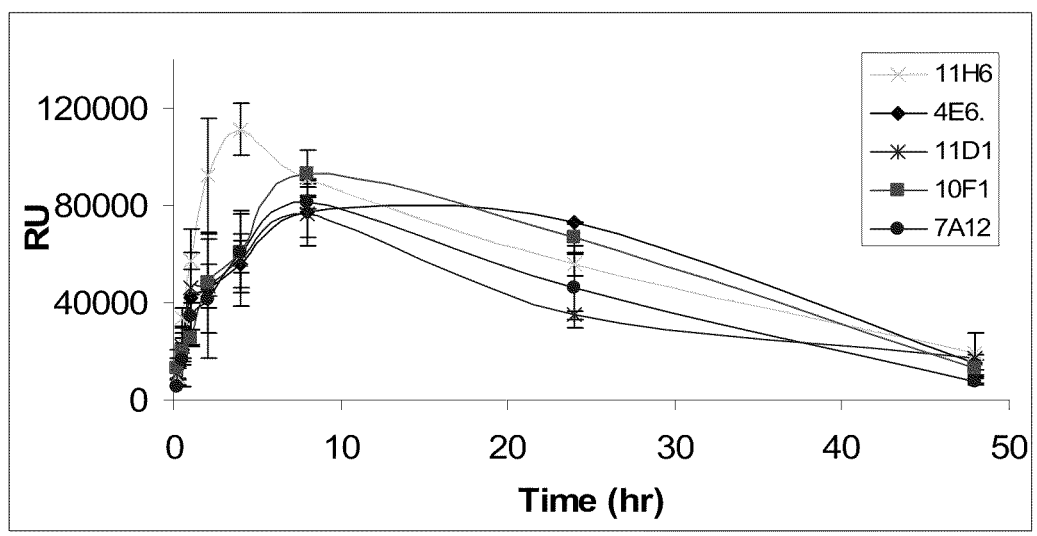
FIG. 2 is a graphic representation of a tumor tissue PD (Caspase3/7 activation) of tetravalent anti-DR5 NB agents.

Caspase 3/7 activity in tumor tissue lysate is evaluated by Caspase glo assay (Promega Catalog no. G8092) according to its user's manual and described as above. All tetramers have similar PD profile (FIG. 2).

An indirect response model is developed to describe the potency ($EC_{50}$), efficacy ($E_{max}$) and time-course of the pharmacological effect of the different NB constructs. The model describes a change in cellular caspase level that results from an enhanced production rate following DR5 receptor binding (i.e., stimulation of the build-up of cellular caspase). The rate of cellular caspase (Response, R) is described by the following equation.

$$\frac{dR}{dt} = k_{in} \cdot \left[1 + \frac{E_{max} \cdot C^n}{EC_{50}^n + C^n}\right] - k_{out} \cdot R \quad \text{(equation 1)}$$

where $k_{in}$ is the zero-order synthesis rate, R is the caspase level, $E_{max}$ is the maximum stimulation, C is the NB construct concentration at the tumor, n is the response shape factor and $k_{out}$ is the caspase first order elimination rate constant.

The tumor concentration-time profiles are first fitted to the pharmacokinetic function that is minimally necessary to provide a reasonable characterization of the concentration-time data (two-compartmental model 3 or model 11 within WinNonlin Software Version 5.1). The pharmacokinetic function obtained for each NB construct is then used as input function for equation 1. The obtained pharmacodynamic parameters are listed in Table 18.

TABLE 18

PK/PD-parameters single dose tetravalent anti-DR5 NB constructs

| Parameter[1] | 10F1 tetra | 7A12 tetra | 4E6 tetra | 11D1 tetra | 11H6 tetra |
| --- | --- | --- | --- | --- | --- |
| $k_{out}$ (1/hr) | 0.319 | 0.301 | 0.412 | 0.416 | 0.356 |
| $EC_{50}$ (ng/mg tissue) | 0.365 | 1.41 | 1.36 | 12.2 | 8.37 |
| $E_{max}$ | 15.8 | 15.3 | 4.74 | 12.2 | 17.5 |
| N | 2.14 | 3.85 | 10.1 | 0.18 | 4.62 |

4.3. In Vivo Test Using Xenograft Model

Figure 3:
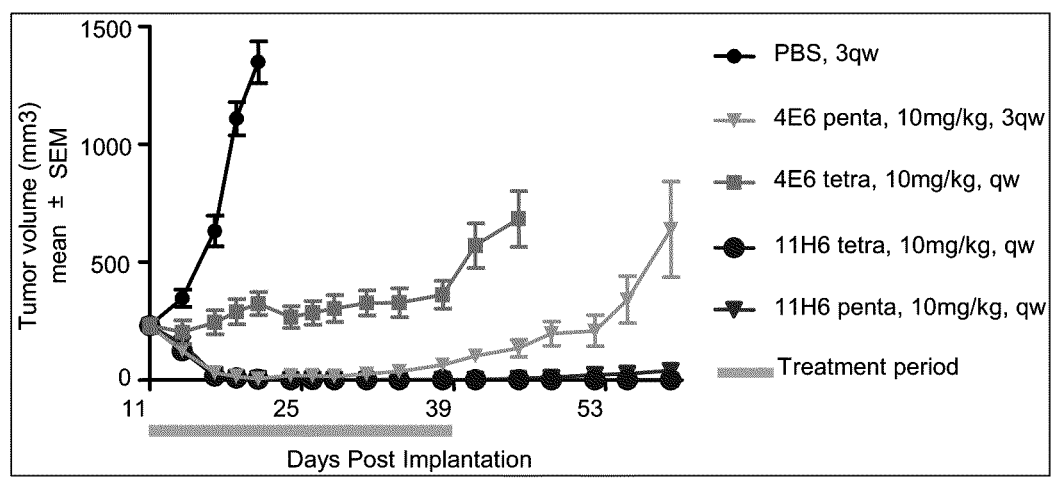
FIG. 3 is a graphic representation of the in vivo efficacy of tetravalent and pentavalent anti-DR5 NB agents in a Colo205 tumors model.
Figure 4A:
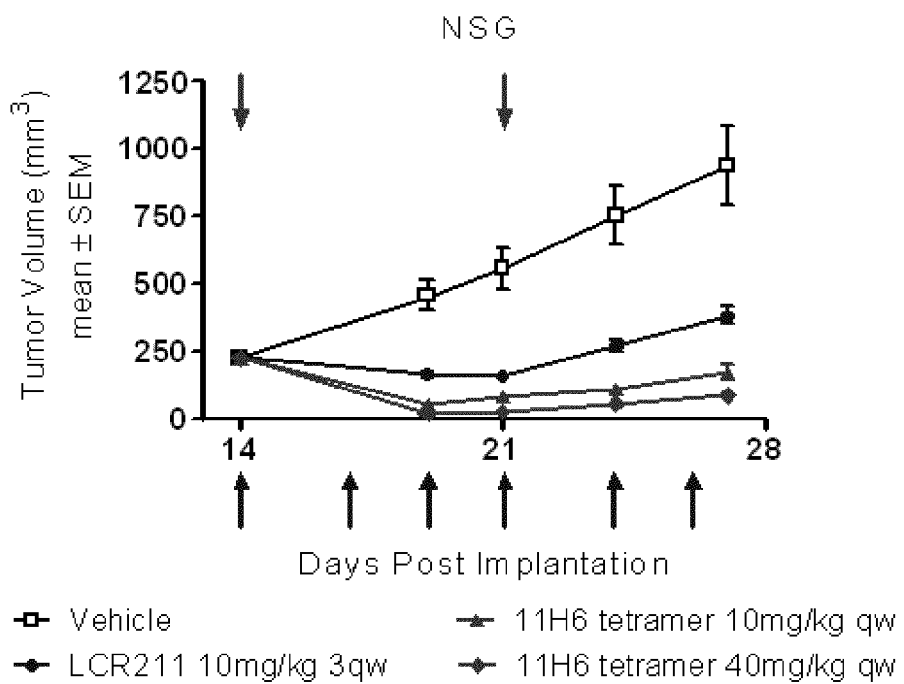
FIGS. 4A and 4B are graphic representations of 11H6 tetramer exhibiting anti-tumor activity in a MiaPaCa pancreatic tumor model grown in NSG hosts (i.e., macrophage/NK deficient hosts) either without (FIG. 4A) or with (FIG. 4B) CSF-1R inhibitor.
Figure 4B:
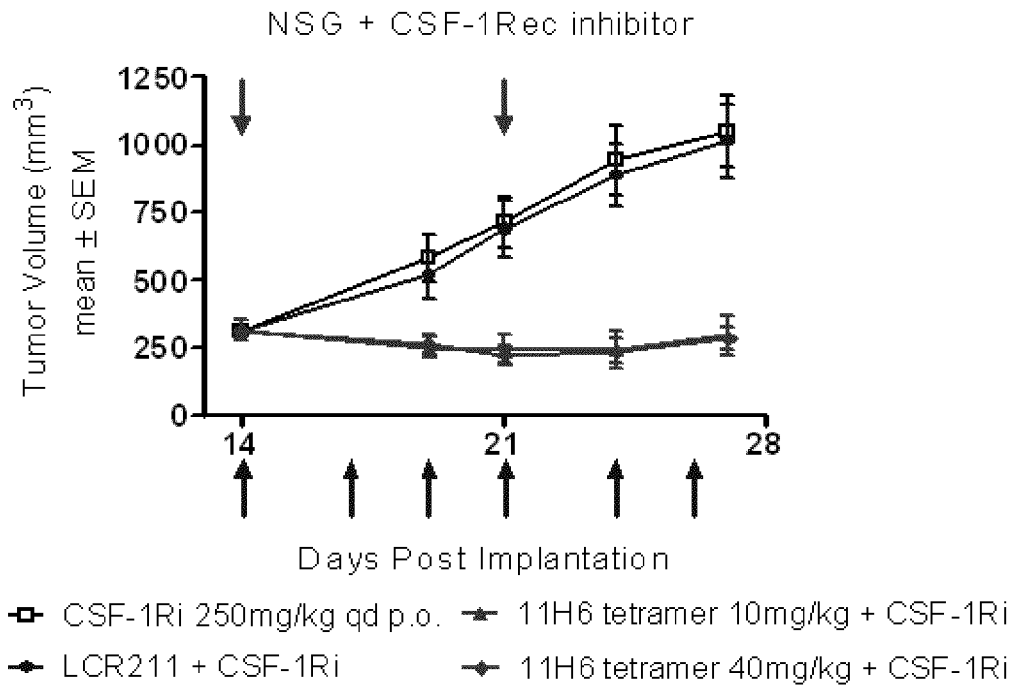

Outbred athymic (nu/nu) female mice (Harlan Sprague Dawley, Indianapolis, Ind.) are implanted s.c. into the right axillary (lateral) region with approximately 1–2×10$^6$ COLO205 tumor cells suspended in 100% Hanks' balanced salt solution (HBSS) in a total volume of 100 ml. Tumors are allowed to grow to 200 mm$^3$ before the dosing is initiated. NB constructs are formulated as a solution in PBS, and dosed either once per week or three times per week on Monday, Wednesday and Friday. Both treatments are administered i.v. for four weeks. Tumors are measured and individual animal body weights are recorded once or twice per week. Experiments are concluded after seven weeks from the initial dosing. Anti-tumor activity is expressed as % T/C (comparing change in tumor volume for treatment group versus vehicle control group). Regression is calculated using the formula: (1−T/T0)×100%, where T is the mean tumor volume for the treatment group at the end of the experiment, and T0 is the mean tumor volume at the beginning of the experiment. Statistical significance of the results is uniformly evaluated using one-way ANOVA test post-hoc Tukey analysis. As shown in FIG. 3, the NB constructs induce tumor stasis or regression in the Colo205 tumor model. Pentameric forms of the NB constructs trend toward more potent efficacy than tetrameric forms.

5. Example V

5.1. Humanization of 4E6

5.1.1. Characterization of 4E6 Humanization Variant

The protein sequence of parent 4E6 is aligned to the human VH3-23 (DP-47) and JH5 germlines (Table 19). Amino acid differences relative to the human germline sequence are represented by letters, identical amino acids by dots. Amino acid differences in framework regions that are underlined are selected for conversion into the human counterpart whereas the others are left untouched.

20). In addition, the variants are analyzed in the thermal shift assay as well (Table 20). 5 µl of each purified monovalent anti-DR5 NB construct (80 µg/ml) is incubated with 5 µl of the fluorescent probe Sypro Orange (Invitrogen, Carlsbad, Calif., catalogue # S6551) (final concentration 10×) in 10 µl of buffer (100 mM phosphate, 100 mM borate, 100 mM citrate, 115 mM NaCl, buffered at different pH's ranging from 3.5 to 9). The samples are then heated in a LightCycler 48011 machine (Roche, Basel, Switzerland), from 37° C. to 90° C. at 4.4° C./s, after which they are cooled down to 37° C. at 2.2° C./s. Upon heat-induced unfolding, hydrophobic patches of the proteins are exposed, to which the Sypro Orange binds resulting in an increase in fluorescence intensity. The inflection point of the first derivative of the fluorescence intensity curve serves as a measure of the melting

TABLE 19

```
Alignment of 4E6 parent and humanized N-glycosylation knock out variants

Kabat #:      1         10        20        30        40        50        60
              |---------|---------|---------|---------|---------|--a------|

VH3-23/JH5:   EVQLLESGGGLVQPGGSLRLSCAASGFTFSSYAMSWVRQAPGKGLEWVSAISGSGGSTYYA

4E6:          ....v.....s..a.d..........r..g.irvg.f..t...er.f.a..nrnd.t....

4E6-hu:       ...................r..g.irvg.f.......r.f....nrnd.t....

Kabat #:      60        70        80        90        100       110
              |---------|---------|--abc----|---------|abcdefghi---------|---

VH3-23/JH5:   DSVKGRFTISRDNSKNTLYLQMNSLRAEDTAVYYCAK----------------WGQGTLVTVSS

4E6:          ..............a...v.m..a..kp.........aglqynrsadrvpvgavy.....q.....

4E6-Hu:       ..................v........p.........aglqynrAadrvpvgavy...........
```

VH3-23/JH5 = SEQ ID NO: 90
4E6 = SEQ ID NO: 1
4E6-Hu = SEQ ID NO: 26

Purified, monovalent material is produced from 4E6, 4E6-Hu and of variant 4E6hx (wherein 4E6hx has the humanized FR regions identical to 4E6-Hu but has the CDR3 of 4E6). These constructs are then characterized in a number of assays for binding on human and cynomolgus DR5, namely FACS saturation binding (apparent Kd) and SPR kinetics (see Table temperature (Tm). For more details, please see Ericsson et al. 2006 (Annals of Biochemistry, 357: 289-298). Overall, the 4E6-hx variant displays affinities similar to the 4E6 parent. In addition, this variant has a 7% increase in Tm compared to the 4E6 parent.

TABLE 20

Monovalent 4E6 humanization and N-glycosylation knock-out variants

| | Human DR5 | | | | |
|---|---|---|---|---|---|
| | Biacore | | | FACS | |
| | $k_a$ (1/Ms) | $k_d$ (1/s) | KD (M) | Apparent KD (M) | Tm @ pH 7 (° C.) |
| 4E6 | $4.4 \times 10^{+06}$ | $1.0 \times 10^{-04}$ | $2.3 \times 10^{-11}$ | $4.2 \times 10^{-10}$ | 73.4 |
| 4E6-hx | $6.0 \times 10^{+06}$ | $1.4 \times 10^{-04}$ | $2.3 \times 10^{-11}$ | $3.4 \times 10^{-10}$ | 79.1 |
| 4E6-Hu | $1.1 \times 10^{+07}$ | $1.1 \times 10^{-04}$ | $9.5 \times 10^{-12}$ | $4.4 \times 10^{-10}$ | ND |

| | Cynomolgus DR5 | | | | |
|---|---|---|---|---|---|
| | Biacore | | | FACS | |
| | $k_a$ (1/Ms) | $k_d$ (1/s) | KD (M) | Apparent KD (M) | Tm @ pH 7 (° C.) |
| 4E6 | $2.1 \times 10^{+06}$ | $1.1 \times 10^{-02}$ | $5.5 \times 10^{-09}$ | $7.3 \times 10^{-09}$ | 73.4 |
| 4E6-hx | $6.1 \times 10^{+06}$ | $2.1 \times 10^{-02}$ | $3.4 \times 10^{-09}$ | $7.1 \times 10^{-09}$ | 79.1 |
| 4E6-Hu | $7.0 \times 10^{+06}$ | $1.1 \times 10^{-02}$ | $1.6 \times 10^{-09}$ | $8.8 \times 10^{-09}$ | ND |

5.1.2. N-Glycosylation Knock-Out Variant of Humanized 4E6

Expression of 4E6-hx in *P. pastoris* followed by SDS PAGE and anti-$V_{HH}$ (polyclonal anti-Nanobody®) western reveals the presence of two products (16 kDa and 21 kDa) compared to only one 16 kDa product when *E. coli* is the expression host. Treatment with PNGaseF and staining with concanavalin reveals that the 21 kDa product is the N-glycosylated form of the 16 kDa product. Cleavage of N-glycosylation moieties from proteins using PNGaseF is done according to the manufacturer's recommendations (New England Biolabs, Ipswich, Mass., catalogue # P0704S). PNGaseF is an amidase that cleaves between the innermost GlcNAc and asparagine residues of high mannose, hybrid, and complex oligosaccharides from N-linked glycoproteins. Detection of protein N-glycosylation is done in a Western assay with Concanavalin A, a lectin that recognizes glycoproteins containing α-D-mannose, α-D-glucose. Blotted proteins are blocked for 2 hours with blocking buffer (PBS, 0.05% Tween-20, 1 mM $CaCl_2$, 1 mM $MnCl_2$), followed by ON incubation with 5 μg/ml of Concanavalin A biotin conjugate (Sigma, St. Louis Mo., catalogue # C2272) at 4° C. in blocking buffer. Detection is done using a 1/2000 dilution of extravidin-HRP conjugate in blocking buffer and DAB as substrate (Sigma, St. Louis Mo., catalogue # E2886 and D6815). The 36 kDa band visible in the coomassie stained gel is the PNGaseF enzyme. Off-rate analysis on human DR5 revealed an >8-fold increase for the *P. pastoris* produced material versus the *E. coli* produced material, suggesting that the N-glycosylation interferes with the binding of 4E6-hu to DR5.

A potential N-glycosylation motif is present in the CDR3 of 4E6 and 4E6-hx (amino acids "nrs"—shown in bold and italics in Table 19). The 4E6-Hu variant (CDR3 with a replaced "A" residue shown in bold capital letter—Table 19) is generated and produced in *E. coli*, purified and assayed for binding to human and cynomolgus DR5 using the FACS saturation binding assay and SPR kinetics (Table 20). The 4E6-Hu has equal binding characteristics to both human and cynomolgus DR5, compared to 4E6-hx. Upon expression in *P. pastoris*, the 4E6-Hu variant yields only the 16 kDa product. This confirms the functional knock-out of the glycosylation motif.

5.1.3. In Vitro Characterization of 4E6-Hu

Purified, tetravalent material is produced from wild type 4E6 and its humanized variant 4E6-Hu. These are then assayed in cell survival assays in Colo205 and Jurkat (Table 21). The potency and efficacy of the humanized variant is relatively equal to the parent 4E6 construct.

TABLE 21

In vitro potency and efficacy of tetravalent wild type 4E6 and 4E6-Hu

| | Colo205 | | Jurkat | |
|---|---|---|---|---|
| | IC50 (M) | Efficacy (% dead cells) | IC50 (M) | Efficacy (% dead cells) |
| 4E6 tetra | $1.9 \times 10^{-11}$ | 94 | $8.7 \times 10^{-12}$ | 79 |
| 4E6-Hu tetra | $1.2 \times 10^{-11}$ | 94 | $2.6 \times 10^{-12}$ | 95 |

5.2. 11H6 Humanization

5.2.1. Characterization of 11H6 Humanization Variant

The protein sequence of wild type 11H6 is aligned to the human VH3-23 (DP-47) and JH5 germlines (Table 22). Amino acid differences relative to the human germline sequence are represented by letters, identical amino acids by dots. Amino acid differences in framework regions that are underlined are selected for conversion into the human counterpart whereas the others are left untouched.

TABLE 22

```
             Alignment 11H6 parent and humanization variant

Kabat #:     1         10        20        30        40        50        60
             |---------|---------|---------|---------|---------|--a-------|

VH3-23/JH5:  EVQLLESGGGLVQPGGSLRLSCAASGFTFSSYAMSWVRQAPGKGLEWVSAISGSGGSTYYA

11H6:        ....v....................tfdkinn.g.y......qrdl.aq.t-p..i.d..

11H6-hu:     .........................tfdkinn.g.y......qrdl.aq.t-p..i.d..

Kabat #:     60        70        80        90        100       110
             |---------|---------|--abc-------|---------|abcdef---------|---

VH3-23/JH5:  DSVKGRFTISRDNSKNTLYLQMNSLRAEDTAVYYCAK--------------WGQGTLVTVSS

11H6:        .............a.d.m.......kp......f.naeilkrayidvyvny.....g.....

11H6-hu:     .........................p........naeilkrayidvyvny...........
```

VH3-23/JH5 = SEQ ID NO: 90
11H6 = SEQ ID NO: 5
11H6-hu = SEQ ID NO: 30

Purified, monovalent material is produced for 11H6 and 11H6-Hu, which is then characterized in a number of assays for binding on human and cynomolgus DR5, namely FACS saturation binding (apparent Kd) and SPR kinetics (Table 23). In addition, the variants are analyzed in the thermal shift assay (Table 23). The 11H6-hu variant retains the parental 11H6 binding characteristics. It also has an 8% increase in melting temperature compared to parent 11H6. Tm is determined at pH 7.

TABLE 23

Characterization of monovalent 11H6 parent and humanization variants

| | Apparent Kd (M) | | Kd (M) | | |
|---|---|---|---|---|---|
| | Human DR5 | Cynomolgus DR5 | Human DR5 | Cynomolgus DR5 | Tm (° C.) |
| 11H6 | $4.6 \times 10^{-09}$ | ND | $4.9 \times 10^{-09}$ | $3.2 \times 10^{-07}$ | 68.5 |
| 11H6-hu | $4.4 \times 10^{-09}$ | ND | $2.3 \times 10^{-09}$ | $1.7 \times 10^{-07}$ | 74.0 |

5.2.2. In Vitro Characterization of 11H6-Hu

Purified, tetravalent material is produced from parental clone 11H6 and its humanized variant 11H6-Hu. These are then assayed in cell survival assays against Colo205 and Jurkat (Table 24). The potency and efficacy of the humanized variant is equal to the parent. Efficacy represents the percentage of dead cells seen.

TABLE 24

In vitro potency and efficacy of tetravalent wild type 11H6 and 11H6-hum

| | Colo205 | | Jurkat | |
|---|---|---|---|---|
| | IC50 (M) | Efficacy | IC50 (M) | Efficacy |
| 11H6 tetra | $1.4 \times 10^{-11}$ | 92 | $1.5 \times 10^{-11}$ | 34 |
| 11H6-hu tetra | $2.0 \times 10^{-11}$ | 94 | $1.6 \times 10^{-11}$ | 54 |

5.3. In Vitro Characterization of 11H6-Hu and 4E6-Hu Tetramers and Pentamers

Cells are plated in a 96 well plate (Costar #3903 white clear bottom) with the intention of achieving about 75% confluence. Cells are plated in a range from 7500-15000 cells/well (depending on cell line) in 100 µl media the day prior to the assay. The day of the assay, the media is removed and fresh media is added. Serially diluted NB agent is then added (starting concentrations may vary depending on the cell line), usually between 1-20 nM starting concentration, which is then diluted 3-4 fold over 10 dilutions in general for a final volume of 150 µl. The cells are then incubated for 24-72 hrs at 37° C. in the $CO_2$ supplied incubator. After incubation, the plated cells and Cell Titer Glo (Promega #G7571) reagents are brought to room temperature (about 30 min). 50 µL of the reconstituted Cell Titer Glo reagent is then added to each well. The plate is shaken for 2-3 minutes and then left to equilibrate in the dark for 10 minutes before reading luminescence on the Spectromax.

Specific examples are provided in Table 25.

6. Example VI 6.1. Ex-Vivo Assay for Leukemia Patients

An ex-vivo assay for leukemia patients is provided as a method to predict which patients will respond to treatment with an NB construct. A blood sample is obtained from a patient prior to treatment and used to assay potential treatment response. The degree and direction of response is used as selection criteria for treatment.

T-cell leukemia (T-ALL) is believed to be generally sensitive to DR5 stimulation. T-ALL samples are treated with NB constructs of the invention and assessed to determine if the number of leukemia cells is decreased (or undergoing apoptosis) with treatment. The assay drug range is from about 20 nm to about 0.0001 nM for treatments Ex-vivo with NB constructs of the invention.

Cell samples from patients diagnosed with other indications may also be obtained and similarly tested.

6.2. General Ex-Vivo Sensitivity Assay

Tumor samples are tested outside of a patient in a laboratory setting as a method to help predict which patients may respond to one or more NB agents.

Primary patient tumor material from blood or tissue is treated in a similar manner to the above assays, depending on the tumor type. Tumor is removed via total blood collection or tissue biopsy and plated into an appropriate tissue culture plate for 0-24 hours. The tumor specimen is then treated with varying concentrations of NB agent(s) over a dilution series (e.g., starting concentration could be 20 nM diluted 3-4 fold over 10 dilutions). The tissue culture plate is then treated with NB agent(s) for 24-72 hrs or for several hours (1-24) at 37° C. in the $CO_2$ supplied incubator. After incubation, the plated specimen is analyzed using a method to detect the response of the specimen to treatment. Such as in the above examples; Cell Titer Glo (Promega #G7571) for cell viability, or

TABLE 25

In vitro characterization of 11H6-hu and 4E6-hu tetramers and pentamers

| | 11H6-Hu | | | 4E6-Hu | | |
|---|---|---|---|---|---|---|
| IC50 (nM) | tetra | penta | fold improvement | tetra | penta | fold improvement |
| Jurkat (72) | 0.0007 | 0.0017 | 4 | 0.0172 | 0.0036 | 5 |
| A549 | >10 | >10 | 1 | >10 | >10 | 1 |
| Colo205 | 0.0036 | 0.0012 | 3 | 0.0034 | 0.0007 | 5 |
| BxPC-3 | 0.0154 | 0.0046 | 3 | 0.0292 | 0.005 | 6 |
| T24 | 0.0222 | 0.0031 | 7 | 0.0447 | 0.0043 | 10 |
| Panc-1 | 0.2317 | 0.0067 | 35 | 0.2291 | 0.0105 | 22 |
| M30 | >10 | >10 | 1 | >10 | >10 | 1 |
| H226 | 0.1718 | 0.0124 | 14 | 0.1293 | 0.0272 | 5 |
| H2122 | 0.0041 | 0.0017 | 2 | 0.0051 | 0.0008 | 7 |
| MiaPaCa-2 | 0.0117 | 0.0031 | 4 | 0.0185 | 0.0038 | 5 |

Caspase 3/7 activation, or AnnexinV staining, or Cell counting, or FACS analysis or other method to determine the growth, death, or response to NB agent treatment are provided.

Either a NB agent-sensitive cell line (e.g., Jurkat) or a NB agent-insensitive cell line (BE13), or PBMC (peripheral blood mononuclear cells, e.g., made fresh from the blood of a healthy volunteer) or the combination of the cell culture (cell line) spiked into the PBMC are treated with various concentrations of NB agent(s) for 3.5 hours at 37° C. in the $CO_2$ supplied incubator, after which Caspase 3/7 activation is assessed (Promega #G7790) by following the directions supplied by the manufacturer.

7. Example VII

7.1. Analysis of the RAF-MEK-ERK Pathway and DR5 Activity

Death Receptor 5 (DR5) is of particular interest in cancer drug discovery, since its activation selectively induces apoptosis in cancer cells while sparing many normal cells. A DR5 specific agonist construct may avoid the limitations of the ligand, namely binding to Decoy Receptors such as DcR1, DcR2 and OPG. A major hurdle for the clinical developments of DR5 agonist antibodies has been the difficulty in identifying biomarkers predictive of efficacy in patient subgroups. The analysis of data from 200 cancer cell lines indicated that no obvious genetic mutations, including those in RAS and RAF, are correlative of sensitivity to LBY135, a DR5 agonist antibody (Novartis AG).

A strategy to screen pooled shRNAs based on DR5 sensitization/rescue is used to identify genes or pathways that modify DR5 mediated apoptosis after genetic perturbation. The screens are conducted in seven cancer cell lines across various lineages, and Solexa based deep sequencing of the integrated hairpins is used to de-convolute the shRNA compositions.

A set of common sensitizers and rescuers are identified as known pathway components, such that shRNAs targeting caspase 8, caspase 3 and DR5 itself are the top rescuers and those targeting BCLxI are the top sensitizers, indicating the robustness of the screens. Interestingly, in addition to these sets of common genes, inhibition of BRAF-MEK-ERK exhibits opposing cell-context-dependent phenotypes on DR5 mediated apoptosis. Specifically, inhibition of BRAF-MEK-ERK pathway sensitizes Miapaca2 cells to DR5 mediated apoptosis, but rescues Colo205 cells from it.

These opposite phenotypes correlate well with different kinetics of caspase 8 and caspase 9 activity, but appear to be independent of DR5 expression level. Pathway dissection reveals that cFLIP and cIAP1, two of the endogenous apoptosis inhibitors, mediate cross-talk between DR5 mediated apoptosis and the BRAF-MEK-ERK pathway. In Miapaca2 cells, combination of U0126 (MEK inhibitor) and DR5 antibody accelerate the degradation of cFLIP and cIAP1 proteins, while in colo205, both cFLIP and cIAP1 mRNAs are up-regulated. Consistently, inhibition of cFLIP or cIAP1 by shRNAs or chemical inhibition eliminate the rescue phenotype in Colo205 cells, and further sensitize Miapaca2 to DR5 mediated apoptosis. Microarray analysis of Miapaca2 and Colo205 cells treated with MEK inhibitor reveal genes that are down-regulated in both cell lines, including DUSP6, ETV5 and ERG1, which are the canonical downstream targets of ERK.

7.2. Bcl-xL, cIAP1 and BRAF-MEK-ERK as Cell-Context Dependent Regulators of DR5 Mediated Apoptosis Many proteins work as cell-context dependent regulators, if it is defined broadly. For examples, ABT737, a Bcl-xL inhibitor, showed a range of phenotypes on LBY135 induced apoptosis. Among 35 cell lines to be examined, it strongly sensitizes the effect of LBY135 on 7 cell lines, mildly sensitizes 9 cell lines, but had no effect on the other 19 cell lines. One of the plausible reasons is that parallel pathways are present in some cell lines that compensate the inhibition of Bcl-xL. For example, analysis of our screens reveal that shRNAs against Bcl-xL sensitize all cell lines except for Miapaca2 cells, which actually are sensitized by shRNAs targeting MCL1. Such kind of regulators would not hinder the development of combination therapy. In this aspect, an inhibitor to cIAP1 is a similar regulator that sensitizes a DR5 agonist antibody in a large number of cell lines (Table 26, plus data not shown). Interesting, cIAP1, not x-IAP, is specifically involved in the cross-talk between DR5 and BRAF-MEK-ERK pathway.

The BRAF-MEK-ERK pathway falls into a category for cell-context-dependent regulators. Its cell-context dependent effects ranged from sensitizer to antagonizer. Such dramatic differences provide an opportunity to gain insight in the signaling networks regulating DR5 mediated apoptosis. However, biomarker should be identified, or such combination will be difficult to develop, even if the sensitizing effects are strong and desirable. Actually for DR5 resistant cell lines, such as ES2 and A375, BRAF/MEK inhibitors are the only partners in the table below that show strong sensitizing effects, whereas inhibitors to Bcl-xL do not. Downregulation of cIAP1 is associated with the sensitizing effects in multiple cell lines, suggesting it as a PD biomarker for such combination strategy. Our results suggest that a triple combination of a DR5 agonist antibody with inhibitors to c1 and BRAF-MEK could be a solution.

Table 26 shows the synergistic effect between DR5 agonist antibody and inhibitors to cIAP1 or Bcl-xL. Thirty five cell lines are treated with LBY135 (DR5 agonist antibody, Novartis AG) alone or in combination with LBW242 (cIAP1 inhibitor) or ABT737 (Bcl-xL inhibitor). Cells are labeled as insensitive where the viability is higher than 70% at 5 nM of LBY135. For combination effects, it is labeled as '+++' where the combination reduces cell viability by more than 30%; and labeled as '++' where the combination reduces cell viability by between 10-30%. It is labeled as "none" when no synergy is observed with the combination treatment.

TABLE 26

Synergistic effect between DR5 agonist and cIAP1 or Bcl-xL inhibitors.

| Cell line | Tumor type | Sensitivity to LBY135 (5 nM) | Sensitized by LBW242 | Sensitized by ABT737 |
|---|---|---|---|---|
| A172 | CNS | sensitive | ++ | ++ |
| Bxpc3 | Pancreatic | insensitive | ++ | ++ |
| Caov3 | ovary | sensitive | ++ | ++ |
| H596 | NSCLC | insensitive | ++ | ++ |
| panc10.05 | Pancreatic | insensitive | ++ | +++ |
| A375 | Melanoma | insensitive | ++ | none |
| DU145 | Prostate | insensitive | ++ | none |
| SK-Mel5 | Melanoma | insensitive | ++ | none |
| colo741 | Colon | insensitive | +++ | ++ |
| HCT116 | Colon | sensitive | +++ | ++ |

TABLE 26-continued

Synergistic effect between DR5 agonist and cIAP1 or Bcl-xL inhibitors.

| Cell line | Tumor type | Sensitivity to LBY135 (5 nM) | Sensitized by LBW242 | Sensitized by ABT737 |
|---|---|---|---|---|
| HT29 | Colon | insensitive | +++ | ++ |
| colo205 | Colon | sensitive | +++ | +++ |
| EBC1 | Lung | sensitive | +++ | +++ |
| colo201 | Colon | sensitive | +++ | none |
| ES2 | ovary | insensitive | +++ | none |
| sw626 | Colon | insensitive | none | ++ |
| H2452 | Mesothelioma | sensitive | none | +++ |
| HPAC | Pancreatic | sensitive | none | +++ |
| LNcap | Prostate | insensitive | none | +++ |
| T24 | Bladder | insensitive | none | +++ |
| A549 | NSCLC | insensitive | none | none |
| Calu6 | Lung | sensitive | none | none |
| H146 | SCLC | insensitive | none | none |
| H358 | NSCLC | sensitive | none | none |
| H520 | NSCLC | insensitive | none | none |
| MDAMB361 | Breast | insensitive | none | none |
| MDA-MB-453 | Breast | sensitive | none | none |
| OPM2 | Multiple Myeloma | sensitive | none | none |
| panc2.03 | Pancreatic | insensitive | none | none |
| Panc3.27 | Pancreatic | sensitive | none | none |
| RKO | Colon | insensitive | none | none |
| RT4 | Bladder | insensitive | none | none |
| SKOV3 | ovary | insensitive | none | none |
| SW480 | Colon | sensitive | none | none |
| U266B1 | Multiple Myeloma | insensitive | none | none |

++: sensitizing;
+++: strong sensitizing;

In addition, 180 genes are also identified as being differentially regulated by MEK inhibition between the two cell lines. A set of transcription factors that could be responsible for regulating those genes are predicted by gene set enrichment analysis (GSEA), followed by individual examination using shRNA to confirm their involvement. Among many transcription factors, only FOXO3 and SP1 are found to be directly involved in the cross-talk between the two pathways, as shown by their role in the regulation of cFLIP or cIAP1 at the mRNA level in Colo205 cells. However, in Miapaca2 cells, cFLIP or cIAP1 are regulated at the protein level in proteasome and caspase 8 dependent manners. Finally, reduced cIAP1 protein levels are associated with the sensitizing effects in additional cell lines. These results identify multiple potent combination strategies for the DR5 agonist antibody LBY135, and reveal a cell-context-dependent regulation of DR5 mediated apoptosis by the BRAF-MEK-ERK pathway.

To validate the shRNA results, chemical inhibitors specific to BRAF and MEK are used to disrupt the BRAF-MEK-ERK pathway. Namely, RAF265 and U0126 are inhibitors of BRAF and MEK, respectively. Inhibition of the BRAF-MEK-ERK pathway with either compound sensitized Miapaca2 cells to LBY135 treatment, but rescued Colo205 cells from it. Other BRAF and MEK specific inhibitors gave similar phenotypes.

Miapaca2 cells have an activating KRAS mutation (G12C), whereas Colo205 cells have an active BRAF mutation (V600E). So it is possible that these mutations are responsible for the different phenotypes. However, H2122, which has the same KRAS mutation as Miapaca2 cells, did not show any sensitizing effect as in Miapaca2. Furthermore, after screening seven additional cell lines, all with BRAF mutations, we found that MEK inhibitors showed no effect in some cell lines while the others are sensitized as in Miapaca2 cells. Taken together, our results indicate that neither BRAF nor KRAS mutations explain the cell-context dependent roles of the BRAF-MEK-ERK pathway on DR5 mediated apoptosis.

Overall, inhibition of BRAF-MEK-ERK is a double-edge sword—it can lead to either a sensitizing or an antagonizing effect when used in combination with a DR5 agonist. Inhibitors of cIAP1 or XIAP, of Bcl-xL or of cFLIP in combination with a DR5 agonist is sufficient for sensitization. However, the combination of a BRAF inhibitor and either a MEK or ERK inhibitor appear to antagonize the effect of pre-treatment with LBY135. While this raises concerns for combination therapy targeting both pathways in the clinic, data suggests that a triple combination with cIAP inhibitors could be a solution for the antagonism. Namely, a triple combination of a DR5 agonist, a cIAP inhibitor (either to cIAP1 or to XIAP) and the choice of a MEK inhibitor or a BRAF inhibitor should also result in synergistic induction of cell death.

7.3. Experimental Protocols

For the shRNA library screen, target cells are infected with a pooled shRNA library targeting kinome and apotome shRNA, selected with puromycin, then treated with cross-linked LBY135 or PBS control. Samples collected at Day 0, 7 and 14 are subjected to DNA extraction, PCR amplification of integrated shRNAs and purification, followed by solexa sequencing. Comparisons between treatments at the same time points reveal shRNAs modulating DR5 mediated apoptosis. Comparisons between time points in PBS controls reveal effects of shRNAs on cell growth. These hits are then subjected to individual validation.

To analyze knock-down of LIMK2 sensitized Miapaca2 and Colo205 to LBY135 induced apoptosis, cells are infected with shRNAs against LIMK2 or control hairpins, selected with puromycin for 5 days, then seeded in 96-well-plates for treatments with serial dilutions of cross-linked LBY135 the next day for 36 hours. Cell viabilities are measured by cell-titer-glow reagent, and normalized to the samples not treated with LBY135. Cell survival rate is plotted as a function of concentrations to generate a dose-response curve. Data includes the mean±SD of triplicates of a representative experiment out of at least two independent experiments.

Chemical inhibitors of MEK and BRAF are used to validate the phenotype of shRNAs in the screen. Miapaca2 and Colo205 are pre-incubated with DMSO, MEK inhibitor U0126 (10 uM) or BRAF inhibitor RAF265 (1 uM) overnight, then treated with serial dilutions of cross-linked LBY135 for 36 hours. Cell viabilities are measured by cell-titer-glow reagent, and normalized to the samples not treated with LBY135. Cell survival rate is plotted as a function of concentrations to generate a dose-response curve. Data are the mean±SD of triplicates of a representative experiment out of at least two independent experiments.

To show that activation of ERK by DR5 remains intact in both cell lines, Miapaca2 and Colo205 cells are pre-incubated with DMSO or U0126 (10 uM) overnight, treated with cross-linked LBY135 (0.25 nM), and collected at 0 h, 1 h, 3 h and 6 h for western blot analysis for ERK and p-ERK. MEK inhibition decreases DR5 induced activities of caspase-8, caspase-9 and caspase-3/7 in Colo205 cells, whereas it increases them in Miapaca2 cells. Colo205 and Miapaca2 are treated with cross-linked LBY-135 at 0 nM, 0.25 nM or 1 nM for 7 hrs. Cells are lysed for analysis of activities of caspase8, caspase9 and caspase3/7. Caspase activities are plotted as a function of LBY135 concentrations. Data is representative experiment out of at least two independent experiments.

Microarray analysis is used to reveal those genes with significant correlation between Colo205 and Miapaca2 cells among genes regulated by MEK. Colo205 and Miapaca2 cells are pre-incubated with DMSO or U0126 overnight in five independent experiments. RNA is extracted for microarray analysis. Relative expression level for each gene in U0126 versus DMSO treated cells are plotted as a function of Colo205 cells on Y-axis and Miapaca2 on X-axis.

7.4. Working Model for Cross-Talk Between DR5 and RAF-MEK-ERK

A working model proposes that treatment with a DR5 agonist activates both caspase-8 and ERK. Cross-talks between these two pathways are mediated by cFLIP and cIAP1, which negatively regulate the activation of caspase-8 and caspase-9 that in turn control the apoptosis induced by DR5 agonist. cFLIP and cIAP1 are regulated at different levels in a manner that is cell-context dependent. In Colo205 cells, they are regulated at their RNA levels through transcription factor FOXO3 and SP1, which themselves are regulated by BRAF-MEK-ERK pathway. In Miapaca2 cells, cFLIP and cIAP1 are regulated by BRAF-MEK-ERK pathway at protein level in proteasome and caspase 8 dependent manners.

8. Example VIII

8.1. Exemplary Biacore Assay

A suitable assay for determining whether an amino acid sequence or other binding agent cross-blocks or is capable of cross-blocking is a Biacore assay. It will be appreciated that the assay can be used with any of the amino acid sequences (or other binding agents such as polypeptides of the invention) described herein.

The Biacore machine (for example the Biacore 3000) is operated in line with the manufacturers recommendations. In one exemplary cross-blocking assay, the target protein is coupled to a CM5 Biacore chip using standard amine coupling chemistry to generate a surface that is coated with the target. Typically 200-800 resonance units of the target would be coupled to the chip (i.e., an amount that gives easily measurable levels of binding but that is readily saturable by the concentrations of test reagent being used).

Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions are in the same buffer and at the same concentration as in the test mix.

The test mixture is passed over the target-coated Biacore chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded.

The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above Biacore cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination.

The Biacore assay described above is a primary assay used to determine if amino acid sequences or other binding agents cross-block each other according to the invention. On rare occasions particular amino acid sequences or other binding agents may not bind to target coupled via amine chemistry to a CM5 Biacore chip (this usually occurs when the relevant binding site on target is masked or destroyed by the coupling to the chip). In such cases cross-blocking can be determined using a tagged version of the target, e.g., a N-terminal His-tagged version (R & D Systems, Minneapolis, Minn., USA; 2005 cat#1406-ST-025). In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged DR5, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

9. Example IX

9.1. Exemplary ELISA Assay

The following generally describes an ELISA assay for determining whether an amino acid sequence or other binding agent directed against a target cross-blocks or is capable of cross-blocking as defined herein. This assay can be used with any of the amino acid sequences (or other binding agents such as polypeptides of the invention) herein.

The general principal of the assay is to have an amino acid sequence or binding agent that is directed against the target coated onto the wells of an ELISA plate. An excess amount of a second, potentially cross-blocking, anti-target amino acid sequence is added in solution (i.e., not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence.

In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e., Ab-Y, is then added to the ELISA plate such that the moles of Ab-Y [target] binding sites per well are at least 10 fold higher than the moles of Ab-X [target] binding sites that are used, per well, during the coating of the ELISA plate. [target] is then added such that the moles of [target] added per well are at least 25-fold lower than the moles of Ab-X [target] binding sites that are used for coating each well. Following a suitable incubation period the ELISA plate is washed and a reagent for detecting the target is added to measure the amount of target specifically bound by the coated anti-[target] amino acid sequence (in this case Ab-X).

The background signal for the assay is defined as the signal obtained in wells with the coated amino acid sequence (in this case Ab-X), second solution phase amino acid sequence (in this case Ab-Y), [target] buffer only (i.e., no target) and target detection reagents. The positive control signal for the assay is defined as the signal obtained in wells with the coated amino acid sequence (in this case Ab-X), second solution phase amino acid sequence buffer only (i.e., no second solution phase amino acid sequence), target and target detection reagents. The ELISA assay may be run in a manner so as to have the positive control signal be at least six times the background signal.

To avoid any artifacts (e.g. significantly different affinities between Ab-X and Ab-Y for [target]) resulting from the choice of which amino acid sequence to use as the coating amino acid sequence and which to use as the second (competitor) amino acid sequence, the cross-blocking assay may to be run in two formats: (1) format 1 is where Ab-X is the amino acid sequence that is coated onto the ELISA plate and Ab-Y is the competitor amino acid sequence that is in solution and (2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal {i.e., the amount of target bound by the coated amino acid sequence) as compared to the target detection signal obtained in the absence of the solution phase anti-target amino acid sequence (i.e., the positive control wells).

10. Example X

10.1. Macrophage Depletion Experiment

All anti-DR5 antibodies in clinical development to date require cross-linking to achieve optimal potency in vitro and in vivo. In vivo, this crosslinking is believed to be mediated via the binding of the Fc portion of the anti-DR5 antibody to Fc receptor expressing immune cells. To investigate the cross-linking effects in vivo of the anti-DR5 antibody LCR211 compared with an NB construct, which is expected to not require this crosslinking, the activity of the mouse IgG1 anti-DR5 antibody LCR211 is compared to 11H6 tetra under tumor associated macrophage (TAM) depletion conditions in the MiaPaCa-2 xenograft model in the NOD/LtSz-scid IL2R gamma$^{null}$ female mice (NSG mouse) background. NSG (NOD-SCID gamma) mice are deficient in T cells, B cells, and have little or no NK cell cytotoxicity activity caused by disrupted cytokine signaling as a result of the deletion of the IL-2R gamma-chain (Shultz, J. of Immunology 2005). Depletion of TAMs is accomplished using a small molecule that inhibits signaling through the CSF-1 receptor. Three doses at 200 mg/kg once per day depletes up to 80% of macrophages, as previously shown. Daily dosing is continued throughout the study.

MiaPaCa cells are harvested in exponential growth. Five million cells mixed 50:50 with Matrigel are subcutaneously implanted into the upper right flank of nude mice. For cell implantation, mice are anesthetized with continuous flow of 2-4% isoflurane/20 oxygen mixture using the integrated multi chambers anesthesia center (IMCAC) and induction chamber (Vetequip. Inc., Pleasanton, Calif.). The tumor take rate is >90% and tumors reach approximately 150-350 mm$^3$ around 14 days post cell implantation. Animals are randomized according to tumor volume such that the mean tumor volume and range are statistically similar between treatment groups (as determined by a Student's t-test). Tumors are measured with digital calipers twice a week at the start of dosing. Tumor volumes are calculated using the ellipsoid formula: (length× width$^2$)/2. LCR211 is dosed at 10 mg/kg 3qw iv and 11H6 tetra is dosed at 10 mg/kg and 40 mg/kg qw iv, with or without the CSF1-R inhibitor (CSF-1Ri) at 250 mg/kg qd po.

Percent treatment/control (T/C) values are calculated using the following formula:

$$\% \ T/C = 100 \times \Delta T / \Delta C \text{ if } \Delta T > 0$$

$$\% \ \text{Regression} = 100 \times \Delta T / T_{initial} \text{ if } \Delta T < 0$$

where:
- T=mean tumor volume of the drug-treated group on the final day of the study;
- ΔT=mean tumor volume of the drug-treated group on the final day of the study−mean tumor volume of the drug-treated group on initial day of dosing;
- $T_{initial}$=mean tumor volume of the drug-treated group on initial day of dosing;
- C=mean tumor volume of the control group on the final day of the study; and
- ΔC=mean tumor volume of the control group on the final day of the study−mean tumor volume of the control group on initial day of dosing.

% T/C calculations are done at the end of study.

As seen in Table 27 and in FIGS. 4A and 4B, 11H6 tetra maintains potent single agent activity in the MiaPaCa-2 xenograft under TAM depletion conditions in the NSG mouse background, while under the same conditions the murine anti-DR5 antibody LCR211 loses efficacy.

TABLE 27

Summary of 11H6 tetra efficacy under TAM depletion conditions

| Molecule | % T/C no TAM depletion | % T/C with TAM depletion |
|---|---|---|
| LCR211 10 mg/kg 3 qw | 22% | 95% |
| 11H6 tetra 10 mg/kg qw | −23.64% | −5.73% |
| 11H6 tetra 40 mg/kg qw | −67.77% | −9.11% |

10.2. Anti-Tumor Activity of a DR5 Agent in LCR211-Insensitive Patient-Derived Tumor Model TPAN1-IFA, a patient-derived pancreatic tumor (Xentech), is implanted subcutaneously (sc) into (80) female nude mice (Harlan, about 8 weeks of age at implant). Animals are randomized at start of treatment into groups of nine. Starting tumor volume is 99 mm³ (range 63-196 mm³). Treatment groups are: (1) Vehicle, once a week (qw), intravenously (i.v.), (2) LCR211, 10 mg/kg, three times a week (3qw), i.v., (3) 11H6 tetramer, 10 mg/kg, qw, i.v., (4) 11H6, 40 mg/kg, qw, i.v., 5. Gemcitabine, 60 mg/kg, twice a week (2qw), i.v. Intravenous dosing volume is 5 ml/kg. Mice are weighted twice a week. Tumors are callipered twice a week and tumor volume (TV) calculated using the formula: TV (mm³)=[length (mm)×width (mm)2]/2 is used, where the length and the width are the longest and the shortest diameters of each tumor, respectively.

Figure 5:
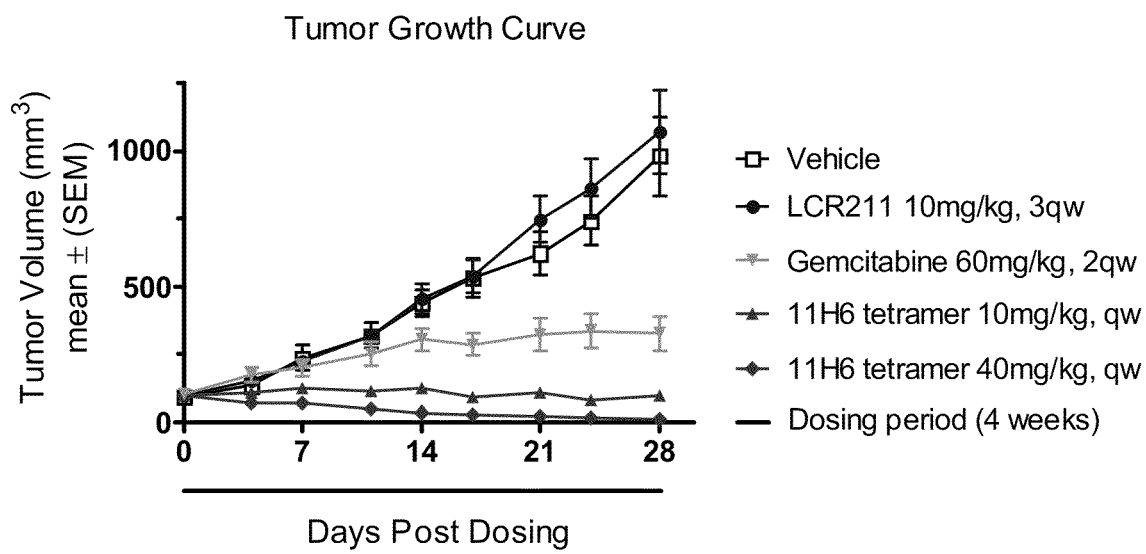
FIG. 5 shows 11H6 tetramer ability to regress patient-derived pancreatic tumor TPAN1-IFA that is insensitive to LCR211, a murine antibody specific to DR5.

As shown in FIG. 5, after 4 weeks of dosing, LCR211 shows no single agent activity, with the mean change in tumor volume of the treatment group over control (T/C)=109%. In contrast, 11H6 dosed at 10 mg/kg weekly and at 40 mg/kg weekly results in 1% and 86% regression, respectively (p<0.05 vs vehicle). Gemcitabine treatment results in a T/C of 25% (p<0.05 vs vehicle). LCR211 and 11H6 treatment is well tolerated with no significant loss of body weight observed. Thus, in a patient-derived cancer that is insensitive to conventional antibody targeting of DR5, the NB constructs show potent tumor regression. In this example, the NB construct has the potential to treat a larger class of patients that could be refractory to conventional targeting approaches for this pathway.

11. Example XI

11.1. X-Ray Crystallographic Structure Determination of the Human DR5/NB Construct Complexes Crystal structures of a human DR5 ECD fragment bound to monomeric constructs 11H6 (SEQ ID NO: 103) and 4E6 (SEQ ID NO: 104) are determined. As detailed below, individual DR5 protein fragments are expressed, purified and mixed to form complexes. Protein crystallography is employed to generate atomic resolution data for the DR5 protein bound to the two examples.

Two variants of DR5 protein are produced for crystallography, namely DR5_54 and DR5_61. Following the sequence numbering of human DR5, GenBank accession number BAA33723.1 (SEQ ID NO: 89), the DR5 sequences correspond to residues 54 to 183, and 61 to 183, respectively. As shown in Table 28, sequences in lower case letters are removed during production. For DR5_54 (SEQ ID NO: 100) and DR5_61 (SEQ ID NO: 101), human DR5 sequence is underlined. In Table 28, "ID" represents the SEQ ID NO.

TABLE 28

Proteins used for crystal structure determination

| Construct | Amino acid sequence in one letter code. | ID |
|---|---|---|
| HuDR5 GenBank: BAA33723.1 | meqrgqnapaasgarkrhgpgpreargarpglrvpktivlvvaavlllvsaesali tqqdlapqqrvapqqkrsspseglcppghhisedgrdcisckygqdysthwndllf clrctrcdsgevelspctttrntvcqceegtfreedspemcrkcrtgcprgmvkvg dctpwsdiecvhkesgtkhsgeapaveetvtsspgtpaspcslsgiiigvtvaavv livavfvcksllwkkvlpylkgicsggggdpervdrssqrpgaednvlneivsilq ptqvpeqemevqepaeptgvnmlspgesehllepaeaersqrrrllvpanegdpte tlrqcfddfadlvpfdsweplmrklglmdneikvakaeaaghrdtlytmlikwvnk tgrdasvhtlldaletlgerlakqkiedhllssgkfmylegnadsams | 89 |
| DR5_54 gp67DR5a54-s183-PH | mvsaivlyvllaaaahsafaadlgslevlfqALITQQDLAPQQRAAPQQKRSSPSE GLCPPGHHISEDGRDCISCKYGQDYSTHWNDLLFCLRCTRCDSGEVELSPCTTTRN TVCQCEEGTFREEDSPEMCRKCRTGCPRGMVKVGDCTPWSDIECVHKESAAALEVL FQgpssgklghhhhhhhhhh | 100 |
| DR5_61 gp67DR5I61-s183-PH | mvsaivlyvllaaaahsafaadlgslevlfqGPSMALAPQQRAAPQQKRSSPSEGL CPPGHHISEDGRDCISCKYGQDYSTHWNDLLFCLRCTRCDSGEVELSPCTTTRNTV CQCEEGTFREEDSPEMCRKCRTGCPRGMVKVGDCTPWSDIECVHKESAAALEVLFQ gpssgklghhhhhhhhhh | 101 |
| 11H6 hu pAX100-11H6 | mkktaiaiavalaglatvaqaEVQLLESGGGLVQPGGSLRLSCAASGTFDKINNMG WYRQAPGKQRDLVAQITPGGITDYADSVKGRFTISRDNSKNTLYLQMNSLRPEDTA VYYCNAEILKRAYIDVYVNYWGQGTLVTVSSAAAEQKLISEEDLNGAAHHHHHH | 102 |
| 4E6 hu pAX111-4E6 | mkktaiaiavalaglatvaqaEVQLLESGGGLVQPGGSLRLSCAASGRTFGSIRVG WFRQAPGKGREFVSAINRNDGTTYYADSVKGRFTISRDNSKNTVYLQMNSLRPEDT AVYYCAAGLQYNRAADRVPVGAVYWGQGTLVTVSSHHHHHH | 103 |

The above proteins are expressed in SF9 cells using a baculovirus expression system, with the expression vector containing the GP67 signal peptide. DR5 protein is purified from the cell growth media following a 2.5 day infection. The media is clarified with the addition of 5 mM CaCl$_2$, 1 mM NiCl$_2$, 50 mM Tris pH 8.0, and 1 μM PMSF. The protein is captured on Ni-NTA resin (Qiagen) equilibrated in 50 mM Tris pH 8.0, 300 mM NaCl using a gravity flow column. The column is washed with 50 mM Tris pH 8.0, 300 mM NaCl, 30 mM imidazole, followed by elution with 50 mM Tris pH 8.0, 300 mM NaCl, 300 mM imidazole. Eluted DR5 from the Ni column is cleaved with PreScission protease (GE Healthcare), followed by gel filtration chromatography using a Superdex 75 column (GE Healthcare) equilibrated in 50 mM HEPES pH 7.6, 150 mM NaCl. DR5 is further purified by ion exchange using a MonoQ column (GE Healthcare) at pH 7.5 with a 20 column volume gradient of 0.03-1 M NaCl. Peak fractions are analyzed by SDS-PAGE and LCMS prior to pooling.

11.2. 4E6 and 11H6 Crystallization with DR5

Both 4E6 (pAX111-4E6, SEQ ID NO:103) and 11H6 (pAX100-11H6, SEQ ID NO:102) are cloned as monomeric NB constructs for expression in E. coli using BL21 (DE3) pLysS cells and BL21 (DE3) Star cells, respectively, and both contain signal sequences for periplasmic localization, as provided in Table 28 above. Following a 3 hour induction with IPTG at 37° C., cells are harvested and lysed. Protein is captured on a Ni-NTA column pre-equilibrated in 50 mM Tris pH 8.0, 300 mM NaCl. The column is washed with 50 mM Tris pH 8.0, 300 mM NaCl, 50 mM imidazole, followed by elution with 50 mM Tris pH 8.0, 300 mM NaCl, 300 mM imidazole. The Ni eluate is further purified via gel filtration chromatography using a Superdex 75 column (GE Healthcare). Whereas this is the final purification step for 11H6, the 4E6 underwent an additional purification step via a MonoS cation exchange column (GE Healthcare).

A complex of DR5_61/4E6 is prepared by mixing DR5_61 and 4E6 in a 1:1 molar ratio (concentration measured via LCUV), incubating on ice for 1 hour, and purifying the complex on a Superdex75 column (GE Healthcare) equilibrated in 20 mM HEPES pH 7.5, 150 mM NaCl. Peak fractions are analyzed by SDS-PAGE and LCMS. Fractions containing DR5_61/4E6 are concentrated to about 10 mg/ml for crystallization.

A complex of DR5_54/11H6 is prepared by mixing DR5_54 and 11H6 in a molar ration of 1:1.3 (concentration estimated by LCUV), incubating on ice for 1 hour, and purifying the complex on a Superdex75 column (GE Healthcare) equilibrated in 25 mM HEPES pH 7.5, 150 mM NaCl. Peak fractions containing the DR5_54/11H6 dimer are pooled and concentrated to about 12.7 mg/ml. The dimer is then Trypsin-treated as follows: 200 µl of dimer (about 2.5 mg) is used to resuspend 20 µg of lyophilized trypsin, which is then incubated at room temperature for 15 minutes. The DR5_54/11H6/trypsin mixture is centrifuged prior to setting up crystallization screens.

Crystals are grown by sitting drop vapor diffusion from drops containing equal volumes of protein and reservoir solution. For DR5_61/4E6 complex a reservoir solution of 22% PEG 3350, 150 mM calcium acetate, 100 mM HEPES pH 7.5 produced crystals upon incubation at 20° C. For trypsin-treated DR5_54/11H6 complex a reservoir solution of 0.2 M ammonium sulfate, 0.1M Tris pH 8.5, 25% PEG 3350 produced crystals upon incubation at 20° C.

The DR5_61/4E6, crystals are transferred to a cryo solution containing 25% PEG 3350, 50 mM HEPES pH 7.5, 150 mM calcium acetate, 15% glycerol, 10% ethylene glycol and flash cooled in liquid nitrogen. The DR5_a54/11H6, crystals are transferred to reservoir solution containing additional 22% glycerol and flash cooled in liquid nitrogen.

For DR5_61/4E6 complex, diffraction data are collected at station PXI-X06SA at the Swiss Light Source (Paul Scherrer Institut, Villigen, Switzerland). Data are processed and scaled at 1.9 Å using autoPROC (Global Phasing, LTD) in space group C121 with cell dimensions a=98.50 Å, b=84.65 Å, c=64.91 Å, alpha=90°, beta=99.38°, gamma=90°. The DR5_61/4E6 structure is solved by molecular replacement using Phaser (McCoy et al., (2007) J. Appl. Cryst. 40: 658-674) with DR5 structure 2H9G and the camelized human VH structure 1OL0 as search models. The final model, which contains 2 molecule of the DR5_61/4E6 complex per asymmetric unit, is built in COOT (Emsley & Cowtan (2004) Acta Cryst. 60: 2126-2132) and refined to R and $R_{free}$ values of 22.2% and 24.1%, respectively, with an rmsd of 0.003 Å and 0.69° for bond lengths and bond angles, respectively, using PHENIX (Adams et al., Acta Cryst. D66, 213-221 (2010)).

For DR5_54/11H6 complex, diffraction data are collected at beamline 17-ID at the Advanced Photon Source (Argonne National Laboratory, USA). Data are processed and scaled at 2.2 Å using autoPROC (Global Phasing, LTD) in space group $P6_5$ with cell dimensions a=99.61 Å, b=99.61 Å, c=107.73 Å, alpha=90°, beta=90°, gamma=120°. The DR5_54/11H6 structure is solved by molecular replacement using Phaser (McCoy et al., (2007) J. Appl. Cryst. 40: 658-674) with DR5 structure 2H9G and NB construct 4E6 as search models. The final model, which contains 2 molecule of the DR5_54/11H6 complex per asymmetric unit, is built in COOT (Emsley & Cowtan (2004) Acta Cryst. 60: 2126-2132) and refined to R and $R_{free}$ values of 19.5% and 22.0%, respectively, with an rmsd of 0.002 Å and 0.64° for bond lengths and bond angles, respectively, using PHENIX (Adams et al., Acta Cryst. D66, 213-221 (2010)).

11.3. 4E6 and 11H6 Recognize Unique Epitopes on DR5

The crystal structure of the 4E6/DR5_61 complex has been used to identify the DR5 epitope for the 4E6 construct. The interaction surface on DR5 is formed by three discontinuous (i.e., noncontiguous) sequences: namely residues 77 through 80, residues 87 through 91, and residues 105 through 114, as detailed in Table 29A. These residues form the three-dimensional surface that is recognized by the NB construct. Interactions include backbone interactions, solvent mediated interactions, and direct sidechain interactions. The amino acids whose sidechains are directly contributing to the interactions noted in Table 29A. The interaction surface contribution from the 4E6 NB construct is formed by its N-terminal residue 2, and three loop regions: residues 28 through 33, residues 53 through 59, and residues 99 through 115. The contact residues are listed in Table 29B.

In Table 29A, DR5 residues that contain atoms in contact with the NB construct, 4E6 are listed. Contact is defined to be within 5 Angstroms of the NB construct to account for potential water mediated interactions. Amino acids whose sidechains contribute directly to the interaction surface are noted with a "+".

TABLE 29A

DR5 Conformational Epitope for 4E6 (Table 29A discloses positions 77-80 as SEQ ID NO: 107, poistions 87-97 as SEQ ID NO: 108, and position 105-112 as SEQ ID NO: 109)

| Protein | Amino acid | Sequence position | Sidechain Interaction |
|---|---|---|---|
| DR5 | S | 77 | |
| DR5 | E | 78 | + |
| DR5 | G | 79 | |
| DR5 | L | 80 | + |
| DR5 | I | 87 | + |
| DR5 | S | 88 | |
| DR5 | E | 89 | |
| DR5 | D | 90 | |

TABLE 29A-continued

DR5 Conformational Epitope for 4E6 (Table 29A discloses positions 77-80 as SEQ ID NO: 107, poistions 87-97 as SEQ ID NO: 108, and position 105-112 as SEQ ID NO: 109)

| Protein | Amino acid | Sequence position | Sidechain Interaction |
|---|---|---|---|
| DR5 | G | 91 | + |
| DR5 | T | 105 | |
| DR5 | H | 106 | + |
| DR5 | W | 107 | + |
| DR5 | N | 108 | |
| DR5 | D | 109 | + |
| DR5 | L | 110 | + |
| DR5 | L | 111 | + |
| DR5 | F | 112 | + |
| DR5 | L | 114 | + |

In Table 29B, residues in the NB construct 4E6 that are in contact with DR5 are listed. Contact is defined to be within 5 Angstroms of the NB construct to account for potential water mediated interactions. Amino acids whose sidechains contribute directly to the interaction surface are noted with a "+".

TABLE 29B

4E6 amino acids in contact with DR5 (Table 29B discloses positions 30-33 as SEQ ID NO: 110 and positions 96-106 as SEQ ID NO: 111)

| Protein | Amino acid | Sequence position | Sidechain Interaction |
|---|---|---|---|
| 4E6 | V | 2 | + |
| 4E6 | T | 28 | + |
| 4E6 | G | 30 | + |
| 4E6 | S | 31 | + |
| 4E6 | I | 32 | + |
| 4E6 | R | 33 | + |
| 4E6 | R | 53 | |
| 4E6 | N | 54 | + |
| 4E6 | Y | 59 | |
| 4E6 | G | 99 | + |
| 4E6 | L | 100 | |
| 4E6 | Q | 101 | + |
| 4E6 | Y | 102 | + |
| 4E6 | N | 103 | |
| 4E6 | R | 104 | |
| 4E6 | A | 105 | + |
| 4E6 | A | 106 | + |
| 4E6 | V | 111 | + |
| 4E6 | V | 114 | + |
| 4E6 | Y | 115 | + |

The crystal structure of the 11H6/DR5__54 complex is used to identify the DR5 epitope for the 11H6 construct. The interaction surface on DR5 is formed by two discontinuous sequences, residues 86 through 102 and residues 111 through 118, and two additional residues 74 and 125 as detailed in Table 30A. These residues form the three-dimensional surface that is recognized by the NB construct. Interactions include backbone interactions, solvent mediated interactions, and direct sidechain interactions. The amino acids whose sidechains are directly contributing to the interactions noted in Table 30A. The interaction surface contribution from the 11H6 construct extends beyond the loop regions observed for the 4E6 construct. Residues 30 through 37, residues 44 through 61 and residues 96 through 112 contribute to the binding surface of the 11H6 construct as detailed in Table 30B. The 11H6 construct's loop from residues 98 to 110 is in a very different conformation than the corresponding loop from the 4E6 construct. This alternate loop position provides a unique interaction surface for DR5 binding.

In Table 30A, DR5 residues that contain atoms in contact with the 11H6 construct are listed. Contact is defined to be within 5 Angstroms of 11H6 to account for potential water mediated interactions. Amino acids whose sidechains contribute directly to the interaction surface are noted with a "+". Buried surface area is determined as a percentage.

TABLE 30A

DR5 Conformational Epitope for 11H6 (Table 30A discloses positions 86-90 as SEQ ID NO: 112)

| Protein | Amino acid | Sequence position | Buried surface area (%) |
|---|---|---|---|
| DR5 | S | 74 | |
| DR5 | H | 86 | + |
| DR5 | I | 87 | |
| DR5 | S | 88 | + |
| DR5 | E | 89 | + |
| DR5 | D | 90 | + |
| DR5 | R | 92 | |
| DR5 | D | 93 | + |
| DR5 | I | 95 | + |
| DR5 | S | 96 | |
| DR5 | K | 98 | + |
| DR5 | G | 100 | |
| DR5 | Q | 101 | + |
| DR5 | D | 102 | + |
| DR5 | L | 111 | + |
| DR5 | F | 112 | + |
| DR5 | C | 113 | |
| DR5 | R | 115 | + |
| DR5 | R | 118 | + |
| DR5 | E | 125 | |

In Table 30B, residues in 11H6 that are in contact with DR5 are listed. Contact is defined to be within 5 Angstroms of the 11H6 construct to account for potential water mediated interactions. Amino acids whose sidechains contribute directly to the interaction surface are noted with a "+".

TABLE 30B

11H6 amino acids in contact with DR5 (Table 30B discloses positions 44-47 as SEQ ID NO: 113 and positions 50-58 as SEQ ID NO: 114)

| Protein | Amino acid | Sequence position | Sidechain Interaction |
|---|---|---|---|
| 11H6 | K | 30 | + |
| 11H6 | N | 32 | + |
| 11H6 | N | 33 | + |
| 11H6 | Y | 37 | + |
| 11H6 | Q | 44 | + |
| 11H6 | R | 45 | |
| 11H6 | D | 46 | + |
| 11H6 | L | 47 | + |
| 11H6 | Q | 50 | + |
| 11H6 | I | 51 | |
| 11H6 | T | 52 | + |
| 11H6 | P | 53 | |
| 11H6 | G | 54 | |
| 11H6 | G | 55 | |
| 11H6 | I | 56 | + |
| 11H6 | T | 57 | |
| 11H6 | D | 58 | + |
| 11H6 | A | 60 | + |
| 11H6 | D | 61 | |
| 11H6 | N | 96 | + |
| 11H6 | E | 98 | + |
| 11H6 | L | 100 | + |
| 11H6 | Y | 104 | |
| 11H6 | D | 106 | |
| 11H6 | V | 107 | + |
| 11H6 | Y | 108 | + |
| 11H6 | N | 110 | + |
| 11H6 | W | 112 | + |

EQUIVALENTS

One embodiment provides an isolated polypeptide comprising at least one monomer of a single variable domain of a NB agent that specifically binds to human DR5.

One embodiment provides the polypeptide, wherein said single variable domain is selected from the group consisting of a) singe variable domains comprising one or more complementarity determining region 3 (CDR3) sequences selected from any one or more of SEQ ID NOs: 63-68; b) single variable domains comprising one or more complementarity determining region 3 (CDR3) sequences with 90% identity to at least one CDR3 selected from any one or more of SEQ ID NOs: 63-68; and c) single variable domains comprising one or more complementarity determining region 3 (CDR3) sequences with at least 95% identity to at least one CDR3 selected from any one or more of SEQ ID NOs: 63-68.

One embodiment provides the polypeptide, wherein said single variable domain is selected from the group consisting of a) singe variable domains comprising one or more complementarity determining region 3 (CDR3) sequences selected from any one or more of SEQ ID NOs: 41-44, 51-55 and 63-68; b) single variable domains comprising one or more complementarity determining region 3 (CDR3) sequences with at least 90% identity to at least one CDR3 selected from any one or more of SEQ ID NOs: 41-44, 51-55 and 63-68; and c) single variable domains comprising one or more complementarity determining region 3 (CDR3) sequences with at least 95% identity to at least one CDR3 selected from any one or more of SEQ ID NOs: 41-44, 51-55 and 63-68 with at least 90% identity.

One embodiment provides the polypeptide, wherein said single variable domain is selected from the group consisting of a) singe variable domains with SEQ ID NOs: 1-5, 26, 30 and 87; and b) single variable domains with at least 95% identity to at least one single variable domain with SEQ ID NOs: 1-5, 26, 30 and 87.

One embodiment provides an isolated polypeptide comprising at least three monomers of a single variables domain that specifically binds to human DR5.

One embodiment provides the polypeptide, wherein said polypeptide comprises three identical monomers of the single variable domain and wherein said single variable domain is selected from the group consisting of a) a single variable domain comprising one or more complementarity determining region 3 (CDR3) sequences selected from any one or more of SEQ ID NOs: 63-68; b) single variable domains comprising one or more complementarity determining region 3 (CDR3) sequences with at least 90% identity to at least one CDR3 selected from any one or more of SEQ ID NOs: 63-68; and c) single variable domains comprising one or more complementarity determining region 3 (CDR3) sequences with at least 95% identity to at least one CDR3 selected from any one or more of SEQ ID NOs: 63-68 with at least 90% identity.

One embodiment provides the polypeptide, wherein said polypeptide comprises three identical monomers of the single variable domain and wherein said single variable domain is selected from the group consisting of a) singe variable domains comprising one or more complementarity determining region 3 (CDR3) sequences selected from any one or more of SEQ ID NOs: 41-44, 51-55 and 63-68; b) single variable domains comprising one or more complementarity determining region 3 (CDR3) sequences with at least 90% identity to at least one CDR3 selected from any one or more of SEQ ID NOs: 41-44, 51-55 and 63-68; and c) single variable domains comprising one or more complementarity determining region 3 (CDR3) sequences with at least 95% identity to at least one CDR3 selected from any one or more of SEQ ID NOs: 41-44, 51-55 and 63-68 with at least 90% identity.

One embodiment provides the polypeptide, wherein said polypeptide comprises three identical monomers of the single variable domain and wherein said single variable domain is selected from the group consisting of a) singe variable domains with SEQ ID NOs: 1-5, 26, 30 and 87; b) single variable domains with at least 90% identity to at least one single variable domain with SEQ ID NOs: 1-5, 26, 30 and 87 and c) single variable domains with at least 95% identity to at least one single variable domain with SEQ ID NOs: 1-5, 26, 30 and 87.

One embodiment provides the polypeptide comprising an amino sequence that is selected from the group consisting of a) amino acid sequences with SEQ ID NO: 6, 9, 12-14, 17, 20, 27 and 31; and b) amino acid sequences with at least 90% identity to said amino acid sequence with SEQ ID NO: 6, 9, 12-14, 17, 20, 27 and 31.

One embodiment provides the polypeptide comprising an amino sequence that is selected from the group consisting of a) amino acid sequences with SEQ ID NO: 6, 9, 12-14, 17, 20, 27 and 31; and b) amino acid sequences with at least 90% identity to said amino acid sequence with SEQ ID NO: 6, 9, 12-14, 17, 20, 27 and 31.

The polypeptide of paragraph 5 comprising an amino sequence that is selected from the group consisting of a) amino acid sequences with SEQ ID NO: 6, 9, 12-14, 17, 20, 27 and 31; and b) amino acid sequences with at least 95% identity to said amino acid sequence with SEQ ID NO: 6, 9, 12-14, 17, 20, 27 and 31.

One embodiment provides an isolated polypeptide comprising at least four monomers of a single variable domain that specifically binds to human DR5.

One embodiment provides the polypeptide, wherein said polypeptide comprises four single variable domains and wherein said single variable domain is selected from one, two, three or four monomers from the group consisting of a) singe variable domains with SEQ ID NOs: 1-5, 26, 30 and 87; b) single variable domains with at least 90% identity to said single variable domain with SEQ ID NOs: 1-5, 26, 30 and 87; and c) single variable domains with 95% identity to said single variable domain with SEQ ID NOs: 1-5, 26, 30 and 87.

One embodiment provides the polypeptide, wherein said polypeptide comprises four identical single variable domains and wherein said single variable domain is selected from the group consisting of a) singe variable domains with SEQ ID NOs: 1-5, 26, 30 and 87; b) single variable domains with at least 90% identity to said single variable domain with SEQ ID NOs: 1-5, 26, 30 and 87; and c) single variable domains with 95% identity to said single variable domain with SEQ ID NOs: 1-5, 26, 30 and 87.

One embodiment provides the polypeptide, wherein said polypeptide comprises four identical single variable domains and wherein said single variable domain is selected from the group consisting of a) singe variable domains with SEQ ID NOs: 1-5, 26, 30 and 87; and b) single variable domains with at least 95% identity to at least one single variable domain with SEQ ID NOs: 1-5, 26, 30 and 87.

One embodiment provides the polypeptide comprising an amino sequence that is selected from the group consisting of a) an amino acid sequence of SEQ ID NO: 88; b) amino acid sequences with at least 90% identity to said amino acid sequence with SEQ ID NO: 88; and c) amino acid sequences with 95% identity to said amino acid sequence with SEQ ID NO: 88.

One embodiment provides the polypeptide comprising an amino sequence that is selected from the group consisting of a) amino acid sequences with SEQ ID NO: 7, 10, 15, 18, 21, 28 and 32; b) amino acid sequences with at least 90% identity to said amino acid sequence with SEQ ID NO: 7, 10, 15, 18, 21, 28 and 32; and c) amino acid sequences with 95% identity to said amino acid sequence with SEQ ID NO: 7, 10, 15, 18, 21, 28 and 32.

The polypeptide comprising a humanized amino sequence that is selected from the group consisting of a) amino acid sequences with SEQ ID NO: 28; b) amino acid sequences with SEQ ID NO: 32; and b) amino acid sequences with at least 95% identity to said amino acid sequence with SEQ ID NO: 28 and 32.

One embodiment provides an isolated polypeptide comprising at least five monomers of a single variable domain that specifically binds to human DR5.

One embodiment provides the polypeptide, wherein said polypeptide comprises five single variable domains and wherein said single variable domain is selected from one, two, three, four or five monomers of the group consisting of a) singe variable domains with SEQ ID NOs: 1-5, 26, 30 and 87; b) single variable domains with at least 90% identity to said single variable domain with SEQ ID NOs: 1-5, 26, 30 and 87; and c) single variable domains with at least 95% identity to said single variable domain with SEQ ID NOs: 1-5, 26, 30 and 87 with at least 90% identity.

One embodiment provides the polypeptide, wherein said polypeptide comprises five identical single variable domains and wherein said single variable domain is selected from the group consisting of a) singe variable domains with SEQ ID NOs: 1-5, 26, 30 and 87; b) single variable domains with at least 90% identity to said single variable domain with SEQ ID NOs: 1-5, 26, 30 and 87; and b) single variable domains with 95% identity to said single variable domain with SEQ ID NOs: 1-5, 26, 30 and 87.

One embodiment provides the polypeptide, wherein said polypeptide comprises five single variable domains and wherein said single variable domain is humanized, and said humanized domain is selected from the group consisting of a) singe variable domains with SEQ ID NOs: 26 and 30; b) single variable domains with at least 90% identity to at least one single variable domain with SEQ ID NOs: 26 and 30; and b) single variable domains with at least 95% identity to at least one single variable domain with SEQ ID NOs: 26 and 30.

One embodiment provides the polypeptide comprising an amino sequence that is selected from the group consisting of a) amino acid sequences with SEQ ID NO: 8, 11, 16, 19, 22, 29 and 33; b) amino acid sequences with at least 90% identity to said amino acid sequence with SEQ ID NO: 8, 11, 16, 19, 22, 29 and 33; and c) amino acid sequences with 95% identity to said amino acid sequence with SEQ ID NO: 8, 11, 16, 19, 22, 29 and 33.

One embodiment provides the polypeptide comprising an amino sequence that is selected from the group consisting of a) amino acid sequence of SEQ ID NO: 29; b) amino acid sequences with at least 90% identity to said amino acid sequence with SEQ ID NO: 29; and b) amino acid sequences with 95% identity to said amino acid sequence with SEQ ID NO: 29.

One embodiment provides the polypeptide comprising an amino sequence that is selected from the group consisting of a) amino acid sequences with SEQ ID NO: 33; b) amino acid sequences with at least 90% identity to said amino acid sequence with SEQ ID NO: 33; and b) amino acid sequences with at least 95% identity to said amino acid sequence with SEQ ID NO: 33.

One embodiment provides an isolated polypeptide comprising three or four or five monomers of a single variable domain that specifically binds to human DR5 and wherein said polypeptide has an in vitro potency ($IC_{50}$) against a panel of at least 2 tumor cell lines selected from the group consisting of Colo205, Jurkat, Molt4, H2122, H226 and H2052 that is equal or lower than 100 nM.

One embodiment provides the polypeptide, wherein said polypeptide has an in vitro potency that is equal or lower than 10 nM.

One embodiment provides the polypeptide, wherein said polypeptide has an in vitro potency that is equal or lower than 1 nM.

One embodiment provides the polypeptide, wherein said polypeptide has an in vitro potency that is equal or lower than 100 pM.

One embodiment provides the polypeptide, wherein said polypeptide has an in vitro potency ($IC_{50}$) against a panel of at least 3 non-tumor cell lines selected from the group consisting of Malme-3, WI-38, ARPE-19, 184A1, Huvec, HAAE-1 that is equal of greater than 20 nM.

One embodiment provides the polypeptide, wherein said polypeptide has an in vitro potency ($IC_{50}$) against a panel of at least 3 non-tumor cell lines selected from the group consisting of Malme-3, WI-38, ARPE-19, 184A1, Huvec, HAAE-1 that is equal of greater than 100 nM.

One embodiment provides the polypeptide, wherein said polypeptide comprises three or four or five monomers of a single variable domain and wherein said single variable domain is selected from the group consisting of a) singe variable domains with SEQ ID NOs: 1-5, 26, 30 and 87; and b) single variable domains with at least 90% identity to said single variable domain with SEQ ID NOs: 1-5, 26, 30 and 87.

The polypeptide, wherein said polypeptide comprises three or four or five monomers of a single variable domain and wherein said single variable domain is humanized and selected from the group consisting of a) singe variable domains with SEQ ID NOs: 26 and 30; b) single variable domains with at least 90% identity to said single variable domain with SEQ ID NOs: 26 and 30; and b) single variable domains with at least 95% identity to said single variable domain with SEQ ID NOs: 26 and 30.

One embodiment provides the polypeptide, wherein said polypeptide is selected from the group consisting of a) the polypeptide selected from any one or more of SEQ ID NOs: 27, 28 and 29; b) a polypeptide with at least 95% identity to at least one polypeptide selected from any one or more of SEQ ID NOs: 27, 28 and 29; c) the polypeptide selected from any one or more of SEQ ID NOs: 31, 32 and 33; and d) a polypeptide with at least 95% identity to at least one polypeptide selected from any one or more of SEQ ID NOs: 31, 32 and 33.

One embodiment provides an isolated polypeptide comprising an amino sequence that is selected from the group consisting of one or more amino acid sequences of SEQ ID NO: 1 through 22, 26 through 33, 87 and 88.

One embodiment provides the isolated polypeptide, wherein said polypeptide does not fully or partially compete with the natural ligand of the DR5 in a competitive binding assay.

One embodiment provides the isolated polypeptide, wherein said polypeptide does fully or partially compete with the natural ligand of the DR5 in a competitive binding assay.

One embodiment provides the isolated polypeptide, comprising at least one complementarity determining region (CDR) having at least 60, 70, 80, 90, 95 or 100 percent sequence identity with at least one of the CDR regions depicted in any of SEQ ID NO: 41 to 44 (CDR1); SEQ ID NO: 51 to 55 (CDR2); SEQ ID NO: 63 to 68 (CDR3), more preferably SEQ ID NO: 51 to 55 and SEQ ID NO: 63 to 68.

One embodiment provides the isolated polypeptide, comprising CDR1 to CDR3 regions having at least 90, 95 or 100 percent sequence identity respectively with the CDR regions depicted in any of SEQ ID NO: 41 to 44 (CDR1); SEQ ID NO: 51 to 55 (CDR2); SEQ ID NO: 63 to 68 (CDR3).

One embodiment provides the isolated polypeptide, comprising or essentially consisting of an amino acid sequence having at least 90, 95 or 100 percent sequence identity with any of sequences as depicted in SEQ ID NO: 26 to 33.

One embodiment provides the isolated polypeptide, comprising a CDR3 region according to SEQ ID NO: 64 or SEQ ID NO: 66.

One embodiment provides the isolated polypeptide, a CDR1, CDR2 and CDR3 region identical respectively to the CDR regions depicted in SEQ ID NO: 41 to 44 (CDR1); SEQ ID NO: 51 to 55 (CDR2); SEQ ID NO: 63 to 68 (CDR3) or variant CDR regions with 1, 2, 3, 4 or 5 amino acid substituted, deleted or inserted when compared to original CDR regions as depicted therein.

One embodiment provides the isolated polypeptide that is an immunoglobulin or a fragment thereof.

One embodiment provides the isolated polypeptide that is a humanized immunoglobulin, a camelized immunoglobulin or an immunoglobulin obtainable by affinity optimization technique, or a fragment thereof.

One embodiment provides the isolated polypeptide that essentially consists of a light chain variable domain sequence, e.g., a $V_L$-sequence; or of a heavy chain variable domain sequence, e.g., a $V_H$-sequence.

One embodiment provides the isolated polypeptide that essentially consists of a heavy chain variable domain sequence that is derived from a conventional four-chain antibody or that essentially consists of a heavy chain variable domain sequence that is derived from heavy chain antibody.

One embodiment provides the isolated polypeptide that essentially consists of a domain antibody, a single domain antibody, a dAb and a camelid antibody or fragment, including but not limited to a $V_{HH}$ sequence.

One embodiment provides the isolated polypeptide essentially consists of a $V_{HH}$ sequence.

One embodiment provides the isolated polypeptide that essentially consists of a $V_{HH}$ sequence that,
a) has at least 90% amino acid identity with at least one of the amino acid sequences of SEQ ID NO's 1-22, 26-40, 87-88, and 102-103, in which for the purposes of determining the degree of amino acid identity, the amino acid residues that form the CDR sequences are disregarded; and in which:
b) optionally one or more of the amino acid positions 11, 37, 44, 45, 47, 83, 84, 103, 104 and 108 according to Kabat numbering are humaneered.

One embodiment provides the isolated polypeptide that essentially consists of a $V_{HH}$ sequence that:
a) has at least 90% amino acid identity with at least one of the amino acid sequences of SEQ ID NO's 1-22, 26-40, 87-88, and 102-103, in which for the purposes of determining the degree of amino acid identity, the amino acid residues that form the CDR sequences are disregarded; and in which
b) optionally the contacts between DR5 and the $V_{HH}$ sequence are selected from:
i) the DR5 conformational epitope comprising the residues in Table 29A;
ii) the DR5 conformational epitope comprising the residues in Table 30A;
iii) the interaction surface of the $V_{HH}$ amino acids as listed in Table 29B; and
iv) the interaction surface of the $V_{HH}$ amino acids as listed in Table 30B.

One embodiment provides the isolated polypeptide that essentially consists of a humanized $V_{HH}$ sequence.

One embodiment provides the compound that comprises or essentially consists of one or more polypeptide, and optionally further comprises one or more other groups, residues, moieties or binding units, wherein said compound is capable of enhancing cell apoptosis.

One embodiment provides the compound, which has an $IC_{50}$ less than 100 nM, preferably less than 10 nM, more preferably less than 1 nM, even more preferably less than 100 pM, e.g. below 10 pM as, e.g., measured in Colo205 cell survival assay.

One embodiment provides the compound, wherein the corresponding monovalent binding polypeptide is not as potent as the multivalent polypeptide as measured, e.g., in Colo205 cell based survival assay.

One embodiment provides the compound, wherein said at least three, four, five or more monovalent binding polypeptides can each bind human DR5 in a monovalent format.

One embodiment provides the compound, wherein said at least three, four, five or more monovalent binding polypeptides can each bind human DR5 in a monovalent format but does not bind to TRAIL-R3 and/or TRAIL-R4 receptors.

One embodiment provides the compound of, wherein said at least three, four, five or more monovalent binding polypeptide can each bind DR5 in a monovalent format and competes in a binding assay with natural TRAIL ligand.

One embodiment provides the compound, wherein said at least three, four, five or more monovalent binding polypeptides are all directed against the same binding region of human DR5.

One embodiment provides the compound, wherein said at least one monovalent binding polypeptide is directed against one binding region of DR5 and at least one other monovalent binding polypeptide is directed against another distinct binding region of DR5 or a binding region of another DR5.

One embodiment provides the compound, wherein said at least three, four, five or more monovalent binding polypeptides have substantially identical amino acid sequences.

One embodiment provides the compound, which essentially consists of a single chain polypeptide and wherein said at least three, four, five or more monovalent binding single variable domains are linked together via peptidic linker.

One embodiment provides the compound, wherein said linker consists essentially of a peptide comprising between 5 and 50 amino acid residues.

One embodiment provides the compound, wherein said one or more other groups, residues, moieties or binding units are polypeptides, optionally linked via one or more linkers.

One embodiment provides the compound, wherein said one or more linkers are peptidic or polypeptidic linkers.

One embodiment provides the compound, wherein said one or more other groups, residues, moieties or binding units are selected from the group consisting of a domain antibody, a single domain antibody, a dAb and a camelid antibody or fragment thereof, including but not limited to a $V_{HH}$ sequence.

One embodiment provides the compound of, wherein said one or more other groups, residues, moieties or binding units provide the compound with an increased half-life when administered in a mammalian organism, compared to the same compound without said one or more other groups, residues, moieties or binding units.

One embodiment provides an isolated nucleic acid that encodes either (1) a polypeptide comprising the amino acid sequence of the polypeptide or (2) a compound.

One embodiment provides a host cell that expresses, or that under suitable circumstances is capable of expressing the nucleic acid.

One embodiment provides a method for producing the DR5 binding polypeptide, or the compound, comprising:
 a) expressing, in a suitable host cell or a non-human host organism, the nucleic acid; and
 b) isolating and/or purifying said DR5 binding polypeptide or compound.

One embodiment provides the polypeptide or compound, for use as a drug.

One embodiment provides the polypeptide, for use as an anti-cancer therapeutic.

One embodiment provides a composition comprising at least a polypeptide, or a compound and at least one pharmaceutically acceptable carrier, diluent or excipient and/or adjuvant.

One embodiment provides a method for the prevention and/or treatment of a disorder that can be treated by enhancement of cell apoptosis, said method comprising administering, to a subject in need thereof, a pharmaceutically effective amount of at least one polypeptide, or of at least one compound.

One embodiment provides the method, wherein said disorder is a proliferative disease.

One embodiment provides the method, wherein said proliferative disease is selected from:
 a) one or more solid cancers selected from primary and metastatic cancers such as renal cell carcinoma, and cancers of the lung (e.g., small cell lung cancer "SCLC" and non-small cell lung cancer "NSCLC"), pancreas, hematopoietic malignancy, glioma, astrocytoma, mesothelioma, colorectal cancers, prostate cancer, osteosarcoma, melanoma, lymphoma lymphoma (including but not limited to Burkitt's Lymphoma), breast cancer, endometrial cancer, liver cancer, gastric cancer, skin cancer, ovarian cancer and squamous cell cancers of any origin (including but not limited to squamous cell cancers of the lung, head and neck, breast, thyroid, cervix, skin, and/or esophageal); and
 b) one or more liquid cancers selected from leukemias including especially a T-cell leukemia such as acute T-cell leukemia (T-ALL), acute B-cell leukemia (B-ALL), chronic myelogenous leukemia (CML), acute myelogenous leukemia (AML), plasma cell myeloma and multiple myeloma (MM).

One embodiment provides the method, wherein said proliferative disease is one or more non-cancer indications, said indications comprising one or more of inflammatory and autoimmune diseases, such as systemic lupus erythematosus, Hashimoto's disease, rheumatoid arthritis, graft-versus-host disease, Sjogren's syndrome, pernicious anemia, Addison disease, scleroderma, Goodpasture's syndrome, Crohn's disease, autoimmune hemolytic anemia, sterility, myasthenia gravis, multiple sclerosis, Basedow's disease, thrombotic throbocytopenia, thrombopenia purpurea, insulin-dependent diabetes mellitus, allergy; asthma, atopic disease; arteriosclerosis; myocarditis; cardiomyopathy; globerula nephritis; and hypoplastic anemia.

One embodiment provides the method, wherein the proliferative disease is pancreatic cancer.

One embodiment provides the method, wherein the proliferative disease is T-ALL.

One embodiment provides the method, wherein the proliferative disease is mesothelioma.

One embodiment provides the method, wherein the proliferative disease is squamous cell carcinoma of any tissue origin.

One embodiment provides the method, wherein the proliferative disease is AML.

One embodiment provides the method of, wherein the proliferative disease is melanoma.

One embodiment provides the method, wherein the proliferative disease is myeloma.

One embodiment provides a composition comprising the polypeptide or at least one compound, said composition in combination with at least one inhibitor of any one or more genes selected from cIAP1, cIAP2, XIAP, cFLIP and Bcl-xL.

One embodiment provides the composition, wherein the inhibitor is an inhibitor of cIAP1.

One embodiment provides the composition further comprising an inhibitor of MEK.

One embodiment provides the composition further comprising an inhibitor of BRAF, One embodiment provides the composition, wherein the inhibitor is an inhibitor of XIAP.

One embodiment provides the composition, wherein the inhibitor is an inhibitor of cFLIP.

One embodiment provides the composition, wherein the inhibitor is a low molecular weight compound selected from LCL161 and ABT263.

One embodiment provides the composition, wherein the inhibitor is a shRNA.

One embodiment provides a method for using any one or more of the compositions, the method comprising administering to a subject in need thereof a pharmaceutically effected amount of said composition or combination thereof for the treatment of a DR5 associated disease.

One embodiment provides the method wherein the DR5 associated disease is selected from one or more of the following:
 a) one or more proliferative diseases selected from solid and liquid cancers,
  (i) wherein solid tumors include primary and metastatic cancers such as renal cell carcinoma, and cancers of the lung (e.g., small cell lung cancer "SCLC" and non-small cell lung cancer "NSCLC"), pancreas, hematopoietic malignancy, glioma, astrocytoma, mesothelioma, colorectal cancers, prostate cancer, osteosarcoma, melanoma, lymphoma including but not limited to Burkitt's lymphoma), breast cancer, endometrial cancer, liver cancer, gastric cancer, skin cancer, ovarian cancer and squamous cell cancers of any origin (including but not limited to squamous cell cancers of the lung, head and neck, breast, thyroid, cervix, skin, and/or esophageal); and
  (ii) wherein liquid cancers comprise leukemias including especially a T-cell leukemia such as acute T-cell leukemia (T-ALL), acute B-cell leukemia (B-ALL), chronic myelogenous leukemia (CML), acute myelogenous leukemia (AML), plasma cell myeloma and multiple myeloma (MM); and
 b) non-cancer indications comprising one or more of inflammatory and autoimmune diseases, such as systemic lupus erythematosus, Hashimoto's disease, rheumatoid arthritis, graft-versus-host disease, Sjogren's syndrome, pernicious anemia, Addison disease, scleroderma, Goodpasture's syndrome, Crohn's disease, autoimmune hemolytic anemia; sterility, myasthenia gravis, multiple sclerosis, Basedow's disease, thrombotic throbocytopenia, thrombopenia purpurea, insulin-dependent diabetes mellitus, allergy; asthma, atopic disease; arteriosclerosis; myocarditis; cardiomyopathy; globerula nephritis; and hypoplastic anemia.

One embodiment provides the isolated polypeptides wherein the CDRs are calculated according to either Kabat and/or Chothia rules.

One embodiment provides the isolated polypeptides wherein the polypeptide binds one or more epitopes as provided in Tables 29A and/or 30A, and/or comprises the interactive surface residues as provided in Tables 29B and/or 30B.

The following claims of the invention are non-limiting. Certain variations to the invention may be contemplated that are within the abilities of one skilled in the art, including but not limited to changes in formulations, delivery, humanization, expression systems and the like. Such variations are considered to be within the scope of the invention.

What is claimed is:

1. An isolated polypeptide comprising at least one monomer of a single variable domain comprising the sequence of the complementarity determining region 3 (CDR3) sequence of SEQ ID NO: 66, the sequence of the complementarity determining region 2 (CDR2) sequence of SEQ ID NO: 53, and the sequence of the complementarity determining region 1 (CDR1) sequence of SEQ ID NO: 43, wherein the isolated polypeptide specifically binds to human DR5.

2. The polypeptide of claim 1, wherein said single variable domain comprises:
(a) the sequence of SEQ ID NO: 30; or
(b) the sequence of SEQ ID NO: 30 wherein one or more of the amino acid positions 1-30, 36-49, 66-97 and/or 112-122 have been substituted, modified or deleted and/or wherein one or more amino acids have been inserted between any amino acids at 1-30, 36-49, 66-97 and/or 112-122.

3. An isolated polypeptide comprising at least three, at least four, or at least five monomeric subunits of a single variable domain that specifically binds to human DR5, wherein said subunits are linked by a linker, and wherein the variable domain comprises the sequence of the complementarity determining region 3 (CDR3) sequence of SEQ ID NO: 66, the sequence of the complementarity determining region 2 (CDR2) sequence of SEQ ID NO: 53, and the sequence of the complementarity determining region 1 (CDR1) sequence of SEQ ID NO: 43.

4. The polypeptide of claim 1, wherein said single variable domain comprises the sequence of SEQ ID NO: 30.

5. The polypeptide of claim 3 wherein the single variable domain comprises the amino acid sequence of SEQ ID NO: 30 wherein one or more of the amino acid positions 1-30, 36-49, 66-97 and/or 112-122 have been substituted, modified or deleted, and/or wherein one or more amino acids have been inserted between any amino acids at 1-30, 36-49, 66-97 and/or 112-122.

6. An isolated polypeptide comprising the amino acid sequence of SEQ ID NO: 5, 20, 21, 22, 30, 31, 32, 33, or 87.

7. A composition comprising an isolated polypeptide comprising at least one monomer of a single variable domain that specifically binds to human DR5, wherein the single variable domain comprises complementarity determining region (CDR) sequences having the sequences of SEQ ID NO: 43 (CDR1); SEQ ID NO: 53 (CDR2); and SEQ ID NO: 66 (CDR3), further comprising at least one pharmaceutically acceptable carrier, diluent or excipient and/or adjuvant.

8. The isolated polypeptide according to claim 1 that is a humanized immunoglobulin, a camelized immunoglobulin or an immunoglobulin obtainable by an affinity optimization technique, or a fragment thereof.

9. An isolated polypeptide that has:
   (a) the amino acid sequence of SEQ ID NO: 30; or
   (b) the amino acid sequence of SEQ ID NO: 30, in which one or more of the amino acid positions 11, 37, 44, 45, 47, 83, 84, 112, 113 and 117 of SEQ ID NO: 30 are humaneered, substituted, modified or deleted and/or wherein one or more amino acids have been inserted between any amino acids at 1-30, 36-49, 66-97 and/or 112-122, wherein the isolated polypeptide specifically binds to human DR5.

10. An isolated polypeptide comprising one or more copies of:
    (a) the sequence of SEQ ID NO: 30; and/or
    (b) the sequence of SEQ ID NO: 30 wherein one or more of the amino acid positions 1-30, 36-49, 66-97 and/or 112-122 have been substituted, modified or deleted, and/or wherein one or more amino acids have been inserted between any amino acids at 1-30, 36-49, 66-97 and/or 112-122, and wherein the isolated polypeptide is capable of enhancing cell apoptosis and wherein the isolated polypeptide specifically binds to human DR5.

11. The polypeptide according to claim 10, wherein the polypeptide comprises at least three, four, five or more copies of the sequence of SEQ ID NO: 30 wherein one or more of the amino acid positions 1-30, 36-49, 66-97 and/or 112-122 have been substituted, modified or deleted, and/or wherein one or more amino acids have been inserted between any amino acids at 1-30, 36-49, 66-97 and/or 112-122, and wherein the copies constitute monovalent binding polypeptides that are all directed against the same binding region of human DR5.

12. An isolated polypeptide comprising at least three, four, five or more copies of the sequence of SEQ ID NO: 30 wherein one or more of the amino acid positions 1-30, 36-49, 66-97 and/or 112-122 have been substituted, modified or deleted and/or wherein one or more amino acids have been inserted between any amino acids at 1-30, 36-49, 66-97 and/or 112-122, wherein the isolated polypeptide is capable of enhancing cell apoptosis and wherein the copies constitute monovalent binding polypeptides that are all directed against the same binding region of human DR5, and wherein the said isolated polypeptide specifically binds to human DR5.

13. The polypeptide according to claim 10 for use as a drug.

14. The polypeptide of claim 10, for use as an anti-cancer therapeutic.

15. A composition comprising the polypeptide of claim 10, further comprising at least one pharmaceutically acceptable carrier, diluent or excipient and/or adjuvant.

16. A polypeptide comprising the CDR1 sequence of SEQ ID NO: 43, the CDR2 sequence of SEQ ID NO: 53, and the CDR3 sequence of SEQ ID NO: 66, wherein the polypeptide is capable of contacting, within 5 Angstroms, amino acids H86, S88, E89, D90, D93, I95, K98, Q101, D102, L111, F112, R115, and R118 of a DR5 polypeptide of SEQ ID NO: 89.

17. The polypeptide of claim 3 wherein the single variable domain comprises the amino acid sequence of SEQ ID NO: 30.

\* \* \* \* \*